United States Patent
Facchini

(10) Patent No.: US 10,662,453 B2
(45) Date of Patent: *May 26, 2020

(54) COMPOSITIONS AND METHODS FOR MAKING (S)-NORCOCLAURINE AND (S)-NORLAUDANOSOLINE, AND SYNTHESIS INTERMEDIATES THEREOF

(71) Applicant: Willow BioSciences Inc., Calgary (CA)

(72) Inventor: Peter James Facchini, Calgary (CA)

(73) Assignee: Willow BioSciences Inc., Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/122,050

(22) Filed: Sep. 5, 2018

(65) Prior Publication Data

US 2019/0062793 A1  Feb. 28, 2019

Related U.S. Application Data

(63) Continuation of application No. 15/319,568, filed as application No. PCT/CA2015/050542 on Jun. 12, 2015, now Pat. No. 10,119,155.

(60) Provisional application No. 62/014,367, filed on Jun. 19, 2014.

(51) Int. Cl.
| | |
|---|---|
| C12N 9/02 | (2006.01) |
| C12N 9/90 | (2006.01) |
| C12N 15/00 | (2006.01) |
| C07H 21/04 | (2006.01) |
| C12P 17/12 | (2006.01) |
| C12N 9/06 | (2006.01) |
| C12P 7/24 | (2006.01) |
| C12P 13/00 | (2006.01) |
| C12N 9/88 | (2006.01) |
| C12P 13/22 | (2006.01) |
| C12N 15/82 | (2006.01) |
| C12P 17/18 | (2006.01) |

(52) U.S. Cl.
CPC ............ *C12P 17/12* (2013.01); *C12N 9/0022* (2013.01); *C12N 9/0059* (2013.01); *C12N 9/88* (2013.01); *C12P 7/24* (2013.01); *C12P 13/001* (2013.01); *C12P 13/22* (2013.01); *C12N 15/8243* (2013.01); *C12P 17/182* (2013.01); *C12Y 201/01128* (2013.01)

(58) Field of Classification Search
CPC .......... C12P 17/12; C12P 17/188; C12N 9/90; C12Y 201/10114
USPC .... 435/18, 108, 193, 320.1, 252.3; 530/370; 536/23.2
See application file for complete search history.

(56) References Cited

U.S. PATENT DOCUMENTS

2007/0298481 A1   12/2007   Sato

FOREIGN PATENT DOCUMENTS

| EP | 2169075 A1 | 3/2010 |
|---|---|---|
| WO | 2008/067070 A2 | 6/2008 |
| WO | 2012/135389 A2 | 10/2012 |
| WO | 2015/066642 A1 | 5/2015 |

OTHER PUBLICATIONS

Devos et al., "Practical Limits of Function Prediction", Proteins: Structure, Function and Genetics, 2000, vol. 41:98-107.
Facchini, P.J. et al., "Decreased cell wall digestibility in canola transformed with chimeric tyrosine decarboxylase genes from opium poppy", Plant Physiology, 1999, vol. 120(3), p. 653-663.
Hagel, J.M. and Facchini, P.J., "Benzylisoquinoline Alkaloid Metabolism: A Century of Discovery and a Brave New World", Plant Cell Physiology, 2013, vol. 54(5), p. 647-672.
Hawkins, K. et al., "Production of benzylisoquinoline alkaloids in *Saccharomyces cerevisiae*", Nature Chemical Biology, vol. 4, No. 9, p. 564-573, Aug. 10, 2008.
Ilari, A. et al., "Structual Basis of Enzymatic (S)-Norcoclaurine Biosynthesis", Journal of Biological Chemistry, 2009, vol. 284(2), p. 897-904.
Kisselev, L. et al., "Polypeptide Release Factors in Prokaryotes and Eukaryotes: Same Function, Different Structure", Structure, 2002, vol. 10 :8-9.
Nakagawa, A. et al., "A bacterial platform for fermentative production of plant alkaloids", Nature Communications, 2011, vol. 2(326).
Roh, J.H. et al., "Purification, cloning, and three-dimensional structure prediction of Micrococcus luteus FAD-containing tyramine oxidase", Biochemical and Biophysical Research Communicat, Elsevier, Amsterdam, NL, vol. 268, No. 2, p. 293-297, Feb. 16, 2000.
Whisstock, J.C. et al., "Prediction of protein function from protein sequence and structure", Quarterly Reviews of Biophysics 2003, vol. 36(3):307-340.
Witkowski, A. et al., "Conversion of a Beta-Ketoacyl Synthase to a Malonyl Decarboxylase by Replacement of teh Active-Site Cysteine with Glutamine", Biochemistry 38:11643-11650, 1999.

*Primary Examiner* — Robert B Mondesi
*Assistant Examiner* — Mohammad Y Meah
(74) *Attorney, Agent, or Firm* — Bereskin & Parr LLP/S.E.N.C.R.L., s.r.l.; Micheline Gravelle

(57) ABSTRACT

Methods that may be used for the manufacture of the chemical compound (S)-norcoclaurine, (S)-norlaudanosoline, and (S)-norcoclaurine or (S)-norlaudanosoline synthesis intermediates are provided. (S)-Norcoclaurine, (S)-norlaudanosoline, and (S)-norcoclaurine or (S)-norlaudanosoline synthesis intermediates are useful as precursor products in the manufacture of certain medicinal agents.

10 Claims, 7 Drawing Sheets

Specification includes a Sequence Listing.

L-tyrosine tyramine

L-DOPA 4-hydroxy-phenylacetaldehyde
(4-HPAA)

dopamine (S)-norcoclaurine 3,4-dihydroxy-phenylacetaldehyde
(3,4-DHPAA)

(S)-norlaudanosoline

SEQUENCE LISTING

<160> NUMBER OF SEQ ID NOS: 231

<210> SEQ ID NO 1
<211> LENGTH: 193
<212> TYPE: PRT
<213> ORGANISM: Papaver bracteatum

<400> SEQUENCE: 1

Met Met Arg Lys Val Ile Lys Tyr Asp Met Glu Val Ala Thr Ser Ala
1               5                   10                  15

Asp Ser Val Trp Ala Val Tyr Ser Pro Asp Ile Pro Arg Leu Leu
            20                  25                  30

Arg Asp Val Leu Leu Pro Gly Val Phe Glu Lys Leu Asp Val Ile Glu
        35                  40                  45

Gly Asn Gly Gly Val Gly Thr Val Leu Asp Ile Ala Phe Pro Pro Gly
    50                  55                  60

Ala Val Pro Arg Ser Tyr Lys Glu Lys Phe Val Asn Ile Asp Arg Val
65                  70                  75                  80

Lys Arg Leu Lys Glu Val Ile Met Ile Glu Gly Gly Tyr Leu Asp Met
                85                  90                  95

Gly Cys Thr Phe Tyr Leu Asp Arg Ile His Val Val Glu Lys Thr Pro
            100                 105                 110

Asn Ser Cys Val Ile Glu Ser Ser Ile Glu Tyr Glu Val Lys Glu Glu
        115                 120                 125

Phe Ala Asp Lys Met Ala Lys Leu Ile Thr Thr Glu Pro Leu Gln Ser
    130                 135                 140

Met Ala Glu Val Ile Ser Gly Tyr Val Leu Lys Lys Arg Leu Gln Val
145                 150                 155                 160

```
Phe Gly Phe Glu Ile Lys Pro Asn Leu Arg Phe Asn Leu Leu Leu Cys
            165                 170                 175
Leu Ile Ile Cys Leu Val Ile Ala Gly Gly Met Leu Ile Gly Arg Val
            180                 185                 190
Pro

<210> SEQ ID NO 2
<211> LENGTH: 363
<212> TYPE: PRT
<213> ORGANISM: Papaver bracteatum

<400> SEQUENCE: 2

Met Met Arg Lys Val Ile Lys Tyr Asp Met Glu Val Ala Thr Ser Ala
1               5                   10                  15
Asp Ser Val Trp Ala Val Tyr Ser Ser Pro Asp Ile Pro Arg Leu Leu
                20                  25                  30
Arg Asp Val Leu Leu Pro Gly Val Phe Glu Lys Leu Asp Val Ile Glu
            35                  40                  45
Gly Asn Gly Gly Val Gly Thr Val Leu Asp Ile Ala Phe Pro Pro Gly
        50                  55                  60
Ala Val Pro Arg Ser Tyr Lys Glu Lys Phe Val Asn Ile Asp Arg Val
65                  70                  75                  80
Lys Arg Leu Lys Glu Val Ile Met Ile Glu Gly Gly Tyr Leu Asp Met
                85                  90                  95
Gly Cys Thr Phe Tyr Leu Asp Arg Ile His Val Val Glu Lys Ala Pro
            100                 105                 110
Ser Ser Cys Val Ile Glu Ser Ser Ile Val Tyr Glu Val Glu Glu Glu
            115                 120                 125
Tyr Ala Asp Val Met Ser Lys Leu Ile Thr Thr Glu Pro Leu Lys Ser
        130                 135                 140
Met Ala Glu Val Ile Ser Asn Tyr Val Ile Gln Lys Glu Ser Val Ser
145                 150                 155                 160
Ala Arg Asn Ile Phe Asn Arg Gln Ser Val Val Lys Lys Glu Ile His
                165                 170                 175
Tyr Asp Leu Glu Val Pro Thr Ser Ala Asp Ser Ile Trp Ala Val Tyr
            180                 185                 190
Ser Asn Pro Asp Ile Pro Arg Leu Leu Arg Asp Val Leu Leu Pro Gly
            195                 200                 205
Val Phe Glu Lys Leu Asp Val Ile Ala Gly Asn Gly Gly Val Gly Thr
        210                 215                 220
Ile Leu Asp Ile Ala Phe Pro Leu Gly Ala Val Pro Arg Arg Tyr Lys
225                 230                 235                 240
Glu Lys Phe Val Lys Ile Asn His Glu Lys Arg Leu Lys Glu Val Ile
                245                 250                 255
Met Ile Glu Gly Gly Tyr Leu Asp Met Gly Cys Thr Phe Tyr Met Asp
            260                 265                 270
Arg Ile His Val Phe Glu Lys Thr Pro Asn Ser Cys Val Ile Glu Ser
            275                 280                 285
Ser Ile Ile Tyr Glu Val Lys Glu Glu Tyr Ala Asp Lys Met Ala Lys
        290                 295                 300
Leu Ile Thr Thr Glu Pro Leu Gln Ser Met Ala Glu Val Ile Ser Gly
305                 310                 315                 320
Tyr Val Leu Lys Lys Arg Leu Gln Val Phe Gly Phe Glu Ile Lys Pro
                325                 330                 335
```

```
Thr Leu Arg Phe Asn Leu Leu Leu Cys Leu Ile Ile Cys Leu Val Ile
            340                 345                 350

Ala Gly Gly Met Leu Ile Gly Arg Val Pro Leu
        355                 360
```

<210> SEQ ID NO 3
<211> LENGTH: 210
<212> TYPE: PRT
<213> ORGANISM: Thalictrum flavum

<400> SEQUENCE: 3

```
Met Met Lys Met Glu Val Val Phe Val Phe Leu Met Leu Leu Gly Thr
1               5                   10                  15

Ile Asn Cys Gln Lys Leu Ile Leu Thr Gly Arg Pro Phe Leu His His
            20                  25                  30

Gln Gly Ile Ile Asn Gln Val Ser Thr Val Thr Lys Val Ile His His
        35                  40                  45

Glu Leu Glu Val Ala Ala Ser Ala Asp Asp Ile Trp Thr Val Tyr Ser
    50                  55                  60

Trp Pro Gly Leu Ala Lys His Leu Pro Asp Leu Leu Pro Gly Ala Phe
65                  70                  75                  80

Glu Lys Leu Glu Ile Ile Gly Asp Gly Val Gly Thr Ile Leu Asp
            85                  90                  95

Met Thr Phe Val Pro Gly Glu Phe Pro His Glu Tyr Lys Glu Lys Phe
            100                 105                 110

Ile Leu Val Asp Asn Glu His Arg Leu Lys Lys Val Gln Met Ile Glu
        115                 120                 125

Gly Gly Tyr Leu Asp Leu Gly Val Thr Tyr Tyr Met Asp Thr Ile His
    130                 135                 140

Val Val Pro Thr Gly Lys Asp Ser Cys Val Ile Lys Ser Ser Thr Glu
145                 150                 155                 160

Tyr His Val Lys Pro Glu Phe Val Lys Ile Val Glu Pro Leu Ile Thr
            165                 170                 175

Thr Gly Pro Leu Ala Ala Met Ala Asp Ala Ile Ser Lys Leu Val Leu
        180                 185                 190

Glu His Lys Ser Lys Ser Asn Ser Asp Glu Ile Glu Ala Ala Ile Ile
    195                 200                 205

Thr Val
    210
```

<210> SEQ ID NO 4
<211> LENGTH: 275
<212> TYPE: PRT
<213> ORGANISM: Argemone mexicane

<400> SEQUENCE: 4

```
Met Ser Lys Leu Ile Thr Thr Ile Pro Leu Lys Ser Met Ser Glu Val
1               5                   10                  15

Ile Ala Asn Tyr Val Leu Lys Asn Gln Ser Val Ile Arg Lys Glu Val
            20                  25                  30

Thr Tyr Glu Leu Glu Val Pro Thr Ser Ala Asp Ser Ile Trp Ala Val
        35                  40                  45

Tyr Ser Ser Pro Asn Ile Pro Thr Leu Leu Arg Asp Val Leu Leu Pro
    50                  55                  60

Gly Val Phe Glu Lys Leu Asp Val Ile Glu Gly Asn Gly Gly Val Gly
65                  70                  75                  80
```

```
Thr Val Leu Asp Ile Val Phe Pro Pro Gly Ala Val Pro Arg Cys Tyr
                85                  90                  95

Lys Glu Lys Phe Ile Asn Ile Asp Asn Lys Lys Arg Leu Lys Glu Val
            100                 105                 110

Ile Met Ile Glu Gly Gly His Leu Asp Met Gly Cys Thr Tyr Tyr Leu
            115                 120                 125

Asp Arg Ile His Val Ile Ala Lys Thr Pro Asn Ser Cys Val Ile Lys
        130                 135                 140

Ser Ser Ile Ile Tyr Asp Val Lys Lys Glu Tyr Ala Glu Ala Met Ser
145                 150                 155                 160

Lys Leu Ile Thr Thr Ile Pro Leu Lys Ser Met Ser Glu Val Ile Ala
                165                 170                 175

Asn Tyr Val Leu Lys Asn Gln Ser Val Ile Arg Lys Glu Val Thr Tyr
                180                 185                 190

Glu Leu Gln Val Pro Thr Ser Ala Asp Ser Ile Trp Ala Val Tyr Ser
            195                 200                 205

Ser Pro Asn Ile Pro Thr Ile Leu Arg Asp Val Leu Leu Pro Gly Val
        210                 215                 220

Phe Glu Arg Leu Asp Val Ile Lys Gly Asn Gly Gly Val Gly Thr Val
225                 230                 235                 240

Leu Asp Ile Val Ser His Pro Gly Asn Ser Met Tyr Tyr Tyr Phe Phe
                245                 250                 255

Thr Ile Tyr Pro Thr Phe Asn Phe Ile Thr Ile Leu Val Thr Met Val
                260                 265                 270

Asn Ser Thr
        275

<210> SEQ ID NO 5
<211> LENGTH: 220
<212> TYPE: PRT
<213> ORGANISM: Argemone mexicane

<400> SEQUENCE: 5

Met Ser Lys Leu Ile Thr Thr Ala Pro Leu Lys Ser Met Ser Glu Ala
1               5                   10                  15

Ile Ala Asn Tyr Val Leu Lys Lys Gln Ser Val Ile Arg Lys Val Val
            20                  25                  30

Thr Tyr Glu Leu Glu Val Pro Ala Ser Ala Asp Ser Ile Trp Ala Val
        35                  40                  45

Tyr Ser Ser Pro Asn Ile Pro Thr Leu Arg Asp Val Leu Leu Pro
50                  55                  60

Gly Val Phe Glu Lys Leu Asp Val Ile Glu Gly Asn Gly Gly Val Gly
65                  70                  75                  80

Thr Val Leu Asp Ile Val Phe Pro Pro Gly Ala Val Pro Arg Arg Tyr
                85                  90                  95

Lys Glu Lys Phe Val Lys Ile Asn Asn Glu Lys Arg Leu Lys Glu Val
            100                 105                 110

Ile Met Ile Glu Gly Gly Tyr Leu Asp Met Gly Cys Thr Ser Tyr Met
            115                 120                 125

Asp Arg Ile His Val Leu Glu Lys Thr Pro Asn Ser Cys Val Ile Glu
        130                 135                 140

Ser Ser Ile Ile Tyr Glu Val Lys Gln Glu Tyr Ala Asp Glu Met Ser
145                 150                 155                 160

Lys Leu Ile Thr Thr Val Pro Leu Lys Ser Met Ser Glu Val Ile Ala
```

```
                    165                 170                 175

Asn Tyr Val Leu Lys Lys Gln Phe Arg Val Phe Gly Tyr Glu Ile Lys
                180                 185                 190

Pro Lys Leu Gly Leu Ser Leu Leu Cys Leu Ile Ile Cys Leu Val
            195                 200                 205

Ile Leu Gly Gly Leu Leu Ile Ala Gly Val Pro Val
        210                 215                 220

<210> SEQ ID NO 6
<211> LENGTH: 206
<212> TYPE: PRT
<213> ORGANISM: Corydalis saxicola

<400> SEQUENCE: 6

Met Gly Lys Arg Ile Gln Lys Lys Glu Ala Lys Lys Ile Leu Arg Lys
1               5                   10                  15

Glu Leu Thr His Glu Leu Glu Val Pro Thr Ser Ala Asp Ser Ile Trp
            20                  25                  30

Ala Val Tyr Gly Ser Pro Asp Ile Pro Arg Leu Leu Arg Asp Val Leu
        35                  40                  45

Leu Pro Gly Val Phe Glu Lys Leu Asp Ile Ile Glu Gly Asn Gly Gly
    50                  55                  60

Val Gly Thr Val Leu Asp Ile Ala Phe Pro Pro Gly Thr Val Pro Arg
65                  70                  75                  80

Ser Tyr Lys Glu Lys Phe Val Lys Val Asp His Asp Lys His Leu Lys
                85                  90                  95

Glu Val Val Met Ile Glu Gly Gly Tyr Leu Asp Leu Gly Cys Thr Phe
            100                 105                 110

Tyr Met Asp Arg Ile His Val Leu Pro Lys Gly Pro Asn Ser Cys Val
        115                 120                 125

Ile Glu Ser Ser Leu Ile Tyr Glu Val Arg Glu Glu Leu Ala Asp Ala
    130                 135                 140

Val Gly Ser Leu Ile Ser Ile Glu Pro Leu Ala Ser Met Ala Glu Val
145                 150                 155                 160

Val Ser Ser Tyr Val Leu Lys Gln Gln Leu Arg Val Phe Gly Val Val
                165                 170                 175

Val Gln Pro Arg Val Gly Leu Ser Leu Leu Cys Leu Ile Leu Cys
            180                 185                 190

Leu Val Ile Leu Gly Gly Leu Leu Ile Gly Gly Val Ser Ile
        195                 200                 205

<210> SEQ ID NO 7
<211> LENGTH: 231
<212> TYPE: PRT
<213> ORGANISM: Papaver somniferum

<400> SEQUENCE: 7

Met Ser Lys Leu Ile Thr Thr Glu Pro Leu Lys Ser Met Ala Glu Val
1               5                   10                  15

Ile Ser Asn Tyr Ala Met Lys Gln Gln Ser Val Ser Glu Arg Asn Ile
            20                  25                  30

Pro Lys Lys Gln Ser Leu Leu Arg Lys Glu Ile Thr Tyr Glu Thr Glu
        35                  40                  45

Val Gln Thr Ser Ala Asp Ser Ile Trp Asn Val Tyr Ser Ser Pro Asp
    50                  55                  60

Ile Pro Arg Leu Leu Arg Asp Val Leu Leu Pro Gly Val Phe Glu Lys
```

```
            65                  70                  75                  80
Leu Asp Val Ile Ala Gly Asn Gly Gly Val Gly Thr Val Leu Asp Ile
                    85                  90                  95

Ala Phe Pro Leu Gly Ala Val Pro Arg Arg Tyr Lys Glu Lys Phe Val
                100                 105                 110

Lys Ile Asn His Glu Lys Arg Leu Lys Glu Val Val Met Ile Glu Gly
            115                 120                 125

Gly Tyr Leu Asp Met Gly Cys Thr Phe Tyr Met Asp Arg Ile His Ile
        130                 135                 140

Phe Glu Lys Thr Pro Asn Ser Cys Val Ile Glu Ser Ser Ile Ile Tyr
145                 150                 155                 160

Glu Val Lys Glu Glu Tyr Ala Gly Lys Met Ala Lys Leu Ile Thr Thr
                165                 170                 175

Glu Pro Leu Glu Ser Met Ala Glu Val Ile Ser Gly Tyr Val Leu Lys
                180                 185                 190

Lys Arg Leu Gln Val Phe Gly Phe Glu Ile Lys Pro Lys Leu Arg Phe
            195                 200                 205

Asn Leu Leu Leu Cys Leu Ile Ile Cys Leu Val Ile Ala Gly Gly Met
        210                 215                 220

Phe Val Ala Gly Val Pro Leu
225                 230

<210> SEQ ID NO 8
<211> LENGTH: 231
<212> TYPE: PRT
<213> ORGANISM: Papaver somniferum

<400> SEQUENCE: 8

Met Ser Lys Leu Ile Thr Thr Glu Pro Leu Lys Ser Met Ala Glu Val
1               5                   10                  15

Ile Ser Asn Tyr Val Ile Gln Arg Glu Ser Phe Ser Ala Arg Asn Ile
                20                  25                  30

Leu Asn Lys Asn Ser Leu Val Lys Lys Glu Ile Arg Tyr Asp Leu Glu
            35                  40                  45

Val Pro Thr Ser Ala Asp Ser Ile Trp Ser Val Tyr Ser Cys Pro Asp
        50                  55                  60

Ile Pro Arg Leu Leu Arg Asp Val Leu Leu Pro Gly Val Phe Gln Lys
65                  70                  75                  80

Leu Asp Val Ile Glu Gly Asn Gly Gly Val Gly Thr Val Leu Asp Ile
                    85                  90                  95

Val Phe Pro Pro Gly Ala Val Pro Arg Ser Tyr Lys Glu Lys Phe Val
                100                 105                 110

Asn Ile Asn His Glu Lys Arg Leu Lys Glu Val Ile Met Ile Glu Gly
            115                 120                 125

Gly Tyr Leu Asp Met Gly Cys Thr Phe Tyr Met Asp Arg Ile His Ile
        130                 135                 140

Phe Glu Lys Thr Pro Asn Ser Cys Val Ile Glu Ser Ser Ile Ile Tyr
145                 150                 155                 160

Glu Val Lys Glu Glu Tyr Ala Gly Lys Met Ala Lys Leu Ile Thr Thr
                165                 170                 175

Glu Pro Leu Glu Ser Met Ala Glu Val Ile Ser Gly Tyr Val Leu Lys
                180                 185                 190

Lys Arg Leu Gln Val Phe Gly Phe Glu Ile Lys Pro Lys Leu Arg Phe
            195                 200                 205
```

```
Asn Leu Leu Cys Leu Ile Ile Cys Leu Val Ile Ala Gly Gly Met
    210             215                 220

Phe Val Ala Gly Val Pro Leu
225             230

<210> SEQ ID NO 9
<211> LENGTH: 196
<212> TYPE: PRT
<213> ORGANISM: Coptis japonica

<400> SEQUENCE: 9

Met Arg Met Glu Val Val Leu Val Val Phe Leu Met Phe Ile Gly Thr
1               5                   10                  15

Ile Asn Cys Glu Arg Leu Ile Phe Asn Gly Arg Pro Leu Leu His Arg
            20                  25                  30

Val Thr Lys Glu Glu Thr Val Met Leu Tyr His Glu Leu Glu Val Ala
        35                  40                  45

Ala Ser Ala Asp Glu Val Trp Ser Val Glu Gly Ser Pro Glu Leu Gly
    50                  55                  60

Leu His Leu Pro Asp Leu Leu Pro Ala Gly Ile Phe Ala Lys Phe Glu
65                  70                  75                  80

Ile Thr Gly Asp Gly Gly Gly Ser Ile Leu Asp Met Thr Phe Pro
                85                  90                  95

Pro Gly Gln Phe Pro His His Tyr Arg Glu Lys Phe Val Phe Phe Asp
            100                 105                 110

His Lys Asn Arg Tyr Lys Leu Val Glu Gln Ile Asp Gly Asp Phe Phe
        115                 120                 125

Asp Leu Gly Val Thr Tyr Tyr Met Asp Thr Ile Arg Val Val Ala Thr
    130                 135                 140

Gly Pro Asp Ser Cys Val Ile Lys Ser Thr Thr Glu Tyr His Val Lys
145                 150                 155                 160

Pro Glu Phe Ala Lys Ile Val Lys Pro Leu Ile Asp Thr Val Pro Leu
                165                 170                 175

Ala Ile Met Ser Glu Ala Ile Ala Lys Val Val Leu Glu Asn Lys His
            180                 185                 190

Lys Ser Ser Glu
            195

<210> SEQ ID NO 10
<211> LENGTH: 371
<212> TYPE: PRT
<213> ORGANISM: Papaver bracteatum

<400> SEQUENCE: 10

Met Met Arg Lys Val Ile Lys Tyr Asp Met Glu Val Ala Thr Ser Ala
1               5                   10                  15

Asp Ser Val Trp Ala Val Tyr Ser Ser Pro Asp Ile Pro Arg Leu Leu
            20                  25                  30

Arg Asp Val Leu Leu Pro Gly Val Phe Glu Lys Leu Asp Val Ile Glu
        35                  40                  45

Gly Asn Gly Gly Val Gly Thr Val Leu Asp Ile Ala Phe Pro Pro Gly
    50                  55                  60

Ala Val Pro Arg Ser Tyr Lys Glu Lys Phe Val Asn Ile Asp Arg Val
65                  70                  75                  80

Lys Arg Leu Lys Glu Val Ile Met Ile Glu Gly Tyr Leu Asp Met
                85                  90                  95
```

-continued

```
Gly Cys Thr Phe Tyr Leu Asp Arg Ile His Val Val Glu Lys Thr Pro
                100                 105                 110

Ser Ser Cys Val Ile Glu Ser Ser Ile Val Tyr Glu Val Glu Glu Glu
            115                 120                 125

Tyr Ala Asp Ala Met Ser Lys Leu Ile Thr Thr Glu Pro Leu Lys Ser
        130                 135                 140

Met Ala Glu Val Ile Ser Asn Tyr Val Ile Gln Lys Glu Ser Val Ser
145                 150                 155                 160

Ala Arg Asn Ile Phe Asn Arg Gln Ser Val Val Lys Lys Glu Ile His
                165                 170                 175

Tyr Asp Leu Glu Val Pro Thr Ser Ala Asp Ser Ile Trp Ala Val Tyr
            180                 185                 190

Ser Asn Pro Asp Ile Pro Arg Leu Leu Arg Asp Val Leu Leu Pro Gly
        195                 200                 205

Val Phe Glu Lys Leu Asp Val Ile Glu Gly Asn Gly Gly Val Gly Thr
210                 215                 220

Val Leu Asp Ile Val Phe Pro Pro Gly Ala Val Pro Arg Cys Tyr Lys
225                 230                 235                 240

Glu Lys Phe Val Thr Met Asp His Gln Lys Arg Leu Lys Glu Val Ile
                245                 250                 255

Met Ile Glu Gly Gly Tyr Leu Asp Met Gly Cys Thr Ser Tyr Leu Asp
            260                 265                 270

Arg Ile His Val Ile Glu Lys Thr Ser Lys Ser Cys Ile Ile Lys Ser
        275                 280                 285

Ser Val Val Tyr Glu Val Lys Gln Glu Cys Ala Glu Ala Ile Ser Lys
        290                 295                 300

Leu Ile Thr Thr Glu Pro Leu Lys Ser Met Ala Glu Val Ile Ser Asn
305                 310                 315                 320

Tyr Val Leu Lys Lys Gln Ser Val Ser Asp Thr Asn Asn Ile Ala Lys
                325                 330                 335

Lys Gln Ser Val Leu Arg Lys Glu Ile Thr Tyr Glu Thr Glu Val Gln
        340                 345                 350

Thr Ser Ala Asp Ser Ile Trp Asn Val Tyr Ser Ser Pro Asp Ile Pro
        355                 360                 365

Pro Thr Thr
    370

<210> SEQ ID NO 11
<211> LENGTH: 320
<212> TYPE: PRT
<213> ORGANISM: Papaver bracteatum

<400> SEQUENCE: 11

Met Asp Ile Ile Glu Gly Asp Gly Gly Val Gly Thr Val Leu Asp Val
1               5                   10                  15

Val Phe Gln Pro Gly Ala Val Pro Gln Ser Tyr Lys Glu Arg Phe Glu
            20                  25                  30

Thr Val Asp His Glu Lys Arg Ile Leu Glu Val Arg Ile Ile Gln Gly
        35                  40                  45

Gly Tyr Leu Glu Met Gly Cys Thr Ser Tyr Leu Asn Arg Met His Val
    50                  55                  60

Ile Glu Ile Thr Ser Lys Ser Cys Val Ile Lys Ser Ser Val Ile Tyr
65                  70                  75                  80

Asp Val Lys Glu Glu Cys Ala Asp Ala Met Ser Lys Leu Ile Thr Thr
                85                  90                  95

Ile Gln Leu Glu Ser Met Ala Lys Val Val Ala Asp Tyr Val Leu Lys
```

```
            100                 105                 110
Lys Gln Ser Ala Ser Asp Thr Ser Ile Pro Lys Lys Gln Ser Leu Met
            115                 120                 125
Arg Lys Glu Ile Thr His Glu Met Glu Val Gln Thr Ser Ala Asp Ser
        130                 135                 140
Ile Trp Asp Ile Tyr Ser Ser Pro Asp Ile Pro Arg Leu Leu Arg Asp
145                 150                 155                 160
Val Leu Leu Pro Gly Ala Phe Glu Lys Leu His Val Ile Gln Gly Asn
                165                 170                 175
Gly Gly Val Gly Thr Val Leu Asp Ile Ala Leu Pro Leu Gly Ala Val
            180                 185                 190
Pro Arg Asn Tyr Lys Glu Lys Phe Val Lys Ile Asn His Glu Lys Arg
        195                 200                 205
Leu Lys Glu Ala Val Met Ile Glu Gly Gly Tyr Ala Asp Met Gly Cys
    210                 215                 220
Thr Phe Tyr Met His Arg Ile His Val Leu Glu Lys Thr Pro Lys Ser
225                 230                 235                 240
Cys Val Ile Glu Ser Ser Ile Val Tyr Glu Val Lys Glu Glu Tyr Ala
                245                 250                 255
Asp Lys Met Ser Lys Leu Ile Thr Thr Glu Pro Leu Gln Ser Met Ala
            260                 265                 270
Glu Ala Ile Ser Ser Tyr Val Leu Lys Lys Gln Phe Gln Val Phe Gly
        275                 280                 285
Leu Glu Val Lys Pro Lys Leu Val Leu Ser Leu Phe Leu Cys Leu Ile
    290                 295                 300
Ile Phe Leu Ala Ile Val Gly Gly Phe Leu Ile Gly Gly Leu Lys Ala
305                 310                 315                 320

<210> SEQ ID NO 12
<211> LENGTH: 276
<212> TYPE: PRT
<213> ORGANISM: Papaver bracteatum

<400> SEQUENCE: 12

Met Ile Glu Gly Gly Tyr Leu Asp Met Gly Cys Thr Phe Tyr Leu Asp
1               5                   10                  15
Arg Ile His Val Val Glu Lys Thr Pro Ser Ser Cys Val Ile Glu Ser
            20                  25                  30
Ser Ile Val Tyr Glu Val Lys Gln Glu Cys Ala Glu Ala Ile Ser Lys
        35                  40                  45
Leu Ile Thr Thr Glu Pro Leu Lys Ser Met Ala Glu Val Ile Ala Asn
    50                  55                  60
Tyr Val Leu Lys Lys Gln Ser Val Ser Asp Thr Asn Ile Pro Lys Lys
65                  70                  75                  80
Gln Ser Val Leu Arg Lys Glu Ile Thr Tyr Glu Thr Glu Val Gln Thr
                85                  90                  95
Ser Val Asp Ser Ile Trp Asn Val Tyr Ser Ser Pro Asp Ile Pro Arg
            100                 105                 110
Leu Leu Arg Asp Val Leu Leu Pro Gly Val Phe Glu Lys Leu Asp Val
        115                 120                 125
Ile Ala Gly Asn Gly Gly Val Gly Thr Val Leu Asp Ile Ala Phe Pro
    130                 135                 140
Leu Gly Ala Val Pro Arg Arg Tyr Lys Glu Arg Phe Val Lys Ile Asn
145                 150                 155                 160
```

```
His Glu Lys Arg Leu Lys Glu Val Val Met Ile Glu Gly Gly Tyr Leu
            165                 170                 175

Asp Met Gly Cys Thr Phe Tyr Met Asp Arg Ile His Val Phe Asp Lys
        180                 185                 190

Thr Pro Asn Ser Cys Val Ile Glu Ser Ser Ile Ile Tyr Glu Val Lys
        195                 200                 205

Glu Glu Tyr Ala Asp Lys Met Ala Lys Leu Ile Thr Thr Glu Pro Leu
    210                 215                 220

Gln Ser Met Ala Glu Val Ile Ser Gly Tyr Val Leu Lys Lys Arg Leu
225                 230                 235                 240

Gln Val Phe Gly Phe Glu Ile Lys Pro Asn Leu Arg Phe Asn Leu Leu
                245                 250                 255

Leu Cys Leu Ile Ile Cys Leu Val Ile Ala Gly Gly Met Leu Ile Gly
                260                 265                 270

Arg Val Pro Leu
            275

<210> SEQ ID NO 13
<211> LENGTH: 532
<212> TYPE: PRT
<213> ORGANISM: Papaver bracteatum

<400> SEQUENCE: 13

Met Met Arg Lys Val Ile Lys Tyr Asp Met Glu Val Ala Thr Ser Ala
1               5                   10                  15

Asp Ser Val Trp Ala Val Tyr Ser Ser Pro Asp Ile Pro Arg Leu Leu
            20                  25                  30

Arg Asp Val Leu Leu Pro Gly Val Phe Glu Lys Leu Asp Val Ile Glu
        35                  40                  45

Gly Asn Gly Gly Val Gly Thr Val Leu Asp Ile Ala Phe Pro Pro Gly
    50                  55                  60

Ala Val Pro Arg Ser Tyr Lys Glu Lys Phe Val Asn Ile Asp Arg Val
65                  70                  75                  80

Lys Arg Leu Lys Glu Val Ile Met Ile Glu Gly Gly Tyr Leu Asp Met
                85                  90                  95

Gly Cys Thr Phe Tyr Leu Asp Arg Ile His Val Val Glu Lys Thr Pro
            100                 105                 110

Ser Ser Cys Val Ile Glu Ser Ser Ile Val Tyr Glu Val Glu Glu Glu
        115                 120                 125

Tyr Ala Asp Ala Met Ser Lys Leu Ile Thr Thr Glu Pro Leu Lys Ser
    130                 135                 140

Met Ala Glu Val Ile Ser Asn Tyr Val Ile Gln Lys Glu Ser Val Ser
145                 150                 155                 160

Ala Arg Asn Ile Phe Asn Arg Gln Ser Val Lys Lys Glu Ile Arg
                165                 170                 175

Tyr Asp Leu Glu Val Pro Thr Ser Ala Asp Ser Ile Trp Ala Val Tyr
            180                 185                 190

Ser Asn Pro Asp Ile Pro Arg Leu Leu Arg Asp Val Leu Leu Pro Gly
        195                 200                 205

Val Phe Glu Lys Leu Asp Val Ile Glu Gly Asn Gly Gly Val Gly Thr
    210                 215                 220

Val Leu Asp Ile Val Phe Pro Pro Gly Ala Val Pro Arg Arg Tyr Lys
225                 230                 235                 240

Glu Lys Phe Val Asn Ile Asn His Glu Lys Arg Leu Lys Glu Val Ile
                245                 250                 255
```

```
Met Ile Glu Gly Gly Tyr Leu Asp Met Gly Cys Thr Phe Tyr Leu Asp
            260                 265                 270

Arg Ile His Val Val Glu Lys Thr Ser Lys Ser Cys Ile Ile Lys Ser
            275                 280                 285

Ser Ile Val Tyr Glu Val Lys Gln Glu Cys Ala Glu Ala Ile Ser Lys
            290                 295                 300

Leu Ile Thr Thr Glu Pro Leu Lys Ser Met Ala Gln Val Ile Ala Asn
305                 310                 315                 320

Tyr Val Leu Lys Lys Gln Ser Val Ser Asp Thr Asn Ile Pro Lys Lys
                325                 330                 335

Gln Ser Val Leu Arg Lys Glu Ile Thr Tyr Glu Thr Glu Val Gln Thr
            340                 345                 350

Ser Val Asp Ser Ile Trp Asn Val Tyr Ser Ser Pro Asp Ile Pro Arg
            355                 360                 365

Leu Leu Arg Asp Val Leu Pro Gly Val Phe Glu Lys Leu Asp Val
            370                 375                 380

Ile Ala Gly Asn Gly Gly Val Gly Thr Val Leu Asp Ile Ala Phe Pro
385                 390                 395                 400

Leu Gly Ala Val Pro Arg Arg Tyr Lys Glu Lys Phe Val Lys Ile Asn
                405                 410                 415

His Glu Lys Arg Leu Lys Glu Val Ile Met Ile Glu Gly Gly Tyr Leu
            420                 425                 430

Asp Met Gly Cys Thr Phe Tyr Met Asp Arg Ile His Val Leu Glu Lys
            435                 440                 445

Thr Pro Asn Ser Cys Val Ile Glu Ser Ser Ile Ile Tyr Glu Val Lys
            450                 455                 460

Glu Glu Phe Ala Asp Lys Met Ala Lys Leu Ile Thr Thr Glu Pro Leu
465                 470                 475                 480

Gln Ser Met Ala Glu Val Ile Ser Ala Tyr Val Leu Arg Lys Arg Phe
                485                 490                 495

Glu Val Phe Gly Leu Glu Ile Lys Gln Lys Leu Arg Tyr Asn Leu Leu
            500                 505                 510

Leu Cys Leu Ile Ile Cys Leu Val Ile Ala Gly Gly Met Leu Ile Gly
            515                 520                 525

Arg Val Pro Leu
        530

<210> SEQ ID NO 14
<211> LENGTH: 193
<212> TYPE: PRT
<213> ORGANISM: Sanguineris canadensis

<400> SEQUENCE: 14

Met Arg Lys Glu Leu Thr His Glu Met Glu Val Pro Ala Ser Ala Asp
1               5                   10                  15

Ala Ile Trp Ala Val Tyr Ser Ser His Asp Ile Pro Arg Leu Leu Lys
            20                  25                  30

Glu Val Leu Leu Pro Gly Val Phe Glu Lys Leu Asp Val Ile Ala Gly
            35                  40                  45

Asp Gly Gly Val Gly Thr Val Leu Asp Ile Ala Phe Pro Pro Gly Ala
        50                  55                  60

Val Pro Arg Arg Tyr Lys Glu Lys Phe Val Lys Ile Asn His Glu Lys
65                  70                  75                  80

Arg Leu Lys Glu Val Glu Met Ile Glu Gly Gly Tyr Leu Asp Met Gly
```

```
                    85                  90                  95
Cys Thr Phe Tyr Met Asp Arg Ile His Val Val Glu Lys Gly Pro Asn
                100                 105                 110

Ser Cys Val Ile Glu Ser Ala Ile Ile Tyr Val Val Lys Asp Glu Cys
            115                 120                 125

Ala Asp Val Val Val Pro Leu Ile Thr Thr Glu Pro Leu Ala Ser Met
130                 135                 140

Ala Glu Val Ile Ser Asn Tyr Val Leu Arg Lys Gln Ile Arg Leu Phe
145                 150                 155                 160

Gly Tyr Val Ile Lys Pro Lys Leu Gly Leu Ser Ile Leu Leu Ser Leu
                165                 170                 175

Ile Leu Cys Leu Val Ile Leu Gly Val Leu Leu Ile Gly Gly Val Pro
                180                 185                 190

Phe

<210> SEQ ID NO 15
<211> LENGTH: 265
<212> TYPE: PRT
<213> ORGANISM: Chelidonium majus

<400> SEQUENCE: 15

Met Ile Glu Gly Gly Tyr Leu Asp Met Gly Cys Thr Phe Tyr Met Asp
1               5                   10                  15

Arg Ile His Val Val Lys Lys Gly Pro Asn Ser Cys Val Ile Ala Ser
                20                  25                  30

Ala Ile Ile Tyr Glu Val Lys Glu Glu Phe Val Asp Val Val Val Pro
            35                  40                  45

Leu Ile Thr Thr Glu Pro Leu Ala Ser Met Ala Glu Val Ile Ser Asn
        50                  55                  60

Tyr Val Leu Lys Lys Gln Arg Arg Val Arg Lys Glu Leu Thr Tyr Glu
65                  70                  75                  80

Met Glu Val Pro Thr Ser Ala Asp Ser Ile Trp Ala Val Tyr Ser Ser
                85                  90                  95

His Asp Ile Pro Arg Leu Leu Lys Glu Val Leu Leu Pro Gly Val Phe
                100                 105                 110

Glu Lys Leu Asp Val Ile Glu Gly Asp Gly Val Gly Thr Val Leu
            115                 120                 125

Asp Ile Ala Phe Pro Pro Gly Ala Val Pro Arg Thr Tyr Lys Glu Lys
130                 135                 140

Phe Val Lys Ile Asn His Glu Lys Arg Leu Lys Glu Val Met Ile
145                 150                 155                 160

Glu Gly Gly Tyr Leu Asp Met Gly Cys Thr Phe Tyr Met Asp Arg Ile
                165                 170                 175

His Val Leu Glu Lys Ser Pro Asn Ser Cys Val Ile Glu Ser Ser Ile
                180                 185                 190

Ile Tyr Glu Val Lys Glu Glu Phe Ala Asp Val Val Gly Pro Leu Ile
            195                 200                 205

Thr Thr Glu Pro Leu Ala Ser Met Ser Glu Val Ile Ser Asn Tyr Val
        210                 215                 220

Leu Lys Lys Gln Ile Arg Met Phe Gly Tyr Val Ile Lys Pro Lys Leu
225                 230                 235                 240

Gly Leu Ser Leu Leu Leu Cys Phe Ile Leu Cys Leu Val Leu Leu Gly
                245                 250                 255

Val Leu Leu Ile Gly Gly Val Pro Leu
```

<210> SEQ ID NO 16
<211> LENGTH: 531
<212> TYPE: PRT
<213> ORGANISM: Chelidonium majus

<400> SEQUENCE: 16

Met Arg Lys Val Ile Lys Tyr Asp Met Glu Val Ala Val Ser Ala Asp
1               5                   10                  15

Ser Val Trp Ala Val Tyr Ser Ser Pro Asp Ile Pro Arg Leu Leu Arg
            20                  25                  30

Asp Val Leu Leu Pro Gly Val Phe Glu Lys Leu Asp Val Ile Glu Gly
        35                  40                  45

Asn Gly Gly Val Gly Thr Val Leu Asp Ile Val Phe Pro Pro Gly Ala
    50                  55                  60

Val Pro Arg Ser Tyr Lys Glu Lys Phe Val Asn Ile Asp Arg Glu Lys
65                  70                  75                  80

Arg Leu Lys Glu Val Ile Met Ile Glu Gly Gly Tyr Leu Asp Met Gly
                85                  90                  95

Cys Thr Phe Tyr Leu Asp Arg Ile His Val Val Glu Lys Thr Lys Ser
            100                 105                 110

Ser Cys Val Ile Glu Ser Ser Ile Val Tyr Asp Val Lys Glu Glu Cys
        115                 120                 125

Ala Asp Ala Met Ser Lys Leu Ile Thr Thr Glu Pro Leu Lys Ser Met
130                 135                 140

Ala Glu Val Ile Ser Asn Tyr Val Ile Gln Lys Glu Ser Phe Ser Ala
145                 150                 155                 160

Arg Asn Ile Leu Ser Lys Gln Ser Val Val Lys Lys Glu Ile Arg Tyr
                165                 170                 175

Asp Leu Glu Val Pro Ile Ser Ala Asp Ser Ile Trp Ser Val Tyr Ser
            180                 185                 190

Cys Pro Asp Ile Pro Arg Leu Leu Arg Asp Val Leu Leu Pro Gly Val
        195                 200                 205

Phe Gln Lys Leu Asp Val Ile Glu Gly Asn Gly Gly Val Gly Thr Val
    210                 215                 220

Leu Asp Ile Val Phe Pro Pro Gly Ala Val Pro Arg Ser Tyr Lys Glu
225                 230                 235                 240

Lys Phe Val Asn Ile Asn His Glu Lys Arg Leu Lys Glu Val Ile Met
                245                 250                 255

Ile Glu Gly Gly Tyr Leu Asp Met Gly Cys Thr Ser Tyr Leu Asp Arg
            260                 265                 270

Ile His Val Val Glu Lys Thr Ser Lys Ser Cys Ile Ile Lys Ser Ser
        275                 280                 285

Val Val Tyr Glu Val Lys Gln Glu Cys Val Glu Ala Met Ser Lys Leu
    290                 295                 300

Ile Thr Thr Glu Pro Leu Lys Ser Met Ala Glu Val Ile Ser Asn Tyr
305                 310                 315                 320

Ala Met Lys Gln Gln Ser Val Ser Glu Arg Asn Ile Pro Lys Lys Gln
                325                 330                 335

Ser Leu Leu Arg Lys Glu Ile Thr Tyr Glu Thr Glu Val Gln Thr Ser
            340                 345                 350

Ala Asp Ser Ile Trp Asn Val Tyr Ser Ser Pro Asp Ile Pro Arg Leu
        355                 360                 365

```
Leu Arg Asp Val Leu Leu Pro Gly Val Phe Glu Lys Leu Asp Val Ile
    370                 375                 380

Ala Gly Asn Gly Gly Val Gly Thr Val Leu Asp Ile Ala Phe Pro Leu
385                 390                 395                 400

Gly Ala Val Pro Arg Arg Tyr Lys Glu Lys Phe Val Lys Ile Asn His
                405                 410                 415

Glu Lys Arg Leu Lys Glu Val Val Met Ile Glu Gly Gly Tyr Leu Asp
                420                 425                 430

Met Gly Cys Thr Phe Tyr Met Asp Arg Ile His Val Phe Glu Lys Thr
            435                 440                 445

Pro Asn Ser Cys Val Ile Glu Ser Ser Ile Ile Tyr Glu Val Lys Glu
            450                 455                 460

Glu Tyr Ala Ala Lys Met Ala Lys Leu Ile Thr Thr Glu Pro Leu Glu
465                 470                 475                 480

Ser Met Ala Glu Val Ile Ser Gly Tyr Val Leu Lys Lys Arg Leu Gln
                485                 490                 495

Val Phe Gly Phe Glu Ile Lys Pro Lys Leu Arg Phe Asn Leu Leu Leu
                500                 505                 510

Cys Leu Ile Ile Cys Leu Val Ile Ala Gly Gly Met Phe Val Ala Gly
            515                 520                 525

Val Pro Leu
530

<210> SEQ ID NO 17
<211> LENGTH: 351
<212> TYPE: PRT
<213> ORGANISM: Stylophorum diphyllum

<400> SEQUENCE: 17

Met Arg Lys Glu Val Arg Tyr Glu Met Glu Val Pro Thr Ser Ala Asp
1               5                   10                  15

Ser Ile Trp Ala Val Tyr Ser Ser His Asp Ile Pro Arg Leu Leu Lys
                20                  25                  30

Glu Val Leu Leu Pro Gly Val Phe Glu Lys Leu Asp Val Ile Glu Gly
            35                  40                  45

Asp Gly Gly Val Gly Thr Val Leu Asp Ile Ala Phe Pro Pro Gly Ala
    50                  55                  60

Val Pro Arg Thr Tyr Lys Glu Lys Phe Val Thr Ile Asn His Glu Lys
65                  70                  75                  80

Arg Leu Lys Glu Val Ile Met Ile Glu Gly Gly Tyr Leu Asp Met Gly
                85                  90                  95

Cys Thr Phe Tyr Met Asp Arg Ile His Val Leu Glu Lys Gly Pro Lys
            100                 105                 110

Ser Cys Ile Ile Ala Ser Ala Ile Tyr Glu Val Lys Glu Glu Phe
            115                 120                 125

Ala Asp Val Val Pro Leu Ile Thr Thr Glu Pro Leu Ala Ser Met
130                 135                 140

Ala Glu Val Ile Ser Asn Tyr Val Leu Lys Lys Gln Arg Arg Val Arg
145                 150                 155                 160

Lys Glu Leu Thr Tyr Glu Met Glu Val Pro Thr Ser Ala Asp Ser Ile
                165                 170                 175

Trp Ala Val Tyr Ser Ser His Asp Ile Pro Arg Leu Leu Lys Glu Val
                180                 185                 190

Leu Leu Pro Gly Val Phe Glu Lys Leu Asp Val Ile Glu Gly Asp Gly
            195                 200                 205
```

Gly Val Gly Thr Val Leu Asp Ile Ala Phe Pro Pro Gly Ala Val Pro
            210                 215                 220

Arg Thr Tyr Lys Glu Lys Phe Val Lys Ile Asn His Glu Lys Arg Leu
225                 230                 235                 240

Lys Glu Val Val Met Ile Glu Gly Gly Tyr Leu Asp Met Gly Cys Thr
                245                 250                 255

Phe Tyr Met Asp Arg Ile His Val Leu Glu Lys Gly Pro Asn Ser Cys
                260                 265                 270

Val Ile Glu Ser Ala Ile Ile Tyr Glu Val Lys Glu Glu Phe Ala Asp
            275                 280                 285

Val Val Val Pro Leu Ile Thr Thr Glu Pro Leu Ala Ser Met Ala Glu
            290                 295                 300

Val Ile Ser Asn Tyr Val Leu Lys Lys Gln Ile His Val Phe Gly Tyr
305                 310                 315                 320

Val Ile Lys Pro Lys Leu Gly Leu Ser Leu Leu Leu Cys Phe Ile Leu
                325                 330                 335

Cys Leu Val Leu Leu Gly Val Leu Leu Ile Gly Gly Val Pro Leu
            340                 345                 350

<210> SEQ ID NO 18
<211> LENGTH: 284
<212> TYPE: PRT
<213> ORGANISM: Eschscholzia californica

<400> SEQUENCE: 18

Met Ile Gly Gly Phe Leu Asp Met Gly Cys Thr Phe Tyr Met Asp Arg
1               5                   10                  15

Ile His Val Val Ala Lys Gly Pro Asn Ser Cys Ile Ile Lys Ser Thr
            20                  25                  30

Leu Ile Tyr Glu Val Lys Glu Glu Tyr Ala Asp Ala Met Ala Ser Leu
        35                  40                  45

Ile Thr Val Glu Pro Leu Ala Ser Met Ala Glu Val Val Ala Asn Tyr
    50                  55                  60

Val Leu His Gln Gln Val Arg Val Leu Gly Ser Val Lys Arg Lys Glu
65                  70                  75                  80

Leu Thr His Glu Leu Glu Val Ala Ala Pro Ala Asp Ala Ile Trp Gly
            85                  90                  95

Val Tyr Ser Ser Pro Asp Ile Pro Arg Leu Leu Arg Asp Val Leu Leu
            100                 105                 110

Pro Gly Val Phe Glu Lys Leu Glu Val Ile Gln Gly Asn Gly Gly Val
            115                 120                 125

Gly Thr Val Leu Glu Ile Val Phe His Pro Gly Ala Ile Pro Arg Arg
        130                 135                 140

Tyr Lys Glu Lys Phe Val Thr Ile Asn His Lys Lys Arg Leu Lys Glu
145                 150                 155                 160

Val Val Met Ile Gly Gly Tyr Leu Asp Met Gly Cys Thr Leu Tyr Met
                165                 170                 175

Asp Arg Ile His Val Val Ser Lys Gly Pro Asn Ser Cys Val Ile Lys
            180                 185                 190

Ser Thr Leu Ile Tyr Glu Val Lys Ala Glu Ser Ala Asp Ala Met Ala
        195                 200                 205

Ser Thr Ile Thr Ile Asp Pro Leu Ala Ser Met Ala Gln Val Ile Ser
    210                 215                 220

Asn Tyr Val Leu Lys Asn Gln Met Gln Val Leu Gly Ser Val Lys Arg

```
             225                 230                 235                 240

Arg Glu Leu Thr His Glu Leu Glu Val Ala Ala Ser Ala Asp Ala Ile
                245                 250                 255

Trp Gly Val Tyr Gly Ser Lys Arg Tyr Ser Lys Ala Ser Gln Gly Cys
                260                 265                 270

Phe Ala Ser Trp Cys Phe Arg Lys Val Arg Ser His
                275                 280

<210> SEQ ID NO 19
<211> LENGTH: 752
<212> TYPE: PRT
<213> ORGANISM: Eschscholzia californica

<400> SEQUENCE: 19

Met Ile Gly Gly Tyr Leu Asp Met Gly Cys Thr Leu Tyr Met Asp Arg
1               5                   10                  15

Ile His Val Val Glu Lys Gly Pro Asn Ser Cys Val Ile Lys Ser Thr
                20                  25                  30

Leu Ile Tyr Glu Val Lys Ala Glu Tyr Ala Asp Ala Met Ala Ser Leu
            35                  40                  45

Ile Thr Val Asp Pro Leu Ala Ser Met Ala Gln Val Ile Ser Asn Tyr
        50                  55                  60

Val Leu Lys Asn Gln Gly Gln Val Leu Gly Ser Ile Lys Arg Arg Glu
65                  70                  75                  80

Leu Lys His Glu Leu Glu Val Ala Val Ser Ala Asp Ala Ile Trp Gly
                85                  90                  95

Val Ile Gly Ser Lys Asp Ile Pro Arg Leu Leu Arg Asp Val Leu Leu
            100                 105                 110

Pro Gly Val Phe Glu Lys Leu Asp Val Ile Glu Gly Asp Gly Gly Val
        115                 120                 125

Gly Thr Val Leu Glu Ile Val Phe Pro Pro Gly Ala Val Pro Arg Lys
    130                 135                 140

Tyr Arg Glu Lys Phe Val Lys Val Asp His Glu Lys Arg Leu Lys Glu
145                 150                 155                 160

Val Ile Met Ile Gly Gly Tyr Leu Asp Met Gly Cys Thr Phe Tyr Met
                165                 170                 175

Asp Arg Ile His Val Val Ala Lys Gly Pro Asn Ser Cys Ile Ile Lys
            180                 185                 190

Ser Thr Leu Ile Tyr Glu Val Lys Glu Glu Tyr Ala Asp Ala Met Ala
        195                 200                 205

Ser Leu Ile Thr Val Glu Pro Leu Ala Ser Met Ala Glu Val Val Ala
    210                 215                 220

Asn Tyr Val Leu His Gln Gln Val Arg Val Leu Gly Ser Val Lys Arg
225                 230                 235                 240

Lys Glu Leu Thr His Glu Leu Glu Val Ala Ala Ser Ala Asp Ala Ile
                245                 250                 255

Trp Gly Val Tyr Ser Ser Pro Asp Ile Pro Arg Leu Leu Arg Asp Val
                260                 265                 270

Leu Leu Pro Gly Val Phe Glu Lys Leu Glu Val Ile Gln Gly Asn Gly
            275                 280                 285

Gly Val Gly Thr Val Leu Glu Ile Val Phe His Pro Gly Ala Ile Pro
        290                 295                 300

Arg Arg Tyr Lys Glu Lys Phe Val Thr Ile Asn His Lys Lys Arg Leu
305                 310                 315                 320
```

```
Lys Glu Val Val Met Ile Gly Gly Tyr Leu Asp Met Gly Cys Thr Leu
                325                 330                 335

Tyr Met Asp Arg Ile His Val Val Ser Lys Gly Pro Asn Ser Cys Val
            340                 345                 350

Ile Lys Ser Thr Leu Ile Tyr Glu Val Lys Ala Glu Ser Ala Asp Ala
        355                 360                 365

Met Ala Ser Thr Ile Thr Ile Asp Pro Leu Ala Ser Met Ala Gln Val
    370                 375                 380

Ile Ser Asn Tyr Val Leu Lys Asn Gln Met Gln Val Leu Gly Ser Val
385                 390                 395                 400

Lys Arg Arg Glu Leu Thr His Glu Leu Glu Val Ala Ala Ser Ala Asp
                405                 410                 415

Ala Ile Trp Gly Val Tyr Gly Ser Lys Asp Ile Pro Arg Leu Leu Arg
            420                 425                 430

Asp Val Leu Leu Pro Gly Val Phe Glu Lys Leu Glu Val Ile Glu Gly
        435                 440                 445

Asp Gly Gly Val Gly Thr Val Leu Gln Ile Val Phe Pro Pro Gly Ala
    450                 455                 460

Ile Pro Arg Arg Tyr Lys Glu Lys Phe Val Lys Val Asp Gln Lys Leu
465                 470                 475                 480

Arg Leu Lys Glu Val Ile Met Ile Gly Gly Tyr Leu Asp Met Gly Cys
                485                 490                 495

Thr Phe Tyr Met Asp Arg Ile His Val Val Pro Lys Gly Leu Asn Ser
            500                 505                 510

Cys Val Ile Lys Ser Thr Leu Ile Tyr Glu Val Lys Asp Glu Tyr Ala
        515                 520                 525

Asp Ala Met Ser Ser Leu Ile Thr Val Glu Pro Leu Ala Ser Met Ala
    530                 535                 540

Glu Val Val Ser Asn Tyr Val Leu Asn Lys Lys Lys Leu Met Ile Thr
545                 550                 555                 560

Arg Lys Glu Leu Thr His Glu Leu Glu Val Ala Ala Ser Ala Asp Ala
                565                 570                 575

Ile Trp Ser Val Tyr Ser Ser Pro Asp Ile Pro Arg Leu Leu Arg Asp
            580                 585                 590

Val Leu Leu Pro Gly Val Phe Glu Lys Leu Glu Val Val Gln Gly Asn
        595                 600                 605

Gly Gly Val Gly Thr Val Leu Glu Ile Val Phe Pro Lys Gly Ser Val
    610                 615                 620

Pro Arg Arg Tyr Lys Glu Lys Phe Val Lys Ile Asn Asp Glu Lys Lys
625                 630                 635                 640

Leu Lys Glu Val Ile Met Ile Glu Gly Gly Tyr Leu Asp Leu Gly Cys
                645                 650                 655

Thr Phe Tyr Met Asp Lys Ile His Val Leu Pro Lys Gly Pro Asn Ser
            660                 665                 670

Cys Val Ile Glu Ser Ser Leu Ile Tyr Glu Val Lys Glu Glu Asn Ala
        675                 680                 685

Lys Ala Met Ala Ser Leu Ile Thr Val Glu Pro Leu Ala Ser Met Ala
    690                 695                 700

Glu Val Val Ala Asn Tyr Val Leu Lys Lys Gln Ile Arg Val Leu Gly
705                 710                 715                 720

Tyr Val Val Lys Pro Arg Val Gly Tyr Ser Val Leu Val Gly Leu Leu
                725                 730                 735

Leu Cys Leu Val Leu Leu Gly Val Leu Leu Leu Ser Gly Val Asn Ile
```

<210> SEQ ID NO 20
<211> LENGTH: 173
<212> TYPE: PRT
<213> ORGANISM: Argemone mexicane

<400> SEQUENCE: 20

Met Arg Lys Glu Val Val Tyr Glu Leu Glu Val Pro Thr Ser Ala Asp
1               5                   10                  15

Ser Ile Trp Ala Val Tyr Ser Ser Pro Asn Ile Pro Thr Leu Leu Arg
            20                  25                  30

Asp Val Leu Pro Gly Val Phe Glu Lys Leu Asp Val Ile Glu Gly
        35                  40                  45

Asn Gly Gly Val Gly Thr Val Leu Asn Ile Val Phe Pro Pro Gly Ala
    50                  55                  60

Val Pro Arg Cys Tyr Lys Glu Lys Phe Ile Asn Ile Asp Asn Lys Lys
65                  70                  75                  80

Arg Leu Lys Glu Val Ile Met Ile Glu Gly Gly Tyr Leu Asp Met Gly
                85                  90                  95

Cys Thr Phe Tyr Met Asp Arg Ile His Val Ile Ala Glu Thr Pro Asn
            100                 105                 110

Ser Cys Val Ile Lys Ser Ser Ile Ile Tyr Asp Val Lys Lys Glu Tyr
        115                 120                 125

Ala Glu Ala Met Ser Lys Leu Ile Thr Thr Ile Pro Leu Lys Ser Met
    130                 135                 140

Ser Glu Val Ile Ala Asn Tyr Val Leu Lys Asn Gln Ser Val Ile Arg
145                 150                 155                 160

Lys Glu Val Thr Tyr Glu Leu Gln Val Pro Thr Ser Asp
                165                 170

<210> SEQ ID NO 21
<211> LENGTH: 156
<212> TYPE: PRT
<213> ORGANISM: Argemone mexicane

<400> SEQUENCE: 21

Met Lys Phe Glu Leu Val Asn Glu Leu Glu Val Pro Ala Ser Ala Asn
1               5                   10                  15

Asp Val Trp Ala Ile Tyr Ser Ser Pro Asp Phe Pro Lys Leu Leu Thr
            20                  25                  30

Lys Leu Val Pro Gly Ile Leu Glu Ser Val Glu Tyr Val Glu Gly Asp
        35                  40                  45

Gly His Leu Gly Thr Val Ile His Leu Val Tyr Val Pro Gly Ser Val
    50                  55                  60

Pro Leu Ser Tyr Lys Glu Lys Phe Val Thr Ile Asp His Glu Lys Arg
65                  70                  75                  80

Leu Lys Glu Ala Val His Val Glu Gly Gly Phe Leu Glu Met Gly Val
                85                  90                  95

Thr Phe Tyr Met Asn Ser Phe Glu Ile Ile Glu Lys Gly Ser Asp Cys
            100                 105                 110

Cys Ile Ile Arg Ser Met Thr Lys Cys Glu Ile Glu Asp Lys Glu Ile
        115                 120                 125

Met Asn Leu Ile Ser His Ile Ser Val Ala Asn Val Thr Val Leu Ala
    130                 135                 140

Met Thr Ile Ser Lys Tyr Val Gln Gln His Lys Lys

<210> SEQ ID NO 22
<211> LENGTH: 215
<212> TYPE: PRT
<213> ORGANISM: Thalictrum flavum

<400> SEQUENCE: 22

Met Lys Met Glu Val Val Phe Val Phe Met Ile Leu Gly Thr Ile
1               5                   10                  15

Asn Cys Gln Lys Leu Ile Leu Thr Gly Arg Pro Phe Leu Asn Arg Gln
                20                  25                  30

Gly Ile Ile Asn Gln Val Ser Thr Val Thr Lys Gly Val His His Glu
            35                  40                  45

Leu Glu Val Ala Ala Ser Ala Asp Asp Ile Trp Ser Val Tyr Ser Trp
        50                  55                  60

Pro Gly Leu Ala Lys His Leu Pro Asp Leu Leu Pro Gly Ala Phe Glu
65                  70                  75                  80

Lys Leu Glu Ile Ile Gly Asp Gly Gly Val Gly Thr Ile Leu Asp Met
                85                  90                  95

Thr Phe Thr Pro Gly Glu Phe Pro His Glu Tyr Lys Glu Lys Phe Ile
                100                 105                 110

Leu Val Asp Asn Glu His Arg Leu Lys Lys Val Gln Met Ile Glu Gly
            115                 120                 125

Gly Tyr Leu Asp Leu Gly Val Thr Tyr Tyr Met Asp Thr Ile Gln Val
        130                 135                 140

Ile Pro Thr Gly Thr Asn Ser Cys Val Ile Lys Ser Ser Thr Glu Tyr
145                 150                 155                 160

His Val Lys Pro Glu Phe Val Lys Ile Val Glu Pro Leu Ile Thr Thr
                165                 170                 175

Gly Pro Leu Ala Ala Met Ala Glu Ala Ile Ser Lys Leu Val Leu Glu
            180                 185                 190

His Lys Tyr Lys Ser Asn Ser Asp Glu Ile Asp Ala Ser Lys Asn Asn
        195                 200                 205

Leu Lys Met Val Ile Asn Met
    210                 215

<210> SEQ ID NO 23
<211> LENGTH: 218
<212> TYPE: PRT
<213> ORGANISM: Thalictrum flavum

<400> SEQUENCE: 23

Met Lys Met Glu Ala Thr Val Phe Val Phe Leu Met Phe Leu Gly Thr
1               5                   10                  15

Ile Asn Cys Gln Lys Leu Ile Met Ala Gly Arg Pro Phe Leu His His
                20                  25                  30

Gln Gly Ile Ile Asn Gln Glu Phe Thr Val Thr Lys Val Leu His His
            35                  40                  45

Glu Leu Glu Val Ala Ala Ser Ala Asp Asp Ile Trp Gly Val Tyr Ser
        50                  55                  60

Ser Pro His Leu Val Phe His Leu Thr Asp Leu Leu Pro Gly Ala Phe
65                  70                  75                  80

Glu Lys Val Gln Val Ile Gly Asp Gly Gly Val Gly Thr Ile Leu Asp
                85                  90                  95

Met Thr Phe Ala Pro Gly Glu Phe Pro His Glu Tyr Lys Glu Lys Phe

```
                    100                 105                 110
Ile Val Val Asp Asn Glu His Arg Leu Lys Lys Val Gln Met Ile Glu
            115                 120                 125

Gly Gly Tyr Leu Asp Leu Gly Val Thr Tyr Tyr Met Asp Thr Ile Gln
            130                 135                 140

Val Val Pro Thr Gly Thr Asn Ser Cys Val Ile Lys Ser Ser Thr Glu
145                 150                 155                 160

Tyr His Val Lys Pro Glu Leu Leu Lys Ile Val Glu Pro Leu Ile Thr
                165                 170                 175

Thr Gly Pro Val Ala Ala Met Ala Glu Ala Ile Ser Lys Leu Val Leu
            180                 185                 190

Glu Tyr Lys Tyr Lys Ser His Ser Asp Glu Ile His Ala Gly Leu Asn
            195                 200                 205

Asn Asn Leu Lys Met Val Ile Asn Asn Ile
            210                 215
```

<210> SEQ ID NO 24
<211> LENGTH: 193
<212> TYPE: PRT
<213> ORGANISM: Thalictrum flavum

<400> SEQUENCE: 24

```
Met Arg Lys Glu Leu Thr His Glu Met Glu Val Pro Ala Ser Ala Asp
1               5                   10                  15

Ala Ile Trp Ala Val Tyr Gly Ser Pro Asp Ile Pro Arg Leu Leu Lys
            20                  25                  30

Glu Val Leu Leu Pro Gly Val Phe Glu Lys Leu Asp Val Ile Glu Gly
        35                  40                  45

Asp Gly Gly Val Gly Thr Val Leu Asp Ile Ala Phe Pro Pro Gly Ala
    50                  55                  60

Val Pro Arg Ala Tyr Lys Glu Lys Phe Met Lys Val Asn His Glu Lys
65                  70                  75                  80

Arg Leu Lys Glu Val Glu Met Ile Glu Gly Gly Tyr Leu Asp Met Gly
                85                  90                  95

Cys Thr Phe Tyr Met Asp Arg Ile His Val Val Glu Lys Gly Pro Asn
            100                 105                 110

Ala Cys Val Ile Glu Ser Ala Ile Ile Tyr Glu Val Lys Asp Glu Phe
            115                 120                 125

Ala Asp Val Val Val Pro Leu Ile Thr Thr Glu Pro Leu Ala Ser Met
        130                 135                 140

Ala Glu Val Ile Ser Asn Tyr Val Leu Lys Asn Gln Phe Arg Val Phe
145                 150                 155                 160

Gly Tyr Val Ile Lys Pro Lys Leu Gly Leu Ser Leu Leu Leu Cys Phe
                165                 170                 175

Ile Leu Cys Leu Val Leu Leu Gly Gly Leu Leu Ile Gly Gly Val Pro
            180                 185                 190

Leu
```

<210> SEQ ID NO 25
<211> LENGTH: 163
<212> TYPE: PRT
<213> ORGANISM: Thalictrum flavum

<400> SEQUENCE: 25

```
Met Arg Lys Glu Leu Thr Asn Glu Met Glu Val Ala Ala Ser Ala Asp
1               5                   10                  15
```

```
Glu Ile Trp Ala Val Tyr Ser Ser Pro Asn Leu Pro Lys Leu Ile Val
            20                  25                  30

Gln Leu Leu Pro Ala Val Phe Glu Arg Ile Tyr Ile Leu Glu Gly Asp
        35                  40                  45

Gly Gly Val Gly Thr Val Leu Tyr Ile Leu Ser Pro Pro Gly Ser Val
 50                  55                  60

Pro Arg Ser Tyr Lys Glu Lys Phe Ile Thr Ile Asp His Glu Lys Arg
 65                  70                  75                  80

Leu Lys Glu Val Gln Glu Ile Glu Gly Gly Tyr Leu Asp Met Gly Val
                85                  90                  95

Thr Phe Tyr Met Asp Thr Phe Tyr Ile Leu Glu Lys Gly Pro Asp Ser
            100                 105                 110

Cys Ile Ile Lys Ser Met Thr Thr Tyr Glu Ile Lys Asp Glu Leu Ala
            115                 120                 125

Asp Lys Val Ala Ser Leu Ile Ser Ile Asp Ser Leu Val Gly Met Ala
 130                 135                 140

Lys Ala Ile Thr Lys Tyr Val Leu Asp Gln Lys Lys Ala Ala Val Asp
 145                 150                 155                 160

Ser Ser Ala

<210> SEQ ID NO 26
<211> LENGTH: 161
<212> TYPE: PRT
<213> ORGANISM: Berberis thunbergii

<400> SEQUENCE: 26

Met Val Val Ala Ala Ser Ala Asp Asp Val Trp Ala Ile Tyr Ser Ser
 1               5                  10                  15

His Asp Leu Pro Lys Leu Ile Val Lys Leu Leu Pro Ser Val Phe Lys
            20                  25                  30

Ser Ile Glu Ile Val Glu Gly Asp Gly Gly Leu Gly Thr Val Leu Asp
        35                  40                  45

Val Lys Tyr Pro Pro Gly Ser Ile Pro Leu His Tyr Arg Glu Lys Phe
 50                  55                  60

Ile Thr Ile Asp Asn Glu Lys Arg Leu Lys Glu Val Arg Gln Ile Glu
 65                  70                  75                  80

Asp Gly Leu Leu Ala Leu Gly Cys Thr Phe Tyr Met Asp Ser Phe His
                85                  90                  95

Ile Leu Glu Lys Asp Cys His His Glu Phe Phe His Ile His Glu Lys
            100                 105                 110

Asn Cys His Lys Lys Cys Ile Ile Lys Ser Thr Thr Val Tyr Glu Val
            115                 120                 125

Pro Asp Glu Leu Ala Tyr Lys Ile Glu Pro Leu Val Thr Ile Asp Ser
 130                 135                 140

Leu Val Gly Met Ala His Ala Ile Ser Lys Tyr Val Leu Asp Lys Ser
 145                 150                 155                 160

Cys

<210> SEQ ID NO 27
<211> LENGTH: 486
<212> TYPE: PRT
<213> ORGANISM: Corydalis chelanthifolia

<400> SEQUENCE: 27

Met Tyr Tyr Phe Leu Glu Phe Phe Glu Lys Leu Asp Val Ile Glu Gly
```

-continued

```
1               5                   10                  15
Asn Gly Gly Val Gly Thr Val Leu Asp Ile Ala Phe Pro Pro Gly Ala
            20                  25                  30

Val Pro Arg Ser Tyr Lys Glu Lys Phe Val Lys Val Asp His Lys Asn
            35                  40                  45

Arg Leu Lys Glu Val Val Met Ile Glu Gly Gly Tyr Leu Asp Leu Gly
            50                  55                  60

Cys Thr Phe Tyr Met Asp Arg Ile His Val Leu Pro Lys Gly Ala Asn
65                  70                  75                  80

Ser Cys Val Ile Lys Ser Thr Leu Ile Tyr Glu Ile Pro Asp Glu Leu
                    85                  90                  95

Val Asp Ser Val Gly Ser Leu Met Ser Thr Glu Pro Leu Ala Ser Met
                100                 105                 110

Ala Lys Val Ile Ser Asp Tyr Val Leu Lys Gln Arg Lys Met Thr Ala
                115                 120                 125

Asn Lys Ile Leu Arg Lys Glu Leu Lys Thr Glu Met Glu Val Ala Thr
            130                 135                 140

Ser Ala Asp Ser Ile Trp Ala Val Tyr Gly Ser Pro Asp Ile Pro Arg
145                 150                 155                 160

Leu Leu Arg Asp Val Leu Leu Pro Gly Val Phe Glu Lys Leu Asp Val
                165                 170                 175

Ile Glu Gly Asn Gly Gly Val Gly Thr Val Leu Asp Ile Ala Phe Pro
                180                 185                 190

Pro Gly Ala Val Pro Arg Thr Tyr Lys Glu Lys Phe Val Lys Val Asp
            195                 200                 205

His Lys Asn Arg Leu Lys Glu Val Val Met Ile Glu Gly Gly Tyr Leu
            210                 215                 220

Asp Leu Gly Cys Thr Phe Tyr Met Asp Arg Ile His Val Leu Pro Lys
225                 230                 235                 240

Gly Pro Asn Thr Cys Val Ile Lys Ser Thr Leu Ile Tyr Glu Val Pro
                245                 250                 255

Asp Glu Phe Ala Asp Ala Val Gly Ser Leu Ile Ser Val Glu Pro Leu
                260                 265                 270

Ala Ser Met Ala Glu Val Ile Ser Gly Tyr Val Leu Lys Gln Lys Lys
            275                 280                 285

Glu Ala Lys Lys Ile Leu Arg Lys Glu Leu Thr His Glu Leu Glu Val
            290                 295                 300

Pro Thr Ser Ala Asp Ser Ile Trp Ala Val Tyr Gly Ser Pro Asp Ile
305                 310                 315                 320

Pro Arg Leu Leu Arg Asp Val Leu Leu Pro Gly Val Phe Glu Lys Leu
                325                 330                 335

Asp Ile Val Glu Gly Asn Gly Gly Val Gly Thr Val Leu Asp Ile Ala
                340                 345                 350

Phe Pro Pro Gly Ala Val Pro Arg Ser Tyr Lys Glu Lys Phe Val Lys
            355                 360                 365

Val Asp His Asp Lys His Leu Lys Glu Val Val Met Ile Glu Gly Gly
            370                 375                 380

Tyr Leu Asp Leu Gly Cys Thr Phe Tyr Met Asp Arg Ile His Val Leu
385                 390                 395                 400

Pro Lys Gly Pro Asn Ser Cys Val Ile Glu Ser Ser Leu Ile Tyr Glu
                405                 410                 415

Val Arg Glu Glu Leu Ala Asp Val Val Gly Ser Leu Ile Ser Ile Glu
                420                 425                 430
```

```
Pro Leu Ala Ser Met Ala Glu Val Ile Ser Ser Tyr Val Leu Lys Gln
        435                 440                 445

Gln Leu Arg Val Phe Gly Val Val Gln Pro Arg Val Gly Leu Ser
    450                 455                 460

Leu Leu Leu Cys Leu Ile Leu Cys Leu Val Ile Leu Gly Gly Leu Leu
465                 470                 475                 480

Ile Gly Gly Val Ser Ile
                485

<210> SEQ ID NO 28
<211> LENGTH: 372
<212> TYPE: PRT
<213> ORGANISM: Corydalis chelanthifolia

<400> SEQUENCE: 28

Met Arg Lys Glu Leu Arg His Glu Leu Glu Val Ala Thr Ser Ala Asp
1               5                   10                  15

Ser Ile Trp Ala Val Tyr Gly Ser Pro Asp Ile Pro Arg Leu Leu Arg
            20                  25                  30

Asp Val Leu Leu Pro Gly Val Phe Glu Lys Leu Asp Val Ile Gln Gly
        35                  40                  45

Asn Gly Gly Val Gly Thr Val Leu Asp Ile Ala Phe Pro Pro Gly Ala
    50                  55                  60

Val Pro Arg Thr Tyr Lys Glu Lys Phe Val Lys Val Asp His Lys Asn
65                  70                  75                  80

Arg Leu Lys Glu Val Val Met Ile Glu Gly Gly Tyr Leu Asp Leu Gly
                85                  90                  95

Cys Thr Phe Tyr Met Asp Arg Ile His Val Leu Pro Ser Gly Pro Asn
            100                 105                 110

Thr Cys Ile Ile Lys Ser Thr Leu Ile Tyr Glu Val Pro Asp Glu Leu
        115                 120                 125

Ala Tyr Ser Val Ala Ser Leu Ile Ser Val Glu Pro Leu Ala Ser Met
    130                 135                 140

Ala Glu Val Ile Ser Gly Tyr Val Leu Arg Gln Arg Lys Met Thr Thr
145                 150                 155                 160

Asn Lys Ile Leu Arg Lys Glu Leu Thr Thr Glu Met Glu Val Pro Thr
                165                 170                 175

Ser Ala Asp Ser Ile Trp Ala Val Tyr Gly Ser Pro Asp Ile Pro Arg
            180                 185                 190

Leu Leu Arg Asp Val Leu Leu Pro Gly Val Phe Glu Arg Leu Asp Val
        195                 200                 205

Ile Glu Gly Asn Gly Gly Val Gly Thr Val Leu Asp Ile Ser Phe Pro
    210                 215                 220

Pro Gly Ala Val Pro Arg Ser Tyr Lys Glu Lys Phe Val Lys Val Asp
225                 230                 235                 240

His Lys Asn Arg Leu Lys Glu Val Val Met Ile Glu Gly Gly Tyr Leu
                245                 250                 255

Asp Leu Gly Cys Thr Phe Tyr Met Asp Arg Ile His Val Ile Pro Lys
            260                 265                 270

Gly Pro Asn Ser Cys Val Ile Lys Ser Thr Leu Ile Tyr Glu Ile Pro
        275                 280                 285

Gly Glu Leu Val Asp Ser Val Gly Ser Leu Met Ser Thr Glu Pro Leu
    290                 295                 300

Ala Ser Met Ala Ala Val Ile Ser Asp Tyr Val Leu Lys Gln Arg Lys
```

```
305                 310                 315                 320
Met Thr Ala Asn Gln Ile Leu Arg Lys Glu Leu Thr Thr Glu Met Glu
                325                 330                 335

Leu Ala Thr Ser Ala Asp Ser Ile Trp Ser Val Tyr Gly Ser Pro Asp
            340                 345                 350

Ile Pro Arg Leu Leu Arg Asp Val Leu Leu Pro Gly Val Phe Glu Arg
            355                 360                 365

Leu Gly Cys His
        370

<210> SEQ ID NO 29
<211> LENGTH: 199
<212> TYPE: PRT
<213> ORGANISM: Corydalis chelanthifolia

<400> SEQUENCE: 29

Met Met Arg Lys Glu Leu Val His Glu Lys Glu Val Cys Ala Ser Ala
1               5                   10                  15

Asp Ala Val Trp Gly Val Tyr Ser Ser Pro Asn Ile Pro Thr Leu Leu
                20                  25                  30

Arg Asp Lys Leu Leu Pro Gly Met Phe Lys Arg Leu Glu Ile Leu Glu
            35                  40                  45

Gly Asp Gly Gly Val Gly Thr Ile Leu Leu Glu Phe Asn Asn Pro
        50                  55                  60

Ala Ile Ile Pro His Thr Tyr Leu Glu Lys Phe Met Lys Leu Asp His
65                  70                  75                  80

Glu Lys Arg Leu Leu Glu Val Glu Val Val Lys Gly Gly Tyr Leu Asp
                85                  90                  95

Leu Gly Cys Thr Phe Tyr Met Ser Arg Ile His Ile Leu Glu Lys Gly
                100                 105                 110

Pro Asn Ser Cys Val Ile Glu Ser Thr Leu Ile Phe Glu Ala Pro Glu
            115                 120                 125

Glu Leu Met Glu Tyr Val Ser Gln Tyr Ala Asn Leu Glu Ser Leu Ile
130                 135                 140

Ser Met Ala Glu Val Ile Ser Lys Tyr Val Leu Glu Gln Gln Phe Arg
145                 150                 155                 160

Val Phe Gly Val Val Lys Lys Leu Lys Leu Gly Leu Ser Thr Ile
                165                 170                 175

Val Leu Leu Cys Ile Phe Ile Phe Leu Val Ile Val Leu Gly Gly Leu
            180                 185                 190

Trp Ile Glu Gly Val Ser Ile
        195

<210> SEQ ID NO 30
<211> LENGTH: 159
<212> TYPE: PRT
<213> ORGANISM: Corydalis chelanthifolia

<400> SEQUENCE: 30

Met Arg Lys His Leu Val Asn Glu Leu Glu Val Val Pro Ala Asp
1               5                   10                  15

Thr Leu Trp Ala Ile Tyr Ser Thr Thr Gln Phe Pro Lys Leu Ile Val
                20                  25                  30

Gln Leu Leu Pro Ile Val Val Gln Asn Ile Glu Ile Asp Gly Asp Gly
            35                  40                  45

Ser Leu Gly Thr Val Leu Asn Val Ile Phe Val Pro Gly Ser Val Pro
```

```
            50                  55                  60
Leu Ser Tyr Lys Glu Lys Ile Val Thr Ile Asp His Glu Lys Arg Leu
 65                  70                  75                  80

Lys Glu Val Val Gln Ile Glu Gly Gly Tyr Leu Asp Leu Gly Cys Ser
                 85                  90                  95

Phe Tyr Met Ser Ser Phe Gln Ile Leu Glu Lys Gly Arg Asp Ser Cys
                100                 105                 110

Ile Ile Lys Ser Met Val Thr Tyr Glu Leu Ala Lys Asp Ala Asp Pro
            115                 120                 125

Ser Val Ala Asp Leu Val Thr Ile Ala Ala His Ala Ala Ile Ala Gln
        130                 135                 140

Val Ile Ser Lys Tyr Val Leu Asp Lys Gln Val Ala Ala Pro
145                 150                 155
```

<210> SEQ ID NO 31
<211> LENGTH: 180
<212> TYPE: PRT
<213> ORGANISM: Corydalis chelanthifolia

<400> SEQUENCE: 31

```
Met Arg Lys Glu Leu Thr Asn Glu Leu Glu Val Ala Ala Pro Ala Asp
 1               5                  10                  15

Ala Val Trp Ala Val Tyr Ser Ser Pro Asp Leu Pro Lys Ile Ile Val
                20                  25                  30

Glu Leu Leu Pro Ser Val Phe Glu Lys Ile Glu Ile Val Glu Gly Asp
            35                  40                  45

Gly Gly Val Gly Thr Val Leu Tyr Val Val Phe Pro Pro Gly Ser Val
        50                  55                  60

Pro Leu Thr Tyr Lys Glu Lys Phe Val Thr Ile Asp His Glu Lys Arg
 65                  70                  75                  80

Leu Lys Glu Val Leu Gln Ile Glu Gly Gly Tyr Leu Asp Leu Gly Cys
                 85                  90                  95

Thr Phe Tyr Met Asp Ser Phe His Ile Leu Glu Lys Asp Cys Asp Ser
                100                 105                 110

Cys Ile Ile Lys Ser Ile Thr Ala Tyr Glu Val Arg Asp Asp Val Val
            115                 120                 125

Asp Asn Val Ser Ser Leu Ile Ser Ile Asp Ser Leu Ala Asn Met Ala
        130                 135                 140

Glu Ala Ile Ser Lys Tyr Val Leu Glu Lys Gln Glu Ala Ala Thr Lys
145                 150                 155                 160

His Gly His Gly Asp Asp Arg Glu Arg Thr Gly Leu Cys Trp Pro Phe
                165                 170                 175

Asn Cys Leu Gly
            180
```

<210> SEQ ID NO 32
<211> LENGTH: 197
<212> TYPE: PRT
<213> ORGANISM: Nandina domestica

<400> SEQUENCE: 32

```
Met Arg Lys Gly Ile Val Phe Leu Phe Leu Val Phe Leu Gly Cys Glu
 1               5                  10                  15

Val Ser Gln Gly Arg Gln Leu Leu Glu Ser Arg Leu Phe Arg Lys Ser
                20                  25                  30

Thr Ile Gln Lys Val Leu His His Glu Leu Pro Val Ala Ala Ser Ala
```

```
                35                  40                  45
Gln Glu Val Trp Asp Val Tyr Ser Ser Pro Glu Leu Pro Lys His Leu
 50                  55                  60

Pro Glu Ile Leu Pro Gly Ala Phe Glu Lys Val Val Thr Gly Asp
 65                  70                  75                  80

Gly Gly Val Gly Thr Val Leu Glu Met Val Phe Pro Pro Gly Glu Val
                 85                  90                  95

Pro Arg Ser Tyr Lys Glu Lys Phe Val Leu Ile Asp Asp Glu Gln Leu
                100                 105                 110

Leu Lys Lys Val Glu Met Ile Glu Gly Gly Tyr Leu Asp Met Gly Cys
            115                 120                 125

Thr Phe Tyr Met Asp Thr Ile Gln Ile Val Pro Thr Gly Pro Asp Ser
130                 135                 140

Cys Ile Ile Lys Ser Ser Thr Glu Tyr Tyr Val Lys Pro Glu Phe Ala
145                 150                 155                 160

Asp Lys Val Val Pro Leu Ile Ser Thr Ile Pro Leu Gln Ala Met Ala
                165                 170                 175

Glu Ala Ile Ser Asn Ile Val Leu Ala Asn Lys Ala Lys Asn Lys Ser
            180                 185                 190

Ile Ile Ile Glu Ile
            195

<210> SEQ ID NO 33
<211> LENGTH: 151
<212> TYPE: PRT
<213> ORGANISM: Nandina domestica

<400> SEQUENCE: 33

Met Val Phe Pro Pro Gly Glu Val Pro Arg Ser Tyr Lys Glu Lys Phe
  1               5                  10                  15

Val Leu Ile Asp Asp Glu Gln Leu Leu Lys Lys Val Glu Met Ile Glu
                 20                  25                  30

Gly Gly Tyr Leu Asn Asp Leu Asp Cys Val His Ile Lys Arg Thr Ser
             35                  40                  45

His Val Gln Ile Ser Thr Phe Asn His Phe Asp Met Gly Cys Thr Phe
 50                  55                  60

Tyr Met Asp Thr Ile Gln Ile Val Pro Thr Gly Pro Asp Ser Cys Ile
 65                  70                  75                  80

Ile Lys Ser Ser Thr Glu Tyr Tyr Val Lys Pro Glu Phe Ala Asp Lys
                 85                  90                  95

Val Val Pro Leu Ile Ser Thr Ile Pro Leu Gln Ala Met Ala Glu Ala
            100                 105                 110

Ile Ser Asn Ile Val Leu Asp Lys Thr Lys Asp Gln Arg Asn Lys Glu
            115                 120                 125

Val Ile Asn Thr Asn Thr Lys Asn Asn Lys Ile His His Arg Tyr Val
130                 135                 140

Ala Thr Ile Val Ile Ile Arg
145                 150

<210> SEQ ID NO 34
<211> LENGTH: 196
<212> TYPE: PRT
<213> ORGANISM: Nandina domestica

<400> SEQUENCE: 34

Met Arg Ser Gly Ile Val Phe Leu Val Leu Phe Phe Leu Gly Cys Glu
```

```
              1               5                  10                 15
            Ile Ser Gln Gly Arg Gln Leu Leu Glu Ser Arg Leu Phe Arg Lys Ser
                            20                 25                 30
            Thr Ile Arg Lys Val Leu His His Glu Leu Pro Val Ala Ala Ser Ala
                            35                 40                 45
            Gln Glu Val Trp Asp Val Tyr Ser Ser Pro Glu Leu Pro Lys His Leu
                            50                 55                 60
            Pro Glu Ile Leu Pro Gly Ala Phe Lys Lys Val Val Thr Gly Asp
            65                              70                 75             80
            Gly Gly Val Gly Thr Val Ile Glu Met Val Phe Pro Pro Gly Val Val
                                85                 90                 95
            Pro His Arg Tyr Lys Glu Lys Phe Val Leu Ile Asp Asp Glu Lys Phe
                               100                105                110
            Leu Lys Lys Val Glu Met Ile Glu Gly Gly Tyr Leu Asp Met Gly Cys
                               115                120                125
            Thr Phe Tyr Met Asp Thr Ile Gln Ile Val Pro Thr Gly Pro Asp Ser
                    130                135                140
            Cys Ile Ile Lys Ser Ser Thr Glu Tyr Tyr Val Lys Pro Glu Phe Ala
            145                 150                155                160
            Asp Lys Val Val Pro Leu Ile Ser Thr Val Pro Leu Gln Ala Met Ala
                                165                170                175
            Glu Ala Ile Ala Lys Ile Val Leu Glu Phe Lys Ala Lys His Lys Gly
                            180                185                190
            Phe Ile Glu Ile
                    195

<210> SEQ ID NO 35
<211> LENGTH: 148
<212> TYPE: PRT
<213> ORGANISM: Nandina domestica

<400> SEQUENCE: 35

Met Glu Val Ala Ala Ser Ala Gly Asp Ile Trp Ala Val Tyr Ser Ser
            1               5                  10                 15
            Pro Asp Leu Pro Arg Leu Ile Val Gln Leu Leu Pro Thr Val Phe Glu
                            20                 25                 30
            Lys Ile Asp Ile Val Glu Gly Asp Gly Val Gly Thr Val Leu His
                            35                 40                 45
            Ile Thr Phe Pro Pro Gly Ser Val Pro Leu Thr Tyr Lys Glu Lys Phe
                    50                 55                 60
            Val Thr Ile Asp Asn Ala Asn Arg Leu Lys Glu Val Leu Gln Ile Glu
            65                  70                 75                 80
            Gly Gly Tyr Leu Glu Leu Gly Cys Thr Phe Tyr Met Asp Ser Phe Gln
                            85                 90                 95
            Ile Phe Glu Lys Gly Ile Asp Ser Cys Ile Ile Lys Ser Met Thr Thr
                           100                105                110
            Tyr Glu Val Pro Asp Glu Leu Ala Asp Lys Val Ala Pro Leu Ile Ser
                           115                120                125
            Ile Asp Ser Leu Val Pro Met Ala Glu Ala Ile Ser Lys Tyr Val Ile
                    130                135                140
            Glu Lys Arg His
            145

<210> SEQ ID NO 36
<211> LENGTH: 154
```

<212> TYPE: PRT
<213> ORGANISM: Cocculus trilobus

<400> SEQUENCE: 36

Met Ile Lys Lys Glu Leu Lys His Glu Met Arg Val Ala Ala Ser Ala
1               5                   10                  15

Asp Asp Ile Trp Ala Val Tyr Ser Ser Pro Asp Leu Pro Asn Leu Ile
            20                  25                  30

Leu Arg Leu Leu Pro Ser Val Phe Asp Asn Ile Glu Ile Val Glu Gly
        35                  40                  45

Asn Gly Gly Val Gly Thr Val Leu His Leu Thr Phe Pro Pro Gly Ser
    50                  55                  60

Val Pro Leu Ser Tyr Lys Glu Lys Phe Val Thr Ile Asn Gly Asn Lys
65                  70                  75                  80

Arg Leu Lys Glu Val Lys Gln Ile Gln Gly Gly Tyr Leu Asp Met Gly
                85                  90                  95

Cys Thr Phe Tyr Met Asp Ser Phe His Ile Glu Glu Lys Gly Cys Asp
            100                 105                 110

Ser Cys Val Ile Val Ser Lys Thr Glu Tyr Glu Val Pro Asn Glu Glu
        115                 120                 125

Ile Ala Asn Gln Val Glu Leu Tyr Ile Ser Ile Asp Ser Leu Ala Ser
    130                 135                 140

Met Ala Gln Gly His Leu Gly Leu Cys Ser
145                 150

<210> SEQ ID NO 37
<211> LENGTH: 205
<212> TYPE: PRT
<213> ORGANISM: Hydrastis canadensis

<400> SEQUENCE: 37

Met Lys Met Ala Ile Leu Phe Val Phe Leu Met Phe Leu Gly Lys Met
1               5                   10                  15

Asn Ser Glu Gly Leu His Leu Ser Gly Arg Pro Leu Leu Arg Ala Ile
            20                  25                  30

Ile Ser Asp Lys Pro Asn Val Ile Lys Val Leu Lys His Glu Leu Ala
        35                  40                  45

Val Pro Ala Ser Ala Asp Lys Val Trp Ala Val Tyr Ser Ala Pro Thr
    50                  55                  60

Leu Ala Phe His Leu Ser Asp Leu Leu Pro Gly Ala Phe Glu Lys Val
65                  70                  75                  80

Glu Val Phe Gly Asp Gly Gly Val Gly Thr Ile Ile Asp Met Thr Phe
                85                  90                  95

Ala Pro Gly Glu Phe Pro His Glu Tyr Lys Glu Lys Phe Ile Leu Ile
            100                 105                 110

Asp Gly Lys Gln Arg Leu Lys Lys Val Gln Met Ile Glu Gly Gly Tyr
        115                 120                 125

Leu Asp Leu Gly Val Thr Tyr Tyr Met Asp Thr Ile His Val Val Pro
    130                 135                 140

Thr Gly Ser Asn Ser Cys Ile Ile Lys Ser Ser Thr Glu Tyr His Val
145                 150                 155                 160

Lys Pro Glu Ala Ala Lys Leu Val Glu Pro Leu Ile Thr Thr Glu Pro
            165                 170                 175

Leu Ala Ala Met Ala Glu Val Ile Thr Lys Ile Val Leu Glu Asn Lys
        180                 185                 190

```
Ser Lys Ser Ser Glu Glu Asn Gln Ser Ser Glu Ala Ile
        195                 200                 205
```

<210> SEQ ID NO 38
<211> LENGTH: 229
<212> TYPE: PRT
<213> ORGANISM: Nigella sativa

<400> SEQUENCE: 38

```
Met Val Gln Phe Ser Arg Glu Ser Lys Gln Ile Ser Ile Ile Ser Asp
1               5                   10                  15

Glu Glu Glu Gly Gly Glu Glu Thr Lys Glu Lys Lys Met Met Lys
            20                  25                  30

Val Gln Val Ala Leu Ala Phe Leu Leu Ile Leu Gly Ala Ala Ser Cys
            35                  40                  45

Gln Glu Leu Ile Leu Gln Gly Arg Pro Leu Leu Gly Gly Ala Arg Ala
    50                  55                  60

Trp Gly Thr Lys Ser Ile Lys Lys Glu Leu Lys His Glu Phe Lys Val
65                  70                  75                  80

Ala Ala Ser Ala Asp Glu Val Trp Ser Val Tyr Ser Ala Pro Glu Leu
                85                  90                  95

Cys Lys His Leu Thr Asp Leu Leu Pro Gly Ala Phe Glu Asp Val Glu
            100                 105                 110

Ile Ile Gly Asp Gly Gly Val Gly Thr Ile Leu His Met Ile Phe Pro
        115                 120                 125

Pro Gly Glu Phe Pro His Glu Tyr Lys Glu Lys Phe Val Val Ile Asp
    130                 135                 140

Asp Lys Gln Arg Leu Lys Lys Val Glu Met Ile Glu Gly Gly Tyr Leu
145                 150                 155                 160

Asp Ile Gly Val Thr Tyr Tyr Met Asp Thr Ile His Val Val Pro Thr
                165                 170                 175

Gly Ser Asp Ser Cys Val Ile Lys Ser Ser Thr Glu Tyr His Val Lys
            180                 185                 190

Pro Glu Phe Glu Lys Ile Val Glu Pro Leu Ile Thr Thr Val Pro Leu
        195                 200                 205

Ala Ala Met Ala Glu Ala Ile Ala Lys Ile Val Leu Asp Asn Lys Thr
    210                 215                 220

His Ser Ile Thr Ile
225
```

<210> SEQ ID NO 39
<211> LENGTH: 199
<212> TYPE: PRT
<213> ORGANISM: Nigella sativa

<400> SEQUENCE: 39

```
Met Val Lys Ile Gln Leu Val Leu Ala Cys Leu Leu Leu Val Val Gly
1               5                   10                  15

Ala Val Asn Cys Gln Lys Leu Ile Leu Gln Gly Arg Pro Leu Leu Gly
            20                  25                  30

Ala Trp Ala Cys Gly Thr Ile Lys Lys Val Leu Lys His Glu Phe Lys
            35                  40                  45

Val Ala Ala Ser Ala Asp Glu Val Trp Ser Val Tyr Ser Ser Pro Glu
    50                  55                  60

Leu Cys Lys His Leu Thr Asp Leu Leu Pro Gly Ala Phe Gln Asp Leu
65                  70                  75                  80
```

```
Glu Ile Ile Gly Asp Gly Gly Val Gly Thr Ile Leu His Met Thr Phe
                85                  90                  95

Pro Pro Gly Glu Phe Pro His Glu Tyr Lys Glu Lys Phe Val Leu Ile
            100                 105                 110

Asp Asp Lys Arg Lys Leu Lys Lys Val Glu Met Ile Lys Gly Gly Tyr
        115                 120                 125

Leu Asp Ile Gly Val Thr Tyr Tyr Met Asp Thr Ile His Val Val Pro
    130                 135                 140

Thr Gly Ser Asp Ser Cys Val Ile Lys Ser Thr Glu Tyr His Val
145                 150                 155                 160

Arg Pro Glu Cys Glu Lys Ile Val Glu Pro Leu Ile Thr Thr Glu Pro
            165                 170                 175

Leu Ala Ala Met Ala Glu Ala Val Ser Lys Ile Val Leu Asp Ala Lys
            180                 185                 190

Ile His Ser Ile Ile Thr Ile
            195

<210> SEQ ID NO 40
<211> LENGTH: 311
<212> TYPE: PRT
<213> ORGANISM: Menispermum canadense

<400> SEQUENCE: 40

Met Ile Lys Lys Glu Leu Lys His Glu Leu Glu Val Ala Thr Ser Ala
1               5                   10                  15

Asp Glu Ile Trp Glu Val Tyr Ser Ser Pro Asp Leu Pro Ile Leu Ile
            20                  25                  30

Val Lys Leu Leu Pro Ser Val Phe Glu Lys Ile Glu Ile Leu Glu Gly
        35                  40                  45

Asp Gly Val Gly Thr Ala Leu Arg Leu Thr Phe Pro Ile Gly Ser
    50                  55                  60

Val Pro Leu Thr Tyr Lys Glu Lys Phe Val Thr Ile Asn Asp Trp Lys
65                  70                  75                  80

Arg Leu Lys Glu Val Lys Gln Ile Glu Gly Gly Tyr Leu Asp Met Gly
                85                  90                  95

Cys Thr Phe Tyr Met Asp Ser Phe His Ile Leu Arg Lys Gly Pro Lys
            100                 105                 110

Ser Cys Val Ile Val Ser Lys Thr Glu Tyr Glu Val Pro Asn Lys Glu
        115                 120                 125

Ile Ala Ser Lys Val Glu Pro Tyr Ile Ser Ile Asp Ser Leu Arg Lys
    130                 135                 140

Met Ala Thr Ala Ile Ser Asp Tyr Val Leu Asn Arg Ala Thr Arg Lys
145                 150                 155                 160

Glu Val Lys His Glu Leu Glu Val Ala Ala Ser Ala Asp Asp Val Trp
                165                 170                 175

Glu Gly Tyr Arg Ser Pro Asp Val Gly Ser Leu Ile Cys Pro His Val
            180                 185                 190

Phe Glu Lys Ile Glu Leu Val Glu Gly Asp Gly Gly Val Gly Thr Ile
        195                 200                 205

Leu Gln Ile Thr His Pro Pro Gly Tyr Val Pro His Thr Tyr Lys Glu
    210                 215                 220

Lys Tyr Val Thr Leu Asp Asp His Lys Arg Leu Leu Glu Val Glu Gln
225                 230                 235                 240

Ile Glu Gly Gly Tyr Leu Glu Met Gly Cys Thr Phe Tyr Met Asp Ser
                245                 250                 255
```

Ile His Val Val Lys Lys Gly Asp Asn Ser Cys Val Ile Val Ser Lys
             260                 265                 270

Ala Lys Tyr Glu Val Pro Lys Glu Leu Ala Ser Gln Val Glu Pro Tyr
         275                 280                 285

Ile Ala Ala Asp Ala Val Ala Asn Met Ala Arg Ile Ile Ser Asn Asn
     290                 295                 300

Val Leu Glu Lys Lys Lys Ser
305                 310

<210> SEQ ID NO 41
<211> LENGTH: 195
<212> TYPE: PRT
<213> ORGANISM: Xanthoriza simplicissima

<400> SEQUENCE: 41

Met Arg Met Glu Val Val Leu Val Val Phe Leu Leu Phe Ile Gly Thr
1               5                   10                  15

Val Asn Cys Glu Arg Met Ile Phe Ser Gly Arg Pro Leu Leu His Arg
            20                  25                  30

Val Thr Asn Glu Glu Thr Val Ile Leu Tyr His Glu Leu Glu Val Pro
        35                  40                  45

Ala Ser Val Asp Glu Leu Trp Ser Val Glu Gly Ser Pro Glu Leu Gly
    50                  55                  60

Lys Asn Leu Pro Asp Leu Leu Pro Gly Ile Phe Ala Asp Phe Lys Ile
65                  70                  75                  80

Thr Gly Asp Gly Gly Glu Gly Ser Ile Leu Asp Met Thr Phe Pro Pro
                85                  90                  95

Gly Gln Phe Pro His His Tyr Arg Glu Lys Phe Val Phe Phe Asp His
            100                 105                 110

Lys Asn His Tyr Lys Leu Val Gln Met Ile Asp Gly Asp Phe Phe Asp
        115                 120                 125

Leu Gly Val Thr Tyr Tyr Met Asp Thr Ile Arg Val Val Ala Thr Gly
    130                 135                 140

Pro Asp Ser Cys Val Ile Lys Ser Ser Thr Glu Tyr His Val Lys Val
145                 150                 155                 160

Glu Phe Ala Lys Ile Val Lys Pro Leu Ile Asp Thr Val Pro Leu Ala
                165                 170                 175

Ile Met Ser Glu Ala Ile Ala Lys Val Val Leu Glu Lys Lys Tyr Lys
            180                 185                 190

Arg Ser Glu
        195

<210> SEQ ID NO 42
<211> LENGTH: 700
<212> TYPE: PRT
<213> ORGANISM: Papaver somniferum

<400> SEQUENCE: 42

Met Arg Lys Val Ile Lys Tyr Asp Met Glu Val Ala Val Ser Ala Asp
1               5                   10                  15

Ser Val Trp Ala Val Tyr Ser Ser Pro Asp Ile Pro Arg Leu Leu Arg
            20                  25                  30

Asp Val Leu Leu Pro Gly Val Phe Glu Lys Leu Asp Val Ile Glu Gly
        35                  40                  45

Asn Gly Gly Val Gly Thr Val Leu Asp Ile Val Phe Pro Pro Gly Ala
    50                  55                  60

```
Val Pro Arg Ser Tyr Lys Glu Lys Phe Val Asn Ile Asp Arg Glu Lys
 65                  70                  75                  80

Arg Leu Lys Glu Val Ile Met Ile Glu Gly Gly Tyr Leu Asp Met Gly
                 85                  90                  95

Cys Thr Phe Tyr Leu Asp Arg Ile His Val Val Glu Lys Thr Lys Ser
                100                 105                 110

Ser Cys Val Ile Glu Ser Ser Ile Val Tyr Asp Val Lys Glu Glu Cys
                115                 120                 125

Ala Asp Ala Met Ser Lys Leu Ile Thr Thr Glu Pro Leu Lys Ser Met
130                 135                 140

Ala Glu Val Ile Ser Asn Tyr Val Ile Gln Lys Glu Ser Phe Ser Ala
145                 150                 155                 160

Arg Asn Ile Leu Ser Lys Gln Ser Val Val Lys Lys Glu Ile Arg Tyr
                165                 170                 175

Asp Leu Glu Val Pro Ile Ser Ala Asp Ser Ile Trp Ser Val Tyr Ser
                180                 185                 190

Cys Pro Asp Ile Pro Arg Leu Leu Arg Asp Val Leu Leu Pro Gly Val
                195                 200                 205

Phe Glu Lys Leu Asp Val Ile Glu Gly Asp Gly Val Gly Thr Val
210                 215                 220

Leu Asp Ile Val Phe Pro Pro Gly Ala Val Pro Arg Ser Tyr Lys Glu
225                 230                 235                 240

Lys Phe Val Asn Ile Asp Arg Glu Lys Arg Leu Lys Glu Val Ile Met
                245                 250                 255

Ile Glu Gly Gly Tyr Leu Asp Met Gly Cys Thr Phe Tyr Leu Asp Arg
                260                 265                 270

Ile His Val Val Glu Lys Ser Leu Ser Ser Cys Val Ile Glu Ser Ser
                275                 280                 285

Ile Val Tyr Glu Val Lys Glu Glu Tyr Ala Asp Ala Met Ser Lys Leu
                290                 295                 300

Ile Thr Thr Glu Pro Leu Lys Ser Met Ala Glu Val Ile Ser Asn Tyr
305                 310                 315                 320

Val Ile Gln Arg Glu Ser Phe Ser Ala Arg Asn Ile Leu Asn Lys Asn
                325                 330                 335

Ser Leu Val Lys Lys Glu Ile Arg Tyr Asp Leu Glu Val Pro Thr Ser
                340                 345                 350

Ala Asp Ser Ile Trp Ser Val Tyr Ser Cys Pro Asp Ile Pro Arg Leu
                355                 360                 365

Leu Arg Asp Val Leu Leu Pro Gly Val Phe Gln Lys Leu Asp Val Ile
                370                 375                 380

Glu Gly Asn Gly Gly Val Gly Thr Val Leu Asp Ile Val Phe Pro Pro
385                 390                 395                 400

Gly Ala Val Pro Arg Ser Tyr Lys Glu Lys Phe Val Asn Ile Asn His
                405                 410                 415

Glu Lys Arg Leu Lys Glu Val Ile Met Ile Glu Gly Gly Tyr Leu Asp
                420                 425                 430

Met Gly Cys Thr Ser Tyr Leu Asp Arg Ile His Val Val Glu Lys Thr
                435                 440                 445

Ser Lys Ser Cys Ile Ile Lys Ser Ser Val Val Tyr Glu Val Lys Gln
                450                 455                 460

Glu Cys Val Glu Ala Met Ser Lys Leu Ile Thr Thr Glu Pro Leu Lys
465                 470                 475                 480
```

Ser Met Ala Glu Val Ile Ser Asn Tyr Ala Met Lys Gln Gln Ser Val
            485                 490                 495

Ser Glu Arg Asn Ile Pro Lys Lys Gln Ser Leu Leu Arg Lys Glu Ile
        500                 505                 510

Thr Tyr Glu Thr Glu Val Gln Thr Ser Ala Asp Ser Ile Trp Asn Val
    515                 520                 525

Tyr Ser Ser Pro Asp Ile Pro Arg Leu Leu Arg Asp Val Leu Leu Pro
    530                 535                 540

Gly Val Phe Glu Lys Leu Asp Val Ile Ala Gly Asn Gly Val Gly
545                 550                 555                 560

Thr Val Leu Asp Ile Ala Phe Pro Leu Gly Ala Val Pro Arg Arg Tyr
                565                 570                 575

Lys Glu Lys Phe Val Lys Ile Asn His Glu Lys Arg Leu Lys Glu Val
            580                 585                 590

Val Met Ile Glu Gly Gly Tyr Leu Asp Met Gly Cys Thr Phe Tyr Met
        595                 600                 605

Asp Arg Ile His Val Phe Glu Lys Thr Pro Asn Ser Cys Val Ile Glu
    610                 615                 620

Ser Ser Ile Ile Tyr Glu Val Lys Glu Glu Tyr Ala Gly Lys Met Ala
625                 630                 635                 640

Lys Leu Ile Thr Thr Glu Pro Leu Glu Ser Met Ala Glu Val Ile Ser
                645                 650                 655

Gly Tyr Val Leu Lys Lys Arg Leu Gln Val Phe Gly Phe Glu Ile Lys
            660                 665                 670

Pro Lys Leu Arg Phe Asn Leu Leu Leu Cys Leu Ile Ile Cys Leu Val
        675                 680                 685

Ile Ala Gly Gly Met Phe Val Ala Gly Val Pro Leu
    690                 695                 700

<210> SEQ ID NO 43
<211> LENGTH: 582
<212> TYPE: DNA
<213> ORGANISM: Papaver bracteatum

<400> SEQUENCE: 43
atgatgagga aagtaatcaa atacgatatg gaggtagcta cctcagctga ttcagtatgg      60
gcagtttaca gttcaccgga tattccaagg cttctcaggg atgttctact tcccggcgtc     120
ttcgagaaat tagacgtcat tgaagggaat ggcggcgtcg gtacagttct tgacattgct     180
tttcctccag gtgcggttcc tcgaagttac aaagagaaat tcgtcaacat cgaccgtgta     240
aagcgattga agaagtgat catgattgaa ggaggatacc tggacatggg atgcacattt      300
tacttggaca ggatccatgt cgtggagaaa accccaaact catgtgtcat tgaatcctct     360
attatctacg aagttaaaga agagtttgct gataaaatgg ctaagctaat cacaacggaa     420
ccattgcagt cgatggcaga agtcatctct ggttatgttc ttaagaaacg actccaagta     480
tttggattcg agattaagcc aaacttaaga ttcaatcttt tgctatgttt gattatctgc     540
ttggttatag ctggaggtat gttgattgga cgtgttccat aa                        582

<210> SEQ ID NO 44
<211> LENGTH: 633
<212> TYPE: DNA
<213> ORGANISM: Thalictrum flavum

<400> SEQUENCE: 44
atgatgaaga tggaagttgt atttgttttc ttaatgttgt taggaacaat aaattgccag      60

```
aaactgattc tgacaggtag gccgtttctg caccaccagg gcataataaa ccaggtgtct    120
acagtcacaa aagtgattca tcatgagttg aagttgctg cttcagctga tgatatatgg     180
actgtttata gctggcctgg cttggccaag catcttcctg acttgctccc tggcgctttt    240
gaaaagctag aaatcattgg tgatggaggt gttggtacca tcctagacat gacatttgta    300
ccaggtgaat ttcctcatga atacaaggag aagtttatat tagtcgataa tgagcatcgt    360
ttaaagaagg tgcaaatgat tgagggaggt tatctggact ggggagtaac atactacatg    420
gacacaatcc atgttgttcc aactggtaaa gattcatgtg ttattaaatc ctcaactgag    480
taccatgtga aacctgagtt tgtcaaaatc gttgaaccac ttatcaccac cggtccatta    540
gctgccatgg cagacgccat ctcaaaactt gttctagaac acaaatccaa aagcaactca    600
gatgaaattg aggccgcaat aataacagtc tga                                 633
```

<210> SEQ ID NO 45
<211> LENGTH: 696
<212> TYPE: DNA
<213> ORGANISM: Papaver somniferum

<400> SEQUENCE: 45

```
atgtctaagt tgatcacgac ggaaccattg aagtcgatgg cagaagttat ctctaattac     60
gctatgaagc aacaatctgt ttctgagaga acattccta agaagcaatc tctactgagg    120
aaggaaatta cttatgaaac ggaggtgcaa acttctgctg attcaatttg gaacgtctac    180
agttctcctg acatccctcg actacttaga gatgttctgc ttcctggtgt ttttgaaaag    240
ctagatgtca tagcaggcaa tggtggagtt ggtacggtac tggatattgc cttccctcta    300
ggtgcagtgc cacggaggta caaggagaaa tttgtgaaga tcaaccatga aagcgattg     360 aaagaagtgg tgatgatcga aggaggatac ttagacatgg ggtgcacatt ttacatggac    420
aggatccata tctttgagaa accccaaac tcatgtgtta tcgaatcctc gatcatttac     480
gaagttaaag aagagtatgc tggtaaaatg gctaagctaa tcacaactga accattggaa    540
tccatggcag aagtcatctc tggttatgtt cttaagaaac gactccaagt attcggattc    600
gagattaagc caaaattaag attcaatctt ttgctatgtt tgattatctg tctggttata    660
gctggaggta tgtttgttgc tggtgttcca ctctaa                              696
```

<210> SEQ ID NO 46
<211> LENGTH: 696
<212> TYPE: DNA
<213> ORGANISM: Papaver somniferum

<400> SEQUENCE: 46

```
atgtctaaat taatcacaac tgaaccattg aagtcgatgg cggaagtcat ctctaattac     60
gttatccaga gagaatcatt ttccgcaaga acattctca acaaaaattc tttggtgaag    120
aaggagattc ggtatgacct ggaggttcca acctcagctg attctatctg gtcagtttac    180
agctgcccgg atattcctcg gcttcttaga gatgttttac ttcccggtgt tttccagaaa    240
ttggatgtta tcgaagggaa tggtggtgtt ggtacagttc ttgatatcgt ttttcctcca    300
ggtgcggtac ctcgtagtta caaggagaaa tttgtgaaca tcaaccacga aaagcgatta    360
aaagaagtga ttatgatcga aggaggatat ttagacatgg gatgcacatt ttacatggac    420
aggatccata tctttgagaa accccaaac tcatgtgtta tcgaatcctc gatcatttac     480
gaagttaaag aagagtatgc tggtaaaatg gctaagctaa tcacaactga accattggaa    540
```

```
tccatggcag aagtcatctc tggttatgtt cttaagaaac gactccaagt attcggattc    600
gagattaagc caaaattaag attcaatctt ttgctatgtt tgattatctg tctggttata    660
gctggaggta tgtttgttgc tggtgttcca ctctaa                              696

<210> SEQ ID NO 47
<211> LENGTH: 591
<212> TYPE: DNA
<213> ORGANISM: Coptis japonica

<400> SEQUENCE: 47
atgaggatgg aagttgttct agttgttttc ttgatgttca taggtacgat aaattgtgaa     60
agattgatat tcaatggacg accgctactc catcgcgtaa caaaagagga gactgtaatg    120
ctttatcatg agctggaagt agctgcttca gccgatgaag tgtggagtgt cgaaggttcg    180
cctgagttgg gcttgcattt gcctgacttg ctccctgctg gtatatttgc aaagtttgaa    240
attactggtg atggaggtga aggttcgatc ctggacatga cattcccccc aggtcagttt    300
ccacatcatt acagggagaa gttcgtgttc ttcgatcaca agaatcgtta caagttagta    360
gaacagatcg atggtgattt tttcgatcta ggtgttacat actatatgga tacaatccga    420
gttgttgcga caggccctga ttcatgtgtc atcaagtcta ctactgaata ccatgtgaaa    480
cctgagtttg ccaaaatcgt caaaccactt attgacactg ttccactagc tatcatgtct    540
gaagcgattg caaaggttgt tctagagaac aaacacaaga gttcagagta a             591

<210> SEQ ID NO 48
<211> LENGTH: 1116
<212> TYPE: DNA
<213> ORGANISM: Papaver bracteatum

<400> SEQUENCE: 48
atgatgagga agtaatcaa atacgatatg gaggtagcta cctcagctga ttcagtctgg     60
gcagtttaca gttcaccgga tattcctaga cttctcaggg atgttctact ccccggcgtc    120
tttgagaaat tagacgtcat tgaagggaat ggcggcgttg gtactgttct tgacattgct    180
ttccctccag gtgcggttcc tcgaagttac aaagagaaat tcgtcaacat cgaccgtgta    240
aagcgattga agaagtgat catgattgaa ggaggatacc tggacatggg atgcacattt    300
tacttggaca ggatccatgt cgtggagaaa actccgagct catgtgttat tgaatcgtct    360
attgtttatg aagtggaaga gagtacgct gatgcgatgt caaaattgat cacyactgaa    420
ccattgaagt cgatggcgga agtgatytct aattacgtta ttcagaaaga atcagtttcc    480
gcaagaaaca ttttcaacag gcaatctgta gtgaagaagg agattcatta cgacctggag    540
gtaccaacct cagctgattc gatctgggca gtttacagca atcccgatat ccctcggcta    600
cttagagatg ttctgcttcc tggcgttttc gagaaattgg atgtcattga agggaatggt    660
ggtgttggca ctgttcttga tattgttttc cctccaggtg cggtgcctcg ttgttacaag    720
gagaagtttg tgaccatgga ccaccaaaag cgactaaaag aagtgattat gatcgaagga    780
ggttacttag acatgggatg cacatcttac ctggacagga tccatgttat agaaaaaaacc    840 tctaaatctt gcatcattaa atcttctgtt gtctacgaag tgaagcaaga gtgtgctgaa    900
gcaatatcta agttgatcac gacggagcca ttgaagtcga tggcagaagt catctcaaat    960
tatgttctta agaacaaatc tgtttccgac acaaacaata ttgctaagaa gcaatctgtg   1020
ttgaggaaag aaattactta tgaaacggag gtgcaaacct cagctgattc gatttggaac   1080
gtctacagtt ctcctgacat tcccccgact acttag                             1116
```

<210> SEQ ID NO 49
<211> LENGTH: 963
<212> TYPE: DNA
<213> ORGANISM: Papaver bracteatum

<400> SEQUENCE: 49

```
atggatatca tagaagggga tggtggagtt ggtactgttc ttgatgttgt tttccaacct      60
ggtgcggtgc ctcaaagtta caaggagaga tttgagaccg tggaccacga gaagcgaata     120
ctggaagtga gaattatcca aggaggatac ttagaaatgg gttgcacatc ttacctgaat     180
aggatgcatg ttattgaaat aacctctaaa tcttgtgtta ttaaatcttc ggttatctac     240
gacgtgaaag aagagtgtgc tgatgcaatg tctaagttaa tcacaaccat acagttggag     300
tcaatggcca agtggtcgc tgattatgtt cttaagaaac aatctgcttc tgacacaagc      360
attcctaaga agcagtctct aatgaggaaa gaaattacac atgagatgga ggtgcaaacc     420
tcagctgatt cgatttggga catctacagt tctcctgaca tccctcgact acttagagat     480
gtcctgcttc ctggtgcttt cgaaaagcta catgtcattc aaggcaatgg tggggttggt     540
actgtactgg acatcgctct ccctctaggt gcagtgccac gaaattacaa ggagaaattt     600
gtgaagatca accacgagaa gcgactaaaa gaagcagtta tgattgaagg gggatacgca     660
gacatggggt gcacatttta catgcacagg atccatgtcc tagagaaaac accaaagtcg     720
tgtgtcattg aatcctccat cgtttacgaa gtgaagaag agtatgctga taaaatgtca     780
aagctaatca caacagaacc attgcagtcc atggcagaag ccatatctag ttatgttctt     840
aagaaacagt tccaagtatt tggattagag gttaaaccga aattagtatt aagtctattt     900
ctatgtttga tcatctttt ggctatagtt ggtggttttt tgattggagg tctaaaagca     960
taa                                                                   963
```

<210> SEQ ID NO 50
<211> LENGTH: 831
<212> TYPE: DNA
<213> ORGANISM: Papaver bracteatum

<400> SEQUENCE: 50

```
atgattgaag gaggataccct ggacatggga tgcacgtttt acttggacag gatccatgtc      60
gtggagaaaa ctccgagctc atgtgttatt gaatcgtcta ttgtttatga agtgaagcaa     120
gagtgtgctg aagcaatatc taagttgatc acgacggagc cattgaagtc gatggcagaa     180
gtcatcgcta attacgttct taagaaacaa tctgtttctg acacaaacat tcctaagaag     240
caatctgtgt tgaggaaaga aattacttat gaaacggagg tgcaaacctc agttgattcg     300
atttggaacg tctacagttc tccagacatc cctcgactac ttagagatgt tctgcttcct     360
ggtgtttttg agaagctaga tgtcattgca ggcaatggtg gcgttgggac tgtactggac     420
attgctttcc ctctaggtgc agtgccgcgg aggtataagg agagatttgt gaagatcaat     480
catgagaagc ggttgaaaga agtggttatg atcgaaggag ggtacttgga catgggctgc     540
acattttaca tggacaggat tcatgtctttt gacaaaaccc caaactcatg tgtcattgaa     600
tcctctatta tctacgaagt taagaagag tatgctgata aaatggctaa gctaatcaca     660
acggaaccat tgcagtcgat ggcagaagtc atctctggtt atgttcttaa gaaacgactc     720
caagtatttg gattcgagat taagccaaac ttaagattca atcttttgct atgtttgatt     780
atctgcttgg ttatagctgg aggtatgttg attggacgtg ttccactcta a             831
```

<210> SEQ ID NO 51
<211> LENGTH: 1599
<212> TYPE: DNA
<213> ORGANISM: Papaver bracteatum

<400> SEQUENCE: 51

| | |
|---|---|
| atgatgagga aagtaatcaa atacgatatg gaggtagcta cctcagctga ttcagtctgg | 60 |
| gcagtttaca gttcaccgga tattccaagg cttctcaggg atgttctact tcccggcgtc | 120 |
| ttcgagaaat tagatgtcat tgaagggaat ggcggcgttg gtactgttct tgacattgct | 180 |
| ttccctccag gtgcggttcc tcgaagttac aaagagaaat tcgtcaacat cgaccgtgta | 240 |
| aagcgattga agaagtgat catgattgaa ggaggatacc tggacatggg atgcacattt | 300 |
| tacttggaca ggatccatgt cgtggagaaa actccgagct catgtgttat tgaatcgtct | 360 |
| attgtttatg aagtggaaga agagtacgct gatgccatgt caaaattgat caccactgaa | 420 |
| ccattgaagt cgatggcgga agtgatttct aattacgtta ccagaaaga atcagtttcc | 480 |
| gcaagaaaca ttttcaacag gcaatctgta gtgaagaagg agattcgata cgacctggag | 540 |
| gtaccaacct cagctgattc tatctgggca gtttacagca atcccgatat ccctcggcta | 600 |
| cttagagatg ttctgcttcc tggcgttttc gagaaattgg atgtcattga agggaatggt | 660 |
| ggtgttggga ctgttcttga tatcgttttt cctccaggtg cggtgcctcg tcgttacaag | 720 |
| gagaaatttg taacatcaa ccacgagaag cgattaaaag aagtgattat gatcgaagga | 780 |
| gggtacttag acatgggatg cacattttac ctggacagga tccatgttgt agaaaaaacc | 840 |
| tctaaatctt gcatcattaa atcttctatt gtttacgaag tgaagcaaga gtgcgctgaa | 900 |
| gcaatatcta agttgatcac gacggagccg ttgaagtcga tggcacaagt catcgctaat | 960 |
| tatgttctta agaaacaatc tgtttctgac acaaacattc ctaagaagca atctgtgttg | 1020 |
| aggaagaaa ttacttatga acggagtg caaacctcag ttgattcgat ttggaacgtc | 1080 |
| tacagttctc cagacatccc tcgactactt agagatgttc tgcttccggg tgttttgaa | 1140 |
| aagctagatg tcattgcagg caatggtggc gttgggactg tactggacat tgctttccct | 1200 |
| ctaggtgcag tgccgcggag gtacaaggaa aaatttgtga agatcaacca tgagaaacga | 1260 |
| ttgaaagaag tgattatgat cgaaggagga tacttagaca tggggtgcac attttacatg | 1320 |
| gacaggattc atgtacttga gaaaccccca aactcatgtg tcattgaatc ctctattatc | 1380 |
| tacgaagtta agaagagtt tgctgataaa atggctaagc taatcacaac ggaaccattg | 1440 |
| cagtcgatgg cagaagtcat ctctgcttat gttcttagga aacgattcga agtatttgga | 1500 |
| ctagagatta agcaaaaatt aagatacaat cttttgctat gtttgattat ctgcttggtt | 1560 |
| atagctggag gtatgttgat tggacgtgtt ccactctaa | 1599 |

<210> SEQ ID NO 52
<211> LENGTH: 582
<212> TYPE: DNA
<213> ORGANISM: Sanguineris canadensis

<400> SEQUENCE: 52

| | |
|---|---|
| atgaggaagg aactgacaca cgagatggag gtgcctgcct cagccgatgc tatttgggca | 60 |
| gtctacagtt cacatgatat tccaaggctg ctcaaagaag ttttgcttcc tggtgttttt | 120 |
| gaaaagctag atgtcattgc aggtgatggt ggtgttggta ctgttctcga cattgctttc | 180 |
| cctccagggg cggtaccgcg tcgttacaag gagaaattcg tgaagatcaa tcacgagaag | 240 |
| cgattgaagg aagtggagat gatcgaagga gggtatttgg atatggggtg tacatttat | 300 |

```
atggacagga ttcatgtcgt agagaaaggt cctaattcat gcgttatcga atcggcgatt      360
atttacgtag tgaaggacga atgcgccgat gtcgtcgttc ctctaattac gactgaacca      420
ctggctagca tggcggaggt catctcaaat tacgttctaa ggaaacaaat ccgattgttt      480
ggatacgtaa ttaaaccaaa attagggtta agtattttgc tctccttgat tctctgccta      540
gttatactag gagtgttatt gattggaggt gttccattct aa                        582
```

<210> SEQ ID NO 53
<211> LENGTH: 798
<212> TYPE: DNA
<213> ORGANISM: Chelidonium majus

<400> SEQUENCE: 53

```
atgattgaag agggtatttt ggatatggga tgtacatttt acatggacag aatccatgtt       60
gtaaagaaag gtcccaattc atgcgttatt gcatcggcta ttatctacga ggtgaaggag      120
gaatttgtcg acgtcgtcgt tcctctaatc acgaccgaac cattggctag catggcagaa      180
gtcatctcaa attacgttct taagaaacaa cgtcgtgtaa ggaaggaact aacatatgag      240
atggaggtgc ctacctcagc tgattcaatt tgggcagtct acagttcaca tgatattcca      300
aggctcctca agaagttcct gctccctggt gtctttgaaa agcttgatgt cattgaaggt      360
gatggtggtg ttggtactgt tcttgacatt gctttcccac caggggcggt accacgcact      420
tacaaggaga aattcgtgaa gatcaatcac gagaagcgat tgaaagaggt ggtgatgatt      480
gaaggagggt atttggatat gggatgtaca ttttacatgg acagaatcca tgtgctagag      540
aaaagtccta actcgtgcgt tattgaatct tctattatct acgaggtgaa ggaggaattt      600
gccgatgtcg tgggtcctct aatcacgacc gagccactag ctagcatgtc agaggtcatc      660
tcaaattacg ttctaaagaa acaaatccgc atgtttggtt atgtaattaa accaaaactt      720
ggtttaagtc ttttgctctg cttcattctc tgcctcgttt tacttggagt tttattgatt      780
gggggtgttc cactctaa                                                    798
```

<210> SEQ ID NO 54
<211> LENGTH: 1596
<212> TYPE: DNA
<213> ORGANISM: Chelidonium majus

<400> SEQUENCE: 54

```
atgaggaaag taatcaaata cgatatggag gtagctgtct cagctgattc agtttgggca       60
gtttacagtt caccggatat tcctagactt ctcagagacg ttctacttcc cggtgtcttc      120
gagaagttag atgttattga agggaatggc ggcgtcggaa cagttcttga cattgttttc      180
cctccaggtg cggttcctcg aagttacaag agagaaatttg tcaatatcga tcgcgaaaag      240
cgattgaaag aagtgatcat gatcgaagga ggatacctgg acatgggatg cacattttac      300
ttggatagga tccatgtagt ggagaaaacc aagagctcat gcgttattga atcgtctatt      360
gtttacgatg tgaaagaaga gtgcgccgat gccatgtcta aattgatcac aactgaacca      420
ttgaagtcca tggcggaagt catttctaat tacgttattc agaaagaatc attttctgcc      480
agaaacattc taagcaagca atctgtagtg aagaaggaga ttcgatacga cctggaggta      540
ccaatctcag ctgattctat ctggtcagtt tacagctgcc cggatattcc tcggcttctt      600
agagatgttt tacttcccgg tgtgttccag aaattggatg ttatcgaagg gaatggtggt      660
gttggtacag ttcttgatat cgttttttcct ccaggtgcgg tacctcgtag ttacaaggag      720
```

```
aaatttgtga acatcaacca cgaaaagcga ttaaagaag tgattatgat cgaaggagga    780
tatttagaca tgggatgcac atcttacctg gacaggatcc atgtagttga aaaaacctct    840
aaatcttgta tcattaaatc ttctgttgtc tatgaagtga agcaagagtg tgttgaggca    900
atgtctaagt tgatcacgac ggaaccattg aagtcgatgg cagaagttat ctctaattac    960
gctatgaagc aacaatctgt ttctgagaga acattccta agaagcaatc tctactgagg   1020
aaggaaatta cttatgaaac ggaggtgcaa acttctgctg attcaatttg aacgtctac   1080 agttctcctg acatccctcg actacttaga gatgttctgc ttcctggtgt ttttgaaaag   1140
ctagatgtca ttgcaggcaa tggtggcgtt ggtactgtac tggatattgc tttccctcta   1200
ggtgcagttc cgcggaggta aggagaaa tttgtgaaga ttaaccatga aagcgactg   1260 aaagaagtgg ttatgatcga aggaggatac ctagacatgg gttgcacatt ctacatggac   1320
aggatccatg tctttgagaa aaccccaaac tcatgtgtta tcgaatcctc gatcatttac   1380
gaagttaaag aagagtatgc tgctaaaatg gctaagctaa tcacaacaga accattggaa   1440
tccatggcag aagtcatctc tggttatgtt cttaagaaac gactccaagt attcggattc   1500
gagattaagc caaaattaag attcaatctt ttgctatgtt tgattatctg tctggttata   1560
gctggaggta tgtttgttgc tggtgttcca ctctaa                             1596

<210> SEQ ID NO 55
<211> LENGTH: 1056
<212> TYPE: DNA
<213> ORGANISM: Stylophorum diphyllum

<400> SEQUENCE: 55
atgaggaagg aagtacgata tgagatggag gtacctacct cagctgattc aatttgggca     60
gtttacagtt cacatgatat tccaaggctc ctcaaagaag ttcttctccc tggtgtcttt    120
gaaaagcttg atgtcattga aggtgatggt ggtgttggta ctgttcttga cattgctttc    180
ccaccagggg cggtaccacg cacttacaag gagaaatttg tgacaatcaa tcatgagaag    240
cgattgaaag aggtgattat gattgaagga gggtatttgg atatgggatg tacattttac    300
atggacagaa tccatgtcct agagaaaggt cccaaatcat gcattattgc atcggctatt    360
atctatgagg tgaaagaaga attcgccgat gtcgtcgttc ctcaatcac gactgaacca    420 ttggctagca tggcagaggt catctccaat tacgttctta agaaacaacg ccgtgtaagg    480
aaggaattaa catatgagat ggaggttcct acctcagctg attcaatttg gcagtttac    540 agttcacatg atattccaag gctcctcaaa gaagtccttc tcctggtgt gtttgaaaag    600 cttgatgtca ttgagggtga tggtggtgtt ggtactgttc ttgacattgc tttccctcca    660
ggtgcggtac cacgcactta caaggagaaa ttcgtgaaga tcaatcacga gaagcgattg    720
aaagaggtgg tgatgattga aggagggtat ttggatatgg gatgtacatt ttacatggac    780
agaatccatg tcctagagaa aggtcctaat tcttgcgtta ttgaatctgc tattatctac    840
gaggtgaaag aagaatttgc tgatgtcgtc gttccactaa tcacgaccga accactagct    900
agcatggcag aggtcatctc aaattacgtt ctaagaaac aaatccatgt gtttggttat    960
gtaattaaac caaaacttgg attaagtctt ttgctctgct tcattctctg cctcgtttta   1020
cttggagttt tattgattgg aggtgttcca ctctaa                              1056

<210> SEQ ID NO 56
<211> LENGTH: 855
<212> TYPE: DNA
<213> ORGANISM: Eschscholzia californica
```

<400> SEQUENCE: 56

```
atgatcggag gattcttaga catgggatgt acattttaca tggacaggat tcatgtcgta      60
gcgaaaggtc ctaattcatg tattatcaaa tcgactctta tctacgaagt gaaagaggaa     120
tatgccgatg ccatggcttc tctaatcact gtagaaccac tagctagcat ggcagaagtt     180
gttgcaaatt acgttcttca tcaacaagtc cgggtgttag gatccgtgaa gaggaaggaa     240
cttacgcatg agttggaagt tgctgcacca gctgatgcta tttggggtgt gtatagctca     300
cctgatattc cgaggcttct gagggatgtt ttgcttccgg tgttttttga aaagttagaa     360
gttatacaag gaaatggagg tgttggtact gttcttgaga ttgttttcca tccaggtgca     420
attccgcgta ggtacaagga gaagtttgtg acgataaatc acaagaagcg actgaaagag     480
gtggtcatga ttggagggta tctagacatg gggtgtacac tttatatgga caggattcat     540
gtagtatcca aggtcctaa ttcatgtgtt atcaaatcga cactcattta tgaagttaaa      600
gcagaatcag cagatgcgat ggcttctaca atcaccatcg acccactcgc tagcatggca     660
caggtcatct caaattatgt tctcaagaat caaatgcaag tcttaggatc tgttaagaga     720
agggaattaa cacatgagtt agaggtagct gcctcagctg acgctatttg gggagtttat     780
ggatcaaaaa gatattccaa ggcttctcag ggatgttttg cttcctggtg ttttcgaaaa     840
gttagaagtc attga                                                      855
```

<210> SEQ ID NO 57
<211> LENGTH: 2259
<212> TYPE: DNA
<213> ORGANISM: Eschscholzia californica

<400> SEQUENCE: 57

```
atgatcggag ggtacctaga catggggtgt actctttata tggacaggat tcatgtggtt      60
gagaaaggtc caaactcatg tgttataaaa tcgacactta tttatgaagt gaaagcagaa     120
tatgcggatg ccatggcttc tctaatcaca gtcgacccac tcgctagcat ggcacaagtg     180
atctcaaatt atgttctcaa gaatcaaggc caagtcttag gatctataaa gagaagggaa     240
ctaaaacatg aattggaggt agctgtctct gctgatgcta tttggggagt tattggttca     300
aaagatatcc caaggcttct tagagatgtt ttgcttcctg tgttttttga gaagttagat     360
gtcattgaag gtgatggagg cgtgggtact gttcttgaaa ttgttttccc tccaggagct     420
gttccgcgaa atacagaga gaagtttgtg aaggtcgatc atgagaaacg actgaaagag     480
gtgatcatga tcggagggta cttagacatg ggatgtacat tttacatgga caggattcat     540
gtcgtagcga aggtcctaa ttcatgtatt atcaaatcga ctcttatcta cgaagtgaaa      600
gaggaatatg ccgatgcaat ggcttctcta atcaccgtag aaccactagc tagcatggca     660
gaagttgttg caaattacgt tctccatcaa caagtccggg tgttaggatc cgtgaagagg     720
aaggaactta cacatgagtt ggaagtagct gcatcagctg atgctatttg gggtgtgtat     780
agctcacctg atattccgag gcttctgagg gatgttttgc ttccgggtgt ttttgaaaag     840
ttagaagtta tacaaggaaa tggaggtgtt ggtactgttc ttgagattgt tttccatcca     900
ggtgcaattc cgcgtaggta caaggagaag tttgtgacga taaatcacaa gaagcgactg     960
aaagaggtgg tcatgattgg agggtatcta gacatggggt gtacactttat atggacagg    1020
attcatgtag tatccaaagg tcctaattca tgtgttatca atcgacact catttatgaa     1080
gttaaagcag aatcagcaga tgccatggct tctacaatca ccatcgaccc actcgctagc    1140
```

| | |
|---|---|
| atggcacagg tcatctcaaa ttacgttctc aagaatcaaa tgcaagtctt aggatctgtt | 1200 |
| aagagaaggg aattaacaca tgagttagag gtagctgcct cagctgacgc tatttgggga | 1260 |
| gtttatggat caaaagatat tccaaggctt ctcagggatg ttttgcttcc tggtgttttc | 1320 |
| gaaaagttag aagtcattga aggcgatgga ggtgttggta ctgttctcca aattgttttt | 1380 |
| cctccagggg caattccacg gaggtacaaa gagaaatttg tgaaagtcga tcagaagctg | 1440 |
| cgactaaaag aagtgatcat gatcggagga tacttggaca tgggttgtac gttttatatg | 1500 |
| gacaggattc atgtagtacc aaaaggtctt aattcatgtg ttatcaaatc aacacttatt | 1560 |
| tatgaagtga agatgaata tgctgatgcc atgtcctctc ttatcactgt cgagccactc | 1620 |
| gctagcatgg ctgaagttgt ttcaaattat gttctgaata aaaagaaact aatgataaca | 1680 |
| aggaaagaac taacacatga gttggaggtg gcagcctcag ccgatgctat ttggagtgtc | 1740 |
| tatagctcac ctgatattcc aaggcttctc agagatgttt tgcttcctgg cgttttgaa | 1800 |
| aagttagaaa ttgttcaagg aaatggtggc gttggtactg ttctcgaaat tgttttccct | 1860 |
| aaaggatctg ttccacggag gtacaaagag aagtttgtga aaatcaacga cgagaaaaag | 1920 |
| ctgaaagagg taatcatgat cgaaggagga tacttggact tgggatgtac attttacatg | 1980 |
| gacaaaattc atgtcttacc taaagggcct aattcatgtg ttatcgaatc gtcacttatt | 2040 |
| tacgaagtta agaagaaaa tgcaaaagcc atggcttctc tgattactgt tgaaccactt | 2100 |
| gctagcatgg ctgaagtcgt tgcaaattac gttcttaaga agcaaatccg tgtgttagga | 2160 |
| tacgtcgtta agccaagagt tggatatagt gttttggttg ggcttttact ctgcttggtt | 2220 |
| ctacttggag tttttattgct ttcaggtgtc aacatctaa | 2259 |

<210> SEQ ID NO 58
<211> LENGTH: 522
<212> TYPE: DNA
<213> ORGANISM: Argemone mexicane

<400> SEQUENCE: 58

| | |
|---|---|
| atgaggaaag aagttgtata tgaattggaa gtaccaactt cagctgattc aatatgggca | 60 |
| gtttacagtt cacccaacat tcctacactt ctaagagatg ttctacttcc tggtgttttt | 120 |
| gagaagttag atgtgattga gggtaatggt ggtgttggaa ctgttcttaa cattgttttc | 180 |
| cctccaggtg ctgtgccccg ttgttacaaa gagaaattca ttaatatcga caacaagaag | 240 |
| aggttaaaag aagtgattat gatcgaagga ggctatttag acatgggatg tacatttac | 300 |
| atggatagga tccatgttat agcggaaact cctaattctt gtgttatcaa atcatctatc | 360 |
| atttacgacg tgaaaaaaga gtatgccgaa gctatgtcta aactaatcac aaccataccct | 420 |
| ttgaaatcca tgtctgaagt catcgctaat tacgttctca agaatcaatc tgtgataaga | 480 |
| aaggaagtta catatgaact gcaagtgcca acctcagact ga | 522 |

<210> SEQ ID NO 59
<211> LENGTH: 471
<212> TYPE: DNA
<213> ORGANISM: Argemone mexicane

<400> SEQUENCE: 59

| | |
|---|---|
| atgaagtttg agctagtaaa tgagttagag gtgcctgcct cagcaaatga tgtatgggca | 60 |
| atttatagct cacctgattt ccctaaaactc cttacgaagt tggttccagg tattctggag | 120 |
| agtgtagaat acgtcgaagg cgatggtcat cttggaactg ttattcatct tgtatacgtt | 180 |
| cctgggagtg tgccacttag ttacaaggaa aagtttgtga cgatcgacca cgaaaaacgt | 240 |

```
ttgaaagagg cagtgcatgt cgaaggagga ttcctagaga tgggtgtaac attttacatg      300
aacagcttcg aaattattga gaaaggttcg gattgttgca taattaggtc aatgactaag      360
tgcgaaattg aggataaaga aatcatgaac ctaatttctc atattagtgt tgcaaatgtg      420
accgtccttg caatgactat ctcaaaatat gttcaacaac acaagaaata a               471
```

```
<210> SEQ ID NO 60
<211> LENGTH: 648
<212> TYPE: DNA
<213> ORGANISM: Thalictrum flavum

<400> SEQUENCE: 60
atgaagatgg aagttgtatt tgttttcttt atgatcttag aacaattaa ttgccagaaa       60 ctgattctga caggtaggcc atttcttaac cgccaaggca taataaacca agtgtctaca      120
gtgacaaaag gggttcatca tgagttggaa gttgctgctt cggctgatga tatatggagt     180
gtttatagct ggcctggttt ggcaaagcat cttcctgact tgctccctgg cgcttttgaa     240
aagctcgaaa tcattggtga tggaggtgtt ggtaccatcc tagacatgac atttacacca     300
ggtgaatttc ctcatgaata caaggagaaa tttattttag tcgataatga gcatcgttta     360
aagaaggtgc aaatgatcga gggaggttat ctggacttag gagtaacata ctacatggac     420
acaatccagg ttattccaac tggtacaaat tcgtgtgtca ttaaatcctc aactgagtac     480
catgtgaaac ctgagtttgt caaaatcgtt gaaccactta tcactactgg tccattagct     540
gccatggcgg aagccatctc aaaacttgtt ttagaacaca atacaaaag caactcagat     600 gagattgatg cctcaaaaaa caatctgaag atggtgatta atatgtaa                  648
```

```
<210> SEQ ID NO 61
<211> LENGTH: 657
<212> TYPE: DNA
<213> ORGANISM: Thalictrum flavum

<400> SEQUENCE: 61
atgaagatgg aagctactgt atttgttttt ttaatgttct taggaacaat aaattgtcag      60
aaattgatta tggcaggtag gccgtttctt catcaccagg gcataataaa ccaggagttt     120
acagttacaa aagtgcttca tcatgagttg aagttgctg cttcggctga tgatatatgg      180
ggtgtttata gctcgcctca cttggttttt catctcactg acttgctccc tggtgctttt     240
gaaaaggtcc aagtcattgg tgatggaggt gttggtacta ttctagacat gacatttgca     300
ccaggtgaat tcctcatga atacaaggag aaatttattg tagtcgataa tgaacatcgt     360
ttaaagaagg tgcaaatgat cgagggaggt tatctggact taggagtaac atactacatg     420
gacacaatcc aggttgttcc aactggtaca aattcgtgtg tcattaaatc ctcaactgag     480
tatcatgtga aacctgagct actcaaaatc gttgaaccac ttatcaccac tggtccagta     540
gctgccatgg cggaagccat ctcaaaactt gttctagaat acaaatacaa aagtcactca     600
gacgagattc atgctggcct caataacaat ctaaagatgg tgatcaataa tatataa       657
```

```
<210> SEQ ID NO 62
<211> LENGTH: 582
<212> TYPE: DNA
<213> ORGANISM: Thalictrum flavum

<400> SEQUENCE: 62
atgaggaagg aactaacaca tgagatggag gtacctgcct cagctgatgc tatttgggca      60
```

```
gtctatggtt ctcctgatat tcccaggctc ctcaaagaag ttttgctccc aggtgtcttt      120
gaaaagctgg atgttattga aggtgatggt ggtgttggta ccgttctcga tattgctttc      180
ccaccaggag cggtgccgcg tgcttacaag gagaaattca tgaaggtcaa tcacgaaaag      240
cgattgaaag aggtggagat gatcgaagga gggtatttgg atatgggttg tacattttac      300
atggacagaa tccatgtcgt agagaaaggt cctaatgcct gtgttattga atcggctatt      360
atatatgaag tgaaggatga attcgccgac gttgttgttc ctctaatcac aactgaacca      420
ctggctagca tggctgaggt catctcaaac tatgttctaa agaatcaatt tcgcgtgttc      480
ggctatgtaa ttaaacctaa actcggatta agtcttttgc tctgcttcat tctctgcctc      540
gttttacttg gagggttgtt gattggaggt gttccactct aa                        582

<210> SEQ ID NO 63
<211> LENGTH: 492
<212> TYPE: DNA
<213> ORGANISM: Thalictrum flavum

<400> SEQUENCE: 63
atgaggaagg aacttacaaa tgagatggag gtggctgcgt ctgctgacga aatttgggca      60
gtctacagct cccccaacct ccccaaactc atcgttcaat tacttcctgc tgtctttgaa      120
aggatatata tccttgaagg agatggtggt gttggtaccg ttctctatat tttatctcct      180
ccaggatcgg ttccgcgtag ttacaaggag aagttcatta caatcgatca tgagaagcgt      240
ctgaaggagg tgcaagagat cgaaggaggg tacttggaca tgggcgttac cttttacatg      300
gacaccttct acatcttaga gaaaggtcct gattcctgca tcatcaaatc catgactacc      360
tacgaaatca aggatgagct ggccgataaa gttgcttctc ttattagcat tgattcacta      420
gttggcatgg ctaaagccat cacaaaatat gtccttgatc agaagaaagc tgctgtggat      480
tcttctgcct ag                                                          492

<210> SEQ ID NO 64
<211> LENGTH: 486
<212> TYPE: DNA
<213> ORGANISM: Berberis thunbergii

<400> SEQUENCE: 64
atggtagtgg ctgcctcagc tgatgatgtt tgggcaatct atagctccca tgatctgccc      60
aaactcattg tgaagttgct tccaagtgtc tttaagagca tagaaattgt tgaaggtgat      120
ggaggtcttg gtacagtttt ggatgttaaa taccctccag gatcaatacc actacattac      180
agggagaaat ttataacaat cgataatgaa aaacgtctta agaagtgag acaaatcgaa      240 gatggacttc tggctttagg atgcacattc tacatggaca gcttccatat ccttgagaaa      300
gattgtcacc atgaattctt ccatatccat gagaagaact gtcataagaa atgtatcatc      360
aagtcgacta cagtatatga atacctgat gagttagctt ataaaatcga acctctagtc      420
accattgatt ccctggttgg tatggctcat gccatctcaa aatatgttct tgacaaatcg      480
tgttaa                                                                486

<210> SEQ ID NO 65
<211> LENGTH: 1461
<212> TYPE: DNA
<213> ORGANISM: Corydalis chelanthifolia

<400> SEQUENCE: 65
atgtactact tcctggagtt cttcgaaaaa ctagatgtca ttgaaggcaa tggaggcgtc      60
```

```
ggcactgttc ttgacattgc ttttcctcca ggggcagtac cacgtagcta caaggagaag      120
ttcgtaaagg ttgaccacaa gaaccgtttg aaggaagtcg tgatgatcga aggaggatat      180
ttagatcttg gatgtacatt ttatatggat agaatccatg tcttaccaaa aggtgcaaat      240
tcatgcgtaa tcaagtcgac cctcatttac gaaattccag atgagcttgt cgactctgtt      300
ggttctctta tgtctactga accactagca agcatggcaa aagtcatctc ggattacgtt      360
ctcaagcaga gaaagatgac agcaaacaaa atattgagga aggaattaaa aacagagatg      420
gaggtggcta cttcagctga ttctatatgg gcagtctacg gttcccctga cattcctaga      480
ctcctcagag atgtattact tcctggagtt tttgagaaac tggatgtcat tgaaggcaat      540
ggaggtgtcg gcactgttct tgatattgct tttcctccag gggcggtacc tcgtacttac      600
aaagagaagt tcgtaaaggt tgatcacaag aaccgtttga aggaagtcgt gatgattgaa      660
ggcggatatc tggacttagg atgtacattt tatatggata gaatccatgt cttaccaaaa      720
ggtcctaata catgcgtaat caaatcgact cttatctatg aagttccaga cgagttcgct      780
gatgcagttg gttctcttat ctccgttgaa ccactagcaa gcatggcaga agtaatatca      840
ggttatgttc tcaagcagaa gaaggaagca aagaaaatat taggaaggaa ttaacacac       900 gaattggagg tgcctacttc agctgattca atatgggcag tctatggttc cctgatatt       960 ccaagattgc tcagagatgt attacttcct ggtgtgtttg aaaagctaga catcgtggaa     1020
ggcaatggag gtgttggtac tgttcttgac attgcttttc ctccaggggc ggtacctcgt     1080
agttacaagg agaagtttgt aaaggttgat cacgataagc atttgaaaga agttgtgatg     1140
atcgaaggag gatatttgga tctaggatgc acattctata tggatagaat ccatgtccta     1200
ccgaaaggtc ctaattcttg tgttatcgaa tcgtctctta tttatgaagt ccgggaagag     1260
ctcgctgatg tcgttggttc tcttatctca attgaaccac ttgctagcat ggcagaagtc     1320
atctcaagtt atgttctcaa acaacaactc cgagtgtttg gagttgtagt tcaaccaaga     1380
gtaggattaa gtcttttgct ctgccttata ctgtgtctag tcatattagg aggtcttttg     1440
atcggcggtg tttcgatata a                                                1461

<210> SEQ ID NO 66
<211> LENGTH: 1119
<212> TYPE: DNA
<213> ORGANISM: Corydalis chelanthifolia

<400> SEQUENCE: 66
atgaggaagg aattaagaca tgaattggag gtggcaactt cagctgattc tatttgggca      60
gtctatggtt cccctgatat cccaagactt ctcagagatg tattgcttcc tggtgtcttt     120
gaaaaactag atgttattca aggcaatgga ggtgtgggta ctgttcttga cattgctttc     180
cctccagggg cggttccacg tacttacaag agaagttcg taaaggtcga tcacaagaat      240
cgtttgaagg aagttgtaat gatcgaagga ggatatctgg acctaggatg tacattttat     300
atggatagaa tccatgtctt gcccagtgga cctaatacat gtataatcaa atctacactt     360
atttacgaag ttccagacga gctcgcctac tccgttgctt ctctaatctc tgttgaacca     420
ctagcaagca tggcagaagt catctcaggt tatgtgctca ggcagagaaa gatgacaaca     480
aacaaaatat tgaggaagga attgacaaca gagatggagg tgcccacttc agctgattca     540
atatgggcag tctatggttc cctgatatt cctagactcc ttagagatgt attacttcct      600
ggagttttcg aaaggctgga tgtcattgaa ggcaatggag gtgtcggcac tgttcttgat     660
```

```
attagttttc caccaggggc ggtaccacgt agttacaagg agaagtttgt gaaggttgat      720
cacaagaacc gtctgaagga agttgtgatg atcgaaggag gatatctaga tctaggatgt      780
acattttata tggatagaat ccatgtaata ccaaaaggcc ctaattcatg cgtaatcaag      840
tcgaccctca tttatgaaat tcctggtgag cttgtggact ctgttggttc tcttatgtct      900
actgaaccac ttgcaagcat ggcagcagtc atctcggatt acgttctcaa acagagaaag      960
atgacagcaa accaaatatt gaggaaggaa ttgacaacag atggagtt ggctacttca       1020 gctgattcta tttggtcagt ttatggttcc cctgatattc ctagactcct cagagatgta    1080
ttacttcctg gagttttcga aagactagga tgtcattga                            1119
```

```
<210> SEQ ID NO 67
<211> LENGTH: 600
<212> TYPE: DNA
<213> ORGANISM: Corydalis chelanthifolia

<400> SEQUENCE: 67
atgatgagga agaactagt acatgaaaag gaagtgtgtg catcagctga tgcagtatgg        60
ggagtgtata gttcacccaa tattccaaca ctccttagag ataaattact tcctggtatg      120
tttaaaaggc ttgagatact tgaaggtgat ggaggagttg gtacaattct cctccttgag      180
ttcaataatc cagcgattat accacataca tatcttgaaa agttcatgaa gctagatcat      240
gagaagcgtt tgttggaagt tgaggtggtc aaaggaggat atttggattt aggatgtaca      300
ttttatatga gtagaataca catcttggag aaaggtccta attcatgcgt aatcgaatcg      360
actcttattt tcgaagcacc ggaggaactc atggaatatg ttagtcaata tgcaaacctt      420
gaatcattaa ttagcatggc agaagttata tcaaagtatg ttcttgagca gcaattccga      480
gttttcggag ttgttgtcaa gaaactgaaa ttgggattat caactattgt gttgctatgc      540 attttttatct ttctggttat tgtattagga ggtctttgga ttgaaggtgt ttcaatctaa     600
```

```
<210> SEQ ID NO 68
<211> LENGTH: 480
<212> TYPE: DNA
<213> ORGANISM: Corydalis chelanthifolia

<400> SEQUENCE: 68
atgaggaagc atcttgttaa cgagttggag gttgttgttc cagccgacac tctttgggca       60
atttacagca ccactcaatt cccaaagcta attgttcaat tgcttcccat tgttgtccaa      120
aatatagaaa ttgatggcga cggaagtctt ggtactgttt tgaatgttat ttttgttcca      180
ggatcggttc cattgtctta caagagaaa atcgtgacga ttgatcatga aagcgtttg        240 aaggaagtgg tgcagatcga aggaggatat ttggatttag gatgttcatt ttacatgagc      300
agctttcaaa tcttggagaa aggtcgtgat tcttgcatca tcaaatccat ggttacatac      360
gagctggcta aggatgctga tcctagtgtt gctgatttgg tcaccattgc tgcacatgct      420
gccatagctc aagtcatctc taagtatgtt cttgacaaac aagtagccgc agctccataa      480
```

```
<210> SEQ ID NO 69
<211> LENGTH: 543
<212> TYPE: DNA
<213> ORGANISM: Corydalis chelanthifolia

<400> SEQUENCE: 69
atgaggaagg aactcacaaa tgagttggag gtcgcagccc ctgctgatgc tgtctgggca       60
gtttacagct ccccggatct cccaaaaatc atagttgaat tacttcctag tgtcttcgaa      120
```

| aagattgaaa tcgttgaagg agacggaggt gttggtaccg ttctgtacgt tgttttcct | 180 |
| ccaggatcag ttccattaac ttacaaggag aagttcgtga cgattgatca cgagaagcgt | 240 |
| ctgaaggagg tgctacagat tgaaggagga tatttggacc tagggtgtac gttttacatg | 300 |
| gacagcttcc atatactaga gaaagattgt gattcatgca tcatcaaatc cataacagca | 360 |
| tacgaagtca gggatgatgt tgttgataat gtttcctctc ttatctccat tgattcgctc | 420 |
| gctaacatgg ctgaagccat ctcaaagtat gtccttgaga acaagaagc cgcaactaag | 480 |
| catggacatg gagatgatag ggaaaggact ggtctttgtt ggcctttcaa ttgtttgggt | 540 |
| taa | 543 |

<210> SEQ ID NO 70
<211> LENGTH: 594
<212> TYPE: DNA
<213> ORGANISM: Nandina domestica

<400> SEQUENCE: 70

| atgaggaagg gaattgtttt cctatttcta gttttcttag gatgtgaagt ttcacaagga | 60 |
| aggcaactgc tagagtcgag attatttagg aaatctacga tacaaaaagt tcttcaccat | 120 |
| gagttgccag ttgctgcgtc ggcccaagaa gtgtgggatg tttatagctc gcccgaattg | 180 |
| ccaaaacacc taccagaaat acttccaggc gcattcgaga aagttgtagt taccggggat | 240 |
| ggtggtgttg gtactgtact tgaaatggta tttcctccag gagaagtacc ccgtagttac | 300 |
| aaggagaaat ttgtgttgat tgatgacgaa cagcttttga agaaggtcga atgattgaa | 360 |
| ggtggatatt tggacatggg atgtacgttt tatatggaca caatccaaat cgttccaaca | 420 |
| ggtcctgatt catgcataat caaatcctca actgaatact acgttaaacc tgaatttgcg | 480 |
| gacaaggttg tacctcttat cagcacaatc ccattgcaag ccatggccga agctatctcg | 540 |
| aacattgttc tagcaaacaa agccaagaac aagagtatta tcatcgaaat ataa | 594 |

<210> SEQ ID NO 71
<211> LENGTH: 456
<212> TYPE: DNA
<213> ORGANISM: Nandina domestica

<400> SEQUENCE: 71

| atggtatttc ctccaggaga agtaccccgt agttacaagg agaaatttgt gttgattgat | 60 |
| gacgaacagc ttttgaagaa ggtcgaaatg attgaaggtg gatatttgaa cgatttggat | 120 |
| tgtgtccata taaaacgtac atcccatgtc caaatatcca ccttcaatca tttcgacatg | 180 |
| ggatgtacgt tttatatgga cacaatccaa atcgttccaa caggtcctga ttcatgcata | 240 |
| atcaaatcct caactgaata ctacgttaaa cctgaattgc cggacaaggt tgtacctctt | 300 |
| atcagcacaa tcccattgca agccatggcc gaagctatct cgaacattgt tctagacaaa | 360 |
| acaaagacc aaagaaacaa agaagtaatt aatacaaata cgaaaaataa taaaatacat | 420 |
| catcgctatg tcgctaccat tgttataatc agataa | 456 |

<210> SEQ ID NO 72
<211> LENGTH: 591
<212> TYPE: DNA
<213> ORGANISM: Nandina domestica

<400> SEQUENCE: 72

| atgaggagtg gaattgtttt cctggttcta ttttcttag gatgtgaaat ttcgcaggga | 60 |

```
agacaattac tggagtcgag actatttagg aagtctacaa tacgaaaagt gcttcaccat    120
gagttgccag tagctgcgtc ggcccaagaa gtgtgggacg tttatagctc gccggaattg    180
ccaaaacacc taccagaaat acttccaggc gcatttaaga aagttgtagt cactggagat    240
ggaggtgttg gtacggtaat tgaaatggta tttcctccag gagtagtacc gcaccgttac    300
aaggaaaagt tgttctaat cgacgatgag aaatttttaa agaaggttga aatgatcgaa    360
ggtggatatt tggacatggg atgtacgttt tacatggaca caatccaaat cgttccaaca    420
ggtcctgatt catgcataat caagtcctca actgagtact atgttaaacc tgaattcgcg    480
gataaggttg tacctttgat cagcactgtt ccgttgcaag ccatggctga agctattgcg    540
aaaatcgttc tagagttcaa agccaagcac aaggggttta tcgaaatata a            591
```

<210> SEQ ID NO 73
<211> LENGTH: 447
<212> TYPE: DNA
<213> ORGANISM: Nandina domestica

<400> SEQUENCE: 73

```
atggaagtgg ctgcgtcggc gggtgatatt tgggctgttt acagttcccc tgatctgcct     60
aggcttatcg tccaattact ccccactgtg tttgaaaaga tagacattgt agaaggcgat    120
ggaggtgttg gtactgtttt acatattaca tttcctcccg gatctgtacc gcttacttac    180
aaggagaaat ttgtgacgat cgataatgca aaccgtttaa agaagtact acagatcgaa    240 ggtggatatt tggagttggg atgtactttc tatatggata gcttccagat cttcgagaaa    300
ggtattgatt catgcatcat caaatcaatg actacttatg aagtaccaga tgagcttgca    360
gacaaagttg ctcctcttat ctccattgat tccctcgttc ccatggctga agccatctca    420
aaatatgtta ttgagaagcg tcattaa                                        447
```

<210> SEQ ID NO 74
<211> LENGTH: 465
<212> TYPE: DNA
<213> ORGANISM: Cocculus trilobus

<400> SEQUENCE: 74

```
atgatcaaga aggaactcaa acacgagatg agagtggctg cctctgcaga tgatatatgg     60
gcagtttaca gctcacctga tttgcccaat ctcatcctca gattgctacc tagtgttttc    120
gacaacatcg aaatcgtcga aggcaacgga ggagtcggaa ctgttctcca cctcactttt    180
cctccaggtt cagtaccact ttcatacaag gagaagttcg tgactattaa tggcaacaaa    240
cgtttgaagg aggtgaagca gattcaagga gggtatcttg acatgggctg cacattctac    300
atggacagct tcatataga agagaaaggt tgtgattcat gtgtgatcgt gtcgaagacc    360
gagtacgaag tacctaatga ggagatagca aaccaagttg agctttatat atctattgat    420
tcactagcta gcatggccca aggccatctc ggattatgtt cttag                    465
```

<210> SEQ ID NO 75
<211> LENGTH: 618
<212> TYPE: DNA
<213> ORGANISM: Hydrastis canadensis

<400> SEQUENCE: 75

```
atgaagatgg caattttgtt tgtgttctta atgttcttgg gaaagatgaa ttctgaaggc     60
ttgcacttga gcgggaggcc gcttctccgg gcgataatat ccgacaagcc caatgtaatc    120
aaagtgctta acatgagtt ggcagtacct gcatccgcgg acaaagtttg gcagtctat    180
```

```
agcgcgccca cgttggcctt ccatctcagc gacttacttc ccggtgcctt tgaaaaggtg      240 gaagttttg gtgatggagg tgttggcact atcatcgaca tgacatttgc cccaggtgaa       300
tttccccatg aatacaagga aaaattcatc ttgatagatg gcaaacaacg tctaaagaaa      360
gtacaaatga tcgaaggagg ttatttggat ctaggagtta catactatat ggacaccatc     420
catgtcgtcc caacaggttc caattcatgc atcatcaaat catctactga ataccatgta    480
aaacctgagg ccgcaaagct agtcgaacct cttatcacaa ctgagccatt agctgccatg    540
gctgaagtta tcacaaagat tgtcttagag aacaaaagca agagctccga agaaaatcag    600
tcatcagaag ccatataa                                                  618

<210> SEQ ID NO 76
<211> LENGTH: 690
<212> TYPE: DNA
<213> ORGANISM: Nigella sativa

<400> SEQUENCE: 76
atggttcagt tcagcagaga aagcaagcaa ataagcatta tctctgacga agaagaagga    60
ggagaagaag aaactaagga gaagaagatg atgaaggtac aagtagcact tgctttctta   120
ctaatattag gtgctgcaag ctgccaagaa ctcatactgc agggaaggcc gcttcttggt   180
ggtgcccgcg cgtggggtac caaatccata agaaagagc tgaaacacga gttcaaagtt    240
gctgcttcag ctgatgaggt ttggagtgtg tatagcgcac cagaactctg caaacatctc   300
actgatcttc tcccaggtgc atttgaggat gttgaaatca ttggtgacgg aggcgttggt   360
accattcttc acatgatttt ccctccaggt gaattcccgc atgaatacaa ggagaagttt   420
gtggtgattg atgacaagca acggttaaag aaggtagaaa tgatcgaagg tgggtatctg   480
gatattggag tgacttacta tatggacacc atccatgttg tgcccactgg ttcagactca   540
tgtgtgatta agtcatccac agaataccat gtaaaacctg agtttgagaa aattgtggaa   600
ccacttatta ctacagttcc attagctgcc atggctgaag ctatcgccaa gattgttcta   660
gacaacaaaa ctcattccat tacaatctga                                    690

<210> SEQ ID NO 77
<211> LENGTH: 600
<212> TYPE: DNA
<213> ORGANISM: Nigella sativa

<400> SEQUENCE: 77
atggtgaaga tacagttagt gcttgcttgt ttactactag tagtaggtgc tgtaaattgc    60
caaaagctta tattgcaggg gaggccactt cttggtgcct gggcgtgtgg taccatcaag   120
aaagtgctga acatgagtt caaagtagct gcttcagctg atgaggtgtg gagtgtgtac    180
agctcaccag aactctgcaa acatctaact gatcttctcc caggtgcatt tcaggatctt   240
gaaattattg gtgatggagg cgttggtacc attctccaca tgacttttcc accaggtgaa   300
ttcccacatg aatacaagga gaaatttgtg ttaattgatg acaagcgaaa gttaaagaag   360
gtagaaatga taagggtgg ctatttggat attggagtga cttactatat ggacaccatc   420
catgttgtgc ccactggttc agattcatgt gtgatcaagt cgtccacaga ataccatgta   480
agacctgagt gtgagaaaat agtggaacca cttattacca ctgaaccatt agctgccatg   540
gctgaagctg tctccaagat tgttctagat gccaaaattc attccataat aacaatctga   600

<210> SEQ ID NO 78
```

<211> LENGTH: 936
<212> TYPE: PRT
<213> ORGANISM: Menispermum canadense

<400> SEQUENCE: 78

```
Ala Thr Gly Ala Thr Cys Ala Gly Ala Gly Gly Ala Gly Cys
1               5                   10                  15

Thr Cys Ala Ala Gly Cys Ala Thr Gly Ala Ala Thr Gly Gly Ala
            20                  25                  30

Gly Gly Thr Ala Gly Cys Thr Ala Cys Cys Thr Cys Thr Gly Cys Gly
            35                  40                  45

Gly Ala Cys Gly Ala Ala Thr Thr Thr Gly Gly Gly Ala Ala Gly
        50                  55                  60

Thr Ala Thr Ala Cys Ala Gly Cys Thr Cys Thr Cys Cys Thr Gly Ala
65                  70                  75                  80

Thr Thr Thr Gly Cys Cys Ala Thr Cys Cys Thr Ala Thr Thr
                85                  90                  95

Gly Thr Thr Ala Ala Thr Thr Gly Cys Thr Cys Cys Ala Ala
            100                 105                 110

Gly Cys Gly Thr Gly Thr Thr Cys Gly Ala Ala Ala Gly Ala Thr
        115                 120                 125

Cys Gly Ala Ala Ala Thr Cys Thr Gly Gly Ala Ala Gly Gly Cys
        130                 135                 140

Gly Ala Thr Gly Gly Ala Gly Gly Cys Gly Thr Thr Gly Gly Thr Ala
145                 150                 155                 160

Cys Thr Gly Cys Thr Cys Thr Thr Cys Gly Ala Cys Thr Cys Ala Cys
                165                 170                 175

Ala Thr Thr Cys Cys Cys Ala Ala Thr Ala Gly Gly Gly Thr Cys Ala
            180                 185                 190

Gly Thr Gly Cys Cys Cys Thr Thr Ala Cys Thr Thr Ala Cys Ala
        195                 200                 205

Ala Gly Gly Ala Gly Ala Ala Gly Thr Thr Thr Gly Thr Gly Ala Cys
        210                 215                 220

Cys Ala Thr Thr Ala Ala Cys Gly Ala Cys Thr Gly Gly Ala Ala Ala
225                 230                 235                 240

Cys Gly Ala Thr Thr Gly Ala Ala Gly Gly Ala Gly Thr Gly Ala
            245                 250                 255

Ala Gly Cys Ala Ala Ala Thr Cys Gly Ala Ala Gly Gly Ala Gly Gly
        260                 265                 270

Gly Thr Ala Cys Cys Thr Thr Gly Ala Thr Ala Thr Gly Gly Gly Cys
        275                 280                 285

Thr Gly Cys Ala Cys Ala Thr Thr Cys Thr Ala Cys Ala Thr Gly Gly
        290                 295                 300

Ala Cys Ala Gly Thr Thr Thr Thr Cys Ala Thr Ala Thr Thr Thr Thr
305                 310                 315                 320

Ala Cys Gly Ala Ala Ala Ala Gly Gly Thr Cys Cys Thr Ala Ala Gly
            325                 330                 335

Thr Cys Gly Thr Gly Thr Gly Thr Gly Ala Thr Gly Thr Gly Thr
        340                 345                 350

Cys Thr Ala Ala Gly Ala Cys Thr Gly Ala Gly Thr Ala Cys Gly Ala
            355                 360                 365

Ala Gly Thr Ala Cys Cys Thr Ala Ala Thr Ala Ala Gly Gly Ala Gly
        370                 375                 380

Ala Thr Ala Gly Cys Ala Ala Gly Cys Ala Ala Ala Gly Thr Thr Gly
```

-continued

```
385                 390                 395                 400

Ala Ala Cys Cys Thr Thr Ala Thr Ala Thr Ala Thr Cys Thr Ala Thr
                405                 410                 415

Thr Gly Ala Thr Thr Cys Ala Cys Thr Cys Ala Gly Gly Ala Ala Gly
            420                 425                 430

Ala Thr Gly Gly Cys Ala Ala Cys Thr Gly Cys Cys Ala Thr Cys Thr
        435                 440                 445

Cys Gly Gly Ala Thr Thr Ala Thr Gly Thr Thr Cys Thr Gly Ala Ala
    450                 455                 460

Cys Ala Gly Gly Gly Cys Gly Ala Cys Cys Ala Gly Gly Ala Ala Gly
465                 470                 475                 480

Gly Ala Ala Gly Thr Gly Ala Ala Gly Cys Ala Cys Gly Ala Ala Thr
                485                 490                 495

Thr Ala Gly Ala Gly Gly Thr Gly Gly Cys Thr Gly Cys Cys Thr Cys
            500                 505                 510

Gly Gly Cys Ala Gly Ala Cys Gly Ala Thr Gly Thr Gly Thr Gly Gly
        515                 520                 525

Gly Ala Gly Gly Gly Cys Thr Ala Cys Ala Gly Gly Thr Cys Ala Cys
    530                 535                 540

Cys Thr Gly Ala Cys Gly Thr Gly Gly Gly Cys Ala Gly Cys Cys Thr
545                 550                 555                 560

Ala Ala Thr Thr Thr Gly Cys Cys Cys Ala Cys Ala Thr Gly Thr Gly
                565                 570                 575

Thr Thr Cys Gly Ala Ala Ala Ala Gly Ala Thr Cys Gly Ala Gly Cys
            580                 585                 590

Thr Thr Gly Thr Ala Gly Ala Ala Gly Gly Thr Gly Ala Thr Gly Gly
        595                 600                 605

Cys Gly Gly Thr Gly Thr Thr Gly Gly Cys Ala Cys Thr Ala Thr Thr
    610                 615                 620

Cys Thr Gly Cys Ala Gly Ala Thr Cys Ala Cys Gly Cys Ala Thr Cys
625                 630                 635                 640

Cys Ala Cys Cys Ala Gly Gly Ala Thr Ala Thr Gly Thr Gly Cys Cys
                645                 650                 655

Ala Cys Ala Thr Ala Cys Thr Thr Ala Cys Ala Ala Gly Gly Ala Gly
            660                 665                 670

Ala Ala Gly Thr Ala Cys Gly Thr Gly Ala Cys Gly Cys Thr Ala Gly
        675                 680                 685

Ala Thr Gly Ala Thr Cys Ala Cys Ala Ala Ala Cys Gly Thr Thr Thr
    690                 695                 700

Gly Thr Thr Gly Gly Ala Gly Gly Thr Ala Gly Ala Gly Cys Ala Ala
705                 710                 715                 720

Ala Thr Cys Gly Ala Ala Gly Gly Ala Gly Gly Ala Thr Ala Cys Cys
                725                 730                 735

Thr Thr Gly Ala Gly Ala Thr Gly Gly Gly Cys Thr Gly Cys Ala Cys
            740                 745                 750

Ala Thr Thr Thr Thr Ala Cys Ala Thr Gly Gly Ala Cys Ala Gly Cys
        755                 760                 765

Ala Thr Thr Cys Ala Cys Gly Thr Thr Gly Thr Ala Ala Ala Gly Ala
    770                 775                 780

Ala Ala Gly Gly Thr Gly Ala Cys Ala Ala Cys Thr Cys Ala Thr Gly
785                 790                 795                 800

Thr Gly Thr Cys Ala Thr Cys Gly Thr Gly Thr Cys Cys Ala Ala Gly
                805                 810                 815
```

```
Gly Cys Ala Ala Ala Gly Thr Ala Cys Gly Ala Ala Gly Thr Thr Cys
                820                 825                 830
Cys Cys Ala Ala Gly Gly Ala Gly Thr Thr Ala Gly Cys Ala Ala Gly
            835                 840                 845
Cys Cys Ala Ala Gly Thr Thr Gly Ala Ala Cys Cys Thr Thr Ala Cys
        850                 855                 860
Ala Thr Thr Gly Cys Cys Gly Cys Thr Gly Ala Thr Gly Cys Ala Gly
865                 870                 875                 880
Thr Thr Gly Cys Ala Ala Cys Ala Thr Gly Gly Cys Cys Ala Ala Gly
                885                 890                 895
Ala Ala Thr Ala Ala Thr Cys Thr Cys Ala Ala Thr Ala Ala Ala Thr
            900                 905                 910
Gly Thr Thr Cys Thr Ala Gly Ala Gly Ala Ala Gly Ala Ala Gly Ala
        915                 920                 925
Ala Ala Thr Cys Ala Thr Gly Ala
    930                 935
```

<210> SEQ ID NO 79
<211> LENGTH: 588
<212> TYPE: DNA
<213> ORGANISM: Xanthoriza simplicissima

<400> SEQUENCE: 79

```
atgaggatgg aagttgttct agttgttttc ttactgttca taggtactgt aaattgtgaa      60
agaatgatat tcagtgggcg tcctctcctc catcgcgtaa caaatgagga gactgtaatc     120
ctttatcatg agctggaagt acctgcttcg gtggatgaac tgtggagtgt cgaaggttcg     180
cctgagttgg gcaagaattt gcctgacctg ctccctggta tatttgcaga cttcaaaatt     240
actggtgacg gaggtgaagg ttccatcctg gatatgacat tccccccagg tcagtttcca     300
catcattaca gggagaagtt cgtgttttc gatcacaaga tcattacaa gttagtacaa       360
atgatcgacg gtgattttt cgatctaggt gttacatact atatggatac aatccgtgtt      420
gttgcaacag gccctgattc atgtgtcatc aagtcttcaa cggaatatca tgtaaaagtt     480
gagtttgcca agatcgtcaa accacttatt gacactgtac cactagctat aatgtctgaa     540
gcgattgcaa aggttgttct tgagaagaaa tacaagagat cagagtaa                 588
```

<210> SEQ ID NO 80
<211> LENGTH: 2103
<212> TYPE: DNA
<213> ORGANISM: Papaver somniferum

<400> SEQUENCE: 80

```
atgaggaaag taatcaaata cgatatggag gtagctgtct cagctgattc agtttgggca      60
gtttacagtt caccggatat tcctagactt ctcagagacg ttctacttcc cggtgtcttc     120
gagaagttag atgttattga agggaatggc ggcgtcggaa cagttcttga cattgttttc     180
cctccaggtg cggttcctcg aagttacaag gagaaatttg tcaatatcga tcgcgaaaag     240
cgattgaaag aagtgatcat gatcgaagga ggatacctgg acatgggatg cacattttac     300
ttggatagga tccatgtagt ggagaaaacc aagagctcat gcgttattga atcgtctatt     360
gtttacgatg tgaaagaaga gtgcgccgat gccatgtcta aattgatcac aactgaacca     420
ttgaagtcca tggcggaagt catttctaat tacgttattc agaaagaatc attttctgcc     480
agaaacattc taagcaagca atctgtagtg aagaaggaga ttcgatacga cctggaggta     540
```

| | |
|---|---|
| ccaatctcag ctgattctat ctggtcagtt tacagctgcc ctgatatccc tcggcttctt | 600 |
| agagatgttc tacttcctgg tgtgttcgag aaattggatg tcattgaagg ggatggtggt | 660 |
| gttgggactg ttcttgacat tgtcttccct ccaggtgcag ttcctcgaag ttacaaagag | 720 |
| aaattcgtta acattgaccg cgagaagcga ttgaaagagg ttatcatgat cgaaggagga | 780 |
| tacttggaca tgggatgcac gttttacttg gacaggatcc atgtagtgga gaaaagcctg | 840 |
| agctcgtgtg ttatcgaatc gtctattgtt tatgaagtaa agaagagta tgctgatgcc | 900 |
| atgtctaaat taatcacaac tgaaccattg aagtcgatgg cggaagtcat ctctaattac | 960 |
| gttatccaga gagaatcatt ttccgcaaga acattctca acaaaaattc tttggtgaag | 1020 |
| aaggagattc ggtatgacct ggaggttcca acctcagctg attctatctg gtcagtttac | 1080 |
| agctgcccgg atattcctcg gcttcttaga gatgttttac ttcccggtgt tttccagaaa | 1140 |
| ttggatgtta tcgaagggaa tggtggtgtt ggtacagttc ttgatatcgt ttttcctcca | 1200 |
| ggtgcggtac tcgtagtta caaggagaaa tttgtgaaca tcaaccacga aaagcgatta | 1260 |
| aaagaagtga ttatgatcga aggaggatat ttagacatgg gatgcacatc ttacctggac | 1320 |
| aggatccatg tagttgaaaa aacctctaaa tcttgtatca ttaaatcttc tgttgtctat | 1380 |
| gaagtgaagc aagagtgtgt tgaggcaatg tctaagttga tcacgacgga accattgaag | 1440 |
| tcgatggcag aagttatctc taattacgct atgaagcaac aatctgtttc tgagagaaac | 1500 |
| attcctaaga agcaatctct actgaggaag gaaattactt atgaaacgga ggtgcaaact | 1560 |
| tctgctgatt caatttggaa cgtctacagt tctcctgaca tccctcgact acttagagat | 1620 |
| gttctgcttc ctggtgtttt tgaaaagcta gatgtcattg caggcaatgg tggagttggt | 1680 |
| acggtactgg atattgcctt ccctctaggt gcagtgccac ggaggtacaa ggagaaattt | 1740 |
| gtgaagatca accatgagaa gcgattgaaa gaagtggtga tgatcgaagg aggatactta | 1800 |
| gacatggggt gcacatttta catggacagg atccatgtct ttgagaaaac cccaaactca | 1860 |
| tgtgttatcg aatcctcgat catttacgaa gttaaagaag agtatgctgg taaaatggct | 1920 |
| aagctaatca aactgaacc attggaatcc atggcagaag tcatctctgg ttatgttctt | 1980 |
| aagaaacgac tccaagtatt cggattcgag attaagccaa aattaagatt caatcttttg | 2040 |
| ctatgtttga ttatctgtct ggttatagct ggaggtatgt ttgttgctgg tgttccactc | 2100 |
| taa | 2103 |

<210> SEQ ID NO 81
<211> LENGTH: 582
<212> TYPE: DNA
<213> ORGANISM: Sanguineris canadensis

<400> SEQUENCE: 81

| | |
|---|---|
| atgaggaagg aactgacaca cgagatggag gtgcctgcct cagccgatgc tatttgggca | 60 |
| gtctacagtt cacatgatat tccaaggctg ctcaaagaag ttttgcttcc tggtgttttt | 120 |
| gaaaagctag atgtcattgc aggtgatggt ggtgttggta ctgttctcga cattgctttc | 180 |
| cctccagggg cggtaccgcg tcgttacaag gagaaattcg tgaagatcaa tcacgagaag | 240 |
| cgattgaagg aagtggagat gatcgaagga gggtatttgg atatggggtg tacattttat | 300 |
| atggacagga ttcatgtcgt agagaaaggt cctaattcat gcgttatcga atcggcgatt | 360 |
| atttacgtag tgaaggacga atgcgccgat gtcgtcgttc ctctaattac gactgaacca | 420 |
| ctggctagca tggcggaggt catctcaaat tacgttctaa ggaaacaaat ccgattgttt | 480 |
| ggatacgtaa ttaaaccaaa attagggtta agtattttgc tctccttgat tctctgccta | 540 |

```
gttatactag gagtgttatt gattggaggt gttccattct aa                             582
```

<210> SEQ ID NO 82
<211> LENGTH: 591
<212> TYPE: DNA
<213> ORGANISM: Nandina domestica

<400> SEQUENCE: 82

```
atgaggagtg gaattgtttt cctggttcta tttttcttag gatgtgaaat ttcgcaggga          60
agacaattac tggagtcgag actatttagg aagtctacaa tacgaaaagt gcttcaccat         120
gagttgccag tagctgcgtc ggcccaagaa gtgtgggacg tttatagctc gccggaattg         180
ccaaaacacc taccagaaat acttccaggc gcatttaaga agttgtagt  cactggagat         240
ggaggtgttg gtacggtaat tgaaatggta tttcctccag gagtagtacc gcaccgttac         300
aaggaaaagt ttgttctaat cgacgatgag aaattttta  agaaggttga aatgatcgaa         360
ggtggatatt tggacatggg atgtacgttt tacatggaca caatccaaat cgttccaaca         420
ggtcctgatt catgcataat caagtcctca actgagtact atgttaaacc tgaattcgcg         480
gataaggttg tacctttgat cagcactgtt ccgttgcaag ccatggctga agctattgcg         540
aaaatcgttc tagagttcaa agccaagcac aagggggttta tcgaaatata a                 591
```

<210> SEQ ID NO 83
<211> LENGTH: 963
<212> TYPE: DNA
<213> ORGANISM: Papaver bracteatum

<400> SEQUENCE: 83

```
atggatatca tagaagggga tggtggagtt ggtactgttc ttgatgttgt tttccaacct          60
ggtgcggtgc ctcaaagtta caaggagaga tttgagaccg tggaccacga gaagcgaata         120
ctggaagtga gaattatcca aggaggatac ttagaaatgg gttgcacatt ttacctgaat         180
aggatgcatg ttattgaaat aacctctaaa tcttgtgtta ttaaatcttc ggttatctac         240
gacgtgaaag aagagtgtgc tgatgcaatg tctaagttaa tcacaaccat acagttggag         300
tcaatggcca aagtggtcgc tgattatgtt cttaagaaac aatctgcttc tgacacaagc         360
attcctaaga agcagtctct aatgaggaaa gaaattacac atgagatgga ggtgcaaacc         420
tcagctgatt cgatttggga catctacagt tctcctgaca tccctcgact acttagagat         480
gtcctgcttc ctggtgcttt cgaaaagcta catgtcattc aaggcaatgg tggggttggt         540
actgtactgg acatcgctct ccctctaggt gcagtgccac gaaattacaa ggagaaattt         600
gtgaagatca accacgagaa gcgactaaaa gaagcagtta tgattgaagg gggatacgca         660
gacatggggt gcacatttta catgcacagg atccatgtcc tagagaaaac accaaagtcg         720
tgtgtcattg aatcctccat cgtttacgaa gtgaagaag  agtatgctga taaaatgtca         780
aagctaatca aacagaacc  attgcagtcc atggcagaag ccatatctag ttatgttctt         840
aagaaacagt tccaagtatt tggattagag gttaaaccga aattagtatt aagtctattt         900
ctatgtttga tcatcttttt ggctatagtt ggtggttttt tgattggagg tctaaaagca         960
taa                                                                       963
```

<210> SEQ ID NO 84
<211> LENGTH: 855
<212> TYPE: DNA
<213> ORGANISM: Eschscholzia californica

<400> SEQUENCE: 84

```
atgatcggag gattcttaga catgggatgt acattttaca tggacaggat tcatgtcata      60
gcgaaaggtc ctaattcatg tattatcaaa tcaactctta tctacgaagt gaaagaggaa     120
tatgccgatg ccatggcttc tctaatcacc atagaaccac tagctagcat ggcagaagtt     180
gttgcaaatt acgttcttca tcaacaagtc cgggtgttag gatccgtgaa gaggaaggaa     240
cttacgcatg agttggaagt tgctgcacca gctgatgcta tttggggtgt gtatagctca     300
cctgatattc cgaggcttct gagggatgtt ttgcttccgg gtgttttga aaagttagaa      360
gttatacaag gaaatggagg tgttggtact gttcttgaga ttgttttcca tccaggtgca     420
attccgcgta ggtacaagga gaagtttgtg acgataaatc acaagaagcg actgaaagag     480
gtggtcatga ttggagggta tctagacatg gggtgtacac tttatatgga caggattcat     540
gtagtatcca aaggtcctaa ttcatgtgtt atcaaatcga cactcattta tgaagttaaa     600
gcagaatcag cagatgccat ggcttctaca atcaccatcg acccactcgc tagcatggca     660
caggtcatct caaattacgt tctcaagaat caaatgcaag tcttaggatc tgttaagaga     720
agggaattaa cacatgagtt agaggtagct gcctcagctg acgctatttg gggagtttat     780
ggatcaaaaa gatattccaa ggcttctcag ggatgttttg cttcctggtg ttttcgaaaa     840
gttagaagtc attga                                                      855
```

<210> SEQ ID NO 85
<211> LENGTH: 798
<212> TYPE: DNA
<213> ORGANISM: Chelidonium majus

<400> SEQUENCE: 85

```
atgattgaag agggtatttt ggatatggga tgtacatttt acatggacag aatccatgtt      60
gtaaagaaag gtcccaattc atgcgttatt gcatcggcta ttatctacga ggtgaaggag     120
gaatttgtcg acgtcgtcgt tcctctaatc acgaccgaac cattggctag catggcagaa     180
gtcatctcaa attacgttct taagaaacaa cgtcgtgtaa ggaaggaact aacatatgag     240
atggaggtgc ctacctcagc tgattcaatt tgggcagtct acagttcaca tgatattcca     300
aggctcctca agaagttcct gctccctggt gtctttgaaa agcttgatgt cattgaaggt     360
gatggtggtg ttggtactgt tcttgacatt gctttcccac caggggcggt accacgcact     420
tacaaggaga aattcgtgaa gatcaatcac gagaagcgat tgaaagaggt ggtgatgatt     480
gaaggagggt atttggatat gggatgtaca ttttacatgg acagaatcca tgtgctagag     540
aaaagtccta actcgtgcgt tattgaatct tctattatct acgaggtgaa ggaggaattt     600
gccgatgtcg tgggtcctct aatcacgacc gagccactag ctagcatgtc agaggtcatc     660
tcaaattacg ttctaaagaa acaaatccgc atgtttggtt atgtaattaa accaaaactt     720
ggtttaagtc ttttgctctg cttcattctc tgcctcgttt tacttggagt tttattgatt     780
gggggtgttc cactctaa                                                   798
```

<210> SEQ ID NO 86
<211> LENGTH: 1107
<212> TYPE: DNA
<213> ORGANISM: Corydalis chelanthifolia

<400> SEQUENCE: 86

```
atgaggaagg aattaagaca tgaattggag gtggcaactt cagctgattc tatttgggca      60
gtctatggtt ccctgatat cccaagactt ctcagagatg tattgcttcc tggtgtcttt     120
```

-continued

```
gaaaaactag atgttattca aggcaatgga ggtgtgggta ctgttcttga cattgctttc      180
cctccagggg cggttccacg tacttacaag gagaagttcg taaaggtcga tcacaagaat      240
cgtttgaagg aagttgtaat gatcgaagga ggatatctgg acctaggatg tacattttat      300
atggatagaa tccatgtctt gcccagtgga cctaatacat gtataatcaa atctacactt      360
atttacgaag ttccagacga gctcgcctac tccgttgctt ctctaatctc tgttgaacca      420
ctagcaagca tggcagaagt catctcaggt tatgtgctca ggcagagaaa gatgacaaca      480
aacaaaatat tgaggaagga attgacaaca gagatggagg tgcccacttc agctgattca      540
atatgggcag tctatggttc ccctgatatt cctagactcc ttagagatgt attacttcct      600
ggagttttcg aaaggctgga tgtcattgaa ggcaatggag gtgtcggcac tgttcttgat      660
attagttttc caccaggggc ggtaccacgt agttacaagg agaagtttgt gaaggttgat      720
cacaagaacc gtctgaagga agttgtgatg atcgaaggag gatatctaga tctaggatgt      780
acattttata tggatagaat ccatgtaata ccaaaaggcc taattcatg cgtaatcaag       840 tcgaccctca tttatgaaat tcctggtgag cttgtggact ctgttggttc tcttatgtct      900
actgaaccac ttgcaagcat ggcagcagtc atctcggatt acgttctcaa acagagaaag      960
atgacagcaa accaaatatt gaggaaggaa ttgacaacag atggagtt ggctacttca       1020 gctgactcta tttggtcagt ttatggttcc cctgatattc ctagactcct cagagatgta     1080
ttacttcctg gagttttcga agactag                                          1107
```

<210> SEQ ID NO 87
<211> LENGTH: 648
<212> TYPE: DNA
<213> ORGANISM: Thalictrum flavum

<400> SEQUENCE: 87

```
atgaagatgg aagttgtatt tgttttcttt atgatcttag gaacaattaa ttgccagaaa       60
ctgattctga caggtaggcc atttcttaac cgccaaggca taataaacca agtgtctaca     120
gtgacaaaag gggttcatca tgagttggaa gttgctgctt cggctgatga tatatggagt     180
gtttatagct ggcctggttt ggcaaagcat cttcctgact tgctccctgg cgcttttgaa     240
aagctcgaaa tcattggtga tggaggtgtt ggtaccatcc tagacatgac atttacacca     300
ggtgaatttc ctcatgaata caaggagaaa tttattttag tcgataatga gcatcgttta     360
aagaaggtgc aaatgatcga gggaggttat ctggacttag gagtaacata ctacatggac     420
acaatccagg ttattccaac tggtacaaat tcgtgtgtca ttaaatcctc aactgagtac     480
catgtgaaac ctgagtttgt caaaatcgtt gaaccactta tcactactgg tccattagct     540 gccatggcg aagccatctc aaaacttgtt ttagaacaca aatacaaaag caactcagat     600
gagattgatg cctcaaaaaa caatctgaag atggtgatta atatgtaa                  648
```

<210> SEQ ID NO 88
<211> LENGTH: 1044
<212> TYPE: DNA
<213> ORGANISM: Corydalis chelanthifolia

<400> SEQUENCE: 88

```
atggaagtgg ctacttcagc tgattctata tgggcagtct acggttcccc tgacattcct       60
agactcctca gagatgtatt acttcctgga gttttgaga actgatgt cattgaaggc        120 agtggaggtg tcggcactgt tcttgatatt gcttttcctc aggggcggt acctcgtact      180
```

```
tacaaagaga agttcgtaaa ggttgatcac aagaaccgtt tgaaggaagt cgtgatgatt        240
gaaggcggat atctggactt aggatgtaca ttttatatgg atagaatcca tgtcttacca        300
aaaggtccta atacatgcgt aatcaaatcg actcttatct atgaagttcc agacgagttc        360
gctgatgcag ttggttctct tatctccgtt gaaccactag caagcatggc agaagtaata        420
tcaggttatg ttctcaagca gaagaaggaa gcaaagaaaa tattaaggaa ggaattaaca        480
cacgaattgg aggtgcctac ttcagctgat tcaatatggg cagtctatgg ttcccctgat        540
attccaagat tgctcagaga tgtattactt cctggtgtgt ttgaaaagct agacatcgtg        600
gaaggcaatg gaggtgttgg tactgttctt gacattgctt ttcctccagg ggcggtacct        660
cgtagttaca aggagaagtt tgtaaaggtt gatcacgata agcatttgaa agaagttgtg        720
atgatcgaag gaggatattt ggatctagga tgcacattct atatggatag aatccatgtc        780
ctaccgaaag gtcctaattc ttgtgttatc gaatcgtctc ttatttatga agtccgggaa        840
gagctcgctg atgtcgttgg ttctcttatc tcaattgaac cacttgctag catggcagaa        900
gtcatctcaa gttatgttct caaacaacaa ctccgagtgt ttggagttgt agttcaacca        960
agagtaggat taagtctttt gctctgcctt atactgtgtc tagtcatatt aggaggtctt       1020
ttgatcggcg gtgtttcgat ataa                                              1044

<210> SEQ ID NO 89
<211> LENGTH: 1056
<212> TYPE: DNA
<213> ORGANISM: Stylophorum diphyllum

<400> SEQUENCE: 89
atgaggaagg aagtacgata tgagatggag gtacctacct cagctgattc aatttgggca        60
gtttacagtt cacatgatat tccaaggctc ctcaaagaag ttcttctccc tggtgtcttt       120
gaaaagcttg atgtcattga aggtgatggt ggtgttggta ctgttcttga cattgctttc       180
ccaccagggg cggtaccacg cacttacaag gagaaatttg tgacaatcaa tcatgagaag       240
cgattgaaag aggtgattat gattgaagga gggtatttgg atatgggatg tacattttac       300
atggacagaa tccatgtcct agagaaaggt cccaaatcat gcattattgc atcggctatt       360
atctatgagg tgaaagaaga attcgccgat gtcgtcgttc ctctaatcac gactgaacca       420
ttggctagca tggcagaggt catctccaat tacgttctta agaaacaacg ccgtgtaagg       480
aaggaattaa catatgagat ggaggttcct acctcagctg attcaatttg gcagtttac         540 agttcacatg atattccaag gctcctcaaa gaagtcccttc tccctggtgt gtttgaagag       600
cttgatgtca ttgagggtga tggtggtgtt ggtactgttc ttgacattgc tttccctcca       660
ggtgcggtac cacgcactta caaggagaaa ttcgtgaaga tcaatcacga gaagcgattg       720
aaagaggtgg tgatgattga aggagggtat ttggatatgg atgtacatt ttacatggac        780 agaatccatg tcctagagaa aggtcctaat tcttgcgtta ttgaatctgc tattatctac       840
gaggtgaaag aagaatttgc tgatgtcgtc gttccactaa tcacgaccga accactagct       900
agcatggcag aggtcatctc aaattacgtt ctaaagaaac aaatccatgt gtttggctat       960
gtaattaaac caaacttggg attaagtctt ttgctctgct tcattctctg cctcgttta       1020 cttggagttt tattgattgg aggtgttcca ctctaa                                 1056

<210> SEQ ID NO 90
<211> LENGTH: 1599
<212> TYPE: DNA
<213> ORGANISM: Papaver bracteatum
```

<400> SEQUENCE: 90

```
atgatgagga aagtaatcaa atacgatatg gaggtagcta cctcagctga ttcagtatgg      60
gcagtttaca gttcaccgga tattccaagg cttctcaggg atgttctact cccggcgtc     120
ttcgagaaat tagacgtcat tgaagggaat ggcggcgtcg gtacagttct tgacattgct    180
tttcctccag gtgcggttcc tcgaagttac aaagagaaat tcgtcaacat cgaccgtgta    240
aagcgattga aagaagtgat catgattgaa ggaggatacc tggacatggg atgcacattt    300
tacctggaca ggatccatgt cgtggagaaa actccgagct catgtgttat tgaatcgtct    360
attgtttatg aagtggaaga agtacgct gatgtcatgt caaaattgat caccactgaa     420
ccattgaagt cgatggcgga agtgatttct aattacgtta ccagaaaga atcagtttcc    480
gcaagaaaca ttttcaacag gcaatctgta gtgaagaagg agattcatta cgacctggag   540
gtaccaacct cagctgattc gatctgggca gtttacagca atcccgatat ccctcgacta   600
cttagagatg ttctgcttcc tggcgttttc gagaaattgg atgtcattga agggaatggt   660
ggtgttggga ctgttcttga tatcgttttt cctccaggtg cggtgcctcg tcgttacaag   720
gagaaatttg tgaacatcaa ccacgagaag cgattaaaag aagtgattat gatcgaagga   780
gggtacttag acatgggatg cacattttac ctggacagga tccatgttgt agaaaaaacc   840
tctaaatctt gcatcattaa atcttctatt gtttatgaag tgaagcaaga gtgtgctgaa   900
gcaatatcta agttgatcac gacggagcca ttgaagtcga tggcagaagt catctctaat   960
tatgttctta agaaacaatc tgtttctgac acaaacattc taagaagca atctgtgttg  1020
aggaaagaaa ttacttatga aacggaggtg caaacgtcag ctgattcgat ttggaacgtc   1080
tacagttctc cagacatccc tcgactactt agagatgttc tgcttcctgg tgtttttgag   1140
aagctagatg tcattgcagg caatggtggc gttgggactg tactggatat cgctttccct   1200
ctaggtgcag tgccgcggag gtacaaggag agatttgtga aaatcaatca cgagaagcgg   1260
ttgaaagaag tggttatgat cgaaggaggg tacttggaca tgggctgcac attttacatg   1320
gacaggattc atgtctttga caaaacccca aactcatgtg tcattgaatc ctctattatc   1380
tacgaagtta agaagagta tgctgataaa atggctaagc taatcacaac agaaccattg   1440
gaatccatgg cagaagtcat ctctggttat gttcttaaga aacgactcca agtatttgga   1500
ttcgagattc agccaacatt aagattcaat cttttgctat gtttgattat ctgcttggtt   1560
atagctggag gtatgttgat tggacgtgtt ccactctaa                         1599
```

<210> SEQ ID NO 91
<211> LENGTH: 831
<212> TYPE: DNA
<213> ORGANISM: Papaver bracteatum

<400> SEQUENCE: 91

```
atgatcgaag gagggtatct ggacatggga tgcacgtttt atctggacag gatccatgta     60
gtggagaaaa ctccgagctc atgtgttatt gaatcgtcta ttgtttatga agtgaagcaa   120
gagtgtgctg aagcaatatc taagttgatc acgacggagc cattgaagtc gatggcagaa   180
gtcatctcta attatgttct taagaaacaa tctgtttctg acacaaacat tcctaagaag   240
caatctgtgt tgaggaaaga aattacttat gaaacggagg tgcaaacgtc agctgattcg   300
atttggaacg tctacagttc tccagacatc cctcgactac ttagagatgt tctgcttcct   360
ggtgtttttg agaagctaga tgtcattgca ggcaatggcg gcgttgggac tgtactggat   420
```

```
atcgctttcc ctctaggtgc agtgccgcgg aggtacaagg agagatttgt gaaaatcaat      480
cacgagaagc ggttgaaaga agtggttatg atcgaaggag ggtacttgga catgggctgc      540 acatttaca tggacaggat tcatgtcttt gacaaaaccc caaactcatg tgtcattgaa       600
tcctctatta tctacgaagt taaagaagag tatgctgata aaatggctaa gctaatcaca      660
acagaaccat tggaatccat ggcagaagtc atctctggtt atgttcttaa gaaacgactc     720
caagtatttg gattcgagat tcagccaaca ttaagattca atcttttgct atgtttgatt      780
atctgcttgg ttatagctgg aggtatgttg attggacgtg ttccactcta a               831
```

<210> SEQ ID NO 92
<211> LENGTH: 543
<212> TYPE: DNA
<213> ORGANISM: Corydalis chelanthifolia

<400> SEQUENCE: 92

```
atgaggaagg aactcacaaa tgagttggag gtcgcagccc ctgctgatgc tgtctgggca      60
gtttacagct ccccggatct cccaaaaatc atagttgaat acttcctag tgtcttcgaa      120 aagattgaaa tcgttgaagg agacggaggt gttggtaccg ttctgtacgt tgttttcct    180 ccaggatcag ttccattaac ttacaaggag aagttcgtga cgattgatca cgagaagcgt     240
ctgaaggagg tgctacagat tgaaggagga tatttggacc tagggtgtac gttttacatg     300
gacagcttcc atatactaga gaagattgt gattcatgca tcatcaaatc cataacagca      360
tacgaagtca gggatgatgt tgttgataat gtttcctctc ttatctccat tgattcgctc     420
gctaacatgc tgaagccat ctcaaagtat gtccttgaga acaagaagc cgcaactaag      480 catggacatg agatgatag ggaaaggact ggtctttgtt ggccttttcaa ttgtttgggt    540 taa                                                                   543
```

<210> SEQ ID NO 93
<211> LENGTH: 588
<212> TYPE: DNA
<213> ORGANISM: Xanthoriza simplicissima

<400> SEQUENCE: 93

```
atgaggatgg aagttgttct agttgttttc ttactgttca taggtactgt aaattgtgaa      60
agaatgatat tcagtgggcg tcctctcctc catcgcgtaa caaatgagga gactgtaatc      120
ctttatcatg agctggaagt acctgcttcg gtggatgaac tgtggagtgt cgaaggttcg     180
cctgagttgg gcaagaattt gcctgacttg ctccctggta tatttgcaga cttcaaaatt      240
actggtgacg gaggtgaagg ttccatcctg gatatgacat tccccccagg tcagtttcca     300
catcattaca gggagaagtt cgtgtttttc gatcacaaga tcattacaa gttagtacaa      360 atgatcgacg gtgattttt cgatctaggt gttacatact atatggatac aatccgtgtt     420
gttgcaacag gccctgattc atgtgtcatc aagtcttcaa cggaatatca tgtaaaagtt     480
gagtttgcca agatcgtcaa accacttatt gacactgtac cactagctat aatgtctgaa    540
gcgattgcaa aggttgttct tgagaagaaa tacaagagat cagagtaa                  588
```

<210> SEQ ID NO 94
<211> LENGTH: 1926
<212> TYPE: DNA
<213> ORGANISM: Papaver somniferum

<400> SEQUENCE: 94

```
atgaggaaag taatcaaata cgatatggag gtagctgtct cagctgattc agtttgggca      60
```

```
gtttacagtt caccggatat tcctagactt ctcagagacg ttctacttcc cggtgtcttc    120
gagaagttag atgttattga agggaatggc ggcgtcggaa cagttcttga cattgttttc    180
cctccaggtg cggttcctcg aagttacaag gagaaatttg tcaatatcga tcgcgaaaag    240
cgattgaaag aagtgatcat gatcgaagga ggatacctgg acatgggatg cacattttac    300
ttggatagga tccatgtagt ggagaaaacc aagagctcat gcgttattga atcgtctatt    360
gtttacgatg cgaaagaaga gtgcgccgat gccatgtcta aattgatcac aactgaacca    420
ttgaagtcca tggcggaagt catttctaat tacgttattc agaaagaatc attttctgcc    480
agaaacattc taagcaagca atctgtagtg aagaaggaga ttcgatacga cctggaggta    540
ccaatctcag ctgattctat ctggtcagtt tacagctgcc ctgatatccc tcggcttctt    600
agagatgttc tacttcctgg tgtgttcgag aaattggatg tcattgaagg ggatggtggt    660
gttgggactg ttcttgacat tgtcttccct ccaggtgcag ttcctcgaag ttacaaagag    720
aaattcgtta acattgaccg cgagaagcga ttgaaagagg ttatcatgat tgaaggagga    780
tacttggaca tgggatgcac gttttacttg gacaggatcc atgtagtgga gaaaagcctg    840
agctcgtgtg ttatcgaatc gtctattgtt tatgaagtaa aagaagagta tgttgatgcc    900
atgtctaaat taatcacaac tgaaccattg aagtcgatgg cggaagtcat ctctaattac    960
gttatccaga gagaatcatt ttccgcaaga aacattctca acaaaaattc tttggtgaag   1020
aaggagattc ggtatgacct ggaggttcca acctcagctg attctatctg gtcagtttac   1080
agctgcccgg atattcctcg gcttcttaga gatgttttac ttcccggtgt gttccagaaa   1140
ttggatgtta tcgaagggaa tggtggtgtt ggtacagttc ttgatatcgt ttttcctcca   1200
ggtgcggtac ctcgtagtta caaggagaaa tttgtgaaca tcaaccacga aaagcgatta   1260
aaagaagtga ttatgatcga aggaggatat ttagacatgg gatgcacatc ttacctggac   1320
aggatccatg tagttgaaaa aacctctaaa tcttgtatca ttaaatcttc tgttgtctat   1380
gaagtgaagc aagagtgtgt tgaggcaatg tctaagttga tcacgacgga accattgaag   1440
tcgatggcag aagttatctc taattacgct atgaagcaac aatctgtttc tgagagaaac   1500
attcctaaga agcaatctct actgaggaag gaaattactt atgaaacgga ggtgcaaact   1560
tctgctgatt caatttggaa cgtctacagt tctcctgaca tccctcgact acttagagat   1620
gttctgcttc ctggtgtttt tgaaaagcta gatgtcattg caggcaatgg tggagttggt   1680
acggtactgg atattgcctt ccctctaggt gcagtgcgac ggaggtacaa ggagaaattt   1740
gtgaagatca accatgagaa gcgattgaaa gaagtggtga tgatcgaagg aggatactta   1800
gacatggggt gcacatttta catggacagg atccatgtct ttgagaaaac cccaaactca   1860
tgtgttatcg aatcctcgat cattacgaag ttaaagaaga gtatgctggt aaaatggcta   1920
agctaa                                                               1926
```

<210> SEQ ID NO 95
<211> LENGTH: 2796
<212> TYPE: DNA
<213> ORGANISM: Micrococcus luteus tyo gene for tyramine oxidase

<400> SEQUENCE: 95

```
gcaccaccga gcgcgggaag gtcatcacca ggctgtgctg ggggccgtcg tagaccagct     60
cgtacgggcg gtaggccgcg tacaggccca gtccgccggg gcccagcacg cactcccgcc    120
cgtcctggca gcacgcgccc ggccctgcag ctgcaggctc agcttgaggt actccccgc     180
```

```
gtcccgggcc accatctcgg cggtgcgcac cacccggtgg gcgctggtgg tcatgtcgaa    240
gaggtggacg tcgtccagtt ccaccgtggt gagatccgca cggaactcgc tgtccacggg    300
agcggtgatc tccagggccg cgaaagaggc gttgatggtc tcgcgccact gcgcgagggt    360
gaggtccgcg cggcgcccgg cggcttcctg gcccgtcatg cgcgccccct ctccgatccg    420
cccgcggcac tgcgggcccg tgtccgcatg ctacgccgcc gcgggccgcg gctccgggcg    480
tcaccgggga acacccgca ccccctgccc ctagagtgtt ctcagaccgc gccgccgccc    540
gccctcgggt gcggctcccc gggcctgcac cgctgcggcc ccgacgtccg gaggaccacc    600
atgtacgccg atcggcgcgg agggcttctc cccgctggtg gtcgtgatgc ccgggatcat    660
catcggctcc ggcgtggtgg gcctgctgtg gggcgaggtg ctgcgccgca cccgcccgga    720
gatctacgcc gggatggacc acgtggacca gatccccgag tccccaggaga tccccgtggt    780 ccccgagcgc cgctgagccc accccgttcc cggacgacga cgccgcaccc ggcccacgga    840
cgccctgcac caccgtgcac cacccgccgg caccgggcgc ccgaggcgcg ctcggcaccc    900
gggtgaccgg gcggcgtcgt ccgcaccctg ttcgtcccga taacccgcaa ccccctggagg    960 tacccgtgag caacccgcat gtcgtgatcg tcggagccgg cttcgccggc ctggtggccg    1020
cccgtgaact gcagatggca ggcgtggacg tggagatcgt ggaggccgc gaccgcgtgg    1080 gcggccgcgc ctggaccgag gagcgcatgg gccgtcccct ggaactgggc gccacgtggg    1140
tgcactggat gcagccgcac gtgtggagcg agatcacccg ctacgaccag agcatctacc    1200
ccagcccgtt ctgcgacgac gcctactgga tcaccggggg ccgggtggag cacggcaccg    1260
aggcggacct ggatgccgct ctggcccgcc ccatggccaa gatcttcgag gactcgcggg    1320
agttcttccc gtacccgtac gagcccctgc acgtgctgga cgagagcagc ggcagcaccc    1380
ccgagctgcg ggacgcttc cgcgcggcgg accagggcag tgtcctggac tgcctcaagg    1440
gcggcgactt cacccaggag gagcgggacc tgtgcgacgc gtactggtcc gccgcgtaca    1500
tcggggaccc gcaccagggg tcaccgctca tggccaagca gtgggcggcg ctgtccgacc    1560
accggttgag cctggtggac gagcagaccc tgcgcttcaa gctcacccac ggcatgcggg    1620
gactgtacga gaacatcgcc gcggacctgc gctgccccat ccgcctgaac accccggtca    1680
cggcggtcga ccaccgctcc gacggcgcca cggtcaccct gggcaccggc gagaagatct    1740
cgtgcgacag cgtgatcgtc acggtgccgg tgggggcgct gccaaccatc gagttcaccc    1800
cgggcctgcc ctcggggatg cgcaccgtga tcgaccagcg ctggaactcc acgggctgca    1860
agatctgggt caaggtcaag ggccaccaca gcatcctggg ctacgccccc acccctcaca    1920
aggccgccgt gttccgcagc gagttcttca tggacgacga caccaccatc tgcgtgggct    1980
tcggctccca ccacgacgcc gtggacctca ccgaccgcg ggacgcccag gcaatcgtgg    2040
accagtggcg ccccgacctt gaggtcgtgg actgcacggg ccacgactgg gtggcggaca    2100
ggtggagcgg tcaggcgtgg gccacgctgc gctcagggca gttcaccaac ggctggcacc    2160
acttccgctc caccgactcg cggctgcgct tcgccggggc ggactgggcg cgcggctggc    2220
gcggcgtggt ggtggacggc gccatcgaga cgggcctgtc caccgcccgg acgtcctcc    2280 gggacatccg cgcctgagcc gcaccgcagg acgacgccgc tcgcgccctt ccggggcgg    2340 gcggcgtccg cgcgtgcgaa ccgtgccggg ccaccaggtg cgcccggtcc gtggccacgc    2400 ggcccctcggt gccgcggcac atgcggtgca cggtgccggt gtgcctgcgg cgcgcgggat    2460
gctccgcgcg gtgcgacacg gaggccgccg ggcggcgtcg tgcgccggca ctttcaggag    2520
gagctgagca cgcggcgtcg gtaggcggtg ggggattccc cgtactcggc cttgaaggcc    2580
```

```
ttgctcacgt gggcgggatc cgtgaggccg cgccgggcgc tgatggtgtg gacggtgtcg    2640
tcccggtggg ccgggtccgc gagctccgct cggatggcgg ccaggcgcac cgcgcgaatg    2700
tgggcggcca ccgtgaggtg ctgcgccgcg aaccggctgt gcagctgacg caccgacacg    2760
tacagggcgc gggcgatgga ccccggggag agctcc                              2796
```

<210> SEQ ID NO 96
<211> LENGTH: 443
<212> TYPE: PRT
<213> ORGANISM: Micrococcus luteus

<400> SEQUENCE: 96

```
Met Ser Asn Pro His Val Val Ile Val Gly Ala Gly Phe Ala Gly Leu
1               5                   10                  15

Val Ala Ala Arg Glu Leu Gln Met Ala Gly Val Asp Val Glu Ile Val
            20                  25                  30

Glu Ala Arg Asp Arg Val Gly Gly Arg Ala Trp Thr Glu Arg Met
        35                  40                  45

Gly Arg Pro Leu Glu Leu Gly Ala Thr Trp Val His Trp Met Gln Pro
    50                  55                  60

His Val Trp Ser Glu Ile Thr Arg Tyr Asp Gln Ser Ile Tyr Pro Ser
65                  70                  75                  80

Pro Phe Cys Asp Asp Ala Tyr Trp Ile Thr Gly Gly Arg Val Glu His
                85                  90                  95

Gly Thr Glu Ala Asp Leu Asp Ala Ala Leu Ala Arg Pro Met Ala Lys
            100                 105                 110

Ile Phe Glu Asp Ser Arg Glu Phe Phe Pro Tyr Pro Tyr Glu Pro Leu
        115                 120                 125

His Val Leu Asp Glu Ser Ser Gly Ser Thr Pro Glu Leu Arg Glu Arg
    130                 135                 140

Phe Arg Ala Ala Asp Gln Gly Ser Val Leu Asp Cys Leu Lys Gly Gly
145                 150                 155                 160

Asp Phe Thr Gln Glu Glu Arg Asp Leu Cys Asp Ala Tyr Trp Ser Ala
                165                 170                 175

Ala Tyr Ile Gly Asp Pro His Gln Gly Ser Pro Leu Met Ala Lys Gln
            180                 185                 190

Trp Ala Ala Leu Ser Asp His Arg Leu Ser Leu Val Asp Glu Gln Thr
        195                 200                 205

Leu Arg Phe Lys Leu Thr His Gly Met Arg Gly Leu Tyr Glu Asn Ile
    210                 215                 220

Ala Ala Asp Leu Arg Cys Pro Ile Arg Leu Asn Thr Pro Val Thr Ala
225                 230                 235                 240

Val Asp His Arg Ser Asp Gly Ala Thr Val Thr Leu Gly Thr Gly Glu
                245                 250                 255

Lys Ile Ser Cys Asp Ser Val Ile Val Thr Val Pro Val Gly Ala Leu
            260                 265                 270

Pro Thr Ile Glu Phe Thr Pro Gly Leu Pro Ser Gly Met Arg Thr Val
        275                 280                 285

Ile Asp Gln Arg Trp Asn Ser Thr Gly Cys Lys Ile Trp Val Lys Val
    290                 295                 300

Lys Gly His His Ser Ile Leu Gly Tyr Ala Pro Thr Pro His Lys Ala
305                 310                 315                 320

Ala Val Phe Arg Ser Glu Phe Phe Met Asp Asp Thr Thr Ile Cys
                325                 330                 335
```

```
Val Gly Phe Gly Ser His His Asp Ala Val Asp Leu Thr Asp Pro Arg
                340                 345                 350

Asp Ala Gln Ala Ile Val Asp Gln Trp Arg Pro Asp Leu Glu Val Val
            355                 360                 365

Asp Cys Thr Gly His Asp Trp Val Ala Asp Arg Trp Ser Gly Gln Ala
        370                 375                 380

Trp Ala Thr Leu Arg Ser Gly Gln Phe Thr Asn Gly Trp His His Phe
385                 390                 395                 400

Arg Ser Thr Asp Ser Arg Leu Arg Phe Ala Gly Ala Asp Trp Ala Arg
                405                 410                 415

Gly Trp Arg Gly Val Val Val Asp Gly Ala Ile Glu Thr Gly Leu Ser
            420                 425                 430

Thr Ala Arg Asp Val Leu Arg Asp Ile Arg Ala
        435                 440

<210> SEQ ID NO 97
<211> LENGTH: 1491
<212> TYPE: DNA
<213> ORGANISM: Artificial Sequence
<220> FEATURE:
<223> OTHER INFORMATION: Polyphenol oxidase with tyrosine hydroxylase
      activity oxidoreductase protein [Ralstonia solanacearum GMI1000]

<400> SEQUENCE: 97
tcaaatgacg gcgacctcga tcgattcggg cgtcacgccg ccgctgctct ccacggcaac      60
gccgggttgg ggtacggcca ccaggttgat cgaaaagttg tcgtcccgga tgttgagcgc     120
cttcagcgtg tcggtcaggt tcaccatggt cgacggcagg gcatggtggt cgtgtcccgc     180
cgcatgcgtc aggaagctga gcgaggtgac gaagtgcggg tcggtttccg gcacatcgag     240
gttggcgttc ggcaggttga cgaagacccg gatgctgatc acgttgtagg ggatcctgat     300
gttcttgatc agggccacga cttcggtggt actgccggta ccaacatcgg cacccagggc     360
acccgtcacg gtgccggcct cgaactggac ggcgctgttg agcggttcga ccgccgtggc     420
aaccggatgt tcccccttca gcacgctgcg cagccggata tgatcggcca gcttgacgct     480
gtcgccggtc ttgaacaggg ccagcagatg ctcggcacgg gcgttgttca ccaccttgtt     540
gtcggcgcgc ggcatgacgt catagcggta gcccagcgcc tcggtgctca gcagatcgct     600
cacgccttgc gtgtagtacc ggccctgcgg atcgatgtag ttgttgggga acttcatgcc     660
cagccacagc gggtcagtcg agttcttgcg gcccagcgcg ttccaggtgg cccatacccg     720
gtcgatattg ccgtggtgca tcatgaacac cgggtcgcgc ggcgaggcgg cggtgggcat     780
gaaggcgccg atgttgttgt ggacggtgtt gtgcggcgtg cgctccagga tgccctggtt     840
gccgcctccc atcggcaccc atttgggagtc gaggctgttc tgtaccagcg gcggccggac     900
cgagcggtcg accgaacggc tggtgccgaa gacttcgaag ttggtttcgg catagatctt     960
gtccatgacc tccttctggc cgacgatggc gtcggtgagc gctagggggc ggtcagctc    1020 attccggttg ggcacgtaga gcgggttcgt cttgccgttg taggtcttgg cggtgaaggc    1080
ttcgggcagc aggcggtctt cggtccagtt ccagtacggc atggcgaagg tcttgtagcc    1140
ggtgagcgcg gccacggcgc gctcgtacat cagcacgaag ccgcggtgcc agggcaggaa    1200
gtaccagtcg ccgtgcgggc agtacttgta gccgccgttg agcgtaccgt gctggttggc    1260
aaagccgagc cagctcagcg cctgcgtctg gtccttgcct ttcatgatgc cgacgaactc    1320
gcgataggcc gacaggtccg ggtcgtccat cttcatgcca tgcaggttgc gccgcacgcg    1380
```
cagcggggcg gcatcggccg caacagcgga gaggccggtc agcttgcccg cgaataccgt 1440
ggcgacactt gtcccggcga ttgccttcag caccgttcta cgcacgacca t 1491

<210> SEQ ID NO 98
<211> LENGTH: 496
<212> TYPE: PRT
<213> ORGANISM: Ralstonia solanacearum

<400> SEQUENCE: 98

Met Val Val Arg Arg Thr Val Leu Lys Ala Ile Ala Gly Thr Ser Val
1 5 10 15

Ala Thr Val Phe Ala Gly Lys Leu Thr Gly Leu Ser Ala Val Ala Ala
20 25 30

Asp Ala Ala Pro Leu Arg Val Arg Arg Asn Leu His Gly Met Lys Met
35 40 45

Asp Asp Pro Asp Leu Ser Ala Tyr Arg Glu Phe Val Gly Ile Met Lys
50 55 60

Gly Lys Asp Gln Thr Gln Ala Leu Ser Trp Leu Gly Phe Ala Asn Gln
65 70 75 80

His Gly Thr Leu Asn Gly Gly Tyr Lys Tyr Cys Pro His Gly Asp Trp
85 90 95

Tyr Phe Leu Pro Trp His Arg Gly Phe Val Leu Met Tyr Glu Arg Ala
100 105 110

Val Ala Ala Leu Thr Gly Tyr Lys Thr Phe Ala Met Pro Tyr Trp Asn
115 120 125

Trp Thr Glu Asp Arg Leu Leu Pro Glu Ala Phe Thr Ala Lys Thr Tyr
130 135 140

Asn Gly Lys Thr Asn Pro Leu Tyr Val Pro Asn Arg Asn Glu Leu Thr
145 150 155 160

Gly Pro Tyr Ala Leu Thr Asp Ala Ile Val Gly Gln Lys Glu Val Met
165 170 175

Asp Lys Ile Tyr Ala Glu Thr Asn Phe Glu Val Phe Gly Thr Ser Arg
180 185 190

Ser Val Asp Arg Ser Val Arg Pro Pro Leu Val Gln Asn Ser Leu Asp
195 200 205

Pro Lys Trp Val Pro Met Gly Gly Gly Asn Gln Gly Ile Leu Glu Arg
210 215 220

Thr Pro His Asn Thr Val His Asn Asn Ile Gly Ala Phe Met Pro Thr
225 230 235 240

Ala Ala Ser Pro Arg Asp Pro Val Phe Met Met His His Gly Asn Ile
245 250 255

Asp Arg Val Trp Ala Thr Trp Asn Ala Leu Gly Arg Lys Asn Ser Thr
260 265 270

Asp Pro Leu Trp Leu Gly Met Lys Phe Pro Asn Asn Tyr Ile Asp Pro
275 280 285

Gln Gly Arg Tyr Tyr Thr Gln Gly Val Ser Asp Leu Leu Ser Thr Glu
290 295 300

Ala Leu Gly Tyr Arg Tyr Asp Val Met Pro Arg Ala Asp Asn Lys Val
305 310 315 320

Val Asn Asn Ala Arg Ala Glu His Leu Leu Ala Leu Phe Lys Thr Gly
325 330 335

Asp Ser Val Lys Leu Ala Asp His Ile Arg Leu Arg Ser Val Leu Lys
340 345 350

Gly Glu His Pro Val Ala Thr Ala Val Glu Pro Leu Asn Ser Ala Val

```
              355                 360                 365
Gln Phe Glu Ala Gly Thr Val Thr Gly Ala Leu Gly Ala Asp Val Gly
    370                 375                 380

Thr Gly Ser Thr Thr Glu Val Val Ala Leu Ile Lys Asn Ile Arg Ile
385                 390                 395                 400

Pro Tyr Asn Val Ile Ser Ile Arg Val Phe Val Asn Leu Pro Asn Ala
                405                 410                 415

Asn Leu Asp Val Pro Glu Thr Asp Pro His Phe Val Thr Ser Leu Ser
            420                 425                 430

Phe Leu Thr His Ala Ala Gly His Asp His His Ala Leu Pro Ser Thr
        435                 440                 445

Met Val Asn Leu Thr Asp Thr Leu Lys Ala Leu Asn Ile Arg Asp Asp
    450                 455                 460

Asn Phe Ser Ile Asn Leu Val Ala Val Pro Gln Pro Gly Val Ala Val
465                 470                 475                 480

Glu Ser Ser Gly Gly Val Thr Pro Glu Ser Ile Glu Val Ala Val Ile
                485                 490                 495

<210> SEQ ID NO 99
<211> LENGTH: 1413
<212> TYPE: DNA
<213> ORGANISM: Pseudomonas putida KT2440 DOPA decarboxylase gene

<400> SEQUENCE: 99 gtgaccccccg aacaattccg ccagtacggc caccaactga tcgacctgat tgccgactac        60
cgccagaccg tgggcgaacg cccggtcatg gcccaggtcg aacctggcta tctcaaggcc       120
gccttgcccg caactgcccc tcaacaaggc gaacctttcg cggccattct cgacgacgtc       180
aataacctgg tcatgcccgg cctgtcccat tggcagcacc cggacttcta tggctatttc       240
ccttccaatg gcaccctgtc ctcggtgctg ggggacttcc tcagtaccgg tctgggcgtg       300
ctgggcctgt cctggcaatc cagcccggcc ctgagcgaac tggaagaaac caccctcgac       360
tggctgcgcc agttgcttgg cctgtctggc cagtggagtg gggtgatcca ggacactgcc       420
tcgaccagca ccctggtggc gctgatcagt gcccgtgaac gcgccactga ctacgccctg       480
gtacgtggtg gcctgcaggc cgagcccaag cctttgatcg tgtatgtcag cgcccacgcc       540
cacagctcgg tggacaaggc tgcactgctg gcaggttttg gccgcgacaa tatccgcctg       600
attcccaccg acgaacgcta cgccctgcgc ccagaggcac tgcaggcggc gatcgaacag       660
gacctggctg ccggcaacca gccgtgcgcc gtggttgcca ccaccggcac cacgacgacc       720
actgccctcg acccgctgcg cccggtcggt gaaatcgccc aggccaatgg gctgtggttg       780
cacgttgact cggccatggc cggttcggcg atgatcctgc ccgagtgccg ctggatgtgg       840
gacggcatcg agctggccga ttcggtggtg gtcaacgcgc acaaatggct gggtgtggcc       900
ttcgattgct cgatctacta cgtgcgcgat ccgcaacacc tgatccgggt gatgagcacc       960
aatcccagct acctgcagtc ggcggtggat ggcgaggtga agaacctgcg cgactggggg      1020
ataccgctgg gccgtcggtt ccgtgcgttg aagctgtggt tcatgttgcg cagcgagggt      1080
gtcgacgcat gcaggcgcg gctgcggcgt gacctggaca atgcccagtg gctggcgggg      1140
caggtcgagg cggcggcgga gtgggaagtg ttggcgccag tacagctgca aaccttgtgc      1200
attcgccatc gaccggcggg gcttgaaggg gaggcgctgg atgcgcatac caagggctgg      1260
gccgagcggg tgaatgcatc cggcgctgct tatgtgacgc cggctacact ggacgggcgg      1320
tggatggtgc gggtttcgat tggtgcgctg ccgaccgagc gggggggatgt gcagcggctg      1380
```
tgggcacgtc tgcaggacgt gatcaagggc tga                                         1413

<210> SEQ ID NO 100
<211> LENGTH: 470
<212> TYPE: PRT
<213> ORGANISM: Pseudomanas putida

<400> SEQUENCE: 100

Met Thr Pro Glu Gln Phe Arg Gln Tyr Gly His Gln Leu Ile Asp Leu
1               5                   10                  15

Ile Ala Asp Tyr Arg Gln Thr Val Gly Glu Arg Pro Val Met Ala Gln
            20                  25                  30

Val Glu Pro Gly Tyr Leu Lys Ala Ala Leu Pro Ala Thr Ala Pro Gln
        35                  40                  45

Gln Gly Glu Pro Phe Ala Ala Ile Leu Asp Asp Val Asn Asn Leu Val
    50                  55                  60

Met Pro Gly Leu Ser His Trp Gln His Pro Asp Phe Tyr Gly Tyr Phe
65                  70                  75                  80

Pro Ser Asn Gly Thr Leu Ser Ser Val Leu Gly Asp Phe Leu Ser Thr
                85                  90                  95

Gly Leu Gly Val Leu Gly Leu Ser Trp Gln Ser Ser Pro Ala Leu Ser
            100                 105                 110

Glu Leu Glu Glu Thr Thr Leu Asp Trp Leu Arg Gln Leu Leu Gly Leu
        115                 120                 125

Ser Gly Gln Trp Ser Gly Val Ile Gln Asp Thr Ala Ser Thr Ser Thr
    130                 135                 140

Leu Val Ala Leu Ile Ser Ala Arg Glu Arg Ala Thr Asp Tyr Ala Leu
145                 150                 155                 160

Val Arg Gly Gly Leu Gln Ala Glu Pro Lys Pro Leu Ile Val Tyr Val
                165                 170                 175

Ser Ala His Ala His Ser Ser Val Asp Lys Ala Ala Leu Leu Ala Gly
            180                 185                 190

Phe Gly Arg Asp Asn Ile Arg Leu Ile Pro Thr Asp Glu Arg Tyr Ala
        195                 200                 205

Leu Arg Pro Glu Ala Leu Gln Ala Ala Ile Glu Gln Asp Leu Ala Ala
    210                 215                 220

Gly Asn Gln Pro Cys Ala Val Val Ala Thr Thr Gly Thr Thr Thr Thr
225                 230                 235                 240

Thr Ala Leu Asp Pro Leu Arg Pro Val Gly Glu Ile Ala Gln Ala Asn
                245                 250                 255

Gly Leu Trp Leu His Val Asp Ser Ala Met Ala Gly Ser Ala Met Ile
            260                 265                 270

Leu Pro Glu Cys Arg Trp Met Trp Asp Gly Ile Glu Leu Ala Asp Ser
        275                 280                 285

Val Val Val Asn Ala His Lys Trp Leu Gly Val Ala Phe Asp Cys Ser
    290                 295                 300

Ile Tyr Tyr Val Arg Asp Pro Gln His Leu Ile Arg Val Met Ser Thr
305                 310                 315                 320

Asn Pro Ser Tyr Leu Gln Ser Ala Val Asp Gly Glu Val Lys Asn Leu
                325                 330                 335

Arg Asp Trp Gly Ile Pro Leu Gly Arg Arg Phe Arg Ala Leu Lys Leu
            340                 345                 350

Trp Phe Met Leu Arg Ser Glu Gly Val Asp Ala Leu Gln Ala Arg Leu
        355                 360                 365

```
Arg Arg Asp Leu Asp Asn Ala Gln Trp Leu Ala Gly Gln Val Glu Ala
            370                 375                 380

Ala Ala Glu Trp Glu Val Leu Ala Pro Val Gln Leu Gln Thr Leu Cys
385                 390                 395                 400

Ile Arg His Arg Pro Ala Gly Leu Glu Gly Glu Ala Leu Asp Ala His
            405                 410                 415

Thr Lys Gly Trp Ala Glu Arg Leu Asn Ala Ser Gly Ala Ala Tyr Val
            420                 425                 430

Thr Pro Ala Thr Leu Asp Gly Arg Trp Met Val Arg Val Ser Ile Gly
            435                 440                 445

Ala Leu Pro Thr Glu Arg Gly Asp Val Gln Arg Leu Trp Ala Arg Leu
            450                 455                 460

Gln Asp Val Ile Lys Gly
465                 470

<210> SEQ ID NO 101
<211> LENGTH: 1875
<212> TYPE: DNA
<213> ORGANISM: Papaver somniferum clone TYDC2 tyrosine/dopa
      decarboxylase mRNA

<400> SEQUENCE: 101
```

| | | | | | |
|---|---|---|---|---|---|
| aacaagtatc | agtacttgct | ccaaggctgt | gcttgttctc | attcttcttc | ctcttaggca | 60 |
| tccaacaaaa | cccattcgtt | ctcttgcaaa | ccaataacct | tctttcacct | gaaaaccacc | 120 |
| tctctttttc | tatctcgaaa | tgggtagtct | taacactgaa | gatgttcttg | aaaacagttc | 180 |
| agctttcggt | gtaacaaatc | cattagaccc | agaagaattc | aggagacaag | gtcatatgat | 240 |
| aatcgacttc | ttagctgatt | attatagaga | tgtcgaaaag | tatccagttc | gaagtcaagt | 300 |
| agaacctggt | tatctacgta | aacgattacc | tgaaacagct | ccctacaatc | agaatcaat | 360 |
| cgaaacaatt | cttcaagatg | tgacaactga | gattatccca | ggattaacac | attggcaaag | 420 |
| tcctaattac | tatgcttatt | ttccttcgag | tggttccgtt | gctggattcc | tcggtgaaat | 480 |
| gcttagtact | ggttttaatg | ttgttggttt | taactggatg | tcttcacctg | ctgctacaga | 540 |
| actcgaaagt | gttgttatgg | attggttcgg | gaaaatgctt | aaccttccag | aatcattctt | 600 |
| gttctctggt | agtggtggtg | gagttttgca | gggaactagt | tgtgaagcaa | tcttatgtac | 660 |
| attaacagct | gcaagggaca | gaaagttaaa | caaaattggt | cgtgaacata | tcggaaggtt | 720 |
| agttgtttat | ggatctgatc | aaacgcactg | tgcactacaa | aaagctgctc | aggtcgcagg | 780 |
| aattaaccca | agaacttcc | gtgctattaa | aacgtttaaa | gaaaactcat | tcggattatc | 840 |
| agctgctacc | ctaagagaag | taattcttga | agacattgaa | gccgggttga | tccctctttt | 900 |
| tgtatgtccc | acggttggaa | ctacatcatc | tactgcagtg | gatcctatca | gtcctatctg | 960 |
| tgaagtggca | aaggaatacg | aaatgtgggt | tcacgtagac | gcagcttacg | ctggaagtgc | 1020 |
| atgtatctgc | cctgagttta | gacacttcat | cgatggagtt | gaggaagctg | attcattcag | 1080 |
| tctcaatgca | cataaatggt | ttttcacaac | tttggattgt | tgctgcctct | gggttaaaga | 1140 |
| tccaagtgcc | cttgttaaag | ctctttccac | aaatcctgaa | tacttgagaa | acaaagctac | 1200 |
| ggagtcaaga | caagttgttg | actacaaaga | ctggcaaatc | gcactcagtc | gccgattccg | 1260 |
| atccttgaaa | ctttggatgg | tcttacgtag | ctatggtgta | actaatttga | gaaatttctt | 1320 |
| aaggagtcat | gttaaaatgg | ctaagacatt | cgagggtctt | attttgtatg | gatgggagatt | 1380 |
| cgaaattact | gtgcctagga | cttttgccat | ggtttgcttt | cgactttac | cgccaaaaac | 1440 |

-continued

```
cataaaggta tacgacaatg gggttcacca gaatggaaac ggggtcgttc cactacgtga    1500
tgaaaatgaa aatttagtgc ttgctaataa gcttaatcag gtttatttgg agacagtcaa    1560
tgcaacggga agtgtttaca tgactcatgc cgttgttggc ggtgtctaca tgattcggtt    1620
tgcagttggt tcaaccctaa cagaggaacg ccatgttatt tatgcatgga agattttgca    1680
agagcatgca gatctgattc ttggtaagtt cagtgaagca gatttttcaa gttagtaata    1740
ttcacatatt ttgtgatatc agatcagatg catttgatga tgaatggtgg gcagttgaga    1800
tttaataaaa tcattccggg tcatccataa tgctggaata agatgaaaaa acaaaaaac     1860 agaataaaat gaatc                                                     1875
```

<210> SEQ ID NO 102
<211> LENGTH: 531
<212> TYPE: PRT
<213> ORGANISM: Papaver somniferum

<400> SEQUENCE: 102

```
Met Gly Ser Leu Asn Thr Glu Asp Val Leu Glu Asn Ser Ser Ala Phe
1               5                   10                  15

Gly Val Thr Asn Pro Leu Asp Pro Glu Glu Phe Arg Arg Gln Gly His
            20                  25                  30

Met Ile Ile Asp Phe Leu Ala Asp Tyr Tyr Arg Asp Val Glu Lys Tyr
        35                  40                  45

Pro Val Arg Ser Gln Val Glu Pro Gly Tyr Leu Arg Lys Arg Leu Pro
    50                  55                  60

Glu Thr Ala Pro Tyr Asn Pro Glu Ser Ile Glu Thr Ile Leu Gln Asp
65                  70                  75                  80

Val Thr Thr Glu Ile Ile Pro Gly Leu Thr His Trp Gln Ser Pro Asn
                85                  90                  95

Tyr Tyr Ala Tyr Phe Pro Ser Ser Gly Ser Val Ala Gly Phe Leu Gly
            100                 105                 110

Glu Met Leu Ser Thr Gly Phe Asn Val Val Gly Phe Asn Trp Met Ser
        115                 120                 125

Ser Pro Ala Ala Thr Glu Leu Glu Ser Val Val Met Asp Trp Phe Gly
    130                 135                 140

Lys Met Leu Asn Leu Pro Glu Ser Phe Leu Phe Ser Gly Ser Gly Gly
145                 150                 155                 160

Gly Val Leu Gln Gly Thr Ser Cys Glu Ala Ile Leu Cys Thr Leu Thr
                165                 170                 175

Ala Ala Arg Asp Arg Lys Leu Asn Lys Ile Gly Arg Glu His Ile Gly
            180                 185                 190

Arg Leu Val Val Tyr Gly Ser Asp Gln Thr His Cys Ala Leu Gln Lys
        195                 200                 205

Ala Ala Gln Val Ala Gly Ile Asn Pro Lys Asn Phe Arg Ala Ile Lys
    210                 215                 220

Thr Phe Lys Glu Asn Ser Phe Gly Leu Ser Ala Ala Thr Leu Arg Glu
225                 230                 235                 240

Val Ile Leu Glu Asp Ile Glu Ala Gly Leu Ile Pro Leu Phe Val Cys
                245                 250                 255

Pro Thr Val Gly Thr Thr Ser Ser Thr Ala Val Asp Pro Ile Ser Pro
            260                 265                 270

Ile Cys Glu Val Ala Lys Glu Tyr Glu Met Trp Val His Val Asp Ala
        275                 280                 285

Ala Tyr Ala Gly Ser Ala Cys Ile Cys Pro Glu Phe Arg His Phe Ile
```

| | | | | | | | | | | | | |
|---|---|---|---|---|---|---|---|---|---|---|---|---|
| | | 290 | | | | 295 | | | | 300 | | |
| Asp | Gly | Val | Glu | Glu | Ala | Asp | Ser | Phe | Ser | Leu | Asn | Ala | His | Lys | Trp |
| 305 | | | | 310 | | | | 315 | | | | 320 |

Asp Gly Val Glu Glu Ala Asp Ser Phe Ser Leu Asn Ala His Lys Trp
305                 310                 315                 320

Phe Phe Thr Thr Leu Asp Cys Cys Cys Leu Trp Val Lys Asp Pro Ser
            325                 330                 335

Ala Leu Val Lys Ala Leu Ser Thr Asn Pro Glu Tyr Leu Arg Asn Lys
            340                 345                 350

Ala Thr Glu Ser Arg Gln Val Val Asp Tyr Lys Asp Trp Gln Ile Ala
        355                 360                 365

Leu Ser Arg Arg Phe Arg Ser Leu Lys Leu Trp Met Val Leu Arg Ser
    370                 375                 380

Tyr Gly Val Thr Asn Leu Arg Asn Phe Leu Arg Ser His Val Lys Met
385                 390                 395                 400

Ala Lys Thr Phe Glu Gly Leu Ile Cys Met Asp Gly Arg Phe Glu Ile
            405                 410                 415

Thr Val Pro Arg Thr Phe Ala Met Val Cys Phe Arg Leu Leu Pro Pro
            420                 425                 430

Lys Thr Ile Lys Val Tyr Asp Asn Gly Val His Gln Asn Gly Asn Gly
        435                 440                 445

Val Val Pro Leu Arg Asp Glu Asn Glu Asn Leu Val Leu Ala Asn Lys
    450                 455                 460

Leu Asn Gln Val Tyr Leu Glu Thr Val Asn Ala Thr Gly Ser Val Tyr
465                 470                 475                 480

Met Thr His Ala Val Gly Gly Val Tyr Met Ile Arg Phe Ala Val
            485                 490                 495

Gly Ser Thr Leu Thr Glu Glu Arg His Val Ile Tyr Ala Trp Lys Ile
            500                 505                 510

Leu Gln Glu His Ala Asp Leu Ile Leu Gly Lys Phe Ser Glu Ala Asp
        515                 520                 525

Phe Ser Ser
    530

<210> SEQ ID NO 103
<211> LENGTH: 969
<212> TYPE: DNA
<213> ORGANISM: Corydalis chelanthifolia

<400> SEQUENCE: 103

```
gtattacttc ctggagtttt tgagaaactg gatgtcattg aaggcagtgg aggtgtcggc      60
actgttcttg atattgcttt tcctccaggg gcggtacctc gtacttacaa agagaagttc     120
gtaaaggttg atcacaagaa ccgtttgaag gaagtcgtga tgattgaagg cggatatctg     180
gacttaggat gtacatttta tatggataga atccatgtct taccaaaagg tcctaataca     240
tgcgtaatca aatcgactct tatctatgaa gttccagacg agttcgctga tgcagttggt     300
tctcttatct ccgttgaacc actagcaagc atggcagaag taatatcagg ttatgttctc     360
aagcagaaga aggaagcaaa gaaaatatta aggaaggaat taacacacga attggaggtg     420
cctacttcag ctgattcaat atgggcagtc tatggttccc ctgatattcc aagattgctc     480
agagatgtat tacttcctgg tgtgtttgaa aagctagaca tcgtggaagg caatggaggt     540
gttggtactg ttcttgacat tgcttttcct ccagggcggt acctcgtagt tacaaggag      600
aagtttgtaa aggttgatca cgataagcat tgaaagaag ttgtgatgat cgaaggagga     660
tatttggatc taggatgcac attctatatg gatagaatcc atgtcctacc gaaaggtcct     720
```

```
aattcttgtg ttatcgaatc gtctcttatt tatgaagtcc gggaagagct cgctgatgtc    780
gttggttctc ttatctcaat tgaaccactt gctagcatgg cagaagtcat ctcaagttat    840
gttctcaaac aacaactccg agtgtttgga gttgtagttc aaccaagagt aggattaagt    900
cttttgctct gccttatact gtgtctagtc atattaggag gtcttttgat cggcggtgtt    960
tcgatataa                                                            969

<210> SEQ ID NO 104
<211> LENGTH: 468
<212> TYPE: DNA
<213> ORGANISM: Corydalis chelanthifolia

<400> SEQUENCE: 104
gatctcccaa aaatcatagt tgaattactt cctagtgtct tcgaaaagat tgaaatcgtt     60
gaaggagacg gaggtgttgg taccgttctg tacgttgttt ttcctccagg atcagttcca    120
ttaacttaca aggagaagtt cgtgacgatt gatcacgaga agcgtctgaa ggaggtgcta    180
cagattgaag gaggatattt ggacctaggg tgtacgtttt acatggacag cttccatata    240
ctagagaaag attgtgattc atgcatcatc aaatccataa cagcatacga agtcagggat    300
gatgttgttg ataatgtttc ctctcttatc tccattgatt cgctcgctaa catggctgaa    360
gccatctcaa agtatgtcct tgagaaacaa gaagccgcaa ctaagcatgg acatggagat    420
gatagggaaa ggactggtct tgttggcct ttcaattgtt tgggttaa                  468

<210> SEQ ID NO 105
<211> LENGTH: 723
<212> TYPE: DNA
<213> ORGANISM: Chelidonium majus

<400> SEQUENCE: 105
aattcatgcg ttattgcatc ggctattatc tacgaggtga aggaggaatt tgtcgacgtc     60
gtcgttcctc taatcacgac cgaaccattg gctagcatgg cagaagtcat ctcaaattac    120
gttcttaaga acaacgtcg tgtaaggaag gaactaacat atgagatgga ggtgcctacc    180
tcagctgatt caatttgggc agtctacagt tcacatgata ttccaaggct cctcaaagaa    240
gttctgctcc ctggtgtctt tgaaaagctt gatgtcattg aaggtgatgg tggtgttggt    300
actgttcttg acattgcttt cccaccaggg gcggtaccac gcacttacaa ggagaaattc    360
gtgaagatca atcacgagaa gcgattgaaa gaggtggtga tgattgaagg agggtatttg    420
gatatgggat gtacatttta catggacaga atccatgtgc tagagaaaag tcctaactcg    480
tgcgttattg aatcttctat tatctacgag gtgaaggagg aatttgccga tgtcgtgggt    540
cctctaatca cgaccgagcc actagctagc atgtcagagg tcatctcaaa ttacgttcta    600
aagaaacaaa tccgcatgtt tggttatgta attaaaccaa acttggtttt aagtcttttg    660
ctctgcttca ttctctgcct cgttttactt ggagttttat tgattggggg tgttccactc    720
taa                                                                  723

<210> SEQ ID NO 106
<211> LENGTH: 780
<212> TYPE: DNA
<213> ORGANISM: Eschscholzia californica

<400> SEQUENCE: 106
tcatgtatta tcaaatcaac tcttatctac gaagtgaaag aggaatatgc cgatgccatg     60
gcttctctaa tcaccataga accactagct agcatggcag aagttgttgc aaaattacgtt    120
```

```
cttcatcaac aagtccgggt gttaggatcc gtgaagagga aggaacttac gcatgagttg      180
gaagttgctg caccagctga tgctatttgg ggtgtgtata gctcacctga tattccgagg      240
cttctgaggg atgttttgct tccgggtgtt tttgaaaagt tagaagttat acaaggaaat      300
ggaggtgttg gtactgttct tgagattgtt ttccatccag gtgcaattcc gcgtaggtac      360
aaggagaagt tgtgacgat aaatcacaag aagcgactga agaggtggt catgattgga       420 gggtatctag acatggggtg tacactttat atggacagga ttcatgtagt atccaaaggt     480
cctaattcat gtgttatcaa atcgacactc atttatgaag ttaaagcaga atcagcagat     540
gccatggctt ctacaatcac catcgaccca ctcgctagca tggcacaggt catctcaaat     600
tacgttctca agaatcaaat gcaagtctta ggatctgtta agagaaggga attaacacat     660
gagttagagg tagctgcctc agctgacgct atttggggag tttatggatc aaaaagatat     720
tccaaggctt ctcagggatg ttttgcttcc tggtgttttc gaaaagttag aagtcattga     780

<210> SEQ ID NO 107
<211> LENGTH: 888
<212> TYPE: DNA
<213> ORGANISM: Papaver bracteatum

<400> SEQUENCE: 107
agttacaagg agagatttga gaccgtggac cacgagaagc gaatactgga agtgagaatt       60
atccaaggag gatacttaga aatgggttgc acattttacc tgaataggat gcatgttatt      120
gaataaccct ctaaatcttg tgttattaaa tcttcggtta tctacgacgt gaaagaagag      180
tgtgctgatg caatgtctaa gttaatcaca accatacagt tggagtcaat ggccaaagtg      240
gtcgctgatt atgttcttaa gaaacaatct gcttctgaca caagcattcc taagaagcag      300
tctctaatga ggaaagaaat tacacatgag atggaggtgc aaacctcagc tgattcgatt      360
tgggacatct acagttctcc tgacatccct cgactactta gagatgtcct gcttcctggt      420
gctttcgaaa agctacatgt cattcaaggc aatggtgggg ttggtactgt actggacatc      480
gctctccctc taggtgcagt gccacgaaat tacaaggaga aatttgtgaa gatcaaccac      540
gagaagcgac taaagaagc agttatgatt gaagggggat acgcagacat ggggtgcaca     600
ttttacatgc acaggatcca tgtcctagag aaaacaccaa agtcgtgtgt cattgaatcc      660
tccatcgttt acgaagtgaa agaagagtat gctgataaaa tgtcaaagct aatcacaaca      720
gaaccattgc agtccatggc agaagccata tctagttatg ttcttaagaa acagttccaa      780
gtatttggat tagaggttaa accgaaatta gtattaagtc tatttctatg tttgatcatc      840
tttttggcta tagttggtgg ttttttgatt ggaggtctaa aagcataa                  888

<210> SEQ ID NO 108
<211> LENGTH: 756
<212> TYPE: DNA
<213> ORGANISM: Papaver bracteatum

<400> SEQUENCE: 108
agctcatgtg ttattgaatc gtctattgtt tatgaagtga agcaagagtg tgctgaagca       60
atatctaagt tgatcacgac ggagccattg aagtcgatgg cagaagtcat ctctaattat      120
gttcttaaga aacaatctgt ttctgacaca acattcctta gaagcaatc tgtgttgagg       180 aaagaaatta cttatgaaac ggaggtgcaa acgtcagctg attcgatttg gaacgtctac      240
agttctccag acatccctcg actacttaga gatgttctgc ttcctggtgt ttttgagaag      300
```

```
ctagatgtca ttgcaggcaa tggcggcgtt gggactgtac tggatatcgc tttccctcta    360
ggtgcagtgc cgcggaggta caaggagaga tttgtgaaaa tcaatcacga gaagcggttg    420
aaagaagtgg ttatgatcga aggagggtac ttggacatgg gctgcacatt ttacatggac    480
aggattcatg tctttgacaa aaccccaaac tcatgtgtca ttgaatcctc tattatctac    540
gaagttaaag aagagtatgc tgataaaatg gctaagctaa tcacaacaga accattggaa    600
tccatggcag aagtcatctc tggttatgtt cttaagaaac gactccaagt atttggattc    660
gagattcagc caacattaag attcaatctt ttgctatgtt tgattatctg cttggttata    720
gctggaggta tgttgattgg acgtgttcca ctctaa                              756

<210> SEQ ID NO 109
<211> LENGTH: 573
<212> TYPE: DNA
<213> ORGANISM: Thalictrum flavum

<400> SEQUENCE: 109
aggccatttc ttaaccgcca aggcataata aaccaagtgt ctacagtgac aaaaggggtt     60
catcatgagt tggaagttgc tgcttcggct gatgatatat ggagtgttta tagctggcct    120
ggtttggcaa agcatcttcc tgacttgctc cctggcgctt ttgaaaagct cgaaatcatt    180
ggtgatggag gtgttggtac catcctagac atgacattta caccaggtga atttcctcat    240
gaatacaagg agaaatttat tttagtcgat aatgagcatc gtttaaagaa ggtgcaaatg    300
atcgagggag gttatctgga cttaggagta acatactaca tggacacaat ccaggttatt    360
ccaactggta caaattcgtg tgtcattaaa tcctcaactg agtaccatgt gaaacctgag    420
tttgtcaaaa tcgttgaacc acttatcact actggtccat agctgccat ggcggaagcc     480 atctcaaaac ttgttttaga acacaaatac aaaagcaact cagatgagat tgatgcctca    540
aaaaacaatc tgaagatggt gattaatatg taa                                573

<210> SEQ ID NO 110
<211> LENGTH: 498
<212> TYPE: DNA
<213> ORGANISM: Xanthoriza simplicissima

<400> SEQUENCE: 110
catcgcgtaa caaatgagga gactgtaatc ctttatcatg agctggaagt acctgcttcg     60
gtggatgaac tgtggagtgt cgaaggttcg cctgagttgg gcaagaattt gcctgacttg    120
ctccctggta tatttgcaga cttcaaaatt actggtgacg gaggtgaagg ttccatcctg    180
gatatgacat tccccccagg tcagtttcca catcattaca gggagaagtt cgtgttttc    240 gatcacaaga atcattacaa gttagtacaa atgatcgacg gtgattttttt cgatctaggt    300 gttacatact atatggatac aatccgtgtt gttgcaacag gccctgattc atgtgtcatc    360
aagtcttcaa cggaatatca tgtaaaagtt gagtttgcca agatcgtcaa accacttatt    420
gacactgtac cactagctat aatgtctgaa gcgattgcaa aggttgttct tgagaagaaa    480
tacaagagat cagagtaa                                                 498

<210> SEQ ID NO 111
<211> LENGTH: 696
<212> TYPE: DNA
<213> ORGANISM: Papaver somniferum

<400> SEQUENCE: 111
atgtctaaat taatcacaac tgaaccattg aagtcgatgg cggaagtcat ctctaattac     60
```

```
gttatccaga gagaatcatt ttccgcaaga aacattctca acaaaaattc tttggtgaag      120
aaggagattc ggtatgacct ggaggttcca acctcagctg attctatctg gtcagtttac      180
agctgcccgg atattcctcg gcttcttaga gatgttttac ttcccggtgt tttccagaaa      240
ttggatgtta tcgaagggaa tggtggtgtt ggtacagttc ttgatatcgt ttttcctcca      300
ggtgcggtac ctcgtagtta caaggagaaa tttgtgaaca tcaaccacga aaagcgatta      360
aaagaagtga ttatgatcga aggaggatat ttagacatgg gatgcacatt ttacatggac      420
aggatccata tctttgagaa aaccccaaac tcatgtgtta tcgaatcctc gatcatttac      480
gaagttaaag aagagtatgc tggtaaaatg gctaagctaa tcacaactga accattggaa      540
tccatggcag aagtcatctc tggttatgtt cttaagaaac gactccaagt attcggattc      600
gagattaagc caaaattaag attcaatctt ttgctatgtt tgattatctg tctggttata      660
gctggaggta tgtttgttgc tggtgttcca ctctaa                                696

<210> SEQ ID NO 112
<211> LENGTH: 576
<212> TYPE: DNA
<213> ORGANISM: Thalictrum flavum

<400> SEQUENCE: 112
atgaaactga ttctgacagg taggccgttt ctgcaccacc agggcataat aaaccaggtg       60
tctacagtca caaaagtgat tcatcatgag ttggaagttg ctgcttcagc tgatgatata      120
tggactgttt atagctggcc tggcttggcc aagcatcttc ctgacttgct ccctggcgct      180
tttgaaaagc tagaaatcat tggtgatgga ggtgttggta ccatcctaga catgacattt      240
gtaccaggtg aatttcctca tgaatacaag gagaagttta ttagtcga taatgagcat      300 cgtttaaaga aggtgcaaat gattgaggga ggttatctgg acttgggagt aacatactac      360
atggacacaa tccatgttgt tccaactggt aaagattcat gtgttattaa atcctcaact      420
gagtaccatg tgaaacctga gtttgtcaaa atcgttgaac cacttatcac caccggtcca      480
ttagctgcca tggcagacgc catctcaaaa cttgttctag aacacaaatc caaaagcaac      540
tcagatgaaa ttgaggccgc aataataaca gtctga                                576

<210> SEQ ID NO 113
<211> LENGTH: 531
<212> TYPE: DNA
<213> ORGANISM: Xanthoriza simplicissima

<400> SEQUENCE: 113
atgagaatga tattcagtgg gcgtcctctc ctccatcgcg taacaaatga ggagactgta       60
atcctttatc atgagctgga agtacctgct tcggtggatg aactgtggag tgtcgaaggt      120
tcgcctgagt tgggcaagaa tttgcctgac ctgctccctg gtatatttgc agacttcaaa      180
attactggtg acgaggtgaa aggttccatc ctggatatga cattcccccc aggtcagttt      240
ccacatcatt acagggagaa gttcgtgttt ttcgatcaca agaatcatta caagttagta      300
caaatgatcg acggtgattt tttcgatcta ggtgttacat actatatgga tacaatccgt      360
gttgttgcaa caggccctga ttcatgtgtc atcaagtctt caacggaata tcatgtaaaa      420
gttgagtttg ccaagatcgt caaaccactt attgacactg taccactagc tataatgtct      480
gaagcgattg caaaggttgt tcttgagaag aaatacaaga gatcagagta a                531

<210> SEQ ID NO 114
```

<211> LENGTH: 25
<212> TYPE: DNA
<213> ORGANISM: Artificial Sequence
<220> FEATURE:
<223> OTHER INFORMATION: Synthetic primers

<400> SEQUENCE: 114
agtgtttcag agagtatgat gagga                                      25

<210> SEQ ID NO 115
<211> LENGTH: 20
<212> TYPE: DNA
<213> ORGANISM: Artificial Sequence
<220> FEATURE:
<223> OTHER INFORMATION: Synthetic primers

<400> SEQUENCE: 115
cccgcaatga catctagctt                                            20

<210> SEQ ID NO 116
<211> LENGTH: 20
<212> TYPE: DNA
<213> ORGANISM: Artificial Sequence
<220> FEATURE:
<223> OTHER INFORMATION: Synthetic primers

<400> SEQUENCE: 116
acatcgaccg tgtaaagcga                                            20

<210> SEQ ID NO 117
<211> LENGTH: 21
<212> TYPE: DNA
<213> ORGANISM: Artificial Sequence
<220> FEATURE:
<223> OTHER INFORMATION: Synthetic primers

<400> SEQUENCE: 117
accttagagt ggaacacgtc c                                          21

<210> SEQ ID NO 118
<211> LENGTH: 22
<212> TYPE: DNA
<213> ORGANISM: Artificial Sequence
<220> FEATURE:
<223> OTHER INFORMATION: Synthetic primers

<400> SEQUENCE: 118
acttcctggt gtcttcgtga aa                                         22

<210> SEQ ID NO 119
<211> LENGTH: 24
<212> TYPE: DNA
<213> ORGANISM: Artificial Sequence
<220> FEATURE:
<223> OTHER INFORMATION: Synthetic primers

<400> SEQUENCE: 119
acttggctta tgcttttaga cctc                                       24

<210> SEQ ID NO 120
<211> LENGTH: 23
<212> TYPE: DNA
<213> ORGANISM: Artificial Sequence
<220> FEATURE:
<223> OTHER INFORMATION: Synthetic primers

<400> SEQUENCE: 120
agtgagtgag tgtttcagag agt                                            23

<210> SEQ ID NO 121
<211> LENGTH: 21
<212> TYPE: DNA
<213> ORGANISM: Artificial Sequence
<220> FEATURE:
<223> OTHER INFORMATION: Synthetic primers

<400> SEQUENCE: 121
accttagagt ggaacacgtc c                                              21

<210> SEQ ID NO 122
<211> LENGTH: 25
<212> TYPE: DNA
<213> ORGANISM: Artificial Sequence
<220> FEATURE:
<223> OTHER INFORMATION: Synthetic primers

<400> SEQUENCE: 122
agagagagaa aatgaggaag gaact                                          25

<210> SEQ ID NO 123
<211> LENGTH: 23
<212> TYPE: DNA
<213> ORGANISM: Artificial Sequence
<220> FEATURE:
<223> OTHER INFORMATION: Synthetic primers

<400> SEQUENCE: 123
accgaactta gaatggaaca cct                                            23

<210> SEQ ID NO 124
<211> LENGTH: 23
<212> TYPE: DNA
<213> ORGANISM: Artificial Sequence
<220> FEATURE:
<223> OTHER INFORMATION: Synthetic primers

<400> SEQUENCE: 124
gtgtttcaga gagaacgatg agg                                            23

<210> SEQ ID NO 125
<211> LENGTH: 21
<212> TYPE: DNA
<213> ORGANISM: Artificial Sequence
<220> FEATURE:
<223> OTHER INFORMATION: Synthetic primers

<400> SEQUENCE: 125
accttagagt ggaacaccag c                                              21

<210> SEQ ID NO 126
<211> LENGTH: 24
<212> TYPE: DNA
<213> ORGANISM: Artificial Sequence
<220> FEATURE:
<223> OTHER INFORMATION: Synthetic primers

<400> SEQUENCE: 126
cacgagaagc gattgaaaga ggtg                                           24

<210> SEQ ID NO 127
<211> LENGTH: 25
<212> TYPE: DNA

```
<213> ORGANISM: Artificial Sequence
<220> FEATURE:
<223> OTHER INFORMATION: Synthetic primers

<400> SEQUENCE: 127
tggaccggac ggtatacatg accat                                        25

<210> SEQ ID NO 128
<211> LENGTH: 26
<212> TYPE: DNA
<213> ORGANISM: Artificial Sequence
<220> FEATURE:
<223> OTHER INFORMATION: Synthetic primers

<400> SEQUENCE: 128
gagaaaatga ggaaggaagt acgata                                       26

<210> SEQ ID NO 129
<211> LENGTH: 22
<212> TYPE: DNA
<213> ORGANISM: Artificial Sequence
<220> FEATURE:
<223> OTHER INFORMATION: Synthetic primers

<400> SEQUENCE: 129
ccggtactta gagtggaaca cc                                           22

<210> SEQ ID NO 130
<211> LENGTH: 20
<212> TYPE: DNA
<213> ORGANISM: Artificial Sequence
<220> FEATURE:
<223> OTHER INFORMATION: Synthetic primers

<400> SEQUENCE: 130
aaccaagaga agcgactcaa                                              20

<210> SEQ ID NO 131
<211> LENGTH: 25
<212> TYPE: DNA
<213> ORGANISM: Artificial Sequence
<220> FEATURE:
<223> OTHER INFORMATION: Synthetic primers

<400> SEQUENCE: 131
acctaaagta actgaaacta tgctg                                        25

<210> SEQ ID NO 132
<211> LENGTH: 26
<212> TYPE: DNA
<213> ORGANISM: Artificial Sequence
<220> FEATURE:
<223> OTHER INFORMATION: Synthetic primers

<400> SEQUENCE: 132
gcgaaaatac agagagaagt ttgtga                                       26

<210> SEQ ID NO 133
<211> LENGTH: 23
<212> TYPE: DNA
<213> ORGANISM: Artificial Sequence
<220> FEATURE:
<223> OTHER INFORMATION: Synthetic primers

<400> SEQUENCE: 133
cccctggagg aaaaacaatt tgg                                          23
```

<210> SEQ ID NO 134
<211> LENGTH: 25
<212> TYPE: DNA
<213> ORGANISM: Artificial Sequence
<220> FEATURE:
<223> OTHER INFORMATION: Synthetic primers

<400> SEQUENCE: 134
agggagagaa aatgaggaaa gaagt                                           25

<210> SEQ ID NO 135
<211> LENGTH: 22
<212> TYPE: DNA
<213> ORGANISM: Artificial Sequence
<220> FEATURE:
<223> OTHER INFORMATION: Synthetic primers

<400> SEQUENCE: 135
cctcaatgac atctaacttt tc                                              22

<210> SEQ ID NO 136
<211> LENGTH: 25
<212> TYPE: DNA
<213> ORGANISM: Artificial Sequence
<220> FEATURE:
<223> OTHER INFORMATION: Synthetic primers

<400> SEQUENCE: 136
caaccctgct atctccaagt atgtt                                           25

<210> SEQ ID NO 137
<211> LENGTH: 26
<212> TYPE: DNA
<213> ORGANISM: Artificial Sequence
<220> FEATURE:
<223> OTHER INFORMATION: Synthetic primers

<400> SEQUENCE: 137
aacaggtagc tagggcagct gtttat                                          26

<210> SEQ ID NO 138
<211> LENGTH: 26
<212> TYPE: DNA
<213> ORGANISM: Artificial Sequence
<220> FEATURE:
<223> OTHER INFORMATION: Synthetic primers

<400> SEQUENCE: 138
aatgaggaag gaactaacac atgaga                                          26

<210> SEQ ID NO 139
<211> LENGTH: 26
<212> TYPE: DNA
<213> ORGANISM: Artificial Sequence
<220> FEATURE:
<223> OTHER INFORMATION: Synthetic primers

<400> SEQUENCE: 139
gtggcctatc tcatcttcac agtact                                          26

<210> SEQ ID NO 140
<211> LENGTH: 27
<212> TYPE: DNA
<213> ORGANISM: Artificial Sequence
<220> FEATURE:

<223> OTHER INFORMATION: Synthetic primers

<400> SEQUENCE: 140
caagttcatc acactaacac aagtaag                                27

<210> SEQ ID NO 141
<211> LENGTH: 27
<212> TYPE: DNA
<213> ORGANISM: Artificial Sequence
<220> FEATURE:
<223> OTHER INFORMATION: Synthetic primers

<400> SEQUENCE: 141
cttcgaattc taggcagaag aatccac                                27

<210> SEQ ID NO 142
<211> LENGTH: 26
<212> TYPE: DNA
<213> ORGANISM: Artificial Sequence
<220> FEATURE:
<223> OTHER INFORMATION: Synthetic primers

<400> SEQUENCE: 142
accaaaggtc ctattaccga agatga                                 26

<210> SEQ ID NO 143
<211> LENGTH: 26
<212> TYPE: DNA
<213> ORGANISM: Artificial Sequence
<220> FEATURE:
<223> OTHER INFORMATION: Synthetic primers

<400> SEQUENCE: 143
ctctagacta catctttcaa gcccca                                 26

<210> SEQ ID NO 144
<211> LENGTH: 25
<212> TYPE: DNA
<213> ORGANISM: Artificial Sequence
<220> FEATURE:
<223> OTHER INFORMATION: Synthetic primers

<400> SEQUENCE: 144
gaatatatat gaagatggaa gctac                                  25

<210> SEQ ID NO 145
<211> LENGTH: 25
<212> TYPE: DNA
<213> ORGANISM: Artificial Sequence
<220> FEATURE:
<223> OTHER INFORMATION: Synthetic primers

<400> SEQUENCE: 145
ccacttaagt acctacaaac cccaa                                  25

<210> SEQ ID NO 146
<211> LENGTH: 26
<212> TYPE: DNA
<213> ORGANISM: Artificial Sequence
<220> FEATURE:
<223> OTHER INFORMATION: Synthetic primers

<400> SEQUENCE: 146
gaattggtaa atgagatggt agtggc                                 26

```
<210> SEQ ID NO 147
<211> LENGTH: 26
<212> TYPE: DNA
<213> ORGANISM: Artificial Sequence
<220> FEATURE:
<223> OTHER INFORMATION: Synthetic primers

<400> SEQUENCE: 147
gtagtatctt gttaacacga tttgtc                                          26

<210> SEQ ID NO 148
<211> LENGTH: 26
<212> TYPE: DNA
<213> ORGANISM: Artificial Sequence
<220> FEATURE:
<223> OTHER INFORMATION: Synthetic primers

<400> SEQUENCE: 148
cagtccatcc cttctcagtc aattaa                                          26

<210> SEQ ID NO 149
<211> LENGTH: 25
<212> TYPE: DNA
<213> ORGANISM: Artificial Sequence
<220> FEATURE:
<223> OTHER INFORMATION: Synthetic primers

<400> SEQUENCE: 149
gtcaatccca taagcctaat aacca                                           25

<210> SEQ ID NO 150
<211> LENGTH: 26
<212> TYPE: DNA
<213> ORGANISM: Artificial Sequence
<220> FEATURE:
<223> OTHER INFORMATION: Synthetic primers

<400> SEQUENCE: 150
agatggaagt ggctacttca gctgat                                          26

<210> SEQ ID NO 151
<211> LENGTH: 26
<212> TYPE: DNA
<213> ORGANISM: Artificial Sequence
<220> FEATURE:
<223> OTHER INFORMATION: Synthetic primers

<400> SEQUENCE: 151
tcttgattga attggatccc ctcaat                                          26

<210> SEQ ID NO 152
<211> LENGTH: 25
<212> TYPE: DNA
<213> ORGANISM: Artificial Sequence
<220> FEATURE:
<223> OTHER INFORMATION: Synthetic primers

<400> SEQUENCE: 152
gagtgtgata gtagaaagaa atgag                                           25

<210> SEQ ID NO 153
<211> LENGTH: 25
<212> TYPE: DNA
<213> ORGANISM: Artificial Sequence
<220> FEATURE:
<223> OTHER INFORMATION: Synthetic primers
```

<400> SEQUENCE: 153
cattgccttc aatgacatcc tagtc                                          25

<210> SEQ ID NO 154
<211> LENGTH: 24
<212> TYPE: DNA
<213> ORGANISM: Artificial Sequence
<220> FEATURE:
<223> OTHER INFORMATION: Synthetic primers

<400> SEQUENCE: 154
cgagagacta aaagtaagga aaag                                           24

<210> SEQ ID NO 155
<211> LENGTH: 26
<212> TYPE: DNA
<213> ORGANISM: Artificial Sequence
<220> FEATURE:
<223> OTHER INFORMATION: Synthetic primers

<400> SEQUENCE: 155
accttgacac cattattagt acttcc                                         26

<210> SEQ ID NO 156
<211> LENGTH: 24
<212> TYPE: DNA
<213> ORGANISM: Artificial Sequence
<220> FEATURE:
<223> OTHER INFORMATION: Synthetic primers

<400> SEQUENCE: 156
tagcaagaat gaggaagcat cttg                                           24

<210> SEQ ID NO 157
<211> LENGTH: 26
<212> TYPE: DNA
<213> ORGANISM: Artificial Sequence
<220> FEATURE:
<223> OTHER INFORMATION: Synthetic primers

<400> SEQUENCE: 157
agctagctag gtgcatccat cataag                                         26

<210> SEQ ID NO 158
<211> LENGTH: 26
<212> TYPE: DNA
<213> ORGANISM: Artificial Sequence
<220> FEATURE:
<223> OTHER INFORMATION: Synthetic primers

<400> SEQUENCE: 158
aatgaggaag gaactcacaa atgagt                                         26

<210> SEQ ID NO 159
<211> LENGTH: 23
<212> TYPE: DNA
<213> ORGANISM: Artificial Sequence
<220> FEATURE:
<223> OTHER INFORMATION: Synthetic primers

<400> SEQUENCE: 159
tctcccaagc aaacaaagca ttg                                            23

<210> SEQ ID NO 160
<211> LENGTH: 26

```
<212> TYPE: DNA
<213> ORGANISM: Artificial Sequence
<220> FEATURE:
<223> OTHER INFORMATION: Synthetic primers

<400> SEQUENCE: 160
tctagtttgc attatcaagg agagga                                              26

<210> SEQ ID NO 161
<211> LENGTH: 26
<212> TYPE: DNA
<213> ORGANISM: Artificial Sequence
<220> FEATURE:
<223> OTHER INFORMATION: Synthetic primers

<400> SEQUENCE: 161
acatagcgat gatgattata tttcga                                              26

<210> SEQ ID NO 162
<211> LENGTH: 24
<212> TYPE: DNA
<213> ORGANISM: Artificial Sequence
<220> FEATURE:
<223> OTHER INFORMATION: Synthetic primers

<400> SEQUENCE: 162
cttgaaatgg tatttcctcc agga                                                24

<210> SEQ ID NO 163
<211> LENGTH: 26
<212> TYPE: DNA
<213> ORGANISM: Artificial Sequence
<220> FEATURE:
<223> OTHER INFORMATION: Synthetic primers

<400> SEQUENCE: 163
agtcgcatac atccacattt tgtttc                                              26

<210> SEQ ID NO 164
<211> LENGTH: 25
<212> TYPE: DNA
<213> ORGANISM: Artificial Sequence
<220> FEATURE:
<223> OTHER INFORMATION: Synthetic primers

<400> SEQUENCE: 164
aatgaggagt ggaattgttt tcctg                                               25

<210> SEQ ID NO 165
<211> LENGTH: 25
<212> TYPE: DNA
<213> ORGANISM: Artificial Sequence
<220> FEATURE:
<223> OTHER INFORMATION: Synthetic primers

<400> SEQUENCE: 165
gattacacta cacgatgcaa ctttg                                               25

<210> SEQ ID NO 166
<211> LENGTH: 25
<212> TYPE: DNA
<213> ORGANISM: Artificial Sequence
<220> FEATURE:
<223> OTHER INFORMATION: Synthetic primers

<400> SEQUENCE: 166
```
gtaaatgaga tggaagtggc tgcgt                                            25

<210> SEQ ID NO 167
<211> LENGTH: 26
<212> TYPE: DNA
<213> ORGANISM: Artificial Sequence
<220> FEATURE:
<223> OTHER INFORMATION: Synthetic primers

<400> SEQUENCE: 167
agcatacatc ttgttaatga cgcttc                                           26

<210> SEQ ID NO 168
<211> LENGTH: 21
<212> TYPE: DNA
<213> ORGANISM: Artificial Sequence
<220> FEATURE:
<223> OTHER INFORMATION: Synthetic primers

<400> SEQUENCE: 168
gcctgcatca gcttagaaca c                                                21

<210> SEQ ID NO 169
<211> LENGTH: 21
<212> TYPE: DNA
<213> ORGANISM: Artificial Sequence
<220> FEATURE:
<223> OTHER INFORMATION: Synthetic primers

<400> SEQUENCE: 169
tggcagtcca cttccaattc a                                                21

<210> SEQ ID NO 170
<211> LENGTH: 25
<212> TYPE: DNA
<213> ORGANISM: Artificial Sequence
<220> FEATURE:
<223> OTHER INFORMATION: Synthetic primers

<400> SEQUENCE: 170
cgatcttgca tctgtaaaca tttca                                            25

<210> SEQ ID NO 171
<211> LENGTH: 26
<212> TYPE: DNA
<213> ORGANISM: Artificial Sequence
<220> FEATURE:
<223> OTHER INFORMATION: Synthetic primers

<400> SEQUENCE: 171
gcgtacgtac tcaaacaagt atttct                                           26

<210> SEQ ID NO 172
<211> LENGTH: 26
<212> TYPE: DNA
<213> ORGANISM: Artificial Sequence
<220> FEATURE:
<223> OTHER INFORMATION: Synthetic primers

<400> SEQUENCE: 172
taaataagat ggttcagttc agcaga                                           26

<210> SEQ ID NO 173
<211> LENGTH: 26
<212> TYPE: DNA
<213> ORGANISM: Artificial Sequence

```
<220> FEATURE:
<223> OTHER INFORMATION: Synthetic primers

<400> SEQUENCE: 173
gagcagaagt tgtgttcctc agattg                                        26

<210> SEQ ID NO 174
<211> LENGTH: 21
<212> TYPE: DNA
<213> ORGANISM: Artificial Sequence
<220> FEATURE:
<223> OTHER INFORMATION: Synthetic primers

<400> SEQUENCE: 174
tgagaggaag caagcacaag g                                             21

<210> SEQ ID NO 175
<211> LENGTH: 21
<212> TYPE: DNA
<213> ORGANISM: Artificial Sequence
<220> FEATURE:
<223> OTHER INFORMATION: Synthetic primers

<400> SEQUENCE: 175
cggtcttgta cctgggatga t                                             21

<210> SEQ ID NO 176
<211> LENGTH: 23
<212> TYPE: DNA
<213> ORGANISM: Artificial Sequence
<220> FEATURE:
<223> OTHER INFORMATION: Synthetic primers

<400> SEQUENCE: 176
gcaagaaggt ttccttagtg caa                                           23

<210> SEQ ID NO 177
<211> LENGTH: 21
<212> TYPE: DNA
<213> ORGANISM: Artificial Sequence
<220> FEATURE:
<223> OTHER INFORMATION: Synthetic primers

<400> SEQUENCE: 177
tcagtagctg ctttgaacca t                                             21

<210> SEQ ID NO 178
<211> LENGTH: 22
<212> TYPE: DNA
<213> ORGANISM: Artificial Sequence
<220> FEATURE:
<223> OTHER INFORMATION: Synthetic primers

<400> SEQUENCE: 178
tcgagtgttt cagagagaac ga                                            22

<210> SEQ ID NO 179
<211> LENGTH: 22
<212> TYPE: DNA
<213> ORGANISM: Artificial Sequence
<220> FEATURE:
<223> OTHER INFORMATION: Synthetic primers

<400> SEQUENCE: 179
acccattttt caaacatcgc ca                                            22
```

<210> SEQ ID NO 180
<211> LENGTH: 26
<212> TYPE: DNA
<213> ORGANISM: Artificial Sequence
<220> FEATURE:
<223> OTHER INFORMATION: Synthetic primers

<400> SEQUENCE: 180
ccaagcttat ggaagtggct acttca                                              26

<210> SEQ ID NO 181
<211> LENGTH: 25
<212> TYPE: DNA
<213> ORGANISM: Artificial Sequence
<220> FEATURE:
<223> OTHER INFORMATION: Synthetic primers

<400> SEQUENCE: 181
gctcgagtat cgaaacaccg ccgat                                               25

<210> SEQ ID NO 182
<211> LENGTH: 26
<212> TYPE: DNA
<213> ORGANISM: Artificial Sequence
<220> FEATURE:
<223> OTHER INFORMATION: Synthetic primers

<400> SEQUENCE: 182
ccaagcttat gaggaaggaa ttaaga                                              26

<210> SEQ ID NO 183
<211> LENGTH: 23
<212> TYPE: DNA
<213> ORGANISM: Artificial Sequence
<220> FEATURE:
<223> OTHER INFORMATION: Synthetic primers

<400> SEQUENCE: 183
gctcgaggtc ttcgaaaact cca                                                 23

<210> SEQ ID NO 184
<211> LENGTH: 26
<212> TYPE: DNA
<213> ORGANISM: Artificial Sequence
<220> FEATURE:
<223> OTHER INFORMATION: Synthetic primers

<400> SEQUENCE: 184
ccaagcttat gaggaaggaa ctcaca                                              26

<210> SEQ ID NO 185
<211> LENGTH: 25
<212> TYPE: DNA
<213> ORGANISM: Artificial Sequence
<220> FEATURE:
<223> OTHER INFORMATION: Synthetic primers

<400> SEQUENCE: 185
gctcgagacc caaacaattg aaagg                                               25

<210> SEQ ID NO 186
<211> LENGTH: 26
<212> TYPE: DNA
<213> ORGANISM: Artificial Sequence
<220> FEATURE:
<223> OTHER INFORMATION: Synthetic primers

<400> SEQUENCE: 186
cgggatccta tgattgaagg agggta                                           26

<210> SEQ ID NO 187
<211> LENGTH: 25
<212> TYPE: DNA
<213> ORGANISM: Artificial Sequence
<220> FEATURE:
<223> OTHER INFORMATION: Synthetic primers

<400> SEQUENCE: 187
gctcgaggag tggaacaccc ccaat                                            25

<210> SEQ ID NO 188
<211> LENGTH: 26
<212> TYPE: DNA
<213> ORGANISM: Artificial Sequence
<220> FEATURE:
<223> OTHER INFORMATION: Synthetic primers

<400> SEQUENCE: 188
ccaagcttat gatcggagga ttctta                                           26

<210> SEQ ID NO 189
<211> LENGTH: 26
<212> TYPE: DNA
<213> ORGANISM: Artificial Sequence
<220> FEATURE:
<223> OTHER INFORMATION: Synthetic primers

<400> SEQUENCE: 189
gctcgagatg acttctaact tttcga                                           26

<210> SEQ ID NO 190
<211> LENGTH: 26
<212> TYPE: DNA
<213> ORGANISM: Artificial Sequence
<220> FEATURE:
<223> OTHER INFORMATION: Synthetic primers

<400> SEQUENCE: 190
ccaagcttat gaggagtgga attgtt                                           26

<210> SEQ ID NO 191
<211> LENGTH: 25
<212> TYPE: DNA
<213> ORGANISM: Artificial Sequence
<220> FEATURE:
<223> OTHER INFORMATION: Synthetic primers

<400> SEQUENCE: 191
gctcgagtat ttcgataaac ccctt                                            25

<210> SEQ ID NO 192
<211> LENGTH: 26
<212> TYPE: DNA
<213> ORGANISM: Artificial Sequence
<220> FEATURE:
<223> OTHER INFORMATION: Synthetic primers

<400> SEQUENCE: 192
ccaagcttat ggatatcata gaaggg                                           26

<210> SEQ ID NO 193

```
<211> LENGTH: 25
<212> TYPE: DNA
<213> ORGANISM: Artificial Sequence
<220> FEATURE:
<223> OTHER INFORMATION: Synthetic primers

<400> SEQUENCE: 193
gctcgagtgc ttttagacct ccaat                                         25

<210> SEQ ID NO 194
<211> LENGTH: 26
<212> TYPE: DNA
<213> ORGANISM: Artificial Sequence
<220> FEATURE:
<223> OTHER INFORMATION: Synthetic primers

<400> SEQUENCE: 194
ccaagcttat gatcgaagga gggtat                                        26

<210> SEQ ID NO 195
<211> LENGTH: 25
<212> TYPE: DNA
<213> ORGANISM: Artificial Sequence
<220> FEATURE:
<223> OTHER INFORMATION: Synthetic primers

<400> SEQUENCE: 195
gctcgaggag tggaacacgt ccaat                                         25

<210> SEQ ID NO 196
<211> LENGTH: 26
<212> TYPE: DNA
<213> ORGANISM: Artificial Sequence
<220> FEATURE:
<223> OTHER INFORMATION: Synthetic primers

<400> SEQUENCE: 196
ccaagcttat gatgaggaaa gtaatc                                        26

<210> SEQ ID NO 197
<211> LENGTH: 23
<212> TYPE: DNA
<213> ORGANISM: Artificial Sequence
<220> FEATURE:
<223> OTHER INFORMATION: Synthetic primers

<400> SEQUENCE: 197
gctcgaggag tggaacacgt cca                                           23

<210> SEQ ID NO 198
<211> LENGTH: 26
<212> TYPE: DNA
<213> ORGANISM: Artificial Sequence
<220> FEATURE:
<223> OTHER INFORMATION: Synthetic primers

<400> SEQUENCE: 198
ccaagcttat gaggaaggaa ctgaca                                        26

<210> SEQ ID NO 199
<211> LENGTH: 25
<212> TYPE: DNA
<213> ORGANISM: Artificial Sequence
<220> FEATURE:
<223> OTHER INFORMATION: Synthetic primers

<400> SEQUENCE: 199
```

```
gctcgaggaa tggaacacct ccaat                                        25

<210> SEQ ID NO 200
<211> LENGTH: 25
<212> TYPE: DNA
<213> ORGANISM: Artificial Sequence
<220> FEATURE:
<223> OTHER INFORMATION: Synthetic primers

<400> SEQUENCE: 200
cggatcctat gaggaaggaa gtacg                                        25

<210> SEQ ID NO 201
<211> LENGTH: 21
<212> TYPE: DNA
<213> ORGANISM: Artificial Sequence
<220> FEATURE:
<223> OTHER INFORMATION: Synthetic primers

<400> SEQUENCE: 201
gctcgaggag tggaacacct c                                            21

<210> SEQ ID NO 202
<211> LENGTH: 26
<212> TYPE: DNA
<213> ORGANISM: Artificial Sequence
<220> FEATURE:
<223> OTHER INFORMATION: Synthetic primers

<400> SEQUENCE: 202
ccaagcttat gaagatggaa gttgta                                       26

<210> SEQ ID NO 203
<211> LENGTH: 26
<212> TYPE: DNA
<213> ORGANISM: Artificial Sequence
<220> FEATURE:
<223> OTHER INFORMATION: Synthetic primers

<400> SEQUENCE: 203
ccaagcttat gaggatggaa gttgtt                                       26

<210> SEQ ID NO 204
<211> LENGTH: 27
<212> TYPE: DNA
<213> ORGANISM: Artificial Sequence
<220> FEATURE:
<223> OTHER INFORMATION: Synthetic primers

<400> SEQUENCE: 204
gctcgagctc tgatctcttg tatttct                                      27

<210> SEQ ID NO 205
<211> LENGTH: 27
<212> TYPE: DNA
<213> ORGANISM: Artificial Sequence
<220> FEATURE:
<223> OTHER INFORMATION: Synthetic primers

<400> SEQUENCE: 205
ccaagcttat gaggaaagta atcaaat                                      27

<210> SEQ ID NO 206
<211> LENGTH: 27
<212> TYPE: DNA
```

```
<213> ORGANISM: Artificial Sequence
<220> FEATURE:
<223> OTHER INFORMATION: Synthetic primers

<400> SEQUENCE: 206
ccaagcttat gaggaaagta atcaaat                                        27

<210> SEQ ID NO 207
<211> LENGTH: 24
<212> TYPE: DNA
<213> ORGANISM: Artificial Sequence
<220> FEATURE:
<223> OTHER INFORMATION: Synthetic primers

<400> SEQUENCE: 207
gctcgaggct tagccatttt acca                                           24

<210> SEQ ID NO 208
<211> LENGTH: 27
<212> TYPE: DNA
<213> ORGANISM: Artificial Sequence
<220> FEATURE:
<223> OTHER INFORMATION: Synthetic primers

<400> SEQUENCE: 208
ccaagcttag ttacaaggag agatttg                                        27

<210> SEQ ID NO 209
<211> LENGTH: 25
<212> TYPE: DNA
<213> ORGANISM: Artificial Sequence
<220> FEATURE:
<223> OTHER INFORMATION: Synthetic primers

<400> SEQUENCE: 209
gctcgagtgc ttttagacct ccaat                                          25

<210> SEQ ID NO 210
<211> LENGTH: 28
<212> TYPE: DNA
<213> ORGANISM: Artificial Sequence
<220> FEATURE:
<223> OTHER INFORMATION: Synthetic primers

<400> SEQUENCE: 210
ccaagctttc atgtattatc aaatcaac                                       28

<210> SEQ ID NO 211
<211> LENGTH: 26
<212> TYPE: DNA
<213> ORGANISM: Artificial Sequence
<220> FEATURE:
<223> OTHER INFORMATION: Synthetic primers

<400> SEQUENCE: 211
gctcgagatg acttctaact tttcga                                         26

<210> SEQ ID NO 212
<211> LENGTH: 28
<212> TYPE: DNA
<213> ORGANISM: Artificial Sequence
<220> FEATURE:
<223> OTHER INFORMATION: Synthetic primers

<400> SEQUENCE: 212
cgggatccta attcatgcgt tattgcat                                       28
```

```
<210> SEQ ID NO 213
<211> LENGTH: 26
<212> TYPE: DNA
<213> ORGANISM: Artificial Sequence
<220> FEATURE:
<223> OTHER INFORMATION: Synthetic primers

<400> SEQUENCE: 213
cgggatccta tgattgaagg agggta                                              26

<210> SEQ ID NO 214
<211> LENGTH: 24
<212> TYPE: DNA
<213> ORGANISM: Artificial Sequence
<220> FEATURE:
<223> OTHER INFORMATION: Synthetic primers

<400> SEQUENCE: 214
ccaagcttga tatcccaaga cttc                                                24

<210> SEQ ID NO 215
<211> LENGTH: 23
<212> TYPE: DNA
<213> ORGANISM: Artificial Sequence
<220> FEATURE:
<223> OTHER INFORMATION: Synthetic primers

<400> SEQUENCE: 215
gctcgaggtc ttcgaaaact cca                                                 23

<210> SEQ ID NO 216
<211> LENGTH: 25
<212> TYPE: DNA
<213> ORGANISM: Artificial Sequence
<220> FEATURE:
<223> OTHER INFORMATION: Synthetic primers

<400> SEQUENCE: 216
ccaagcttag gccatttctt aaccg                                               25

<210> SEQ ID NO 217
<211> LENGTH: 26
<212> TYPE: DNA
<213> ORGANISM: Artificial Sequence
<220> FEATURE:
<223> OTHER INFORMATION: Synthetic primers

<400> SEQUENCE: 217
ccaagcttat gaggatggaa gttgtt                                              26

<210> SEQ ID NO 218
<211> LENGTH: 28
<212> TYPE: DNA
<213> ORGANISM: Artificial Sequence
<220> FEATURE:
<223> OTHER INFORMATION: Synthetic primers

<400> SEQUENCE: 218
ccaagcttag ctcatgtgtt attgaatc                                            28

<210> SEQ ID NO 219
<211> LENGTH: 25
<212> TYPE: DNA
<213> ORGANISM: Artificial Sequence
<220> FEATURE:
```

```
<223> OTHER INFORMATION: Synthetic primers

<400> SEQUENCE: 219
gctcgaggag tggaacacgt ccaat                                          25

<210> SEQ ID NO 220
<211> LENGTH: 26
<212> TYPE: DNA
<213> ORGANISM: Artificial Sequence
<220> FEATURE:
<223> OTHER INFORMATION: Synthetic primers

<400> SEQUENCE: 220
ccaagcttga tctcccaaaa atcata                                         26

<210> SEQ ID NO 221
<211> LENGTH: 25
<212> TYPE: DNA
<213> ORGANISM: Artificial Sequence
<220> FEATURE:
<223> OTHER INFORMATION: Synthetic primers

<400> SEQUENCE: 221
gctcgagacc caaacaattg aaagg                                          25

<210> SEQ ID NO 222
<211> LENGTH: 22
<212> TYPE: DNA
<213> ORGANISM: Artificial Sequence
<220> FEATURE:
<223> OTHER INFORMATION: Synthetic primers

<400> SEQUENCE: 222
ccaagcttgg gcgtcctctc ct                                             22

<210> SEQ ID NO 223
<211> LENGTH: 27
<212> TYPE: DNA
<213> ORGANISM: Artificial Sequence
<220> FEATURE:
<223> OTHER INFORMATION: Synthetic primers

<400> SEQUENCE: 223
ccaagcttat gaggaaagta atcaaat                                        27

<210> SEQ ID NO 224
<211> LENGTH: 40
<212> TYPE: DNA
<213> ORGANISM: Artificial Sequence
<220> FEATURE:
<223> OTHER INFORMATION: Synthetic primers

<400> SEQUENCE: 224
taaagggcgg ccgcaaaaat gaggaaggaa ctgacacacg                          40

<210> SEQ ID NO 225
<211> LENGTH: 58
<212> TYPE: DNA
<213> ORGANISM: Artificial Sequence
<220> FEATURE:
<223> OTHER INFORMATION: Synthetic primers

<400> SEQUENCE: 225
agactgagat cttcaatggt gatggtgatg atggaatgga acacctccaa tcaataac      58
```

```
<210> SEQ ID NO 226
<211> LENGTH: 40
<212> TYPE: DNA
<213> ORGANISM: Artificial Sequence
<220> FEATURE:
<223> OTHER INFORMATION: Synthetic primers

<400> SEQUENCE: 226
tcaagtgcgg ccgcaaaaat gaggagtgga attgttttcc                            40

<210> SEQ ID NO 227
<211> LENGTH: 54
<212> TYPE: DNA
<213> ORGANISM: Artificial Sequence
<220> FEATURE:
<223> OTHER INFORMATION: Synthetic primers

<400> SEQUENCE: 227
gtacctagat cttcaatggt gatggtgatg atgtatttcg ataaacccct tgtg            54

<210> SEQ ID NO 228
<211> LENGTH: 40
<212> TYPE: DNA
<213> ORGANISM: Artificial Sequence
<220> FEATURE:
<223> OTHER INFORMATION: Synthetic primers

<400> SEQUENCE: 228
taaagggcgg ccgcaaaaat gaggaaggaa ttaagacatg                            40

<210> SEQ ID NO 229
<211> LENGTH: 53
<212> TYPE: DNA
<213> ORGANISM: Artificial Sequence
<220> FEATURE:
<223> OTHER INFORMATION: Synthetic primers

<400> SEQUENCE: 229
cgcgatacta gttcaatggt gatggtgatg atggtcttcg aaaactccag gaa             53

<210> SEQ ID NO 230
<211> LENGTH: 43
<212> TYPE: DNA
<213> ORGANISM: Artificial Sequence
<220> FEATURE:
<223> OTHER INFORMATION: Sythetic primers

<400> SEQUENCE: 230
ttaagggcgg ccgcaaaaat gatgaggaaa gtaatcaaat acg                        43

<210> SEQ ID NO 231
<211> LENGTH: 52
<212> TYPE: DNA
<213> ORGANISM: Artificial Sequence
<220> FEATURE:
<223> OTHER INFORMATION: Synthetic primers

<400> SEQUENCE: 231
gtactcagat cttcaatggt gatggtgatg atggagtgga acacgtccaa tc              52
```

COMPOSITIONS AND METHODS FOR MAKING (S)-NORCOCLAURINE AND (S)-NORLAUDANOSOLINE, AND SYNTHESIS INTERMEDIATES THEREOF

RELATED APPLICATIONS

This application is a continuation of U.S. application Ser. No. 15/319,568 filed Dec. 16, 2016, U.S. Pat No. 10,119,155, which is a national phase entry application of Patent Cooperation Treaty Application No. PCT/CA2015/050542, which claims the benefit under 35 USC § 119 (e) from U.S. Provisional Patent Application No. 62/014,367, filed on Jun. 19, 2014, both of which are incorporated by reference herein in their entirety.

FIELD OF THE DISCLOSURE

The compositions and methods disclosed herein relate to secondary metabolites and processes for manufacturing the same. More particularly, the present disclosure relates to (S)-norcoclaurine and (S)-norlaudanosoline, and synthesis intermediates thereof and methods for manufacturing (S)-norcoclaurine, (S)-norlaudanosoline, and synthesis intermediates thereof.

BACKGROUND OF THE DISCLOSURE

The following paragraphs are provided by way of background to the present disclosure. They are not however an admission that anything discussed therein is prior art or part of the knowledge of persons skilled in the art.

The biochemical pathways of living organisms are commonly classified as being either part of primary metabolism or part of secondary metabolism. Pathways that are part of a living cell's primary metabolism are involved in catabolism for energy production or in anabolism for building block production for the cell. On the other hand, secondary metabolites are produced by living cells and may lack any obvious anabolic or catabolic function. It has however long been recognized that many secondary metabolites are useful in many respects, including for example as therapeutic agents.

The secondary metabolite (S)-norcoclaurine is produced by opium poppy (*Papaver somniferum*) and by other members mainly of the Papaveraceae, Ranunculaceae, Berberidaceae and Menispermaceae families of plants. (S)-norlaudansoline has not been found in nature, but is structurally similar to (S)-norcoclaurine and can be synthesized using the same suite of natural enzymes. (S)-norcoclaurine, (S)-norlaudanosoline, and synthesis intermediates thereof may be used as a raw material to manufacture alkaloid compounds that are useful as medicinal compounds, as well as recreational drugs or stimulants. Examples of such alkaloid compounds include the narcotic analgesics codeine and morphine, the antimicrobial agents sanguinerine and berberine, the muscle relaxants papaverine and (+)-tubocurarine, and the cough suppressant and potential anticancer drug noscapine.

Currently (S)-norcoclaurine and certain (S)-norcoclaurine synthesis intermediates may be harvested from natural sources, such as opium poppy. Alternatively these compounds may be prepared synthetically. (S)-norlaudanosoline may be prepared synthetically. However, the existing manufacturing methods for (S)-norcoclaurine, (S)-norlaudanosoline, and synthesis intermediates thereof suffer from low yields of (S)-norcoclaurine, (S)-norlaudanosoline, and synthesis intermediates and/or are expensive. In addition, synthetic manufacturing methods commonly lead to high volumes of waste materials such as organic solvents and metal catalysts. There exists therefore in the art a need for improved methods for the synthesis of (S)-norcoclaurine, (S)-norlaudanosoline, and synthesis intermediates thereof.

SUMMARY OF THE DISCLOSURE

The following paragraphs are intended to introduce the reader to the more detailed description that follows and not to define or limit the claimed subject matter of the present disclosure.

The present disclosure relates to the secondary metabolite (S)-norcoclaurine, the non-naturally occurring compound (S)-norlauranosoline, and synthesis intermediates thereof, as well as to methods of making (S)-norcoclaurine, (S)-norlaudanosoline, and synthesis intermediates thereof. The current disclosure further relates to certain enzymes capable of catalyzing reactions resulting in the conversion of certain synthesis intermediates to form (S)-norcoclaurine and/or (S)-norlaudanosoline.

Accordingly, the present disclosure provides, in at least one aspect, at least one embodiment of making (S)-norcoclaurine, (S)-norlaudanosoline, or synthesis intermediates thereof comprising:

(a) providing at least one (S)-norcoclaurine or (S)-norlaudanosoline pathway precursor selected from L-tyrosine or a first L-tyrosine derivative; and (b) contacting the (S)-norcoclaurine or (S)-norlaudanosoline pathway precursor with at least one of the enzymes selected from the group of enzymes consisting of (i) TYR; (ii) TYDC; (iii) DODC; (iv); MAO and (v) NCS under reaction conditions permitting the catalysis of the pathway precursor to form (S)-norcoclaurine, (S)-norlaudanosoline, or a synthesis intermediate thereof, wherein the (S)-norcoclaurine or (S)-norlaudanosoline synthesis intermediate is a second L-tyrosine derivative; and wherein the first and second L-tyrosine derivative have the chemical formula (I):

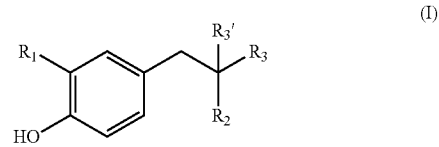

(I)

wherein $R_1$ represents hydrogen or hydroxyl;
wherein $R_2$ represents hydrogen or an amino group $-(NH_2)$; and
wherein $R_3$ represents a carboxyl group $-(COOH)$, or an amino group $-(NH_2)$;
wherein $R_3'$ represents a hydrogen atom; or
$R_3$ and $R_3'$ taken together, form a carbonyl group.

In preferred embodiments of the disclosure, the first and/or second L-tyrosine derivative is L-DOPA; tyramine; dopamine; 4-hydroxyphenylacetaldehyde; or 3,4-dihydroxyphenylacetaldehyde.

In a further aspect, the present disclosure provides at least one embodiment of making (S)-norcoclaurine, (S)-norlaudanosoline, and each of the following synthesis intermediates: tyramine, dopamine, L-DOPA, 4-hydroxyphenylacetaldehyde, and 3,4-dihydroxyphenylacetaldehyde. Accordingly, the present disclosure further provides, in at least one aspect:
(I) at least one embodiment of making (S)-norcoclaurine comprising:
  (a) providing L-tyrosine; and
  (b) contacting L-tyrosine with a mixture of enzymes comprising catalytic quantities of the enzymes TYR, DODC, TYDC, MAO, and NCS under reaction conditions permitting an enzyme catalyzed chemical conversion of L-tyrosine to (S)-norcoclaurine.
(II) at least one embodiment of making dopamine comprising:
  (a) providing L-tyrosine; and
  (b) contacting L-tyrosine with a mixture of enzymes comprising catalytic quantities of the enzymes TYR and DODC under reaction conditions permitting an enzyme catalyzed chemical conversion of L-tyrosine to dopamine.
(III) at least one embodiment of making 4-hydroxyphenylacetaldehyde comprising:
  (a) providing L-tyrosine; and
  (b) contacting L-tyrosine with catalytic quantities of enzymes TYDC and MAO under reaction conditions permitting an enzyme catalyzed chemical conversion of L-tyrosine to 4-hydroxyphenylacetaldehyde; and
(IV) at least one embodiment of making L-DOPA comprising:
  (a) providing L-tyrosine; and
  (b) contacting L-tyrosine with catalytic quantities of the enzyme TYR under reaction conditions permitting an enzyme catalyzed chemical conversion of L-tyrosine to L-DOPA;
(V) at least one embodiment of making tyramine comprising:
  (a) providing L-tyrosine; and
  (b) contacting L-tyrosine with catalytic quantities of the enzyme TYDC under reaction conditions permitting an enzyme catalyzed chemical conversion of L-tyrosine to tyramine;
(VI) at least one embodiment of making (S)-norlaudanosoline comprising:
  (a) providing L-tyrosine; and
  (b) contacting L-tyrosine with a mixture of enzymes comprising catalytic quantities of the enzymes TYR, DODC, MAO, and NCS under reaction conditions permitting an enzyme catalyzed chemical conversion of L-tyrosine to (S)-norlaudanosoline; and
(VII) at least one embodiment of making 3,4-dihydroxyphenylacetaldehyde comprising:
  (a) providing L-tyrosine; and
  (b) contacting L-tyrosine with a mixture of enzymes comprising catalytic quantities of the enzymes TYR, DODC and MAO under reaction conditions permitting an enzyme catalyzed chemical conversion of L-tyrosine to 3,4-dihydroxy-phenylacetaldehyde.

In yet a further aspect, the present disclosure provides in at least one embodiment, the aforementioned embodiments wherein the enzyme, or mixtures comprising catalytic quantities of enzymes, as the case may be, and the (S)-norcoclaurine and/or (S)-norlaudanosoline synthesis intermediates are brought together under in vitro reaction conditions. In another embodiment, the enzyme, or mixtures comprising catalytic quantities of enzymes, as the case may be, and the (S)-norcoclaurine and/or (S)-norlaudanosoline synthesis intermediates are brought together under in vivo reaction conditions.

The present disclosure further provides in substantially pure form (S)-norcoclaurine and (S)-norlaudanosoline, and the following (S)-norcoclaurine and/or (S)-norlaudanosoline synthesis intermediates: L-DOPA; dopamine; tyramine; 4-hydroxyphenylacetaldehyde, and 3,4-hydroxyphenylacetaldehyde.

Other features and advantages of the present disclosure will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

For a better understanding of the various example embodiments described herein, and to show more clearly how these various embodiments may be carried into effect, reference will be made, by way of example, to the accompanying figures which show at least one example embodiment, and the figures will now be briefly described. It should be understood that the figures herein are provided for illustration purposes only and are not intended to limit the present disclosure.

FIG. 6B) and truncated NCS sequences FIG. 6C. Intact NCS sequences used are SCANCS1 (SEQ.ID. NO: 14); SDINSC1 (SEQ.ID. NO: 17); CCHNCS2 (SEQ.ID. NO: 28); NDONCS3 (SEQ.ID. NO: 34); PBRNCS5 (SEQ.ID. NO: 13); and PSONCS3 (SEQ.ID.

NO: 42), TFLNCS2 (SEQ.ID. NO: 87); CMANCS1 (SEQ.ID. NO: 85); PBRNSC3 (SEQ.ID. NO: 83); ECANCS1 (SEQ.ID. NO: 56); CCHNCS1 (SEQ.ID. NO: 65); PBRNCS4 (SEQ.ID. NO: 50); CCHNCS5 (SEQ.ID. NO: 92); XSINCS1 (SEQ.ID. NO: 93). Truncated sequences are TFINCSΔ19 (SEQ.ID NO: 112); TFINCS2Δ25 (SEQ.ID. NO: 109); CMANCS1Δ25 (SEQ.ID. NO: 105); PBRNCS3Δ25 (SEQ.ID. NO: 107); ECANCS1Δ25 (SEQ.ID. NO: 106); CCHNCS1Δ25 (SEQ.ID. NO: 103); PBRNCS4Δ25 (SEQ.ID. NO: 108); CCHNCS5Δ25 (SEQ.ID. NO: 104); XSINCS1Δ25 (SEQ.ID. NO: 113).

Figure 7A:
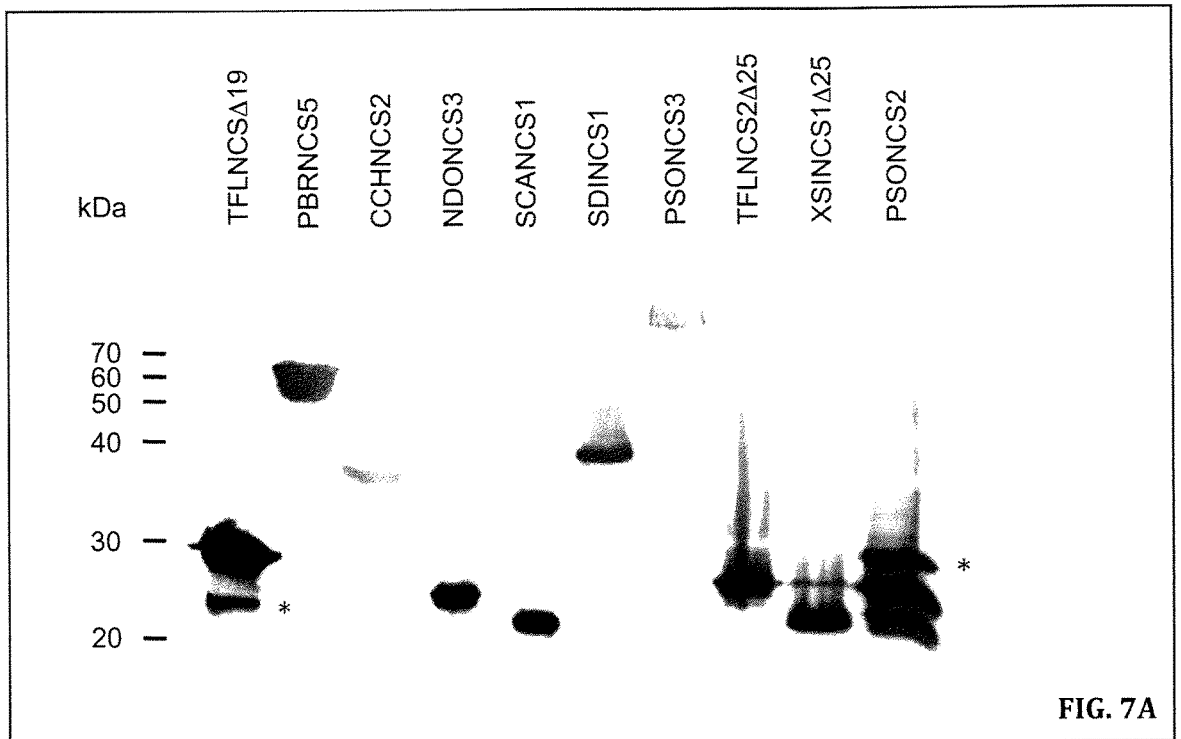
Figure 7B:
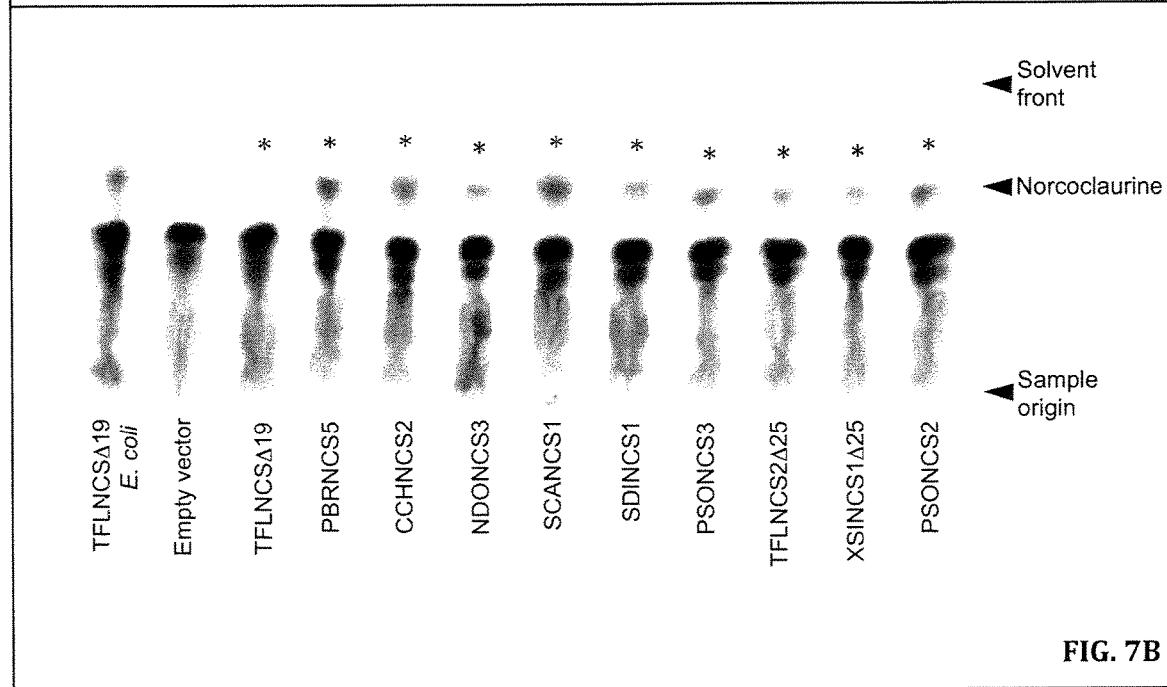

FIG. 7A-B depicts an immunoblot using anti-His-tag antibodies showing expression of NCS polypeptides in yeast (FIG. 7A) and TLPC plates showing norcoclaurine production in yeast using various NCS polypeptides (FIG. 7B). Expression is shown using TFINCSΔ19 (SEQ.ID. NO: 112); PBRNCS5 (SEQ.ID. NO: 13); CCHNCS2 (SEQ.ID. NO: 28); NDONCS3 (SEQ.ID. NO: 34); SCANCS1 (SEQ.ID. NO: 14); SDINCS1 (SEQ.ID.NO: 89), PSONCS3 (SEQ.ID.NO: 42); TFINCS2Δ25 (SEQ.ID. NO: 109); XSINCS1Δ25 (SEQ.ID. NO: 113) and PSONCS2 (SEQ.ID. NO: 111) polypeptides. PBRNCS5 (SEQ.ID. NO: 13); CCHNCS2 (SEQ.ID. NO: 28); NDONCS3 (SEQ.ID. NO: 34); and SCANCS1 (SEQ.ID. NO: 14) polypeptides. Norcoclaurine production is shown using TFINCSΔ19 (SEQ.ID. NO: 112); PBRNCS5 (SEQ.ID. NO: 13); CCHNCS2 (SEQ.ID. NO: 28); NDONCS3 (SEQ.ID. NO: 34); SCANCS1 (SEQ.ID. NO: 14); SDINCS1 (SEQ.ID.NO: 89), PSONCS3 (SEQ.ID.NO: 42); TFINCS2Δ25 (SEQ.ID. NO: 109); XSINCS1Δ25 (SEQ.ID. NO: 113) and PSONCS2 (SEQ.ID. NO: 111) PBRNCS5 (SEQ.ID. NO: 13); CCHNCS2 (SEQ.ID. NO: 28); NDONCS3 (SEQ.ID. NO: 34); and SCANCS1 (SEQ.ID. NO: 14) polypeptides. Controls as are yeast transformed with a vector not comprising an NCS gene ("empty vector"); and yeast and *E. coli* expressing TFLNCSΔ19 (SEQ.ID. NO: 112).

DETAILED DESCRIPTION OF THE DISCLOSURE

Various compositions and methods will be described below to provide an example of an embodiment of each claimed subject matter. No embodiment described below limits any claimed subject matter and any claimed subject matter may cover methods, processes, compositions or systems that differ from those described below. The claimed subject matter is not limited to compositions or methods having all of the features of any one composition, method, system or process described below or to features common to multiple or all of the compositions, systems or methods described below. It is possible that a composition, system, method or process described below is not an embodiment of any claimed subject matter. Any subject matter disclosed in a composition, system, method or process described below that is not claimed in this document may be the subject matter of another protective instrument, for example, a continuing patent application, and the applicants, inventors or owners do not intend to abandon, disclaim or dedicate to the public any such subject matter by its disclosure in this document.

All publications, patents and patent applications are herein incorporated by reference in their entirety to the same extent as if each individual publication, patent or patent application was specifically and individually indicated to be incorporated by reference in its entirety.

Definitions

Figure 3A:
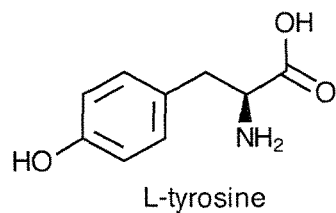
FIG. 3A-H depicts the chemical structures for (S)-norcoclaurine (FIG. 3F), (S)-norlaudanosoline (FIG. 3H), and the following synthesis intermediates thereof: L-tyrosine (FIG. 3A); tyramine (FIG. 3B); L-DOPA (FIG. 3C); dopamine (FIG. 3E), 4-hydroxyphenylacetaldehyde (FIG. 3D); and 3,4-dihydroxyphenylacetaldehyde (FIG. 3G), respectively.
Figure 3B:
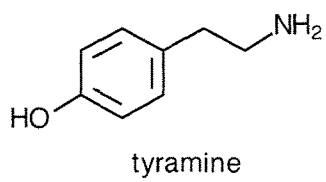
Figure 3C:
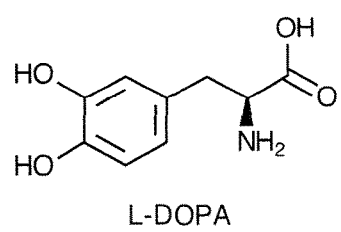
Figure 3D:
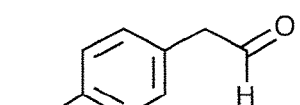
Figure 3E:
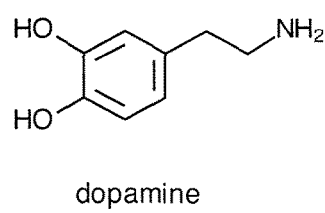
Figure 3F:
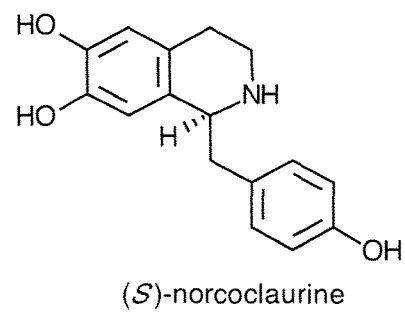

The term "(S)-norcoclaurine" as used herein refers to a chemical compound having the chemical structure depicted in FIG. 3F.

Figure 3G:
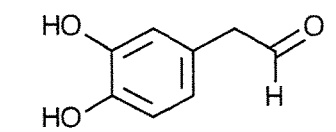
Figure 3H:
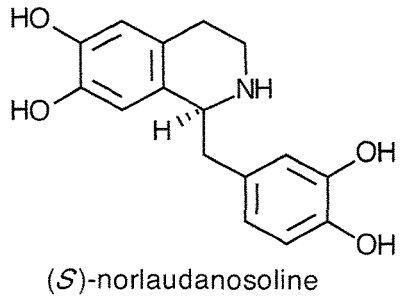

The term "(S)-norlaudanosoline" as used herein refers to a chemical compound having the chemical structure depicted in FIG. 3H.

The term "L-tyrosine" as used herein refers to a chemical compound having the chemical structure depicted in FIG. 3A.

The term "tyramine" as used herein refers to a chemical compound having the chemical structure depicted in FIG. 3B.

The terms "L-DOPA" and "L-3,4-dihydroxyphenylalanine", which may be used interchangeably herein, refer to a chemical compound having the chemical structure depicted in FIG. 3C.

The term "dopamine" as used herein refers to a chemical compound having the chemical structure depicted in FIG. 3E.

The terms "4-hydroxyphenylacetaldehyde" or "4HPAA", which may be used interchangeably herein, refer to a chemical compound having the chemical structure depicted in FIG. 3D.

The terms "3,4-dihydroxyphenylacetaldehyde" or "3,4DHPAA", which may be used interchangeably herein, refer to a chemical compound having the chemical structure depicted in FIG. 3G.

Figure 1:
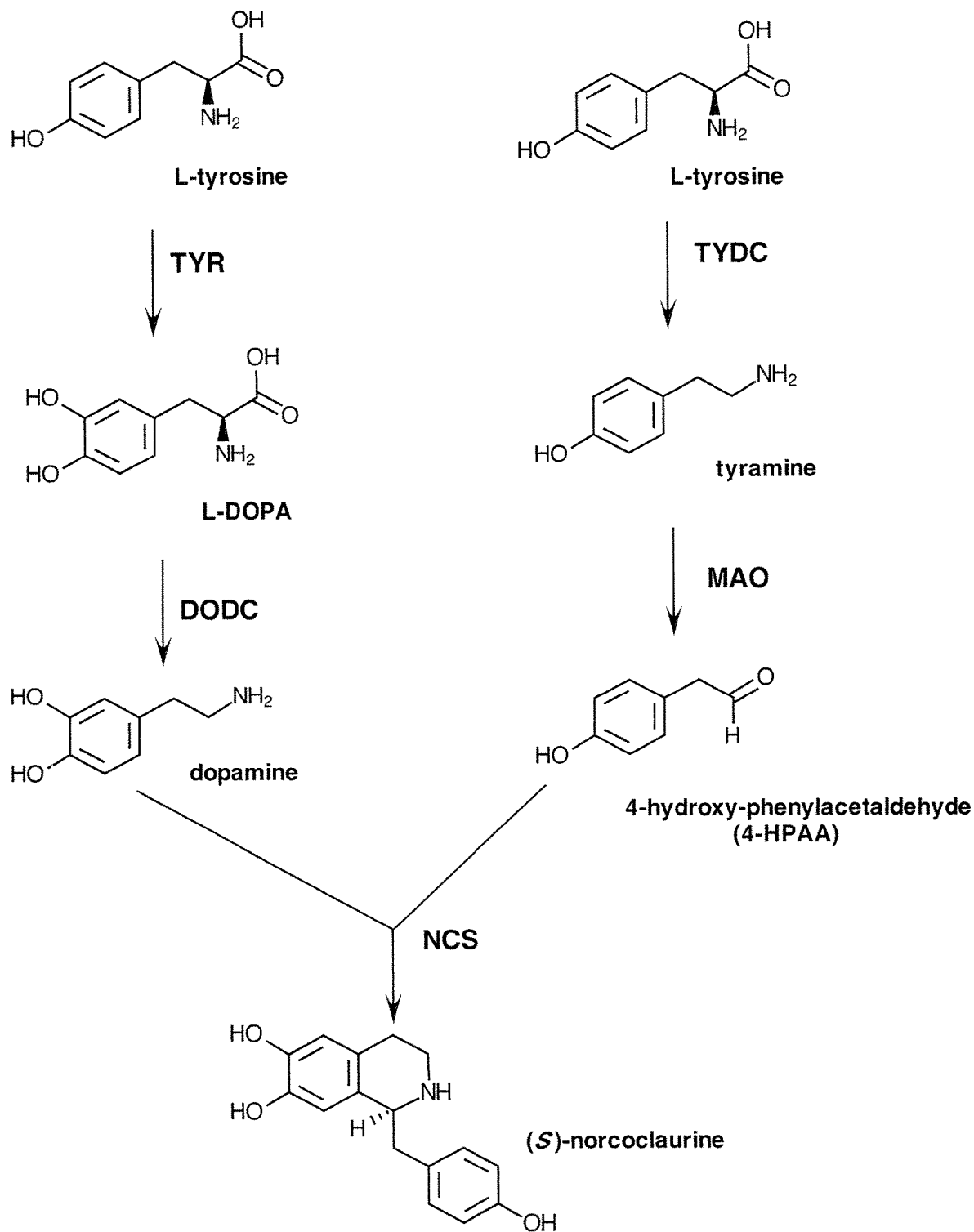
FIG. 1 depicts a synthesis pathway for the manufacture of (S)-norcoclaurine and synthesis intermediates thereof. Included are the chemical structures of the synthesis intermediates and enzymes capable of catalyzing chemical conversion of the synthesis intermediates.
Figure 2:
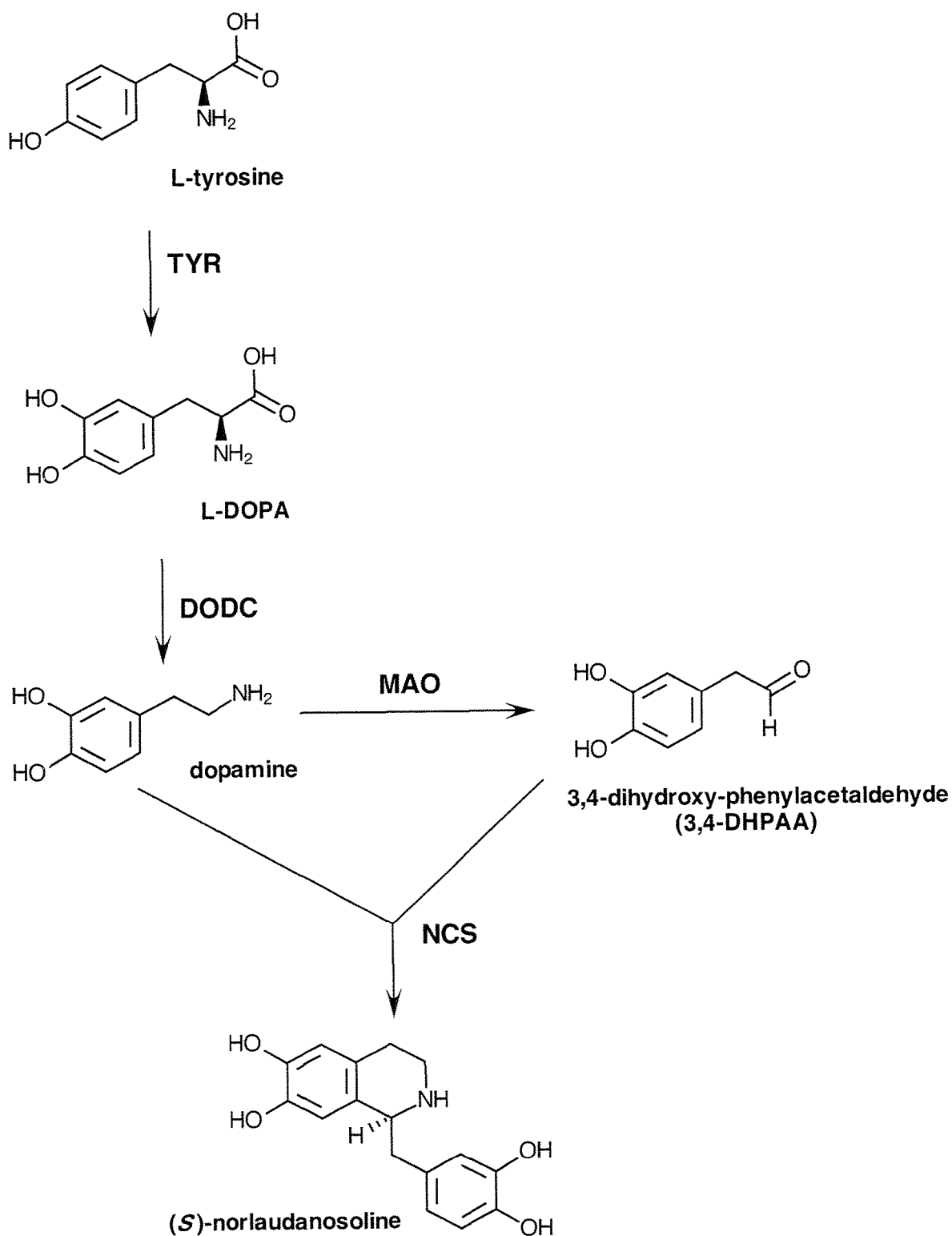
FIG. 2 depicts a synthesis pathway for the manufacture of (S)-norlaudanosoline and synthesis intermediates thereof. Included are the chemical structures of the synthesis intermediates and enzymes capable of catalyzing chemical conversion of the synthesis intermediates.

The terms "(S)-norcoclaurine synthesis pathway" and "(S)-norlaudanosoline synthesis pathway", refer to the metabolic pathway for the synthesis of "(S)-norcoclaurine" depicted in FIG. 1, and "(S)-norlaudanosoline" depicted in FIG. 2, respectively. When a first chemical compound within the (S)-norcoclaurine or (S)-norlaudanosoline synthesis pathways is referenced as "upstream" of a second chemical compound in the pathway, it is meant herein that synthesis of the first chemical compound precedes synthesis of the second chemical compound. Conversely, when a first chemical compound is referenced as "downstream" from a second chemical compound in the (S)-norcoclaurine or (S)-norlaudanosoline synthesis pathways, it is meant herein that synthesis of the second chemical compound precedes synthesis of the first chemical compound.

The terms "(S)-norcoclaurine pathway precursor" and "(S)-norlaudanosoline pathway precursor", as used herein, refer to any of the chemical compounds in the (S)-norcoclaurine or (S)-norlaudanosoline synthesis pathways set forth in FIG. 3A; FIG. 3B; FIG. 3C; FIG. 3D; FIG. 3E; and FIG. 3G; in conjunction with the term "(S)-norcoclaurine synthesis intermediate", "(S)-norcoclaurine pathway precursor" refers to a compound synthesized upstream of a (S)-norcoclaurine synthesis intermediate.

The terms "(S)-norcoclaurine synthesis intermediate" and "(S)-norlaudanosoline synthesis intermediate" as used herein refer to any of the chemical compounds in the (S)-norcoclaurine or (S)-norlaudanosoline synthesis pathways set forth in FIG. 3B; FIG. 3C; FIG. 3D; FIG. 3E and FIG. 3G; in conjunction with the terms "(S)-norcoclaurine pathway precursor" or "(S)-norlaudanosoline pathway precursor", "(S)-norcoclaurine synthesis intermediate" and "(S)-norlaudanosoline synthesis intermediate" refer to a compound synthesized downstream of a (S)-norcoclaurine or (S)-norlaudanosoline pathway precursor.

The terms "tyrosine hydroxylase", polyphenol oxidase" and "TYR", which may be used interchangeably herein, refer to any and all enzymes comprising a sequence of amino acid residues which is (i) substantially identical to the amino acid sequences constituting any TYR polypeptide set forth herein, including, for example, SEQ.ID. NO: 98, or (ii) encoded by a nucleic acid sequence capable of hybridizing under at least moderately stringent conditions to any nucleic acid sequence encoding any TYR polypeptide set forth herein, but for the use of synonymous codons.

The terms "tyrosine decarboxylase" and "TYDC", as may be used interchangeably herein, refer to any and all enzymes comprising a sequence of amino acid residues which is (i) substantially identical to the amino acid sequences constituting any TYDC polypeptide set forth herein, including, for example, SEQ.ID. NO: 102 or (ii) encoded by a nucleic acid sequence capable of hybridizing under at least moderately stringent conditions to any nucleic acid sequence encoding any TYDC polypeptide set forth herein, but for the use of synonymous codons.

The terms "dihydroxyphenylalanine decarboxylase", "DOPA decarboxylase" and "DODC", as may be used interchangeably herein, refer to any and all enzymes comprising a sequence of amino acid residues which is (i) substantially identical to the amino acid sequences constituting any DODC polypeptide set forth herein, including, for example, SEQ.ID. NO: 100 or (ii) encoded by a nucleic acid sequence capable of hybridizing under at least moderately stringent conditions to any nucleic acid sequence encoding any DODC polypeptide set forth herein, but for the use of synonymous codons.

The terms "monoamine oxidase" or "MAO", as may be used interchangeably herein, refer to any and all enzymes comprising a sequence of amino acid residues which is (i) substantially identical to the amino acid sequences constituting any MAO polypeptide set forth herein, including, for example, SEQ.ID. NO: 96, or (ii) encoded by a nucleic acid sequence capable of hybridizing under at least moderately stringent conditions to any nucleic acid sequence encoding any MAO polypeptide set forth herein, but for the use of synonymous codons.

The terms "norcoclaurine synthase" and "NCS", as may be used interchangeably herein, refer to any and all enzymes comprising a sequence of amino acid residues which is (i) substantially identical to the amino acid sequences constituting any NCS polypeptide set forth herein, including, for example, SEQ.ID. NO: 1 to SEQ.ID. NO: 42, or (ii) encoded by a nucleic acid sequence capable of hybridizing under at least moderately stringent conditions to any nucleic acid sequence encoding any NCS polypeptide set forth herein, but for the use of synonymous codons.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present disclosure may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil, and xanthine and hypoxanthine.

The herein interchangeably used terms "nucleic acid sequence encoding TYR" and "nucleic acid sequence encoding a TYR polypeptide", refer to any and all nucleic acid sequences encoding a TYR polypeptide, including, for example, SEQ.ID. NO: 97. Nucleic acid sequences encoding a TYR polypeptide further include any and all nucleic acid sequences which (i) encode polypeptides that are substantially identical to the TYR polypeptide sequences set forth herein; or (ii) hybridize to any TYR nucleic acid sequences set forth herein under at least moderately stringent hybridization conditions or which would hybridize thereto under at least moderately stringent conditions but for the use of synonymous codons.

The herein interchangeably used terms "nucleic acid sequence encoding TYDC" and "nucleic acid sequence encoding a TYDC polypeptide", refer to any and all nucleic acid sequences encoding a TYDC polypeptide, including, for example, SEQ.ID. NO: 101. Nucleic acid sequences encoding a TYDC polypeptide further include any and all nucleic acid sequences which (i) encode polypeptides that are substantially identical to the TYDC polypeptide sequences set forth herein; or (ii) hybridize to any TYDC nucleic acid sequences set forth herein under at least moderately stringent hybridization conditions or which would hybridize thereto under at least moderately stringent conditions but for the use of synonymous codons.

The herein interchangeably used terms "nucleic acid sequence encoding MAO" and "nucleic acid sequence encoding a MAO polypeptide", refer to any and all nucleic acid sequences encoding an MAO polypeptide, including, for example, SEQ.ID. NO: 95. Nucleic acid sequences encoding a MAO polypeptide further include any and all nucleic acid sequences which (i) encode polypeptides that are substantially identical to the NCS polypeptide sequences set forth herein; or (ii) hybridize to any MAO nucleic acid sequences set forth herein under at least moderately stringent hybridization conditions or which would hybridize thereto under at least moderately stringent conditions but for the use of synonymous codons.

The herein interchangeably used terms "nucleic acid sequence encoding NCS" and "nucleic acid sequence encoding an NCS polypeptide", refer to any and all nucleic acid sequences encoding an NCS polypeptide, including, for example, SEQ.ID. NO: 43 to SEQ.ID. NO: 80. Nucleic acid sequences encoding an NCS polypeptide further include any and all nucleic acid sequences which (i) encode polypeptides that are substantially identical to the NCS polypeptide sequences set forth herein; or (ii) hybridize to any NCS nucleic acid sequences set forth herein under at least moderately stringent hybridization conditions or which would hybridize thereto under at least moderately stringent conditions but for the use of synonymous codons.

By the term "substantially identical" it is meant that two polypeptide sequences preferably are at least 70% identical, and more preferably are at least 85% identical and most preferably at least 95% identical, for example 96%, 97%, 98% or 99% identical. In order to determine the percentage of identity between two polypeptide sequences the amino acid sequences of such two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990: 215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences wherein at least 50% of the total length of one of the two sequences is involved in the alignment.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/1), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5× Denhardt's solution/1.0% SDS at Tm (based on the above equation)−5° C., followed by a wash of 0.2×SSC/ 0.1% SDS at 60° C. Moderately stringent hybridization conditions include a washing step in 3×SSC at 42° C. It is understood however that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1.-6.3.6 and in: Sambrook et al., Molecular Cloning, a Laboratory Manual, Cold Spring Harbor Laboratory Press, 1989, Vol. 3.

The term "chimeric" as used herein in the context of nucleic acid sequences refers to at least two linked nucleic acid sequences, which are not naturally linked. Chimeric nucleic acid sequences include linked nucleic acid sequences of different natural origins. For example, a nucleic acid sequence constituting a yeast promoter linked to a nucleic acid sequence encoding a TYR protein is considered chimeric. Chimeric nucleic acid sequences also may comprise nucleic acid sequences of the same natural origin, provided they are not naturally linked. For example, a nucleic acid sequence constituting a promoter obtained from a particular cell-type may be linked to a nucleic acid sequence encoding a polypeptide obtained from that same cell-type, but not normally linked to the nucleic acid sequence constituting the promoter. Chimeric nucleic acid sequences also include nucleic acid sequences comprising any naturally occurring nucleic acid sequence linked to any non-naturally occurring nucleic acid sequence.

The terms "substantially pure" and "isolated", as may be used interchangeably herein describe a compound, e.g., a pathway synthesis intermediate or a polypeptide, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis.

The term "in vivo" as used herein to describe methods of making (S)-norcoclaurine, (S)-norlaudanosoline, or synthesis intermediates thereof refers to contacting a (S)-norcoclaurine pathway precursor, or a (S)-norlaudanosoline pathway precursor with an enzyme capable of catalyzing conversion of a (S)-norcoclaurine or (S)-norlaudanosoline precursor within a living cell, including, for example, a microbial cell or a plant cell, to form a (S)-norcoclaurine synthesis intermediate or a (S)-norlaudanosoline synthesis intermediate, or to form (S)-norcoclaurine or (S)-norlaudanosoline.

The term "in vitro" as used herein to describe methods of making (S)-norcoclaurine, (S)-norlauanosoline, or synthesis intermediates thereof refer to contacting a (S)-norcoclaurine pathway precursor or a (S)-norlauanosoline pathway precursor with an enzyme capable of catalyzing conversion of a (S)-norcoclaurine or (S)-norlauanosoline precursor in an environment outside a living cell, including, without limitation, for example, in a microwell plate, a tube, a flask, a beaker, a tank, a reactor and the like, to form a (S)-norcoclaurine synthesis intermediate or (S)-norlauanosoline synthesis intermediate, or to form (S)-norcoclaurine or (S)-norlauanosoline.

It should be noted that terms of degree such as "substantially", "about" and "approximately" as used herein mean a reasonable amount of deviation of the modified term such that the end result is not significantly changed. These terms of degree should be construed as including a deviation of the modified term if this deviation would not negate the meaning of the term it modifies.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

General Implementation

As hereinbefore mentioned, the present disclosure relates to the secondary metabolites (S)-norcoclaurine, (S)-norlaudanosoline, and synthesis intermediates thereof, as well as to methods of making (S)-norcoclaurine, (S)-norlaudanosoline, and synthesis intermediates thereof. The current disclosure further relates to certain enzymes capable of catalyzing chemical reactions resulting in the conversion of (S)-norcoclaurine and (S)-norlaudanosoline synthesis intermediates to form (S)-norcoclaurine and (S)-norlaudanosoline, respectively. The herein provided methods represent a novel and efficient means of manufacturing (S)-norcoclaurine, (S)-norlaudanosoline, and synthesis intermediates thereof. The methods provided herein do not rely on chemical synthesis and may be conducted at commercial scale. To the best of the inventor's knowledge, the current disclosure provides for the first time a methodology to manufacture NCS, (S)-norcoclaurine, and (S)-norlaudanosoline using yeast cells not normally capable of synthesizing (S)-norcoclaurine or (S)-norlaudanosoline. Such cells may be used as a source whence (S)-norcoclaurine and/or (S)-norlaudanosoline may be economically extracted. (S)-norcoclaurine and/or (S)-norlaudanosoline produced in accordance with the present disclosure is useful inter alia in the manufacture of pharmaceutical compositions.

Accordingly, the present disclosure provides, in at least one aspect, at least one embodiment of making (S)-norcoclaurine, (S)-norlaudanosoline, or a synthesis intermediate thereof comprising:
- (a) providing at least one (S)-norcoclaurine or (S)-norlaudanosoline biosynthetic precursor selected from L-tyrosine or a first L-tyrosine derivative; and
- (b) contacting the (S)-norcoclaurine or (S)-norlaudanosoline biosynthetic precursor with at least one of the enzymes selected from the group of enzymes consisting of (i) TYR; (ii) TYDC; (iii) DODC; (iv) MAO; and (v) NCS under reaction conditions permitting the catalysis of the (S)-norcoclaurine or (S)-norlaudanosoline biosynthetic precursor to form (S)-norcoclaurine, (S)-norlaudanosoline, or a synthesis intermediate thereof, wherein the synthesis intermediate is a second L-tyrosine derivative; and
wherein the first and second L-tyrosine derivative have the chemical formula (I):

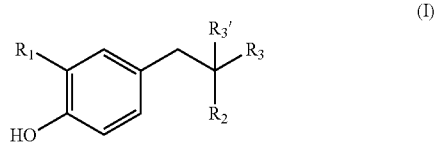

wherein $R_1$ represents hydrogen or hydroxyl;
wherein $R_2$ represents hydrogen or an amino group —($NH_2$); and
wherein $R_3$ represents a carboxyl group —(COOH), or an amino group —($NH_2$);
wherein $R_3'$ represents a hydrogen atom; or
$R_3$ and $R_3'$ taken together, form a carbonyl group.

In preferred embodiments of the disclosure, the first and/or second L-tyrosine derivative is L-DOPA; tyramine; dopamine; 4-hydroxyphenylacetaldehyde, or 3,4-dihydroxyphenylacetaldehyde.

(S)-Norcoclaurine Synthesis

In one embodiment of the present disclosure, there is provided a method of making (S)-norcoclaurine comprising:
- (a) providing L-tyrosine; and
- (b) contacting L-tyrosine with a mixture of enzymes comprising catalytic quantities of the enzymes (i) TYR; (ii) TYDC; (iii) DODC; (iv) MAO; and (v) NCS; under reaction conditions permitting an enzyme catalyzed chemical conversion of L-tyrosine to (S)-norcoclaurine.

In a further embodiment, there is provided a method of making (S)-norcoclaurine comprising:
- (a) providing L-DOPA and L-tyrosine; and
- (b) contacting the L-DOPA and L-tyrosine with a mixture of enzymes comprising catalytic quantities of the enzymes (i) TYDC; (ii) DODC; (iv) MAO; and (iv) NCS under reaction conditions permitting an enzyme catalyzed chemical conversion of L-DOPA and L-tyrosine to (S)-norcoclaurine.

In a further embodiment, there is provided a method of making (S)-norcoclaurine comprising:
- (a) providing dopamine and L-tyrosine; and
- (b) contacting the dopamine and L-tyrosine with a mixture of enzymes comprising catalytic quantities of the enzymes (i) TYDC; (ii) MAO; and (iii) NCS; under reaction conditions permitting an enzyme catalyzed chemical conversion of dopamine and L-tyrosine to (S)-norcoclaurine.

In a further embodiment there is provided a method of making (S)-norcoclaurine comprising:
- (a) providing dopamine and tyramine; and
- (b) contacting dopamine and tyramine with catalytic quantities of the enzymes (i) MAO and (ii) NCS under reaction conditions permitting an enzyme catalyzed chemical conversion of dopamine and tyramine to (S)-norcoclaurine.

In a further embodiment, there is provided a method of making (S)-norcoclaurine comprising:
- (a) providing L-tyrosine and tyramine; and
- (b) contacting dopamine and tyramine with catalytic quantities of the enzymes (i) TYR, (ii) DODC; (iii) MAO and (iv) NCS under reaction conditions permitting an enzyme catalyzed chemical conversion of L-tyrosine and tyramine to (S)-norcoclaurine.

In a further embodiment, there is provided a method of making (S)-norcoclaurine comprising:
- (a) providing L-DOPA and tyramine; and
- (b) contacting L-DOPA and tyramine with catalytic quantities of the enzymes (i) DODC; (ii) MAO and (iii) NCS under reaction conditions permitting an enzyme catalyzed chemical conversion of L-DOPA and tyramine to (S)-norcoclaurine.

In a further embodiment, there is provided a method of making (S)-norcoclaurine comprising:
- (a) providing L-tyrosine and 4-hydroxyphenylacetaldehyde; and
- (b) contacting L-tyrosine and 4-hydroxyphenylacetaldehyde with catalytic quantities of the enzymes (i) TYR; (ii) DODC and (iii) NCS under reaction conditions permitting an enzyme catalyzed chemical conversion of L-tyrosine and 4-hydroxyphenylacetaldehyde to (S)-norcoclaurine.

In a further embodiment, there is provided a method of making (S)-norcoclaurine comprising:
- (a) providing L-DOPA and 4-hydroxyphenylacetaldehyde; and
- (b) contacting L-DOPA and 4-hydroxyphenylacetaldehyde with catalytic quantities of the enzymes (i) DODC and (iii) NCS under reaction conditions permitting an enzyme catalyzed chemical conversion of L-DOPA and 4-hydroxyphenylacetaldehyde to (S)-norcoclaurine.

In a further embodiment, there is provided a method of making (S)-norcoclaurine comprising:
- (a) providing dopamine and 4-hydroxyphenylacetaldehyde; and
- (b) contacting the dopamine and 4-hydroxyphenylacetaldehyde with catalytic quantities of the enzyme NCS under reaction conditions permitting an enzyme catalyzed chemical conversion of dopamine and 4-hydroxyphenylacetaldehyde to (S)-norcoclaurine.

The foregoing embodiments of the disclosure to make (S)-norcoclaurine are further illustrated in Table A.

The foregoing reactions may be performed under in vivo or in vitro conditions as hereinafter further detailed.

Dopamine Synthesis

In one embodiment of the disclosure, there is provided a method making dopamine. Accordingly there is provided a method of making dopamine comprising:

(a) providing L-tyrosine; and
(b) contacting the L-tyrosine, with a mixture of enzymes comprising catalytic quantities of the enzymes (i) DODC; and (ii) TYR under reaction conditions permitting an enzyme catalyzed chemical conversion of L-tyrosine to dopamine;

In a further embodiment, there is provided a method of making dopamine comprising:
(a) providing L-DOPA; and
(b) contacting the L-DOPA with catalytic quantities of the enzyme DO DC under reaction conditions permitting an enzyme catalyzed chemical conversion of L-DOPA to dopamine.

The foregoing reactions may be performed under in vivo or in vitro conditions as hereinafter further detailed.

4-Hydroxyphenylacetaldehyde Synthesis

In one embodiment of the disclosure, there is provided a method making 4-hydroxyphenylacetaldehyde. Accordingly, there is provided a method of making 4-hydroxyphenylacetaldehyde comprising:
(a) providing L-tyrosine; and
(b) contacting the L-tyrosine with catalytic quantities of the enzymes (i) TYDC and (ii) MAO under reaction conditions permitting an enzyme catalyzed chemical conversion of L-tyrosine to 4-hydroxyphenylacetaldehyde.

In a further embodiment, there is provided a method of making 4-hydroxyphenylacetaldehyde comprising:
(a) providing tyramine; and
(b) contacting the tyramine with catalytic quantities of the enzyme MAO under reaction conditions permitting an enzyme catalyzed chemical conversion of tyramine to 4-hydroxyphenylacetaldehyde.

The foregoing reaction may be performed under in vivo or in vitro conditions as hereinafter further detailed.

L-DOPA Synthesis

In one embodiment of the disclosure, there is provided a method making L-DOPA. Accordingly, there is provided a method of making L-DOPA comprising:
(a) providing-tyrosine; and
(b) contacting the L-tyrosine with catalytic quantities of the enzyme TYR under reaction conditions permitting an enzyme catalyzed chemical conversion of L-tyrosine to form L-DOPA.

The foregoing reaction may be performed under in vivo or in vitro conditions as hereinafter further detailed.

Tyramine Synthesis

In one embodiment of the disclosure, there is provided a method making tyramine. Accordingly, there is provided a method of making tyramine comprising:
(a) providing L-tyrosine; and
(b) contacting the L-tyrosine with catalytic quantities of the enzyme TYDC under reaction conditions permitting an enzyme catalyzed chemical conversion of L-tyrosine to form tyramine.

The foregoing reaction may be performed under in vivo or in vitro conditions as hereinafter further detailed.

(S)-Norlaudanosoline Synthesis

In a further embodiment, there is provided a method of making (S)-norlaudanosoline comprising:
(a) providing L-tyrosine; and
(b) contacting the L-tyrosine with catalytic quantities of the enzymes (i) TYR; (ii) DODC; (iii) MAO and (iv) NCS under reaction conditions permitting an enzyme catalyzed chemical conversion of L-tyrosine to (S)-norlaudanosoline.

In a further embodiment, there is provided a method of making (S)-norlaudanosoline comprising:
(a) providing L-DOPA; and
(b) contacting the L-DOPA with catalytic quantities of the enzymes (i) DODC; (ii) MAO and (iii) NCS under reaction conditions permitting an enzyme catalyzed chemical conversion of L-DOPA to (S)-norlaudanosoline.

In a further embodiment, there is provided a method of making (S)-norlaudanosoline comprising:
(a) providing dopamine; and
(b) contacting the dopamine with catalytic quantities of the enzymes (i) MAO and (ii) NCS under reaction conditions permitting an enzyme catalyzed chemical conversion of dopamine to (S)-norlaudanosoline;

In a further embodiment, there is provided a method of making (S)-norlaudanosoline comprising:
(a) providing dopamine and 3,4-dihydroxyphenylacetaldehyde; and
(b) contacting the dopamine and 3,4-dihydroxyphenylacetaldehyde with catalytic quantities of the enzyme NCS under reaction conditions permitting an enzyme catalyzed chemical conversion of dopamine and 4-hydroxyphenylacetaldehyde to (S)-norlaudanosoline.

In a further embodiment, there is provided a method of making (S)-norlaudanosoline comprising:
(a) providing L-tyrosine and 3,4-dihydroxyphenylacetaldehyde; and
(b) contacting the L-tyrosine and 3,4-dihydroxyphenylacetaldehyde with catalytic quantities of the enzymes (i) TYR; (ii) DODC and (iii) NCS under reaction conditions permitting an enzyme catalyzed chemical conversion of L-tyrosine and 4-hydroxyphenylacetaldehyde to (S)-norlaudanosoline.

In a further embodiment, there is provided a method of making (S)-norlaudanosoline comprising:
(a) providing L-DOPA and 3,4-dihydroxyphenylacetaldehyde; and
(b) contacting the L-DOPA and 3,4-dihydroxyphenylacetaldehyde with catalytic quantities of the enzymes (i) DODC and (ii) NCS under reaction conditions permitting an enzyme catalyzed chemical conversion of L-DOPA and 4-hydroxyphenylacetaldehyde to (S)-norlaudanosoline.

The foregoing embodiments of the disclosure to make (S)-norlaudanosoline are further illustrated in Table B.

The foregoing reactions may be performed under in vivo or in vitro conditions as hereinafter further detailed.

3,4-Dihydroxyphenylacetaldehyde Synthesis

In one embodiment of the disclosure, there is provided a method making 3,4-dihydroxyphenylacetaldehyde. Accordingly there is provided a method of making 3,4-dihydroxyphenylacetaldehyde comprising:
(a) providing L-tyrosine; and
(b) contacting the L-tyrosine with catalytic quantities of the enzymes (i) TYR; (ii) DODC; and (iii) MAO under reaction conditions permitting an enzyme catalyzed chemical conversion of L-tyrosine to 3,4-dihydroxyphenylacetaldehyde.

In a further embodiment, there is provided a method of making 3,4-dihydroxyphenylacetaldehyde comprising:
(a) providing L-DOPA; and
(b) contacting the L-DOPA with catalytic quantities of the enzymes (i) DODC; and (ii) MAO under reaction conditions permitting an enzyme catalyzed chemical conversion of L-DOPA to 3,4-dihydroxyphenylacetaldehyde.

In a further embodiment, there is provided a method of making 3,4-dihydroxyphenylacetaldehyde comprising:
(a) providing dopamine; and
(b) contacting the dopamine with catalytic quantities of the enzyme MAO under reaction conditions permitting an enzyme catalyzed chemical conversion of dopamine to 3,4-dihydroxyphenylacetaldehyde.

The foregoing reaction may be performed under in vivo or in vitro conditions as hereinafter further detailed.

In Vitro Production of (S)-Norcoclaurine, (S)-Norlaudanosoline, and Synthesis Intermediates Thereof In accordance with certain aspects of the present disclosure, (S)-norcoclaurine and (S)-norlaudanosoline synthesis precursors and/or (S)-norcoclaurine and (S)-norlaudanosoline synthesis intermediates are brought in contact with catalytic quantities of one or more of the enzymes TYR; DODC; TYDC; MAO; and NCS under reaction conditions permitting an enzyme catalyzed chemical conversion of (S)-norcoclaurine and (S)-norlaudanosoline synthesis precursors and/or (S)-norcoclaurine and (S)-norlaudanosoline synthesis intermediates under in vitro reaction conditions. Under such in vitro reaction conditions the initial reaction constituents are provided in more or less pure form and are mixed under conditions that permit the requisite chemical reactions, upon enzyme catalysis, to substantially proceed. Substantially pure forms of the initial (S)-norcoclaurine and (S)-norlaudanosoline synthesis precursors and/or (S)-norcoclaurine and (S)-norlaudanosoline synthesis intermediates may be chemically synthesized or isolated from natural sources including *Papaver somniferum* and other members of the Papaveraceae, Ranunculacae, Berberidaceae and Menispermaceae families of plants comprising such compounds as desired. Suitable Papaveraceae members include, but are not limited to, species belonging to the genus *Papaver; Argenome; Corydalis; Chelidonium; Eschscholzia; Glaucium; Romeria; Sanguineria;* and *Stylophorum*. Such species may be able to make (S)-norcoclaurine, include, but are not limited to, plant species selected from *Argemone mexicana; Chelidonium majus; Corydalis bulbosa; Corydalis cava; Chordyalis cheilanthifolia; Corydalis ochotenis; Corydalis ophiocarpa; Corydalis platycarpa; Corydalis saxicola; Corydalis tuberosa; Eschscholzia californica; Glaucium flavum; Papaver armeniacum; Papaver bracteatum, Papaver cylindricum; Papaver decaisnei; Papaver fugax; Papaver oreophyllum; Papaver orientate; Papaver paeonifolium; Papaver persicum; Papaver pseudoorientale; Papaver rhoeas; Papaver rhopalothece; Papaver setigerum; Papaver somniferum; Papaver tauricolum; Papaver triniaefolium; Romeria carica; Sanguineria canadensis; Stylophorum diphyllum*. Suitable Ranunculacaea members include, but are not limited to, species belonging to the genus *Thalictrum; Hydrastis; Nigella; Coptis* and *Xanthoriza*. Such species may be able to make (S)-norcoclaurine, include, but not are not limited to, plant species selected from: *Thalictrum flavum; Hydrastis canadensis; Nigella sativa; Coptis japonica* and *Xanthorhiza simplicissima*. Suitable Berberidaceae members include, but are not limited to, species belonging to the genus *Berberis; Mahonia; Jeffersonia* and *Nandina*. Such species may be able to make (S)-norcoclaurine, include, but not are not limited to, plant species selected from *Berberis thunbergii; Mahonia aquifolium; Jeffersonia diphylla,* and *Nandina domestica*. Suitable Menispermaceae members, include, but are not limited to, plant species selected from: *Menispermum, Cocculus, Tinospora* and *Cissempelos*. Such species may be able to make (S)-norcoclaurine, include, but not are not limited to, plant species selected from *Menispermum canadense; Coccolus trilobus; Tinospora cordifolia* and *Cissempelos mucronata*. All of the aforementioned plant species may be able to produce norcoclaurine synthesis pathway precursors and/or (S)-norcoclaurine synthesis intermediates.

In accordance herewith more or less pure forms, of the enzymes may be isolated from natural sources, microbial species, and the hereinbefore mentioned plant species, including *Papaver somniferum,* or they may be prepared recombinantly. Thus, provided herein is further a method for preparing an enzyme selected from the group of enzymes consisting of TYR; DODC; TYDC; MAO; and NCS comprising:
(a) providing a chimeric nucleic acid sequence comprising as operably linked components:
(i) one or more nucleic acid sequences encoding one or more of the polypeptides selected from the group of polypeptides consisting of TYR; DODC; TYDC; MAO; and NCS; and
(ii) one or more nucleic acid sequences capable of controlling expression in a host cell;
(b) introducing the chimeric nucleic acid sequence into a host cell and growing the host cell to produce one or more of the polypeptide selected from the group of polypeptides consisting of TYR; DODC; TYDC; MAO; and NCS; and
(c) recovering TYR; DODC; TYDC; MAO; and NCS from the host cell.

In preferred embodiments, the enzymes are polypeptides having a polypeptide sequence represented by SEQ.ID. NO: 98 (TYR); SEQ.ID. NO: 100 (DODC); SEQ.ID. NO: 102 (TYDC); SEQ.ID. NO: 96 (MAO); and SEQ.ID. NO: 1 to SEQ.ID. NO: 42 (NCS).

Growth of the host cells leads to production of the TYR; DODC; TYDC; MAO and/or NCS. The polypeptides subsequently may be recovered, isolated and separated from other host cell components by a variety of different protein purification techniques including, e.g. ion-exchange chromatography, size exclusion chromatography, affinity chromatography, hydrophobic interaction chromatography, reverse phase chromatography, gel filtration, etc. Further general guidance with respect to protein purification may for example be found in: Cutler, P. Protein Purification Protocols, Humana Press, 2004, Second Ed. Thus substantially pure preparations of the TYR; DODC; TYDC; MAO and/or NCS polypeptides may be obtained. Combinations and mixtures of the TYR; DODC; TYDC; MAO and NCS polypeptides may be prepared and selected in accordance and any and all of the combinations of the enzymes set forth herein in are specifically included.

In accordance herewith, norcoclaurine synthesis pathway precursors or (S)-norcoclaurine synthesis intermediates are brought in contact with catalytic quantities of one or more of the enzymes TYR; DODC; TYDC; MAO and/or NCS under reaction conditions permitting an enzyme catalyzed chemical conversion of the (S)-norcoclaurine and (S)-norlaudanosoline synthesis precursors and/or (S)-norcoclaurine and (S)-norlaudanosoline synthesis intermediates. In preferred embodiments, the agents are brought in contact with each other and mixed to form a mixture. In preferred embodiments, the mixture is an aqueous mixture comprising water and further optionally additional agents to facilitate enzyme catalysis, including buffering agents, salts, pH modifying agents, as well as co-factors, for example NAD+ and NADP+. The reaction may be performed at a range of different temperatures. In preferred embodiments the reaction is performed at a temperature between about 18° C. and 37° C. Upon completion of the in vitro reaction (S)-norcoclaurine, (S)-norlaudanosoline or synthesis intermediates thereof may be obtained in more or less pure form. It is noted that in embodiments of the present disclosure where (S)-norlaudanosoline synthesis requires that a portion of the available dopamine substrate is converted to 3,4-DHPAA, and a portion is used to be coupled to 3,4-DHPAA in order to produce (S)-norlaudanosoline in the presence of NCS, activity of MAO may be regulated in order to obtain a stoichiometric balance of the both NCS substrates. Such regulation may be achieved at for example the transcriptional or translational level.

In Vivo Production of (S)-Norcoclaurine, (S)-Norlaudanosoline, and Synthesis Intermediates Thereof In accordance with certain aspects of the present disclosure (S)-norcoclaurine synthesis pathway precursors and/or (S)-norcoclaurine synthesis intermediates are brought in contact with catalytic quantities of one or more of the enzymes TYR; DODC; TYDC; MAO: and/or NCS under reaction conditions permitting an enzyme catalyzed chemical conversion of the (S)-norcoclaurine and (S)-norlaudanosoline synthesis precursors, and (S)-norcoclaurine and (S)-norlaudanosoline synthesis intermediates under in vivo reaction conditions. Under such in vivo reaction conditions living cells are modified in such a manner that they produce (S)-norcoclaurine, (S)-norlaudanosoline, or synthesis intermediates thereof. In certain embodiments, the living cells are microorganisms, including bacterial cells and fungal cells. In other embodiments, the living cells are multicellular organisms, including plants.

In one embodiment, the living cells are selected to be host cells capable of producing at least one of the (S)-norcoclaurine or (S)-norlaudanosoline synthesis intermediates of the present disclosure, but are unable to produce (S)-norcoclaurine, or one or more of (S)-norcoclaurine, (S)-norlaudanosoline, or synthesis intermediates of the present disclosure. Such cells include, without limitation, bacteria, yeast, other fungal cells, plant cells, or animal cells. Thus, by way of example only, a host cell may be a yeast host cell capable of producing L-tyrosine, but not dopamine, (S)-norcoclaurine, or (S)-norlaudanosoline. In order to modulate such host cells in such a manner that they produce (S)-norcoclaurine, (S)-norlaudanosoline, or synthesis intermediates thereof, one or more of the enzymes selected from the group of enzymes consisting of TYR; DODC; TYDC; MAO and NCS in accordance herewith may be heterologously introduced and expressed in the host cells.

In other embodiments, the living cells naturally produce one or more of the (S)-norcoclaurine and (S)-norlaudanosoline synthesis precursors, and/or synthesis intermediates, thereof, and/or (S)-norcoclaurine, and/or (S)-norlaudanosoline of the present disclosure, however the living cells are modulated in such a manner that the levels of one or more of the (S)-norcoclaurine and (S)-norlaudanosoline synthesis intermediates, or (S)-norcoclaurine and/or (S)-norlaudanosoline produced in the cells is modulated, relative to the levels produced by the cells without heterologous introduction of any of the aforementioned enzymes in such living cells.

In order to produce (S)-norcoclaurine, (S)-norlaudanosoline, or a (S)-norcoclaurine or (S)-norlaudanosoline synthesis intermediate, provided herein is further a method for preparing (S)-norcoclaurine, (S)-norlaudanosoline, and/or one or more of (S)-norcoclaurine or (S)-norlaudanosoline synthesis intermediates selected from the group of (S)-norcoclaurine or (S)-norlaudanosoline synthesis intermediates consisting of: tyramine; L-DOPA; 4-hydroxyphenylacetaldehyde, 3,4-dihydroxyphenylacetaldehyde; and dopamine comprising:

(a) providing a chimeric nucleic acid sequence comprising as operably linked components:
(i) one or more nucleic acid sequences encoding one or more of the polypeptides selected from the group of polypeptides consisting of TYR; DODC; TYDC, MAO; and NCS; and
(ii) one or more nucleic acid sequences capable of controlling expression in a host cell;
(b) introducing the chimeric nucleic acid sequence into a host cell and growing the host cell to produce the polypeptide selected from the group of polypeptides consisting of TYR; DODC; TYDC; MAO; and NCS and to produce one or more of (S)-norcoclaurine, (S)-norlaudanosoline, or one of the (S)-norcoclaurine or (S)-norlaudanosoline synthesis intermediates; and
(c) recovering (S)-norcoclaurine, (S)-norlaudanosoline, or a (S)-norcoclaurine of (S)-norlaudanosoline synthesis intermediate.

In some embodiments, the nucleic acid sequences may be isolated from the hereinbefore mentioned plant species, including *Popover somniferum,* or from microbial species. In preferred embodiments, the nucleic acid sequences are selected from the nucleic acid sequences set forth herein as one or more of SEQ.ID. NO: 43 to SEQ. ID. NO.: 80; SEQ. ID. NO: 95; SEQ. ID. NO: 97; SEQ. ID. NO: 99; or SEQ. ID. NO: 101. In certain embodiments, the nucleic acid sequence encoding the TYR, DODC, TYDC, MAO or NCS may contain multiple nucleic acids sequences encoding a TYR, DODC, TYDC, MAO or NCS polypeptide, e.g. 2, 3, 4, or 5 nucleic acid sequences. Specific nucleic acid sequences that encode multiple NCS sequences that may be used in accordance herewith include SEQ. ID. NO: 80; SEQ. ID. NO: 48; SEQ. ID. NO: 51; SEQ. ID. NO: 53; SEQ ID. NO: 54; SEQ. ID. NO: 65; SEQ ID. NO: 66; SEQ. ID. NO: 55; and SEQ ID. NO: 57. It will be clear to those of skill in the art that a nucleic acid sequence encoding fewer NCS coding regions (e.g. 1 coding region, 2 coding regions, 3 coding regions, 4 coding regions, 5 coding regions or 6 coding) than those provided for by the multiple coding region containing nucleic acid sequences may be isolated from the aforementioned nucleic acid sequences. In this respect, FIG. 4 identifies the NCS coding regions of each of these nucleic acid sequences. Furthermore, a single coding region may be selected, e.g. one of the coding regions shown in FIG. 4, and used to prepare multimers (e.g. a homo-dimer, homo-trimer, homo-tetramer, homo-pentamer or homo-hexamer). In other embodiments, two or more coding regions, from the same or different organisms, may be selected and combined to prepare multimers (e.g. a hetero-dimer, hetero-trimer, hetero-tetramer, hetero-pentamer or hetero-hexamer). It is further noted that a nucleic acid sequence encoding full length or truncated forms of TYR, DODC, TYDC, MAO and NSC may be used, for example the N-terminal signal peptides, representing typically no more than up to 30 amino acids, may be removed from the N-termini, as provided in or SEQ. ID. NO: 103-SEQ. ID. NO: 110. As illustrated in Example 3, truncated sequences may provide more significant levels of norcoclaurine than the intact sequence, and thus be used in preferred embodiments of the present disclosure. The hereinbefore mentioned polypeptide or polypeptides are selected are selected in accordance with the specific (S)-norcoclaurine or (S)-norlaudanosoline synthesis intermediate(s), or (S)-norcoclaurine or (S)-norlaudanosoline that is desirable to obtain. Thus, by way of non-limiting example, if one wishes to prepare (S)-norcoclaurine one may introduce in a host cell capable of producing L-tyrosine, a chimeric nucleic acid sequence into a host cell encoding the polypeptides TYR; DODC; TYDC; MAO; and NCS (i.e. a nucleic acid sequence comprising SEQ.ID. NO: 97 (TYR); SEQ.ID. NO: 99 (DODC); SEQ.ID. NO: 101 (TYDC); SEQ.ID. NO: 95 (MAO); and one of SEQ.ID. NO: 43-SEQ.ID. NO: 80 (NCS).

It is further noted that in certain embodiments of the present disclosure, the chimeric nucleic acid sequence may encode multiple TYR, DODC, TYDC; MAO; and/or NCS polypeptides. Thus in certain embodiments of the present disclosure, the chimeric nucleic acid sequence may additionally encode, a second; second and third; second, third and fourth; second, third, fourth and fifth; or a second, third, fourth, fifth and sixth polypeptide selected from the group of polypeptides consisting of TYR; DODC; TYDC; MAO and NCS. In embodiments were chimeric nucleic acid sequences encoding multiple polypeptides are provided, each of the additional nucleic acid sequences and/or the polypeptides may be identical or non-identical. Nucleic acid sequences that may be used in accordance with these embodiments are CCHNCS2 (SEQ.ID. NO: 66); CMANCS1 (SEQ.ID. NO: 85); CCHNCS1 (SEQ.ID. NO: 65); PBRNCS5 (SEQ.ID. NO: 90); and PSONCS3 (SEQ.ID. NO: 94) (of which expression and (S)-norcoclaurine production is shown in Example 2 and Example 3, respectively) and PBRNCS2 (SEQ.ID. NO: 48), SDINCS1 (SEQ.ID. NO: 89) and CMANSC2 (SEQ.ID. NO: 54).

In accordance herewith, the nucleic acid sequence encoding TYR; DODC; TYDC; MAO; and/or NCS is linked to a nucleic acid sequence capable of controlling expression of TYR; DODC; TYDC; MAO; and/or NCS in a host cell. Accordingly, the present disclosure also provides a nucleic acid sequence encoding TYR; DODC; TYDC; MAO; and/or NCS linked to a promoter capable of controlling expression in a host cell. Nucleic acid sequences capable of controlling expression in host cells that may be used herein include any transcriptional promoter capable of controlling expression of polypeptides in host cells. Generally, promoters obtained from bacterial cells are used when a bacterial host is selected in accordance herewith, while a fungal promoter will be used when a fungal host is selected, a plant promoter will be used when a plant cell is selected, and so on. Further nucleic acid elements capable elements of controlling expression in a host cell include transcriptional terminators, enhancers and the like, all of which may be included in the chimeric nucleic acid sequences of the present disclosure.

In accordance with the present disclosure, the chimeric nucleic acid sequences comprising a promoter capable of controlling expression in host cell linked to a nucleic acid sequence encoding TYR; DODC; TYDC; MAO; and NCS, can be integrated into a recombinant expression vector which ensures good expression in the host cell. Accordingly, the present disclosure includes a recombinant expression vector comprising in the 5' to 3' direction of transcription as operably linked components:

(i) a nucleic acid sequence capable of controlling expression in a host cell; and
(ii) a nucleic acid sequence encoding TYR; DODC; TYDC; MAO; and NCS, wherein the expression vector is suitable for expression in a host cell. The term "suitable for expression in a host cell" means that the recombinant expression vector comprises the chimeric nucleic acid sequence of the present disclosure linked to genetic elements required to achieve expression in a host cell. Genetic elements that may be included in the expression vector in this regard include a transcriptional termination region, one or more nucleic acid sequences encoding marker genes, one or more origins of replication and the like. In preferred embodiments, the expression vector further comprises genetic elements required for the integration of the vector or a portion thereof in the host cell's genome, for example if a plant host cell is used the T-DNA left and right border sequences which facilitate the integration into the plant's nuclear genome.

Pursuant to the present disclosure, the expression vector may further contain a marker gene. Marker genes that may be used in accordance with the present disclosure include all genes that allow the distinction of transformed cells from non-transformed cells, including all selectable and screenable marker genes. A marker gene may be a resistance marker such as an antibiotic resistance marker against, for example, kanamycin or ampicillin. Screenable markers that may be employed to identify transformants through visual inspection include β-glucuronidase (GUS) (U.S. Pat. Nos. 5,268,463 and 5,599,670) and green fluorescent protein (GFP) (Niedz et al., 1995, Plant Cell Rep., 14: 403).

One host cell that particularly conveniently may be used is *Escherichia coli*. The preparation of the *E. coli* vectors may be accomplished using commonly known techniques such as restriction digestion, ligation, electrophoresis, DNA sequencing, the Polymerase Chain Reaction (PCR) and other methodologies. A wide variety of cloning vectors is available to perform the necessary steps required to prepare a recombinant expression vector. Among the vectors with a replication system functional in *E. coli,* are vectors such as pBR322, the pUC series of vectors, the M13 mp series of vectors, pBluescript etc. Typically, these cloning vectors contain a marker allowing selection of transformed cells. Nucleic acid sequences may be introduced in these vectors, and the vectors may be introduced in *E. coli* by preparing competent cells, electroporation or using other well known methodologies to a person of skill in the art. *E. coli* may be grown in an appropriate medium, such as Luria-Broth medium and harvested. Recombinant expression vectors may readily be recovered from cells upon harvesting and lysing of the cells. Further, general guidance with respect to the preparation of recombinant vectors and growth of recombinant organisms may be found in, for example: Sambrook et al., Molecular Cloning, a Laboratory Manual, Cold Spring Harbor Laboratory Press, 2001, Third Ed.

Further included in the present disclosure are a host cell wherein the host cell comprises a chimeric nucleic acid sequence comprising in the 5' to 3' direction of transcription as operably linked components one or more nucleic acid sequences encoding one or more of the polypeptides selected from the group of polypeptides consisting of TYR; DODC; TYDC; MAO; and NCS. As hereinbefore mentioned the host cell is preferably a host cell capable of producing at least one of the (S)-norcoclaurine or (S)-norlaudanosoline synthesis intermediates, or (S)-norcoclaurine or (S)-norlaudanosoline precursors of the present disclosure, but is unable to produce (S)-norcoclaurine, (S)-norlaudanosoline, or one or more of (S)-norcoclaurine or (S)-norlaudanosoline, or other (S)-norcoclaurine and (S)-norlaudanosoline synthesis intermediates of the present disclosure, but for the introduction of the chimeric nucleic acid sequences of the present disclosure. Combinations of nucleic acid sequences in order to produce (S)-norcoclaurine or (S)-norlaudanosoline in accordance herewith may be selected by referring to Table A and Table B, any and all of the combinations of nucleic acid sequences encoding the polypeptides set forth in Tables A and Table B are specifically included herein.

As hereinbefore mentioned, in other embodiments, the living cells naturally produce one or more of the (S)-norcoclaurine and (S)-norlaudanosoline synthesis intermediates, (S)-norcoclaurine and (S)-norlaudanosoline precursors, or (S)-norcoclaurine and (S)-norlaudanosoline of the present disclosure, however the living cells are modulated in such a manner that the levels of one or more of the (S)-norcoclaurine or (S)-norlaudanosoline synthesis intermediates, or (S)-norcoclaurine or (S)-norlaudanosoline produced in the cells is modulated, without heterologous introduction of any of the aforementioned enzymes in such living cells. Such modulations may be achieved by a variety of modification techniques, including, but not limited to, the modulation of one or more of the enzymatic activities of TYR; DODC; TYDC; MAO; and NCS, for example by modulating the native nucleic acid sequences encoding TYR; DODC; TYDC; MAO; and NCS, for example by gene silencing methodologies, such as antisense methodologies; or by the use of modification techniques resulting in modulation of activity of the enzymes using for example site directed mutagenesis, targeted mutagenesis, random mutagenesis, virus-induced gene silencing, the addition of organic solvents, gene shuffling or a combination of these and other techniques known to those of skill in the art, each methodology designed to alter the activity of the enzymes of TYR; DODC; TYDC; MAO; and NCS, in such a manner that the accumulation of one or more of (S)-norcoclaurine or the (S)-norcoclaurine or (S)-norlaudanosoline intermediates in the living cells increases. Thus the present disclosure further includes embodiments which involve modulating living cells by reducing the production of NCS in order to produce dopamine and/or 4-hydroxyphenylacetaldehyde and/or 3,4-dihydroxyphenylacetaldehyde; modulating living cells by reducing the production of DODC in order to produce L-DOPA; modulating living cells by reducing the production of TYR in order to produce L-tyrosine; modulating living cells by reducing the production of TYDC in order to produce L-tyrosine; modulating living cells by reducing the production of MAO in order to produce dopamine. Thus it will be clear that in accordance with the foregoing embodiments, (S)-norcoclaurine or (S)-norlaudanosoline synthesis intermediates, and (S)-norcoclaurine or (S)-norlaudanosoline precursors may be produced by inhibiting an enzyme that converts the (S)-norcoclaurine or (S)-norlaudanosoline synthesis intermediate immediately downstream of the desired (S)-norcoclaurine or (S)-norlaudanosoline synthesis intermediate, or the desired (S)-norcoclaurine or (S)-norlaudanosoline precursor, and providing the (S)-norcoclaurine or (S)-norlaudanosoline intermediate or the (S)-norcoclaurine or (S)-norlaudanosoline precursor immediately upstream (as depicted in FIG. 1 and FIG. 2) of the desired (S)-norcoclaurine or (S)-norlaudanosoline synthesis intermediate, or (S)-norcoclaurine or (S)-norlaudanosoline precursor under conditions that permit the production of the desired (S)-norcoclaurine or (S)-norlaudanosoline synthesis intermediate, or (S)-norcoclaurine or (S)-norlaudansoline precursors from the immediate upstream component. Thus, strictly by way of example, one may select a plant comprising the entire synthesis pathway depicted in FIG. 1 (*Papaver somniferum*, for example), and inhibit NCS in such plant, thereby providing L-DOPA and/or tyramine under conditions that permit the production of dopamine or 4-hydroxyphenylacetaldehyde, respectively; or, and again, strictly by way of example, one may select a plant comprising the entire synthesis pathway depicted in FIG. 1 (*Papaver somniferum*, for example), and inhibit DODC in such plant, thereby providing L-tyrosine under conditions that permit the production of L-DOPA.

Provided herein is further a method for preparing an (S)-norcoclaurine or (S)-norlaudanosoline synthesis intermediate, or an (S)-norcoclaurine or (S)-norlaudanosoline precursor selected from the group of (S)-norcoclaurine or (S)-norlaudanosoline synthesis intermediates and (S)-norcoclaurine or (S)-norlaudanosoline precursors consisting of: L-tyrosine; L-DOPA; dopamine; tyramine; 4-hydroxyphenylacetaldehyde, and 3,4-dihydroxyphenylacetaldehyde; and comprising:

(a) providing a chimeric nucleic acid sequence comprising (i) one or more nucleic acid sequences complementary all or a portion of the mRNA synthesized by the nucleic acid sequence encoding the polypeptides selected from the group of polypeptides consisting of TYR; DODC; TYDC; MAO; and NCS; and (ii) one or more elements capable of controlling transcription of the complementary nucleic acid sequence, wherein the chimeric nucleic acid sequence is capable of producing an antisense RNA complementary all or a portion of the mRNA of the nucleic acid sequence encoding the polypeptides selected from the group of polypeptides consisting of TYR; DODC; TYDC; MAO; and NCS;

(b) introducing the chimeric nucleic acid sequence into a host cell;

(c) growing the host cell to produce the antisense RNA and inhibit synthesis of the polypeptide selected from the group of polypeptides consisting of TYR; DODC; TYDC; MAO; and NCS and to produce one or more of an (S)-norcoclaurine or (S)-norlaudanosoline synthesis intermediate or a (S)-norcoclaurine p or (S)-norlaudanosoline pathway precursor selected from the group of (S)-norcoclaurine or (S)-norlaudanosoline synthesis intermediates and (S)-norcoclaurine or (S)-norlaudanosoline precursors consisting of L-tyrosine; L-DOPA; dopamine; tyramine; 4-hydroxyphenylacetaldehyde, and 3,4-dihydroxyphenylacetaldehyde; and (d) recovering a (S)-norcoclaurine or (S)-norlaudanosoline synthesis intermediate, or (S)-norcoclaurine or (S)-norlaudanosoline precursor selected from the group of (S)-norcoclaurine or (S)-norlaudanosoline synthesis intermediates, and (S)-norcoclaurine or (S)-norlaudanosoline precursors consisting of L-tyrosine; L-DOPA; dopamine; tyramine; 4-hydroxyphenylacetaldehyde, and 3,4-dihydroxyphenylacetaldehyde.

Compositions Comprising (S)-Norcoclaurine and (S)-Norlaudanosoline Synthesis Intermediates In accordance with present disclosure, methods are provided to make various (S)-norcoclaurine or (S)-norlaudanosoline synthesis intermediates. Accordingly, further included in the present disclosure are substantially pure or isolated forms of such (S)-norcoclaurine or (S)-norlaudanosoline intermediates. Included in the present disclosure are substantially pure or isolated tyramine having the chemical formula set forth in FIG. 3B; substantially pure or isolated L-DOPA having the chemical formula set forth in FIG. 3C; a substantially pure or isolated dopamine having the chemical formula set forth in FIG. 3E; substantially pure or isolated 4-hydroxyphenylacetaldehyde having the chemical formula set forth in FIG. 3D; and substantially pure or isolated 3,4-dihydroxyphenylacetaldehyde having the chemical formula set forth in FIG. 3G; and substantially pure or isolated (S)-norlaudanosoline having the chemical formula set forth in FIG. 3H.

Nucleic Acid Sequences Encoding Polypeptides, and Polypeptides Involved in (S)-Norcoclaurine, (S)-Norlaudanosoline, and Synthesis Intermediates Thereof The present disclosure relates to nucleic acid sequences encoding polynucleotides involved in (S)-norcoclaurine, (S)-norlaudanosoline, and synthesis intermediates thereof. Accordingly the present disclosure provides the following nucleic acid sequences encoding NCS polypeptides: SEQ. ID. NO: 1 to SEQ. ID. NO: 42. The foregoing nucleotide sequences may be obtained in pure or substantially pure form and be provided in expression vectors. Accordingly the present disclosure further comprises an expression vector comprising any one of SEQ. ID. NO: 1 to SEQ. ID. NO: 41.

The present disclosure also provides the following NCS polypeptides: SEQ. ID. NO: 42 to SEQ. ID. NO: 79. The foregoing polypeptides in accordance with the present disclosure may be obtained in more or less pure form in accordance with the present disclosure.

Use of (S)-Norcoclaurine, (S)-Norlaudanosoline, and Synthesis Intermediates Thereof The (S)-norcoclaurine, (S)-norlaudanosoline, and synthesis intermediates thereof obtained in accordance with the present disclosure may be formulated for use as a source material or chemical intermediate to manufacture a pharmaceutical drug, recreational drug, stimulant, therapeutic agent or medicinal agent, including the stimulants caffeine and nicotine, the stimulant and local anesthetic cocaine, the anti-malarial drug quinine, the analgesic morphine, the antimicrobials sanguinerine and berberine, the muscle relaxant papaverine, and the cough suppressant noscapine, and derivatives of any of the foregoing. Further (S)-norcoclaurine, (S)-norlaudanosoline, and (S)-norcoclaurine or (S)-norlaudanosoline synthesis intermediates may be used as a pharmaceutical drug, recreational drug, stimulant, therapeutic agent or medicinal agent. Thus the present disclosure further includes a pharmaceutical composition or pharmaceutical precursor composition comprising (S)-norcoclaurine, (S)-norlaudanosoline, and synthesis intermediates thereof prepared in accordance with the methods of the present disclosure. Pharmaceutical or pharmaceutical precursor drug preparations comprising (S)-norcoclaurine, (S)-norlaudanosoline, and synthesis intermediates thereof in accordance with the present disclosure preferably further comprise vehicles, excipients and auxiliary substances, such as wetting or emulsifying agents, pH buffering substances and the like. These vehicles, excipients and auxiliary substances are generally pharmaceutical agents that may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, phosphates, sulfates, and the like; and the salts of organic acids such as acetates, propionates, benzoates, and the like. It is also preferred, although not required, that the preparation will contain a pharmaceutically acceptable excipient that serves as a stabilizer. Examples of suitable carriers that also act as stabilizers for peptides include, without limitation, pharmaceutical grades of dextrose, sucrose, lactose, sorbitol, inositol, dextran, and the like. Other suitable carriers include, again without limitation, starch, cellulose, sodium or calcium phosphates, citric acid, glycine, polyethylene glycols (PEGs), and combinations thereof. The pharmaceutical composition may be formulated for oral and intravenous administration and other routes of administration as desired. Dosing may vary.

In further embodiments, the present disclosure provides methods for treating a patient with a pharmaceutical composition comprising (S)-norcoclaurine, (S)-norlaudanosoline, and synthesis intermediates thereof prepared in accordance with the present disclosure. Accordingly, the present disclosure further provides a method for treating a patient with (S)-norcoclaurine, (S)-norlaudanosoline, and synthesis intermediates thereof prepared according to the methods of the present disclosure, said method comprising administering to the patient a composition comprising (S)-norcoclaurine, (S)-norlaudanosoline, and synthesis intermediates thereof, wherein (S)-norcoclaurine, (S)-norlaudanosoline, and synthesis intermediates thereof are administered in an amount sufficient to ameliorate a medical condition in the patient.

The present disclosure also provides a use of a composition comprising (S)-norcoclaurine, (S)-norlaudanosoline, and synthesis intermediates thereof, for ameliorating a medical condition in a patient. The present disclosure further provides (S)-norcoclaurine, (S)-norlaudanosoline, and synthesis intermediates thereof for use in ameliorating a medical condition in a patient. (S)-norcoclaurine may be used to improve vascular relaxation and as a bronchodilatory stimulant.

EXAMPLES

Hereinafter are provided examples of specific embodiments for performing the methods of the present disclosure, as well as embodiments representing the compositions of the present disclosure. The examples are provided for illustrative purposes only, and are not intended to limit the scope of the present disclosure in any way.

Example 1

Isolation of Candidate Nucleic Acid Sequences Encoding NCS

Figure 4:
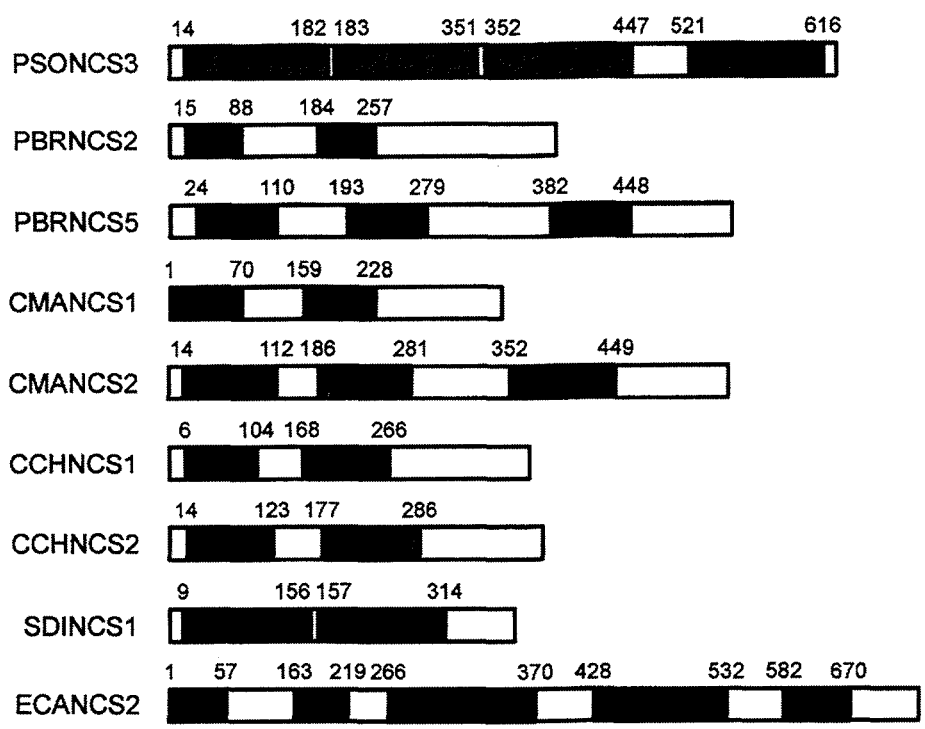
FIG. 4 depicts nucleic acid sequence fragments obtained from various plant species encoding multiple NCS polypeptides. NCS coding regions are represented by black boxes. PSON=*Papaver somniferum;* PBR=*Papaver bracteatum;* CMA=*Chelidonium majus;* CCH=*Chordyalis cheilantifolia;* SDI=*Stylophorum diphyllum;* and ECA=*Eschscholzia californica.*

Full-length NCS candidate genes were identified by web-based BLAST searches with query sequences including PsNSCs (see: SEQ. ID. NO: 7; SEQ. ID. NO: 8), TfNCS (see: SEQ. ID. NO: 3) and AmNCSs (SEQ. ID. NO: 4; SEQ. ID. NO: 5). The first strand cDNA was synthesized from total RNA of each of 20 plant species using reverse transcriptase and oligo-dT primers, and cDNAs encoding full-length NCS candidate genes were amplified by the polymerase chain reaction (PCR) using the forward and reverse primers listed in Table C. The following plant species were used: *Argenome mexicana; Chelidonium majus; Chordyalis cheilanthifolia; Eschscholzia californica; Glaucium flavum; Papaver bracteatum; Sanguineria canadensis; Stylophorum majus; Thalictrum flavum; Hydrastis canadensis; Nigella sativa; Xanthorhiza simplicissima; Berberis thunbergii; Mahonia aquifolium; Jeffersonia diphylla; Nandina domestica; Menispermum canadense; Coccolus trilobus; Tinospora cordifolia* and *Cissempelos mucronata*. Thirty cycles of the PCR consisting of 94° C. for 30 seconds, 52° C. for 30 seconds and extension at 72° C. for 2 min were performed. The reaction contained each deoxynucleoside triphosphate at a concentration of 0.3 mM, 0.3 mM of each primer, 50 ng f template and 5× KAPAhifi reaction buffer, and KAPA Hifi DNA polymerase (Kapa biosystems). Each amplified product was cloned in the pGEM-T easy vector and used as a template for further PCR reaction. To obtain the coding region of NCS candidate genes cloned into an expression vector, primers were designed to include either HindIII or BamHI or XhoI in their sequences as provided in Table D. PCR was performed under the conditions described for these constructs, then they were cloned into pGEMT-easy vector first and the resulting plasmid was digested with either HindIII and XhoI or BamHI and XhoI. The internal NCS candidate gene fragment [SEQ. ID. NO: 80-SEQ. ID. NO: 93] was subcloned in the pET 29b vector and was ligated to T4 DNA ligase (Invitrogen), and the ligation mixture was transformed into either *E. coli* BL21 pLysS or ER2566 pLysS. To obtain truncated versions of NCS candidate genes which lack 25 amino acid residues of the intact protein, forward primers were designed, except the primer for truncated SDINCS1 protein missing the first 30 amino acid residues as provided in Table E [SEQ.ID. NO: 103 to SEQ.ID. NO: 110]. After PCR for truncated NCS candidate genes, the resulting PCR products were purified and ligated into the pGEM-T easy vector. The resulting plasmid was sub-cloned using HindIII/XhoI or BamHI/XhoI restriction sites into pET 29 b vector and BL21 pLys. Nucleic acid sequences of 32 NCS encoding nucleic acid sequence fragments (SEQ. ID. NO: 48-SEQ. ID. NO: 80) were determined and the deduced amino acid sequences (SEQ. ID. NO: 10-SEQ. ID. NO: 42) were obtained. In certain instances the nucleotide fragment encoding the NCS polypeptide comprise multiple (i.e. 2, 3, 4 or 5) NCS coding regions. These fragments and relative orientation of multiple NCS coding regions are shown in FIG. 4.

Example 2

Expression of NCS Polypeptides in *Escherichia Coli*

Figure 5:
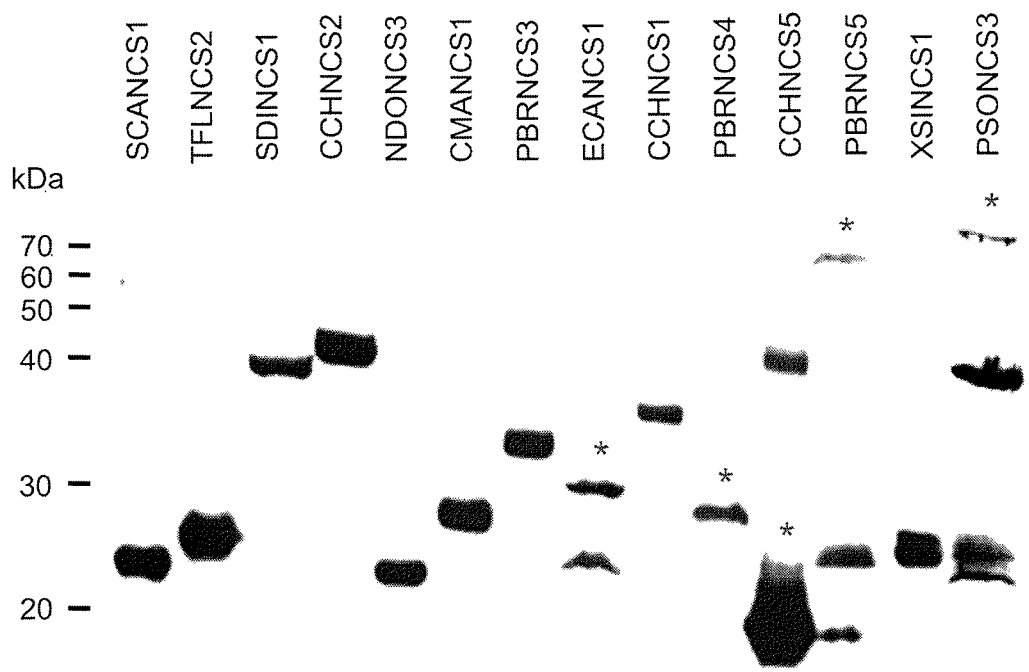
FIG. 5 depicts an immunoblot using anti-His-tag antibodies showing expression of NCS polypeptides of various plant species in *E. coli.* Polypeptide sequences used are: SCANCS1 (SEQ.ID. NO: 14); TFLNCS2 (SEQ.ID. NO: 22); SDINSC1 (SEQ.ID. NO: 17); CCHNCS2 (SEQ.ID. NO: 28); NDONCS3 (SEQ.ID. NO: 34); CMANCS1 (SEQ.ID. NO: 53); (PBRNSC3 (SEQ.ID. NO: 11); ECANCS1 (SEQ.ID. NO: 18); CCHNCS1 (SEQ.ID. NO: 27); PBRNCS4 (SEQ.ID. NO: 12); CCHNCS5 (SEQ.ID. NO: 31); PBRNCS5 (SEQ.ID. NO: 13); XSINCS1 (SEQ.ID. NO: 41); and PSONCS3 (SEQ.ID. NO: 42).

A total of 14 6×-His fusion protein constructs containing either full-length or truncated NCS candidate cDNAs were expressed in *E. coli* by induction with 0.5 mM IPTG for 4.5 h at 37° C. For PSONCS3 protein, low temperature induction (4° C.) for overnight was applied. The following nucleic acid sequences were used: SCANCS1 (SEQ.ID. NO: 52); TFLNCS2 (SEQ.ID. NO: 87); SDINSC1 (SEQ.ID. NO: 89); CCHNCS2 (SEQ.ID. NO: 66); NDONCS3 (SEQ.ID. NO: 72); CMANCS1 (SEQ.ID. NO: 85); (PBRNSC3 (SEQ.ID. NO: 83); ECANCS1 (SEQ.ID. NO: 56); CCHNCS1 (SEQ.ID. NO: 65); PBRNCS4 (SEQ.ID. NO: 50); CCHNCS5 (SEQ.ID. NO: 92); PBRNCS5 (SEQ.ID. NO: 90); XSINCS1 (SEQ.ID. NO: 93); and PSONCS3 (SEQ.ID. NO: 94). Cultures were harvested by centrifugation at 8,000 g for 10 min and resuspended in cold 20 mM Tris, pH 7.5, 100 mM KCl, 10% glycerol. The cells were routinely disrupted by sonication, followed by separation into soluble and insoluble proteins by centrifugation. Recombinant protein from each lysate was separated on SDS-PAGE (12% gels) and examined by immunoblot using anti-His-tag antibody. The immunoblot showing 14 expressed NCS polypeptides (SCANCS1 (SEQ.ID. NO: 14); TFLNCS2 (SEQ.ID. NO: 22); SDINSC1 (SEQ.ID. NO: 17); CCHNCS2 (SEQ.ID. NO: 28); NDONCS3 (SEQ.ID. NO: 34); CMANCS1 (SEQ.ID. NO: 53); (PBRNSC3 (SEQ.ID. NO: 11); ECANCS1 (SEQ.ID. NO: 18); CCHNCS1 (SEQ.ID. NO: 27); PBRNCS4 (SEQ.ID. NO: 12); CCHNCS5 (SEQ.ID. NO: 31); PBRNCS5 (SEQ.ID. NO: 13); XSINCS1 (SEQ.ID. NO: 41); and PSONCS3 (SEQ.ID. NO: 42)) is shown in FIG. 5.

Example 3

Norcoclaurine Production in Recombinant *Escherichia Coli* Expressing NCS

Figure 6A:
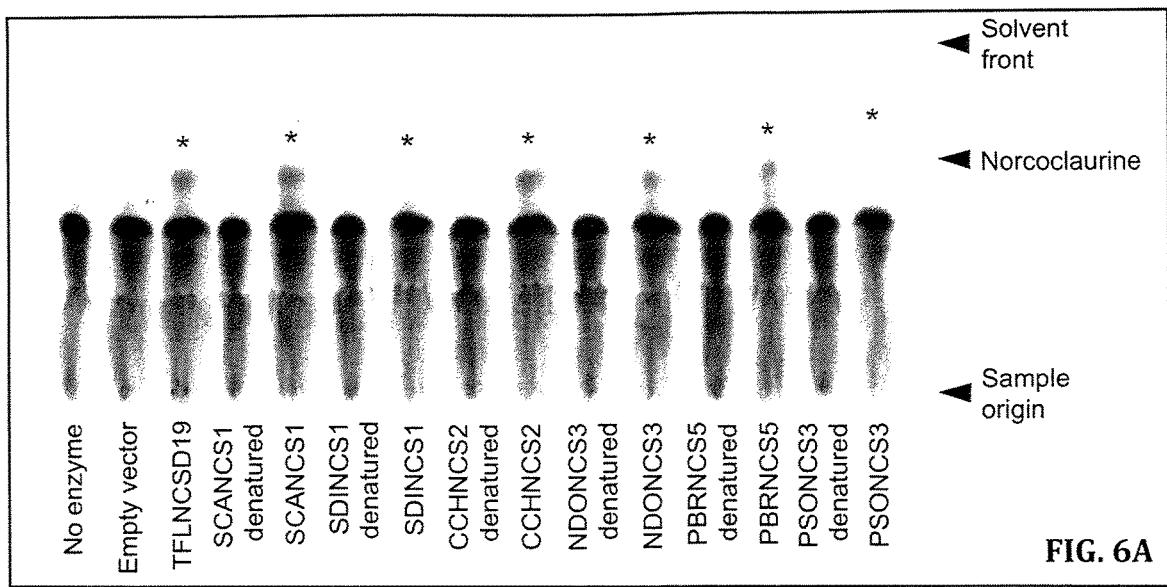
FIG. 6A-C depicts TLPC plates showing norcoclaurine production in *E. coli* using various intact NCS polypeptide sequences (FIG. 6A.
Figure 6B:
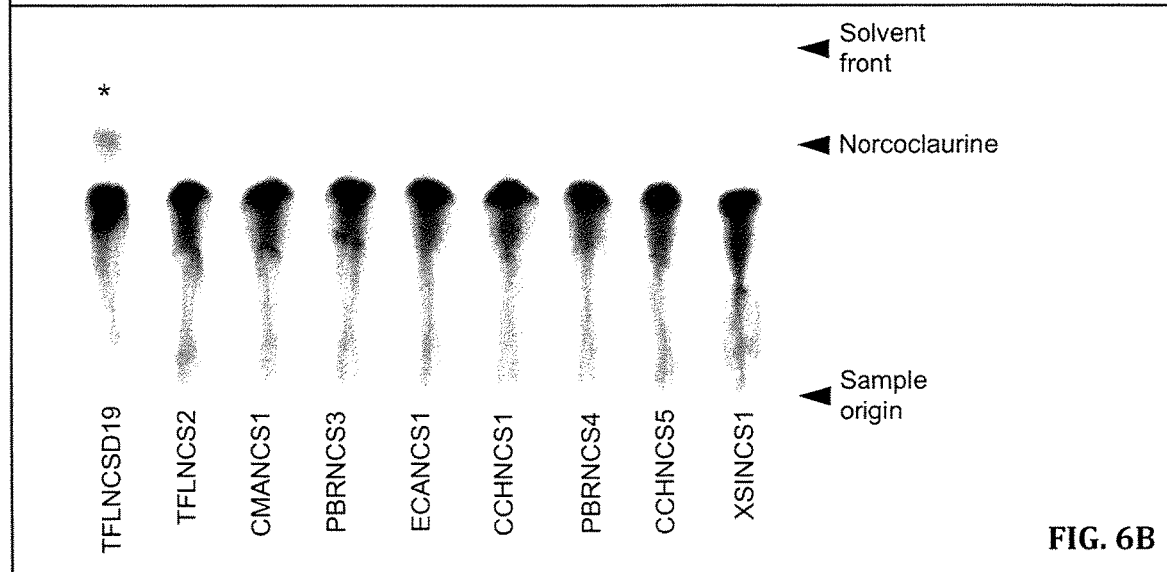
Figure 6C:
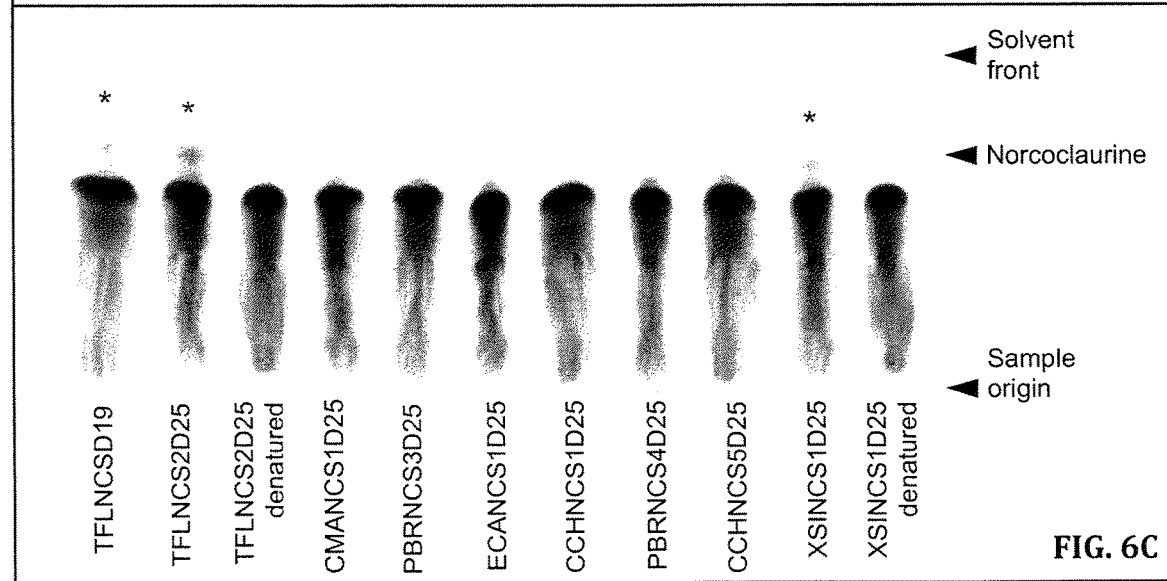

NCS activity was measured as described by Liscombe, D K, Macleod B P, Loukanina N, Nandi O I, and Facchini P J, 2005. Erratum to "Evidence for the monophyletic evolution of bensoisoquinoline alkaloid biosynthesis in angiosperms" Phytochemistry 66: 1374-1393. In summary, reaction mixtures containing each recombinant protein with 1 nmol [8-$^{14}$C] dopamine and 10 nmol 4-HPAA were incubated for 1.5 hr at 37° C. The reaction mixtures were spotted onto a silica gel 60 $F_{254}$ TLC and developed in n-BuOH:HOAC:H$_2$O (4:1:5, v/v/v). The TLC plates were visualized and analyzed using a Bio-Imaging Analyzer. The Results are shown in FIG. 6. A total of 14 *E. coli* strains, each expressing one of the polypeptides isolated in Example 1 were analyzed. FIG. 6A Shows the results obtained using *E. coli* expressing the 6 intact NCS polypeptide sequences: SCANCS1 (SEQ.ID. NO: 14); NDONCS3 (SEQ.ID. NO: 34); CCHNCS2 (SEQ.ID. NO: 28); SDINSC1 (SEQ.ID. NO: 17); PBRNCS5 (SEQ.ID. NO: 13); and PSONCS3 (SEQ.ID. NO: 42) and that all provided for substantial levels of norcoclaurine production. FIG. 6B shows the results obtained using *E. coli* expressing 8 intact polypeptide sequences: TFLNCS2 (SEQ.ID. NO: 87); CMANCS1 (SEQ.ID. NO: 85); (PBRNSC3 (SEQ.ID. NO: 83); ECANCS1 (SEQ.ID. NO: 56); CCHNCS1 (SEQ.ID. NO: 65); PBRNCS4 (SEQ.ID. NO: 50); CCHNCS5 (SEQ.ID. NO: 92); XSINCS1 (SEQ.ID. NO: 93) and that all provided for no visually detectable norcoclaurine production. Truncated nucleic acid sequences [see: SEQ.ID. NO: 103-SEQ.ID. NO: 110] were prepared using the following intact NCS encoding nucleic acid sequences: TFLNCS2 (SEQ.ID. NO: 87), (generating TFLNCS2Δ25 (SEQ. ID. NO: 109)); CMANCS1 (SEQ.ID. NO: 85), (generating TMANCS1Δ25 (SEQ.ID. NO: 105)); (PBRNCS3 (SEQ.ID. NO: 83) (generating PBRNCS3Δ25 (SEQ.ID. NO: 107)); ECANCS1 (SEQ.ID. NO: 56) (generating ECANSC1Δ25 (SEQ.ID. NO: 106)); CCHNCS1 (SEQ.ID. NO: 65) (generating CCHNCS1Δ25 (SEQ.ID. NO: 103)); PBRNCS4 (SEQ.ID. NO: 50) (generating PBRNCS4Δ25 (SEQ.ID. NO: 108)); CCHNCS5 (SEQ.ID. NO: 92) (generating CCHNCS5Δ25 (SEQ.ID. NO: 104)); and XSINCS1 (SEQ.ID. NO: 93) (generating XSINCSΔ25 (SEQ.ID. NO: 113)); An NCS gene from *Thalictrum flavum* (TFLNCS) was used as a control. Norcoclaurine production of the truncated sequences is shown in FIG. 6C. It is noted that truncation of two sequences (TLFNCS 2 (SEQ.ID. NO: 87) and XSIN (SEQ.ID. NO: 93) resulted in a more substantial production of norcoclaurine is obtained when the truncated form is expressed, relative to when the intact form of these proteins is expressed in *E. coli*.

Example 4

Expression of NCS Polypeptides in Yeast

The synthetic SDINCS1 gene included a C-terminal His$_6$-tag and was flanked by NotI and SacI restriction sites for direct insertion into the pESC-leu2d yeast expression vector (Agilent). C-terminal His$_6$-tags were fused to other NCS candidates by re-amplifying NCS gene candidates by PCR using reverse primers that included sequences encoding the His$_6$-tag (Table F). Amplicons were ligated into pESC-leu2d using NotI and BglII, NotI and SpeI, SpeI and PacI, or NotI and SacI, and expression vectors were used to transform *Saccharomyces cerevisiae* strain YPH 499 (Gietz and Schiestl, 2007). A single transformed yeast colony was used to inoculate 2 mL of Synthetic Complete (SC) medium lacking leucine, but containing 2% (w/v) glucose, and grown overnight at 30° C. and 200 rpm. A flask containing 50 mL of SC medium lacking leucine, but containing 1.8% (w/v) galactose, 0.2% (w/v) glucose and 0.1% (w/v) raffinose, was inoculated with 1 mL of the overnight culture and grown at 30° C. and 200 rpm for approximately 55 h. Yeast cells were collected by centrifugation and suspended in 3 mL of 50 mM phosphate buffer, pH 7.3. Cells were lysed by sonication, cell debris was removed at 4° C. by centrifugation for 30 min at 20,000×g, and the supernatant was used for enzyme assays. FIG. 7A shows the expression results using TFLNCSΔ19 (SEQ.ID. NO: 112); PBRNCS5 (SEQ.ID. NO: 13); CCHNCS2 (SEQ.ID. NO: 28); NDONCS3 (SEQ.ID. NO: 34); SCANCS1 (SEQ.ID. NO: 14); SDINCS1 (SEQ-.ID.NO: 89), PSONCS3 (SEQ.ID.NO: 42); TFLNCS2Δ25 (SEQ.ID. NO: 109); XSINCS1Δ25 (SEQ.ID. NO: 113) and PSONCS2 (SEQ.ID. NO: 111) polypeptides.

Example 5

Norcoclaurine Synthase Activity in Recombinant Yeast Expressing NCS

NCS reaction mixtures containing crude recombinant protein, 1 nmol [8-$^{14}$C] dopamine and 10 nmol 4-HPAA were incubated for 1.5 h at 37° C. The reaction mixtures were spotted onto a silica gel 60 $F_{254}$ TLC and developed in n-BuOH:HOAc:H$_2$O (4:1:5, v/v/v). The TLC plate was visualized and analyzed using a Bio-Imaging Analyzer. FIG. 7B shows norcoclaurine production for TFLNCSΔ19 (SE-Q.ID. NO: 112); PBRNCS5 (SEQ.ID. NO: 13); CCHNCS2 (SEQ.ID. NO: 28); NDONCS3 (SEQ.ID. NO: 34); SCANCS1 (SEQ.ID. NO: 14); SDINCS1 (SEQ.ID.NO: 89), PSONCS3 (SEQ.ID.NO: 42); TFLNCS2Δ25 (SEQ.ID. NO: 109); XSINCS1Δ25 (SEQ.ID. NO: 113) and PSONCS2 (SEQ.ID. NO: 111). Controls as are yeast transformed with a vector not comprising an NCS gene ("empty vector"); and yeast and *E. coli* expressing TFLNCSΔ19 (SEQ.ID. NO: 112).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE A

| (S)-norcoclaurine | | | | | |
|---|---|---|---|---|---|
| | TYR | TYDC | DODC | MAO | NCS |
| L-tyrosine | ✓ | ✓ | ✓ | ✓ | ✓ |
| L-tyrosine | | ✓ | ✓ | ✓ | ✓ |

TABLE A-continued

| (S)-norcoclaurine | | | | | |
|---|---|---|---|---|---|
| | TYR | TYDC | DODC | MAO | NCS |
| L-DOPA | | | | | |
| dopamine | | ✓ | | ✓ | ✓ |
| L-tyrosine | | | | | |
| dopamine | | | ✓ | | ✓ |
| tyramine | | | | | |
| dopamine | | | | | ✓ |
| 4-hydroxy-phenylacetaldehyde (4-HPAA) | | | | | |

TABLE B

| (S)-norlaudanosoline | | | | |
|---|---|---|---|---|
| | TYR | DODC | MAO | NCS |
| L-tyrosine | ✓ | ✓ | ✓ | ✓ |

TABLE B-continued

(S)-norlaudanosoline

| | TYR | DODC | MAO | NCS |
|---|---|---|---|---|
| 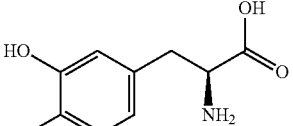 L-DOPA | | ✓ | ✓ | ✓ |
| 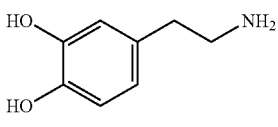 dopamine | | | ✓ | ✓ |
| 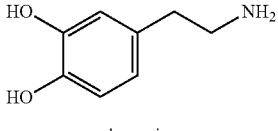 dopamine | | | | ✓ |
| 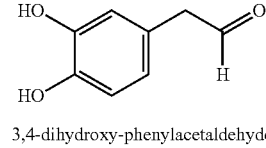 3,4-dihydroxy-phenylacetaldehyde (3,4-DHPAA) | | | | |

TABLE B-continued

(S)-norlaudanosoline

| | TYR | DODC | MAO | NCS |
|---|---|---|---|---|
| 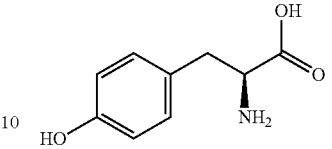 L-tyrosine | ✓ | ✓ | | ✓ |
| 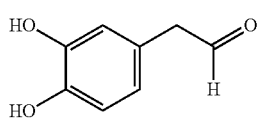 3,4-dihydroxy-phenylacetaldehyde (3,4-DHPAA) | | | | |
| 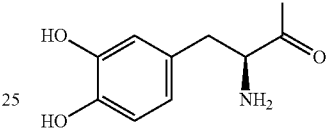 L-DOPA | | ✓ | | ✓ |
| 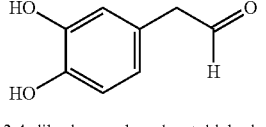 3,4-dihydroxy-phenylacetaldehyde (3,4-DHPAA) | | | | |

TABLE C

| Primers | Description | SEQ ID NO. |
|---|---|---|
| PBR_rep_c6824-F (PBRNCS2) | AGTGTTTCAGAGAGTATGATGAGGA | 114 |
| PBR_rep_c6824-R (PBRNCS2) | CCCGCAATGACATCTAGCTT | 115 |
| PBRContig25754-F (PBRNCS4) | ACATCGACCGTGTAAAGCGA | 116 |
| PBRContig25754-R (PBRNCS4) | ACCTTAGAGTGGAACACGTCC | 117 |
| PBR_rep_c8842-F (PBRNCS3) | ACTTCCTGGTGTCTTCGTGAAA | 118 |
| PBR_rep_c8842-R (PBRNCS3) | ACTTGGCTTATGCTTTTAGACCTC | 119 |
| PBRContig45733-F (PBRNCS5) | AGTGAGTGAGTGTTTCAGAGAGT | 120 |
| PBRContig45733-R (PBRNCS5) | ACCTTAGAGTGGAACACGTCC | 121 |
| SCAContig30427-F (SCANCS1) | AGAGAGAGAAAATGAGGAAGGAACT | 122 |
| SCAContig30427-R (SCANCS1) | ACCGAACTTAGAATGGAACACCT | 123 |
| CMAContig5713-F (CMANCS2) | GTGTTTCAGAGAGAACGATGAGG | 124 |
| CMAContig5713-R (CMANCS2) | ACCTTAGAGTGGAACACCAGC | 125 |
| CMA_rep_c1557-F (CMANCS1) | CACGAGAAGCGATTGAAAGAGGTG | 126 |
| CMA_rep_c1557-R (CMANCS1) | TGGACCGGACGGTATACATGACCAT | 127 |
| SDI_rep_c489-F (SDINCS1) | GAGAAAATGAGGAAGGAAGTACGATA | 128 |

TABLE C-continued

| Primers | Description | SEQ ID NO. |
|---|---|---|
| SDI_rep_c489-R (SDINCS2) | CCGGTACTTAGAGTGGAACACC | 129 |
| ECAContig18893-F (ECANCS2) | AACCAAGAGAAGCGACTCAA | 130 |
| ECAContig18893-R (ECANCS2) | ACCTAAAGTAACTGAAACTATGCTG | 131 |
| ECA_rep_c12486-F (ECANCS1) | GCGAAAATACAGAGAGAAGTTTGTGA | 132 |
| ECA_rep_c12486-R (ECANCS1) | CCCCTGGAGGAAAAACAATTTGG | 133 |
| AME_rep_c2186-F (AMENCS1) | AGGGAGAGAAAATGAGGAAAGAAGT | 134 |
| AME_rep_c2186-R (AMENCS1) | CCTCAATGACATCTAACTTTTC | 135 |
| AMEcomp935-F (AMENCS2) | CAACCCTGCTATCTCCAAGTATGTT | 136 |
| AMEcomp935-R (AMENCS2) | AACAGGTAGCTAGGGCAGCTGTTTAT | 137 |
| TFLcomp2119-F (TFLNCS4) | AATGAGGAAGGAACTAACACATGAGA | 138 |
| TFLcomp2119-R (TFLNCS4) | GTGGCCTATCTCATCTTCACAGTACT | 139 |
| TFLcomp21856-F (TFLNCS5) | CAAGTTCATCACACTAACACAAGTAAG | 140 |
| TFLcomp21856-R (TFLNCSS) | CTTCGAATTCTAGGCAGAAGAATCCAC | 141 |
| TFL_rep_c456-F (TFLNCS2) | ACCAAAGGTCCTATTACCGAAGATGA | 142 |
| TFL_rep_c456-R (TFLNCS2) | CTCTAGACTACATCTTTCAAGCCCCA | 143 |
| TFL_rep_c2110-F (TFLNCS3) | GAATATATATGAAGATGGAAGCTAC | 144 |
| TFL_rep_c2110-R (TFLNCS3) | CCACTTAAGTACCTACAAACCCCAA | 145 |
| BTH_c15840-F (BTHNCS1) | GAATTGGTAAATGAGATGGTAGTGGC | 146 |
| BTH_c15840-R (BTHNCS2) | GTAGTATCTTGTTAACACGATTTGTC | 147 |
| MCAcomp5594-F (MCANCS1) | CAGTCCATCCCTTCTCAGTCAATTAA | 148 |
| MCAcomp5594-R (MCANCS1) | GTCAATCCCATAAGCCTAATAACCA | 149 |
| CCH_rep_c1173-F (CCHNCS1) | AGATGGAAGTGGCTACTTCAGCTGAT | 150 |
| CCH_rep_c1173-R (CCHNCS1) | TCTTGATTGAATTGGATCCCCTCAAT | 151 |
| CCH_rep_c7133-F (CCHNCS2) | GAGTGTGATAGTAGAAAGAAATGAG | 152 |
| CCH_rep_c7133-R (CCHNCS2) | CATTGCCTTCAATGCATCCTAGTC | 153 |
| CCH_rep_c1524-F (CCHNCS3) | CGAGAGACTAAAAGTAAGGAAAAG | 154 |
| CCH_rep_c1524-R (CCHNCS3) | ACCTTGACACCATTATTAGTACTTCC | 155 |
| CCH_rep_c156-F (CCHNCS4) | TAGCAAGAATGAGGAAGCATCTTG | 156 |
| CCH_rep_c156-R (CCHNCS4) | AGCTAGCTAGGTGCATCCATCATAAG | 157 |
| CCH_rep_c2691-F (CCHNCS5) | AATGAGGAAGGAACTCACAAATGAGT | 158 |
| CCH_rep_c2691-R (CCHNCS5) | TCTCCCAAGCAAACAAAGCATTG | 159 |
| NDO_rep_c12880-F (NDONCS1) | TCTAGTTTGCATTATCAAGGAGAGGA | 160 |
| NDO_rep_c12880-R (NDONCS1) | ACATAGCGATGATGATTATATTTCGA | 161 |
| NDO_rep_c17645-F (NDONCS2) | CTTGAAATGGTATTTCCTCCAGGA | 162 |
| NDO_rep_c17645-R (NDONCS2) | AGTCGCATACATCCACATTTTGTTTC | 163 |
| NDO_rep_c11505-F (NDONCS3) | AATGAGGAGTGGAATTGTTTTCCTG | 164 |
| NDO_rep_c11505-R (NDONCS3) | GATTACACTACACGATGCAACTTTG | 165 |
| NDO_rep_c14985-F (NDONCS4) | GTAAATGAGATGGAAGTGGCTGCGT | 166 |
| NDO_rep_c14985-R (NDONCS4) | AGCATACATCTTGTTAATGACGCTTC | 167 |

TABLE C -continued

| Primers | Description | SEQ ID NO. |
|---|---|---|
| CTR_c5246-1-F (CTRNCS1) | GCCTGCATCAGCTTAGAACAC | 168 |
| CTR_c5246-1-R (CTRNCS1) | TGGCAGTCCACTTCCAATTCA | 169 |
| HCA_rep_c19-F (HCANCS1) | CGATCTTGCATCTGTAAACATTTCA | 170 |
| HCA_rep_c19-R (HCANCS1) | GCGTACGTACTCAAACAAGTATTTCT | 171 |
| NCA_rep_c28-F (NCANCS1) | TAAATAAGATGGTTCAGTTCAGCAGA | 172 |
| NCA_rep_c28-R (NCANCS1) | GAGCAGAAGTTGTGTTCCTCAGATTG | 173 |
| NCA_rep_c877-F (NCANCS2) | TGAGAGGAAGCAAGCACAAGG | 174 |
| NCA_rep_c877-R (NCANCS2) | CGGTCTTGTACCTGGGATGAT | 175 |
| XSIcomp133-F (XSINCS1) | GCAAGAAGGTTTCCTTAGTGCAA | 176 |
| XSIcomp133-R (XSINCS1) | TCAGTAGCTGCTTTGAACCAT | 177 |
| PSO_rep_c3975-F (PSONCS3) | TCGAGTGTTTCAGAGAGAACGA | 178 |
| PSO_rep_c3975-R (PSONCS3) | ACCCATTTTTCAAACATCGCCA | 179 |

TABLE D

| Primers | Description | SEQ. ID. NO. |
|---|---|---|
| CCHNCS1-HindIII | CCAAGCTTATGGAAGTGGCTACTTCA | 180 |
| CCHNCS1-XhoI | GCTCGAGTATCGAAACACCGCCGAT | 181 |
| CCHNCS2-HindIII | CCAAGCTTATGGAGGAAGGAATTAAGA | 182 |
| CCHNCS2-XhoI | GCTCGAGGTCTTCGAAAACTCCA | 183 |
| CCHNCS5-HindIII | CCAAGCTTATGGAGGAAGGAACTCACA | 184 |
| CCHNCS5-XhoI | GCTCGAGACCCAAACAATTGAAAGG | 185 |
| CMANCS1-BamHI | CGGGATCCTATGATTGAAGGAGGGTA | 186 |
| CMANCS1-XhoI | GCTCGAGGAGTGGAACACCCCCAAT | 187 |
| ECANCS1-HindIII | CCAAGCTTATGATCGGAGGATTCTTA | 188 |
| ECANCS1-XhoI | GCTCGAGATGACTTCTAACTTTTCGA | 189 |
| NDONCS3-HindIII | CCAAGCTTATGAGGAGTGGAATTGTT | 190 |
| NDONCS3-XhoI | GCTCGAGTATTTCGATAAACCCCTT | 191 |
| PBRNCS3-HindIII | CCAAGCTTATGGATATCATAGAAGGG | 192 |
| PBRNCS3-XhoI | GCTCGAGTGCTTTTAGACCTCCAAT | 193 |
| PBRNCS4-HindIII | CCAAGCTTATGATCGAAGGAGGGTAT | 194 |
| PBRNCS4-XhoI | GCTCGAGGAGTGGAACACGTCCAAT | 195 |
| PBRNCS5-HindIII | CCAAGCTTATGATGAGGAAAGTAATC | 196 |
| PBRNCS5-XhoI | GCTCGAGGAGTGGAACACGTCCA | 197 |
| SCANCS1-HindIII | CCAAGCTTATGAGGAAGGAACTGACA | 198 |
| SCANCS1-XhoI | GCTCGAGGAATGGAACACCTCCAAT | 199 |
| SDINCS1-BamHI | CGGATCCTATGAGGAAGGAAGTACG | 200 |
| SDINCS1-XhoI | GCTCGAGGAGTGGAACACCTC | 201 |
| TFLNCS1-HindIII | CCAAGCTTATGAAGATGGAAGTTGTA | 202 |
| TFLNCS1-XhoI | CCAAGCTTATGAGGATGGAAGTTGTT | 203 |
| XSINCS1-HindIII | GCTCGAGCTCTGATCTCTTGTATTTCT | 204 |
| XSINCS1-XhoI | CCAAGCTTATGAGGAAAGTAATCAAAT | 205 |
| PSONCS3-HindIII | CCAAGCTTATGAGGAAAGTAATCAAAT | 206 |
| PSONCS3-XhoI | GCTCGAGGCTTAGCCATTTTACCA | 207 |

TABLE E

| Primers | Description | SEQ. ID. NO. |
|---|---|---|
| PBRNCS3-25-HindIII | CCAAGCTTAGTTACAAGGAGAGATTTG | 208 |
| PBRNCS3-XhoI | GCTCGAGTGCTTTTAGACCTCCAAT | 209 |
| ECANCS1-25-HindIII | CCAAGCTTTCATGTATTATCAAATCAAC | 210 |
| ECANCS1-XhoI | GCTCGAGATGACTTCTAACTTTTCGA | 211 |

TABLE E -continued

| Primers | Description | SEQ. ID. NO. |
|---|---|---|
| CMANCS1-25-BamHI | CGGGATCCTAATTCATGCGTTATTGCAT | 212 |
| CMANCS1-BamHI | CGGGATCCTATGATTGAAGGAGGGTA | 213 |
| CCHNCS2-25-HindIII | CCAAGCTTGATATCCCAAGACTTC | 214 |
| CCHNCS2-XhoI | GCTCGAGGTCTTCGAAAACTCCA | 215 |
| TFLNCS2-25-HindIII | CCAAGCTTAGGCCATTTCTTAACCG | 216 |
| TFLNCS1-XhoI | CCAAGCTTATGAGGATGGAAGTTGTT | 217 |
| PBRNCS4-25-HindIII | CCAAGCTTAGCTCATGTGTTATTGAATC | 218 |
| PBRNCS4-XhoI | GCTCGAGGAGTGGAACACGTCCAAT | 219 |
| CCHNCS5-25-HindIII | CCAAGCTTGATCTCCCAAAAATCATA | 220 |
| CCHNCS5-XhoI | GCTCGAGACCCAAACAATTGAAAGG | 221 |
| XSINCS1-25-HindIII | CCAAGCTTGGGCGTCCTCTCCT | 222 |
| XSINCS1-XhoI | CCAAGCTTATGAGGAAAGTAATCAAAT | 223 |

TABLE F

| Primer | Description | SEQ. ID. NO. |
|---|---|---|
| SCANCS1-NotI | TAAAGGGCGGCCGCAAAAATGAGGAAGGAACTGACACACG | 224 |
| SCANCS1-BglII | AGACTGAGATCTTCAATGGTGATGGTGATGATGGAATGGAACACCTCCAATCAATAAC | 225 |
| NDONCS3-NotI | TCAAGTGCGGCCGCAAAAATGAGGAGTGGAATTGTTTTCC | 226 |
| NDONCS3-BglII | GTACCTAGATCTTCAATGGTGATGGTGATGATGTATTTCGATAAACCCCTTGTG | 227 |
| CCHNCS2-NotI | TAAAGGGCGGCCGCAAAAATGAGGAAGGAATTAAGACATG | 228 |
| CCHNCS2-SpeI | CGCGATACTAGTTCAATGGTGATGGTGATGATGGTCTTCGAAAACTCCAGGAA | 229 |
| PBRNCS5-NotI | TTAAGGGCGGCCGCAAAAATGATGAGGAAAGTAATCAAATACG | 230 |
| PBRNCS5-BglII | GTACTCAGATCTTCAATGGTGATGGTGATGATGGAGTGGAACACGTCCAATC | 231 |

The invention claimed is:

1. A host cell comprising a heterologous chimeric nucleic acid sequence comprising a promoter capable of controlling expression in the host cell linked to a nucleic acid sequence encoding norcoclaurine synthase (NCS), wherein norcoclaurine synthase (NCS) is a polypeptide having a sequence selected from the group of sequences set forth in SEQ ID NO:13; SEQ ID NO:14; SEQ ID NO:17; SEQ ID NO:28; SEQ ID NO:34; and SEQ ID NO:42; or is encoded by SEQ ID NO:109; or SEQ ID NO:113.

2. The host cell according to claim 1, wherein the host cell is able to produce at least one of L-tyrosine, L-DOPA, dopamine, tyramine, 4-hydroxy-phenylacetaldehyde (4-HPAA), and 3,4-dihydroxy-phenylacetaldehyde (3,4-DHPAA), and wherein the host cell is unable to produce (S)-norcoclaurine or (S)-norlaudanosoline, in the absence of the chimeric nucleic acid sequence.

3. The host cell according to claim 1 wherein the nucleic acid sequence encoding NCS further comprises a nucleic acid sequence selected from the group consisting of a nucleic acid sequence encoding tyrosine hydroxylase (TYR), a nucleic acid sequence encoding tyrosine decarboxylase (TYDC) and a nucleic acid sequence encoding dihydroxyphenylalanine decarboxylase (DODC).

4. The host cell according to claim 1, wherein the host cell is a microbial cell or a plant cell.

5. The host cell according to claim 4, wherein the microbial cell is a bacterial cell or a yeast cell.

6. A recombinant expression vector comprising in the 5' to 3' direction of transcription as operably linked components:
   (i) a nucleic acid sequence capable of controlling expression in a host cell; and
   (ii) a nucleic acid sequence encoding norcoclaurine synthase (NCS), wherein the norcoclaurine synthase (NCS) is a polypeptide having a sequence selected from the group of sequences set forth in SEQ ID NO:13; SEQ ID NO:14; SEQ ID NO:17; SEQ ID NO:28; SEQ ID NO:34; and SEQ ID NO:42; or is encoded by SEQ ID NO:109; or SEQ ID NO:113.

7. The recombinant expression vector according to claim 6 wherein the vector further comprises a nucleic acid sequence selected from the group consisting of a nucleic acid sequence encoding tyrosine hydroxylase (TYR), a nucleic acid sequence encoding tyrosine decarboxylase (TYDC) and a nucleic acid sequence encoding dihydroxyphenylalanine decarboxylase (DODC).

8. The host cell according to claim 2 wherein the nucleic acid sequence encoding NCS further comprises a nucleic acid sequence selected from the group consisting of a nucleic acid sequence encoding tyrosine hydroxylase (TYR), a nucleic acid sequence encoding tyrosine decarboxylase (TYDC) and a nucleic acid sequence encoding dihydroxyphenylalanine decarboxylase (DODC).

9. The host cell according to claim 2, wherein the host cell is a microbial cell or a plant cell.

10. The host cell according to claim 3, wherein the host cell is a microbial cell or a plant cell.

* * * * *